United States Patent
Burgdorf et al.

(10) Patent No.: US 10,570,149 B2
(45) Date of Patent: Feb. 25, 2020

(54) TRICYCLIC HETEROCYLIC DERIVATIVES

(71) Applicant: MERCK PATENT GMBH, Darmstadt (DE)

(72) Inventors: Lars Burgdorf, Frankfurt am Main (DE); Dieter Dorsch, Ober-Ramstadt (DE); Christos Tsaklakidis, Weinheim (DE)

(73) Assignee: MERCK PATENT GMBH, Darmstadt (DE)

(*) Notice: Subject to any disclaimer, the term of this patent is extended or adjusted under 35 U.S.C. 154(b) by 0 days.

(21) Appl. No.: 16/302,873

(22) PCT Filed: May 22, 2017

(86) PCT No.: PCT/EP2017/062221
§ 371 (c)(1),
(2) Date: Nov. 19, 2018

(87) PCT Pub. No.: WO2017/202748
PCT Pub. Date: Nov. 30, 2017

(65) Prior Publication Data
US 2019/0300547 A1 Oct. 3, 2019

(30) Foreign Application Priority Data
May 24, 2016 (EP) .................................. 16171025

(51) Int. Cl.
*C07D 487/14* (2006.01)
*A61K 31/5383* (2006.01)
*A61P 35/00* (2006.01)
*C07D 498/14* (2006.01)
*A61K 45/06* (2006.01)

(52) U.S. Cl.
CPC ........ *C07D 498/14* (2013.01); *A61K 31/5383* (2013.01); *A61K 45/06* (2013.01); *A61P 35/00* (2018.01)

(58) Field of Classification Search
CPC ............... C07D 498/14; C07D 519/00; A61K 31/5383; A61K 31/553; A61P 35/00

USPC ........................................ 544/101; 514/229.8
See application file for complete search history.

(56) References Cited

U.S. PATENT DOCUMENTS 9,453,931 B2 * 9/2016 Hillesund ............ G01V 1/3835

FOREIGN PATENT DOCUMENTS

WO 2014140644 A1 9/2014

OTHER PUBLICATIONS

Sundar et al., Curr Probl Cancer 41, 302-315, 2017.*
Cecil Textbook of Medicine, edited by Bennet, J.C., and Plum F., 20th edition,vol. 1, 1004-101 O, 1996.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
International Search Report PCT/EP2017/062221 dated Jul. 5, 2018 (pp. 1-2).

* cited by examiner

*Primary Examiner* — Venkataraman Balasubramanian
(74) *Attorney, Agent, or Firm* — Millen White Zelano and Branigan, PC; John Sopp

(57) ABSTRACT

Compounds of the formula I

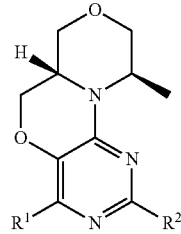

in which $R^1$ and $R^2$ have the meanings indicated in Claim 1, are inhibitors of ATR, and can be employed for the treatment of diseases such as cancer.

14 Claims, No Drawings

TRICYCLIC HETEROCYLIC DERIVATIVES

BACKGROUND OF THE INVENTION

The invention had the object of finding novel compounds having valuable properties, in particular those which can be used for the preparation of medicaments.

The present invention relates to 8,12-dioxa-1,3,5-triazatricyclo[8.4.0.0$^{2,7}$]tetradeca-2,4,6-triene derivatives which inhibit ATR (Ataxia telangiectasia mutated and Rad3-related kinase). The compounds of this invention are therefore useful in treating diseases such as cancer.

The present invention also provides methods for preparing these compounds, pharmaceutical compositions comprising these compounds, and methods of treating diseases utilizing pharmaceutical compositions comprising these compounds.

The tricyclic chemical entities of the present invention are inhibitors of ATR and have a number of therapeutic applications, particularly in the treatment of cancer.

Cancers are the consequence of uncontrolled cell growth of a wide variety of different tissues. In many cases the new cells penetrate into existing tissue, or they metastasize into remote organs. Cancers occur in a wide variety of organs and often progress in a manner specific to the tissue. The term "cancer" as a generic term therefore describes a large group of defined diseases of different organs, tissue and cell types.

In 2008, over 12 million people worldwide were diagnosed with cancer. In the same year, approx. 7.5 million deaths were assumed to be a consequence of these diseases (Globocan 2008 Report). In the USA alone, in 2012, more than 1.6 million new cases and more than 500 000 deaths were predicted from cancers. The majority of these new cases relate to cancers of the colon (~100 000), lung (~230 000), breast (~230 000) and prostate (~240 000) (American Cancer Society, Cancer Facts and Figures 2012).

Many current cancer treatments, including chemotherapeutic agents and ionizing radiation, induce DNA damage and replication fork stalling, thereby activating cell cycle checkpoint pathways and leading to cell cycle arrest. A variety of studies have shown that this response is an important mechanism that helps cancer cells survive the treatments. These findings have prompted the development of agents targeting DNA damage response signalling pathways.

ATR is a member of phosphatidylinositol kinase-related kinase (PIKK) protein family, and is activated by a wide variety of DNA damage events. In particular, ATR is essential to coordinate the response to replicative stress (RS), which stands for the pathological accumulation of single stranded DNA (ssDNA). The recombinogenic nature of ssDNA leads to chromosomal rearrangements that are a hallmark of cancer. In response to RS, ATR triggers arrest of the cell cycle in the S and G2/M stages by phosphorylation of CHK1.

ATR can prevent cancer development, as the ATR checkpoint response might limit the expansion of precancerous cells undergoing RS as a result of oncogene activation. Moreover, because the ATR-CHK1 checkpoint pathway serves to ensure cell survival after RS, a normal and robust ATR-CHK1 checkpoint may be a mechanism of resistance to chemotherapy and may allow cancer cells to survive with high endogenous levels of RS.

Inhibition of ATR-CHK1 pathway components could potentially enhance the effectiveness of replication inhibitors. In addition, ATR inhibition may be particularly toxic for cells with high levels of RS, such as those expressing oncogenes or lacking tumour suppressors. In these cells, strong limitation of ATR activity (for example, by use of an ATR inhibitor) would generate lethal amounts of RS leading to cell death.

A potential advantage of sensitizing cells in this way would be the capacity to lower the doses of the replication inhibitors. This would result in reduced toxicity to haematological and gastrointestinal organ systems among others, if the normal cells are not sensitized to the same extent. Specificity of the replication inhibitor for causing cancer cell death may be assisted by the fact that untransformed cells have more robust S and G2 checkpoints than tumour cells. For example, many cancers have mutations in p53 or other components of the p53 pathway, leading to reliance on the S and G2 checkpoints to arrest the cell cycle and provide for repair and survival. Inhibition of the S and G2 checkpoints may then preferentially kill these p53 deficient tumour cells.

The listing or discussion of an apparently prior-published document in this specification should not necessarily be taken as an acknowledgement that the document is part of the state of the art or is common general knowledge.

There is a lack of potent inhibitors of ATR. Therefore, a need exists for chemical entities that selectively inhibit ATR for clinical use or for further study of the ATR response.

It has been found that an (R) methyl group on the tricyclic pyrimidine core improves significantly the ATR inhibition potency. Furthermore, 5' substituted azaindoles can improve ATR potency and decrease hERG activity.

An (R) methyl group on the 8,12-dioxa-1,3,5-triazatricyclo[8.4.0.0$^{2,7}$]tetradeca-2,4,6-triene core significantly improves cellular ATR potencies.

It has been found that the compounds according to the invention and salts thereof have very valuable pharmacological properties while being well tolerated.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow active agents such as anti IgM to induce a cellular response such as expression of a surface marker, usually between about one hour and one week. In vitro testing can be carried out using cultivated cells from blood or from a biopsy sample. The amount of surface marker expressed is assessed by flow cytometry using specific antibodies recognising the marker.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

PRIOR ART

Other 8,12-dioxa-1,3,5-triazatricyclo[8.4.0.0$^{2,7}$]tetradeca-2,4,6-triene derivatives have been described as ATR inhibitors in WO 2014/140644.

SUMMARY OF THE INVENTION

The invention relates to compounds of the formula I

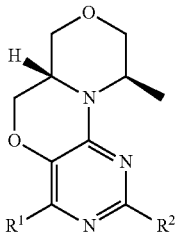

I in which
R¹ denotes C(CH₃)₂SO₂A', CH₂OSO₂A', C(CH₃)₂OH, —[C(R³)₂]ₙHet¹, or 1-methylsulfonyl-cycloprop-1-yl,
R² denotes Het², NR³(CH₂)ₙHet², OHet², Ar¹, CONHHet³, COHet³ or CONHA,
R³ denotes H or A',
Het¹ denotes imidazolyl, pyrazolyl, triazolyl or pyridyl, each of which is unsubstituted or monosubstituted by COOH, COOA', CH₂OH, CH₂OA' or A,
Het² denotes 1H-pyrrolo[2,3-b]pyridinyl, 1H-pyrrolo[2,3-c]pyridinyl, indolyl, benzimidazolyl, imidazolyl, 1,2,3,4-tetrahydroisoquinolyl, pyridyl, triazolyl, pyrazolyl, quinolyl, isoquinolyl, quinazolinyl or 1,3-dihydro-2lamda6-2,2-dioxo-1-benzothiazolyl, each of which is unsubstituted or mono- or disubstituted by Hal, A', —[C(R³)₂]ₙOR³, CONH₂, SO₂phenyl, benzyl, CN, —[C(R³)₂]ₙNH₂, —[C(R³)₂]ₙNHA, oxetanyl-NH— and/or NHCOA,
Het³ denotes triazolyl, pyridazinyl, pyrimidinyl, pyrazolyl or pyrrolidinyl each of which is unsubstituted or monosubstituted by —[C(R³)₂]ₙOR³, —[C(R³)₂]ₙNH₂ or =O,
Ar¹ denotes phenyl monosubstituted by —[C(R³)₂]ₙOR³, imidazolyl, —[C(R³)₂]ₙNH₂, pyrazolyl, aziridinyl or oxetanyl, each of which may be unsubstituted or monosubstituted by —[C(R³)₂]ₙOR³ or —[C(R³)₂]ₙNH₂,
A denotes unbranched or branched alkyl having 1-6 C-atoms, in which 1-7 H atoms may be replaced by OH, F, Cl and/or Br and/or in which one or two non-adjacent CH₂ groups may be replaced by O and/or NH groups,
A' denotes unbranched or branched alkyl having 1-4 C-atoms,
Hal denotes F, Cl, Br or I,
n denotes 0, 1, 2 or 3,
and pharmaceutically acceptable salts, tautomers and stereoisomers thereof, including mixtures thereof in all ratios.

The invention also relates to the optically active forms (stereoisomers), the enantiomers, the racemates, the diastereomers and the hydrates and solvates of these compounds.

Moreover, the invention relates to pharmaceutically acceptable derivatives of compounds of formula I.

The term solvates of the compounds is taken to mean adductions of inert solvent molecules onto the compounds which form owing to their mutual attractive force. Solvates are, for example, mono- or dihydrates or alkoxides.

It is understood, that the invention also relates to the solvates of the salts.

The term pharmaceutically acceptable derivatives is taken to mean, for example, the salts of the compounds according to the invention and also so-called prodrug compounds.

As used herein and unless otherwise indicated, the term "prodrug" means a derivative of a compound of formula I that can hydrolyze, oxidize, or otherwise react under biological conditions (in vitro or in vivo) to provide an active compound, particularly a compound of formula I. Examples of prodrugs include, but are not limited to, derivatives and metabolites of a compound of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution.

The invention relates to the compounds of the formula I and salts thereof and to a process for the preparation of compounds of the formula I and pharmaceutically acceptable salts, solvates, tautomers and stereoisomers thereof, characterised in that a)
a compound of the formula II

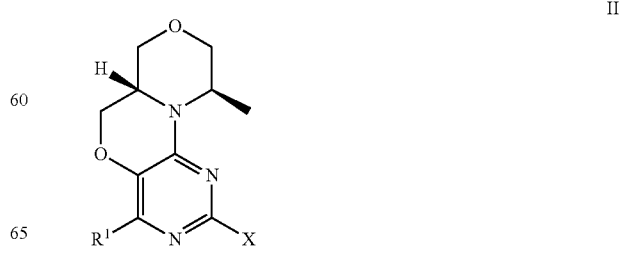

II in which R¹ has the meanings indicated in Claim 1,
and X denotes Cl or Br,
is reacted
with a compound of formula III $$L-R^2 \qquad \text{III}$$

in which R² has the meanings indicated in Claim 1,
and L denotes H, a boronic acid or a boronic acid ester group,
or
b)
a compound of the formula IIb in which R¹ has the meaning indicated in Claim 1, and R³ denotes unbranched or branched alkyl having 1-4 C-atoms,
is reacted
with a compound of formula III $$X-R^2 \qquad \text{III}$$

in which R² has the meanings indicated in Claim 1,
and X denotes Cl, Br or I,
and/or
a base or acid of the formula I is converted into one of its salts.

Above and below, the radicals R¹ and R² have the meanings indicated for the formula I, unless explicitly stated otherwise.

A denotes alkyl, this is unbranched (linear) or branched, and has 1, 2, 3, 4, 5, 6, 7 or 8 C atoms. A preferably denotes methyl, ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Moreover, A denotes preferably $CH_2OCH_3$, $CH_2CH_2OH$ or $CH_2CH_2OCH_3$.

A' denotes alkyl, this is unbranched (linear) or branched, and has 1, 2, 3 or 4 C atoms. A' preferably denotes methyl, ethyl, propyl, isopropyl, butyl, isobutyl, sec-butyl or tert-butyl.

R¹ preferably denotes $C(CH_3)_2SO_2CH_3$, $CH_2OSO_2CH_3$, $C(CH_3)_2OH$, $—[C(R^3)_2]_n\text{Het}^1$ or 1-methylsulfonyl-cycloprop-1-yl; most preferably $C(CH_3)_2SO_2CH_3$ or $C(CH_3)_2OH$.

R² preferably denotes Het².

R³ preferably denotes H or $CH_3$, most preferably H.

The heterocyclic substituent pyridyl=pyridinyl.

Het¹ preferably denotes imidazolyl, pyrazolyl, triazolyl or pyridyl, each of which is unsubstituted or monosubstituted by COOH or $COOCH_3$.

Het¹ most preferably denotes triazolyl which is unsubstituted or monosubstituted by COOH or $COOCH_3$.

Het² preferably denotes 1H-pyrrolo[2,3-b]pyridinyl, 1H-pyrrolo[2,3-c]pyridinyl, indolyl, benzimidazolyl or imidazolyl, each of which is mono- or disubstituted by Hal, $—[C(R^3)_2]_nNH_2$ and/or $—[C(R^3)_2]_nNHA$.

Het² most preferably denotes 1H-pyrrolo[2,3-b]pyridinyl, 1H-pyrrolo[2,3-c]pyridinyl or benzimidazolyl, each of which is unsubstituted or monosubstituted by Hal, NHCOA', $—[C(R^3)_2]_nNH_2$ or $—[C(R^3)_2]_nNHA'$.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Il, which conform to the formula I and in which the radicals not designated in greater detail have the meaning indicated for the formula I, but in which in Ia R¹ denotes $C(CH_3)_2SO_2A'$ or $C(CH_3)_2OH$;
in Ib R¹ denotes $C(CH_3)_2SO_2CH_3$, $CH_2OSO_2CH_3$, $C(CH_3)_2OH$, $—[C(R^3)_2]_n\text{Het}^1$ or 1-methylsulfonyl-cycloprop-1-yl;
in Ic R¹ denotes $C(CH_3)_2SO_2CH_3$ or $C(CH_3)_2OH$;
in Id R² denotes Het²;
in Ie R³ denotes H;
in If A denotes unbranched or branched alkyl having 1-6 C-atoms, in which 1-5 H atoms may be replaced by OH and/or F;
in Ig Het¹ denotes imidazolyl, pyrazolyl, triazolyl or pyridyl, each of which is unsubstituted or monosubstituted by COOH or $COOCH_3$;
in Ih Het² denotes 1H-pyrrolo[2,3-b]pyridinyl, 1H-pyrrolo[2,3-c]pyridinyl, indolyl, benzimidazolyl or imidazolyl, each of which is mono- or disubstituted by Hal, $—[C(R^3)_2]_nNH_2$ and/or $—[C(R^3)_2]_nNHA$,
in Ii R¹ denotes $C(CH_3)_2SO_2A'$ or $C(CH_3)_2OH$;
R² denotes Het²,
Het² denotes 1H-pyrrolo[2,3-b]pyridinyl, 1H-pyrrolo[2,3-c]pyridinyl, indolyl, benzimidazolyl or imidazolyl, each of which is unsubstituted or mono- or disubstituted by Hal, OH, $—[C(R^3)_2]_nNH_2$, $—[C(R^3)_2]_nNHA$, oxetanyl-NH— and/or NHCOA,
A denotes unbranched or branched alkyl having 1-6 C-atoms, in which 1-5 H atoms may be replaced by OH and/or F,
A' denotes unbranched or branched alkyl having 1-4 C-atoms,
Hal denotes F, Cl, Br or I,
n denotes 0, 1, 2 or 3;
in Ij R¹ denotes $C(CH_3)_2SO_2CH_3$, $CH_2OSO_2CH_3$, $C(CH_3)_2OH$, $—[C(R^3)_2]_n\text{Het}^1$ or 1-methylsulfonyl-cycloprop-1-yl,
R² denotes Het²,
R³ denotes H, Het² denotes 1H-pyrrolo[2,3-b]pyridinyl, 1H-pyrrolo[2,3-c]pyridinyl, indolyl, benzimidazolyl or imidazolyl, each of which is unsubstituted or mono- or disubstituted by Hal, OH, —[C(R³)₂]ₙNH₂, —[C(R³)₂]ₙNHA, oxetanyl-NH— and/or NHCOA, A denotes unbranched or branched alkyl having 1-6 C-atoms, in which 1-5 H atoms may be replaced by OH and/or F, A' denotes unbranched or branched alkyl having 1-4 C-atoms, Hal denotes F, Cl, Br or I, n denotes 0, 1, 2 or 3;

in Ik R¹ denotes C(CH₃)₂SO₂CH₃ or C(CH₃)₂OH,

R² denotes Het²,

R³ denotes H,

Het² denotes 1H-pyrrolo[2,3-b]pyridinyl, 1H-pyrrolo[2,3-c]pyridinyl, indolyl, benzimidazolyl or imidazolyl, each of which is mono- or disubstituted by Hal, —[C(R³)₂]ₙNH₂ and/or —[C(R³)₂]ₙNHA, A denotes unbranched or branched alkyl having 1-6 C-atoms, in which 1-5 H atoms may be replaced by OH and/or F, A' denotes unbranched or branched alkyl having 1-4 C-atoms, Hal denotes F, Cl, Br or I, n denotes 0, 1, 2 or 3;

in Il R¹ denotes C(CH₃)₂SO₂CH₃,

R² denotes Het²,

R³ denotes H,

Het² denotes 1H-pyrrolo[2,3-b]pyridinyl, 1H-pyrrolo[2,3-c]pyridinyl or benzimidazolyl, each of which is unsubstituted or monosubstituted by Hal, NHCOA', —[C(R³)₂]ₙNH₂ or —[C(R³)₂]ₙNHA', A' denotes unbranched or branched alkyl having 1-4 C-atoms, Hal denotes F, Cl, Br or I, n denotes 0 or 1;

and pharmaceutically acceptable salts, tautomers and stereoisomers thereof, including mixtures thereof in all ratios.

Most preferred compounds according to the invention are "A1", "A20", "A11", "A15", "A13", "A29", "A24" and "A34".

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The starting compounds of the formula II and III are generally known. If they are novel, however, they can be prepared by methods known per se.

Compounds of the formula I can preferably be obtained by reacting a compound of the formula II with a compound of the formula III.

In the compounds of the formula III, L preferably denotes H,

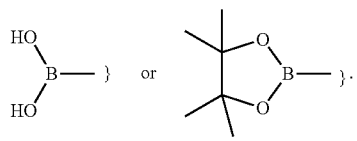

This coupling is generally carried out at elevated temperature using a palladium catalyst, a base and an inert solvent. An overview of catalysts and reaction conditions can be found in the literature [see, for instance, S. Kotha et al., Tetrahedron 2002, 58, 9633-9695; T. E. Barder et al., J. Am. Chem. Soc. 2005, 127, 4685-4696]. The preferred catalyst in this reaction is tetrakis(triphenylphosphine)-palladium(0). The preferred base is sodium carbonate employed as an aqueous solution. The reaction is carried out in organic solvents that are inert under the reaction conditions, such as 1,4-dioxane, acetonitrile, N,N-dimethylformamide (DMF) or dimethylsulfoxide (DMSO), or in water or in mixtures of these solvents. Preferably, the reaction is carried out in a mixture of 1,4-dioxane and water or acetonitrile and water. The reaction is generally performed at temperatures between +100° C. and +250° C., preferably at +110° C. to +150° C. Heating is preferably effected by a singlemode microwave device. The reactions are usually run under an inert gas atmosphere, preferably under argon.

The azaindole group preferably is protected during the reaction steps by means of a phenylsulfonyl group. This group preferably is cleaved off with Cs₂CO₃ in CF₃CH₂OH/THF.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, formate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese (III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Isotopes

There is furthermore intended that a compound of the formula I includes isotope-labelled forms thereof. An isotope-labelled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. A compound of the formula I or a pharmaceutically acceptable salt of either which contains one or more of the above-mentioned isotopes and/or other isotopes of other atoms is intended to be part of the present invention. An isotope-labelled compound of the formula I can be used in a number of beneficial ways. For example, an isotope-labelled compound of the formula I into which, for example, a radioisotope, such as $^3$H or $^{14}$C, has been incorporated is suitable for medicament and/or substrate tissue distribution assays. These radioisotopes, i.e. tritium ($^3$H) and carbon-14 ($^{14}$C), are particularly preferred owing to simple preparation and excellent detectability. Incorporation of heavier isotopes, for example deuterium ($^2$H), into a compound of the formula I has therapeutic advantages owing to the higher metabolic stability of this isotope-labelled compound. Higher metabolic stability translates directly into an increased in vivo half-life or lower dosages, which under most circumstances would represent a preferred embodiment of the present invention. An isotope-labelled compound of the formula I can usually be prepared by carrying out the procedures disclosed in the synthesis schemes and the related description, in the example part and in the preparation part in the present text, replacing a non-isotope-labelled reactant by a readily available isotope-labelled reactant.

Deuterium ($^2$H) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus cause a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a compound of the formula I that is susceptible to oxidation, the profile of this compound in vivo can be drastically modified and result in improved pharmacokinetic properties.

When discovering and developing therapeutic agents, the person skilled in the art attempts to optimise pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t½), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent of the extent to which the improvement in resistance to oxidative metabolism has improved. In this way, it is deter-mined that the half-life of the parent compound can be extended by up to 100% as the result of deuterium-hydrogen exchange of this type.

Deuterium-hydrogen exchange in a compound of the formula I can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The invention furthermore relates to medicaments comprising at least one compound of the formula I and/or pharmaceutically acceptable salts, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and pharmaceutically salts, tautomers and stereoisomers thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, tautomers and stereoisomers thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

A combined treatment of this type can be achieved with the aid of simultaneous, consecutive or separate dispensing of the individual components of the treatment. Combination products of this type employ the compounds according to the invention.

The invention furthermore relates to medicaments comprising at least one compound of the formula I and/or pharmaceutically acceptable salts, tautomers and stereoisomers thereof, including mixtures thereof in all ratios, and at least one further medicament active ingredient.

The invention also relates to a set (kit) consisting of separate packs of
(a) an effective amount of a compound of the formula I and/or pharmaceutically acceptable salts, tautomers and stereoisomers thereof, including mixtures thereof in all ratios,
and
(b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically acceptable salts, tautomers and stereoisomers thereof, including mixtures thereof in all ratios, and an effective amount of a further medicament active ingredient in dissolved or lyophilised form.

"Treating" as used herein, means an alleviation, in whole or in part, of symptoms associated with a disorder or disease, or slowing, or halting of further progression or worsening of those symptoms, or prevention or prophylaxis of the disease or disorder in a subject at risk for developing the disease or disorder.

The term "effective amount" in connection with a compound of formula (I) can mean an amount capable of alleviating, in whole or in part, symptoms associated with a disorder or disease, or slowing or halting further progression or worsening of those symptoms, or preventing or providing prophylaxis for the disease or disorder in a subject having or at risk for developing a disease disclosed herein, such as inflammatory conditions, immunological conditions, cancer or metabolic conditions.

In one embodiment an effective amount of a compound of formula (I) is an amount that inhibits ATR in a cell, such as, for example, in vitro or in vivo. In some embodiments, the effective amount of the compound of formula (I) inhibits tankyrase in a cell by 10%, 20%, 30%, 40%, 50%, 60%, 70%, 80%, 90% or 99%, compared to the activity of ATR in an untreated cell. The effective amount of the compound of formula (I), for example in a pharmaceutical composition, may be at a level that will exercise the desired effect; for example, about 0.005 mg/kg of a subject's body weight to about 10 mg/kg of a subject's body weight in unit dosage for both oral and parenteral administration.

Use

The present compounds are suitable as pharmaceutical active ingredients for mammals, especially for humans. in the treatment of cancer.

The present invention encompasses the use of the compounds of the formula I and/or pharmaceutically acceptable salts, tautomers and stereoisomers thereof for the preparation of a medicament for the treatment or prevention of cancer.

Moreover, the present invention encompasses the compounds for use of the formula I and/or pharmaceutically acceptable salts, tautomers and stereoisomers thereof for treatment or prevention of cancer, Also encompassed is the use of the compounds of the formula I and/or pharmaceutically acceptable salts, tautomers and stereoisomers thereof for the preparation of a medicament for the treatment or prevention of a ATR-induced disease or a ATR-induced condition in a mammal, in which to this method a therapeutically effective amount of a compound according to the invention is administered to a sick mammal in need of such treatment. The therapeutic amount varies according to the specific disease and can be determined by the person skilled in the art without undue effort.

The present invention specifically relates to compounds of the formula I and pharmaceutically acceptable salts, tautomers and stereoisomers thereof, including mixtures thereof in all ratios, for the use for the treatment of diseases in which the inhibition, regulation and/or modulation inhibition of ATR plays a role.

The present invention specifically relates to compounds of the formula I and pharmaceutically acceptable salts, tautomers and stereoisomers thereof, including mixtures thereof in all ratios, for the use for the inhibition of ATR.

Representative cancers that compounds of formula I are useful for treating or preventing include, but are not limited to, cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, brain, central nervous system, solid tumors and blood-borne tumors.

Preferably, the present invention relates to a method wherein the disease is a cancer.

Particularly preferable, the present invention relates to a method wherein the disease is a cancer, wherein administration is simultaneous, sequential or in alternation with administration of at least one other active drug agent.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating Agents such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone;

apaziquone, fotemustine, glufosfamide, palifosfamide, pipobroman, trofosfamide, uramustine, TH-302[4], VAL-083[4];

[4] no INN.

Platinum Compounds such as carboplatin, cisplatin, eptaplatin, miriplatine hydrate, oxaliplatin, lobaplatin, nedaplatin, picoplatin, satraplatin;

lobaplatin, nedaplatin, picoplatin, satraplatin;

DNA Altering Agents such as amrubicin, bisantrene, decitabine, mitoxantrone, procarbazine, trabectedin, clofarabine;

amsacrine, brostallicin, pixantrone, laromustine[1,3];

[1] Prop. INN (Proposed International Nonproprietary Name)
[2] Rec. INN (Recommended International Nonproprietary Names)
[3] USAN (United States Adopted Name)

Topoisomerase Inhibitors such as etoposide, irinotecan, razoxane, sobuzoxane, teniposide, topotecan;

amonafide, belotecan, elliptinium acetate, voreloxin;

Microtubule Modifiers such as cabazitaxel, docetaxel, eribulin, ixabepilone, paclitaxel, vinblastine, vincristine, vinorelbine, vindesine, vinflunine;

fosbretabulin, tesetaxel;

Antimetabolites such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur;

doxifluridine, elacytarabine, raltitrexed, sapacitabine, tegafur[2,3], trimetrexate;

Anticancer Antibiotics such as bleomycin, dactinomycin, doxorubicin, epirubicin, idarubicin, levamisole, miltefosine, mitomycin C, romidepsin, streptozocin, valrubicin, zinostatin, zorubicin, daunurobicin, plicamycin;

aclarubicin, peplomycin, pirarubicin;

Hormones/Antagonists such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol;

acolbifene, danazol, deslorelin, epitiostanol, orteronel, enzalutamide[1,3];

Aromatase Inhibitors such as aminoglutethimide, anastrozole, exemestane, fadrozole, letrozole, testolactone;

formestane;

Small Molecule Kinase Inhibitors such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib;

afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];

Photosensitizers such as methoxsalen[3];

porfimer sodium, talaporfin, temoporfin;

Antibodies such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3];

catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1];

tabalumab[1,3], EMD-525797[4], nivolumab[1,3];

Cytokines such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates such as denileukin diftitox, ibritumomab tiuxetan, iobenguane I123, prednimustine, trastuzumab emtansine, estramustine, gemtuzumab, ozogamicin, aflibercept;

cintredekin besudotox, edotreotide, inotuzumab ozogamicin, naptumomab estafenatox, oportuzumab monatox, technetium (99mTc) arcitumomab[1,3], vintafolide[1,3];

Vaccines such as sipuleucel[3]; vitespen[3], emepepimut-S[3], oncoVAX[4], rindopepimut[3], troVax[4], MGN-1601[4], MGN-1703[4];

Miscellaneous alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat;

celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4];

PARP Inhibitors

Olaparib, Veliparib.

The following abbreviations refer respectively to the definitions below:

aq (aqueous), h (hour), g (gram), L (liter), mg (milligram), MHz (Megahertz), min. (minute), mm (millimeter), mmol (millimole), mM (millimolar), m.p. (melting point), eq (equivalent), mL (milliliter), L (microliter), ACN (acetonitrile), AcOH (acetic acid), $CDCl_3$ (deuterated chloroform), $CD_3OD$ (deuterated methanol), $CH_3CN$ (acetonitrile), c-hex (cyclohexane), DCC (dicyclohexyl carbodiimide), DCM (dichloromethane), DIC (diisopropyl carbodiimide), DIEA (diisopropylethyl-amine), DMF (dimethylformamide), DMSO (dimethylsulfoxide), DMSO-$d_6$ (deuterated dimethylsulfoxide), EDC (1-(3-dimethyl-amino-propyl)-3-ethylcarbodiimide), ESI (Electro-spray ionization), EtOAc (ethyl acetate), $Et_2O$ (diethyl ether), EtOH (ethanol), HATU (dimethylamino-([1,2,3]triazolo[4,5-b]pyridin-3-yloxy)-methylene]-dimethylammonium hexafluorophosphate), HPLC (High Performance Liquid Chromatography), i-PrOH (2-propanol), $K_2CO_3$ (potassium carbonate), LC (Liquid Chromatography), MeOH (methanol), $MgSO_4$ (magnesium sulfate), MS (mass spectrometry), MTBE (Methyl tert-butyl ether), $NaHCO_3$ (sodium bicarbonate), $NaBH_4$ (sodium borohydride), NMM (N-methyl morpholine), NMR (Nuclear Magnetic Resonance), PyBOP (benzotriazole-1-yloxy-trispyrrolidino-phosphonium hexafluorophosphate), Pd dba (Tris(dibenzylideneacetone)dipalladium(0)), $PdCl_2[P(cy)_3]_2$ (Dichlorobis(tricyclohexylphosphine)palladium(II)), RT (room temperature), Rt (retention time), SPE (solid phase extraction), TBTU (2-(1-H-benzotriazole-1-yl)-1,1,3, 3-tetramethyluromium tetrafluoro borate), TEA (triethylamine), TFA (trifluoroacetic acid), THF (tetrahydrofuran), TLC (Thin Layer Chromatography), UV (Ultraviolet), Xantphos (4,5-Bis(diphenylphosphino)-9,9-dimethylxanthene).

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the residue is purified by chromatography on silica gel and/or by crystallisation. Rf values on silica gel; eluent:ethyl acetate/methanol 9:1.

$^1H$ NMR was recorded on Bruker DPX-300, DRX-400, AVII-400 or on a 500 MHz spectrometer, using residual signal of deuterated solvent as internal reference. Chemical shifts (δ) are reported in ppm relative to the residual solvent signal (δ=2.49 ppm for $^1H$ NMR in DMSO-$d_6$). $^1H$ NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

HPLC data provided in the examples described below (retention time given) were obtained as followed.

Method A: 1 min 99% A. In 2.5 min from 99% A to 100% B. Followed by 1.5 min 100% B and 1 min 99% A. Column Chromolith SpeedRod RP-18e; 50-4.6 mm; detection 220 nM (Solvent A: H20 (0.1% TFA), Solvent B: ACN (0.1% TFA)

Method A: Column: XBridge C8 (50×4.6 mm, 3.5 μm); A—0.1% TFA in $H_2O$, B—0.1% TFA in ACN: Flow—2.0 mL/min.

LCMS data provided in the examples are given with retention time, purity and/or mass in m/z. The results were obtained as followed: Mass spectrum: LC/MS Waters ZMD (ESI) or Hewlett Packard System of the HP 1100 series (Ion source: Electrospray (positive mode) or Waters Acquity H Class SQD; Scan: 100-1000 m/z; Fragmentation-voltage: 60 V; Gas-temperature: 300° C., DAD: 220 nm. Flow rate: 2.4 ml/Min. The used splitter reduced the flow rate after the DAD for the MS to 0.75 ml/Min; Column: Chromolith Speed ROD RP-18e 50-4.6; Solvent: LiChrosolv-quality from the company Merck KGaA or as mentioned in the method.

Method A: Column: XBridge C8 (50×4.6 mm); A—0.1% TFA in $H_2O$, B—0.1% TFA in ACN: Flow—2.0 ml/min; Column: XBridge C8 (50×4.6 mm 3.5 Um, +ve mode.

Method B: Column: XBridge C8 (50×4.6 mm); A—0.1% $NH_4HCO_3$ in $H_2O$, B—ACN: Flow—1.0 mL/min.

Method C: Column: Chromolith SpeedROD RP-18e 50-4.6 mm; Solvent A: water+0.05% formic acid; Solvent B: acetonitrile+0.04% formic acid, Flow: 3.3 ml/min; Gradient: within 2 min from 0% B to 100% B.

Method D: Column: Chromolith Speed Rod RP18e-50-4.6; Flow: 2.0 ml/min; Solvent A: Water+0.1% TFA; Solvent B: Acetonitril+0.1% TFA; WL: 220 nm, Gradient: within 0.2 min from 0% B to 1% and within 3.6 min: from 1% B to 100% B, followed by 0.4 min 100% B.

Method E: Column Kinetex EVO-C 18 1.7 μm 50-2.1 mm; Solvent A: H2O+0.05% HCOOH, B: MeCN+0.04% HCOOH; Flow: 0.9 ml/min; Gradient 1%→100% B: 0→1.0 min|100% B: 1.0→1.3 min.

Method F: Column: BEH C-18 2.1-50 1.7 μm; column temp.: 40° C., solvent A: water+0.1% HCOOH, solvent B acetonitrile+0.08% HCOOH; flow: 0.9 ml/min; gradient: 0 min 4% B, in 1 min up to 100% B, till 1.3 min 100% B, till 1.4 min to 4% B, till 2 min 4% B.

Preparative HPLC was performed on a Agilent 1200. Column: Chromolith prep RP 18e Merck KGaA. Mobile phase: 0.1% formic acid in water/0.1% formic acid in acetonitrile.

Preparative column chromatography on normal phase.

The microwave chemistry is performed on a single mode microwave reactor Emrys™ Optimiser from Personal Chemistry.

ATR/ATRIP Kinase Assay—Measurement of ATR/ATRIP Inhibition

The $IC_{50}$ value was determined by an ATR/ATRIP enzymatic assay. The assay comprises two steps: the enzymatic reaction and the detection step. First, a mixture of ATR/ATRIP protein (Ataxia Telangiectasia and Rad3-related protein/ATR interacting protein), the compound in question at different concentrations, p53 as substrate protein and adenosine triphosphate (ATP) are incubated in assay buffer. ATR phosphorylates p53 at Ser15 and other residues. The amount of phosphorylated p53 is then detected using specific antibodies and the TR-FRET assay technology.

In detail: The ATR/ATRIP enzymatic assay is performed as a TR-FRET-(HTRF™, Cisbio Bioassays) based 384-well assay. In a first step, purified human recombinant ATR/ATRIP (human ATR, full length, GenBank ID: NM_001184.3, and human ATRIP, full length, GenBank ID AF451323.1, co-expressed in a mammalian cell line) is incubated in assay buffer for 15 minutes at 22° C. with test compound at different concentrations or without test compound (as a negative control). The assay buffer contains 25 mM HEPES pH 8.0, 10 mM Mg(CH$_3$COO)$_2$, 1 mM MnCl$_2$, 0.1% BSA, 0.01% Brij® 35, and 5 mM dithiothreitol (DTT). An Echo 555 (Labcyte) is used for dispensing of compound solutions. Then, in a second step, purified human recombinant cmyc-tagged p53 (human p53, full length, GenBank ID: BC003596, expressed in Sf21 insect cells) and ATP are added and the reaction mixture is incubated for 25-35 minutes, typically 25 minutes, at 22° C. The pharmacologically relevant assay volume is 5 µl. The final concentrations in the assay during incubation of the reaction mixture are 0.3-0.5 nM, typically 0.3 nM, ATR/ATRIP, 50 nM p53, and 0.5 µM ATP. The enzymatic reaction is stopped by the addition of EDTA. The generation of phosphorylated p53 as a result of the ATR mediated reaction in the presence of ATP is detected by using specific antibodies [labeled with the fluorophores europium (Eu) as donor and d2 as acceptor (Cisbio Bioassays)] enabling FRET. For this purpose, 2 µl of antibody-containing stop solution (12.5 mM HEPES pH 8.0, 125 mM EDTA, 30 mM sodium chloride, 300 mM potassium fluoride, 0.006% Tween-20, 0.005% Brij® 35, 0.21 nM anti-phospho-p53(Ser15)-Eu antibody, 15 nM anti-cmyc-d2 antibody) are added to the reaction mixture. Following signal development for 2 h the plates are analyzed in an EnVision (PerkinElmer) microplate reader using the TRF mode with laser excitation. Upon excitation of the donor europium at 340 nm the emitted fluorescence light of the acceptor d2 at 665 nm as well as from the donor Eu at 615 nm are measured. The amount of phosphorylated p53 is directly proportional to the ratio of the amounts of emitted light i.e. the ratio of the relative fluorescence units (rfu) at 665 nm and 615 nm. Data are processed employing the Genedata Screener software. In particular, IC$_{50}$ values are determined in the usual manner by fitting a dose-response curve to the data points using nonlinear regression analysis.

IC$_{50}$=half maximal inhibitory concentration
ATP=Adenosine triphosphate
TR-FRET=Time-Resolved Fluorescence Resonance Energy Transfer
HTRF®=Homogeneous Time Resolved Fluorescence
HEPES=2-(4-(2-Hydroxyethyl)-1-piperazinyl)-ethanesulfonic acid
Mg(CH3COO)$_2$=Magnesium acetate
MnCl$_2$=Manganese(II)-chloride
BSA=Bovine Serum Albumin
EDTA=Ethylendiamine Tetraacetate
TRF=Time Resolved Fluorescence pCHK1 Cellular Assay Chk1 kinase acts downstream of ATR and has a key role in DNA damage checkpoint control. Activation of Chk1 involves phosphorylation of Ser317 and Ser345 (regarded as the preferential target for phosphorylation/activation by ATR) and occurs in response to blocked DNA replication and certain forms of genotoxic stress. Phosphorylation at Ser 345 serves to localize Chk1 to the nucleus following checkpoint activation.

This assay measures a decrease in phosphorylation of Chk1 (Ser 345) in HT29 colon adenocarcinoma cells following treatment with compound and hydroxyurea (which promotes fork stalling because of dNTP depletion) and using an immunocytochemical procedure and high content imaging.

For the assay HT29 cells are plated in culture medium (DMEM high Glucose (no phenol red), 2 mM Glutamax, 1 mM Pyruvate, 10% FCS into Greiner 384 well plates, black, µclear #781090 (2500 cells/well/30 µl) and incubated for at least 20 hours at 37° C., 10% CO2 and 90% rH. Diluted test compounds (1 nM-30 µM final) and hydroxyurea (3 mM final) are added simultaneously and cells are incubated for 4 h at 37° C. After fixation/prmeabilisation with 100% MeOH (−20° C. cold) and permeabilisation with 0.2% Triton X-100 a complete immunocytochemical procedure is performed using a specific anti-pChk1 antibody (Cell Signaling, #2348BF) and fluorescently labelled secondary antibody (Alexa Fluor® 488 goat anti-rabbit F(ab')2 fragment, Invitrogen A11070) and parallel nuclear staining for cell counting.

The nuclear localised pChk1 signal is detected on an ImageXpress Ultra confocal high content reader and reported as % positive cells (nuclei).

gH2AX-TopBP1ER Cellular Assay

ATR activity is restricted to replicating cells and many of its targets can also be phosphorylated by other PIKKs. These restrictions have limited the development of selective cellular assays in the past. In order to overcome these limitations, a previously developed genetically engineered cellular system in which ATR, and only ATR, can be activated at will in every cell (Toledo et al Genes Dev. 22, 297-302 2008) was used. In this system, the addition of 4-hydroxytamoxifen (4-OHT), promotes the nuclear translocation of a fragment of TopBP1 which then activates ATR. The phosphorylation of H2AX that follows 4-OHT addition in these cells is a direct and selective readout of ATR activity, which is not influenced by the rest of PIKKs. This property has been used in a screen for compounds with ATR inhibitory capacity. U2OS-TopBP1-ER cells stably express the TopBP1 activation domain (aa 978-1286) fused to a mutated estrogen receptor ligand binding domain. Nuclear accumulation of the TopBP1-ER-LBD fusion protein is induced by the synthetic ER antagonist 4-hydroxytamoxifen (4-OHT) (and not by natural ER agonists) mediating specific ATR activation that is independent of DNA damage or cell cycle. In the assay phosphorylation of the ATR substrate H2AX ("gH2AX") at Serin 139 is detected using an immunecytochemical procedure and high content imaging. For the assay U2OS-TopBP1-ER cells are plated in culture medium (DMEM high Glucose (no phenol red), 2 mM Glutamax, 1 mM Pyruvate, 10% FCS into Greiner 384 well plates, black, µclear #781090 (4000 cells/well/30 µl) and incubated for at least 20 hours at 37° C., 10% CO2 and 90% rH. Diluted test compounds (1 nM-30 µM final) and 4-OHT (1 µM final) are added simultaneously and cells are incubated for 2 h at 37° C. After fixation with 4% formaldehyde and permeabilisation with 0.2% Triton X-100 a complete immunocytochemical procedure is performed using a specific anti-gH2AX-antibody (Millipore 05-636, clone JBW301) and fluorescently labelled secondary antibody (Alexa Fluor® 488 goat anti-mouse F(ab')2 fragment, Invitrogen A11017) and parallel nuclear staining for cell counting. The nuclear localised gH2AX signal is detected on an ImageXpress Ultra confocal high content reader and reported as % positive cells (nuclei).

Kv11.1 (hERG) Ion Channel Activity

In this assay, a potential in vitro effect of test compounds on the Kv11.1 (hERG) ion channel current is investigated which mediates the rapidly activating, delayed rectifier cardiac potassium current (IKr). The assay is performed with a stable Kv11.1 (hERG) transfected human embryonic kidney cell line (HEK293) by whole cell patch clamp technique carried out at room temperature.

The Kv11.1 (hERG) ion channel blocker quinidine is used as reference compound. The effects of the test compounds and quinidine are normalized to the corresponding vehicle control. The whole cell recordings are carried out with an automated patch clamp device Patchliner™, Nanion Technologies, Munich). Hereby the Patch Clamp measurements run on silicate-coated chips with a hole of a defined diameter. Solutions, cell suspension and compounds are applied by a Teflon-laminated pipette needle through microfluidic silicate-laminated channels. Commercial patch clamp amplifiers (EPC10, HEKA Elektronik Dr. Schulze GmbH, Germany) are used for the patch clamp recordings. HEK293 cells stably expressing the hERG gene are held at −80 mV. Steady-state inhibition of Kv11.1 (hERG) potassium current due to test/reference compound application is measured using a pulse pattern with fixed amplitudes: 51 ms/−80 mV, 500 ms/+40 mV, 500 ms/−40 mV, 200 ms/−80 mV. The hERG-specific voltage protocol is repeated at 10 s intervals. The leak current is subtracted by a P4 leak subtraction. Cells are resuspended in extracellular patch clamp solution (EC) and applied into the chip. After trapping the cell, the EC is exchanged by seal enhancer solution (SE) to improve the sealing procedure. When the whole cell configuration is attained, seal enhancer is washed out by the application of EC. The recording is started in EC for 1.5 min. Afterwards DMSO (vehicle control, 0.1% DMSO) is applied and the control current is measured for 3 min. Following control steady-state current, test compound is applied twice at the same concentration and the tail current is measured for 3.5 min each. For the determination of a concentration-relationship, the test compound is applied as a cumulative concentration-response curve and each concentration is measured for 5 min. The reference compound quinidine is treated in the same way. The effect on Kv11.1 (hERG) ion channel activity is judged from the tail current amplitude monitored at −40 mV (current of interest, COI). Results are calculated from the last recorded current traces. Changes in Kv11.1 (hERG) ion channel activity between control value, defined as 100% Kv11.1 (hERG) ion channel activity, application of test compound and application of quinidine is reported as percent change of control value of COI. An aliquot of test compound is collected for concentration verification during the recording. The sample is immediately measured by HPLC and the final compound concentration within the assay is calculated according to a calibration curve.

Pharmacological Data

TABLE 1

Inhibition ($IC_{50}$) of ATR-ATRIP; pCHK1 cellular assay; gH2AX-TopBP1-ER cellular assay

| Compound No. | ATR-ATRIP $IC_{50}$ [M] | pCHK1 $IC_{50}$ [M] | gH2AX-TopBP1-ER $IC_{50}$ [M] |
|---|---|---|---|
| "A1" | xxxx | xxx | xx |
| "A2" | xx | | |
| "A3" | x | | |
| "A4" | xxx | | |
| "A5" | xx | | |
| "A6" | xxxx | xx | xx |
| "A7" | xxx | x | x |
| "A8" | xxx | x | |
| "A9" | xxxx | xx | x |
| "A10" | xx | xx | x |
| "A11" | xxxx | xx | x |
| "A12" | xx | | |
| "A13" | xxxx | xx | xx |
| "A14" | xx | | |
| "A15" | xxxx | xxx | xxx |
| "A16" | xx | | |
| "A17" | x | | |
| "A18" | xxx | | |
| "A19" | x | | |
| "A20" | xxxx | xx | xx |
| "A21" | xxxx | x | xx |

TABLE 1-continued

Inhibition ($IC_{50}$) of ATR-ATRIP; pCHK1 cellular assay; gH2AX-TopBP1-ER cellular assay

| Compound No. | ATR-ATRIP $IC_{50}$ [M] | pCHK1 $IC_{50}$ [M] | gH2AX-TopBP1-ER $IC_{50}$ [M] |
|---|---|---|---|
| "A22" | xx | | |
| "A23" | xxx | xx | x |
| "A24" | xxxx | xx | x |
| "A25" | xxxx | xx | x |
| "A26" | xxxx | xx | xx |
| "A27" | xxxx | xxx | |
| "A28" | | | |
| "A29" | xxxx | xx | |
| "A30" | | | |
| "A31" | | | |
| "A32" | | | |
| "A33" | | | |
| "A34" | xxxx | xx | |
| "A35" | | | |
| "A36" | | | |
| "A37" | xxxx | x | |
| "A38" | o | | |
| "A39" | xxxx | xx | |
| "A40" | xxx | | |
| "A41" | xxxx | | |
| "A42" | xxx | xx | |
| "A43" | x | | |
| "A44" | xxxx | x | |
| "A45" | xx | | |
| "A46" | xxxx | xx | |
| "A47" | o | | |
| "A48" | o | | |
| "A49" | o | | |
| "A50" | | | |
| "A51" | o | | |
| "A52" | | | |
| "A53" | o | | |
| "A54" | o | | |
| "A55" | xx | | |
| "A56" | o | | |
| "A57" | o | | |
| "A58" | o | | |
| "A59" | | | |
| "A60" | xx | | |
| "A61" | o | o | |
| "A62" | o | | |
| "A63" | o | o | |
| "A64" | o | o | |
| "A65" | o | | |
| "A66" | xx | | |
| "A67" | xx | o | |
| "A68" | o | | |
| "A69" | xx | x | |
| "A70" | xx | | |
| "A71" | x | | |
| "A72" | xxxx | x | |
| "A73" | xxxx | xx | |
| "A74" | xx | xx | |
| "A75" | xx | | |
| "A76" | xx | | |
| "A77" | xx | | |
| "A78" | xx | x | |
| "A79" | xx | | |
| "A80" | x | | |
| "A81" | xxx | x | |

TABLE 1-continued

Inhibition ($IC_{50}$) of ATR-ATRIP; pCHK1 cellular
assay; gH2AX-TopBP1-ER cellular assay

| Compound No. | ATR-ATRIP $IC_{50}$ [M] | pCHK1 $IC_{50}$ [M] | gH2AX-TopBP1-ER $IC_{50}$ [M] |
|---|---|---|---|
| "A82" | xx | | |
| "A83" | | | |
| "A84" | | | |
| "A85" | | | |
| "A86" | | | |
| "A87" | xx | | |
| "A88" | xx | | |
| "A89" | xxx | | |
| "A90" | xxx | xx | |
| "A91" | xxxx | x | |
| "A92" | | | |
| "A93" | xxx | xx | |

ATR-ATRIP:
xxxx: <1 nM
xxx: 1-10 nM
xx: 10-100 nM
x: 100-500 nM
o: 500-30000
pCHK1:
xxx: <10 nM
xx: 10-100 nM
x: 100-1000 nM
o: 1000-30000
gH2AX-TopBP1-ER:
xxx: <10 nM
xx: 10-100 nM
x: 100-1000 nM The compounds shown in Table 1 are particularly preferred compounds according to the invention.

Surprisingly and unexpectedly, a (R) methyl group on the 8,12-dioxa-1,3,5-triazatricyclo[8.4.0.0$^{2,7}$]tetradeca-2,4,6-triene core significantly improves cellular ATR potencies.

TABLE 2

| Example | pCHK1 $IC_{50}$ [M] | gH2AX-TopBP1-ER $IC_{50}$ [M] |
|---|---|---|
| WO 2014/140644 Example 66 | 6.40E−08 | 6.90E−07 |
| "A26" | 2.5E−08 | 3.7E−08 |
| WO 2014/140644 Example 11 | 1.10E−08 | 8.90E−08 |
| "A15" | 2.90E−09 | 7.40E−09 |

Furthermore, the 5-amino azaindoles decrease the hERG Ki value which results in improved safety risk.

TABLE 3

| Example | pCHK1 $IC_{50}$ [M] | hERG Ki [M/% effect @ conc] |
|---|---|---|
| WO 2014/140644 Example 16 | 2.30E−07 | 1.6E−5 (−65% effect @ 30 μM and −30% effect @ 10 μM) |
| "A13" | 2.00E−08 | 6.5E−6 (−55% effect @ 10 μM) |
| "A1" | 6.20E−09 | >3E−5 (−50% @ 30 μM) |
| "A20" | 3.60E−08 | >1E−5 (−19% effect @ 10 μM) |

Synthesis

The chemical entities according to general formula (I) are prepared using conventional synthetic methods, or according to the routes outlined in Scheme 1.

Scheme 1:

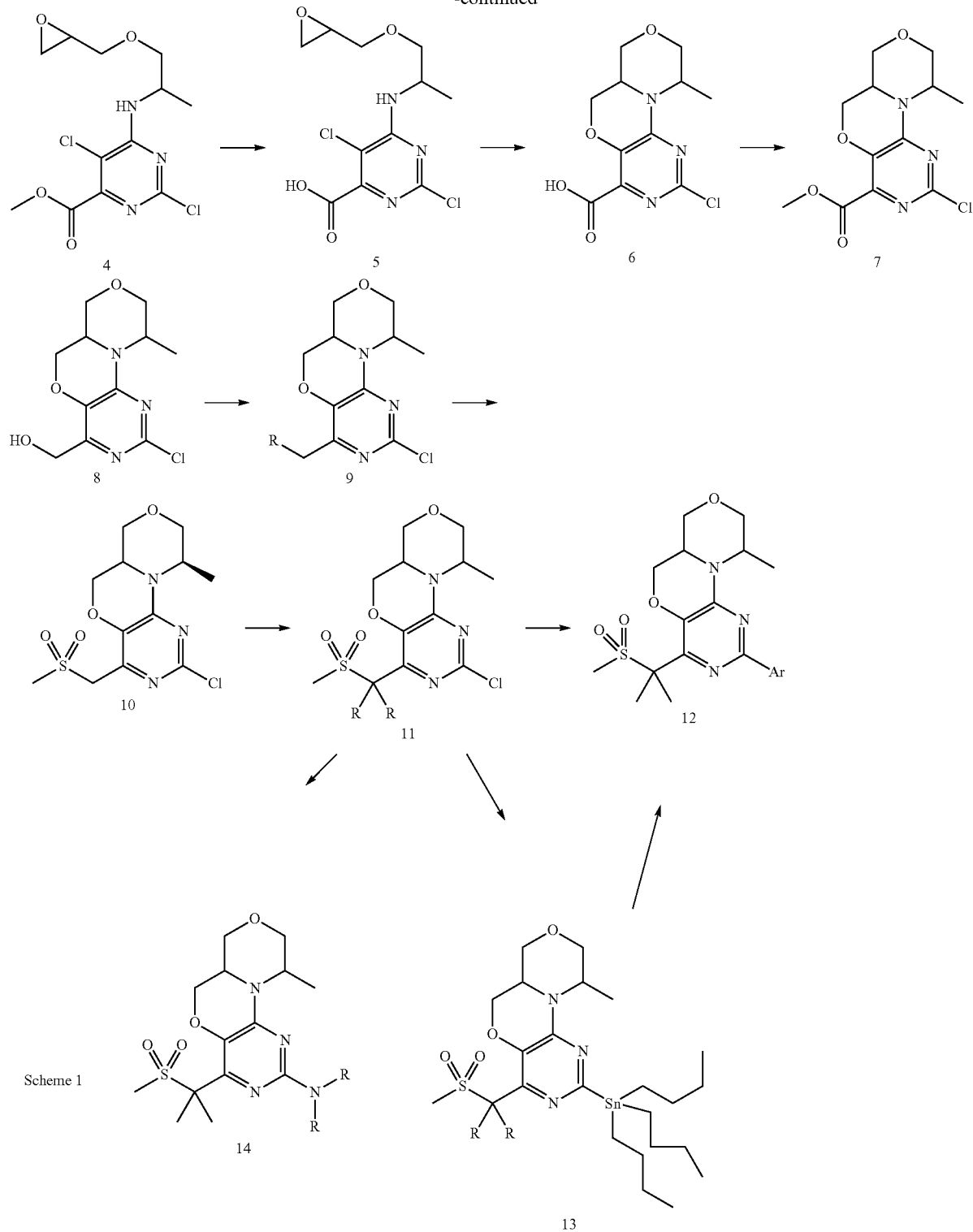

Scheme 1

Protected alaninol, like Boc-D-alaninol, can be reacted with activated [(2R)oxiran-2-yl]methyl, like 3-nitro-benzenesulfonic acid (S)-1-oxiranylmethyl ester with optional addition of a suitable base to ether 1. Depending on the reaction conditions for the removal of the protecting group, the oxiran might open to the amino-chloride 2. 2 can react under typical nucleophilic aromatic replacement or Buchwald Hartwig conditions to pyrimidine 3. Formation of the oxiran 4 is possible under basic conditions. Afterwards, the ester can be saponified to acid 5. The tricycle is now formed under basic conditions to 6. After typical esterification conditions to 7 and reduction with a suitable Hydrid, like LiBH4, the alcohol 8 is obtained. The alcohol can be converted into a leaving group R 9, like chloride or mesylate. R 9 can be reacted with methansulfinic acid to the sulfone 10. Under typical alkylating conditions, substituted sulfone 11 can be obtained. Aromatic C—C bond formation to 12 can be achieved under typical Suzuki conditions. Alternatively, the chloride 12 can be converted to Sn derivative 13 which can be converted under typical Stille conditions to 12. Furthermore, intermediate 11 can be reacted under Buchwald conditions or via nucleophilic aromatic replacement under basic conditions to amine derivative 14.

Intermediate 4 can be alternatively synthesized as described in Scheme 2.

Scheme 2:

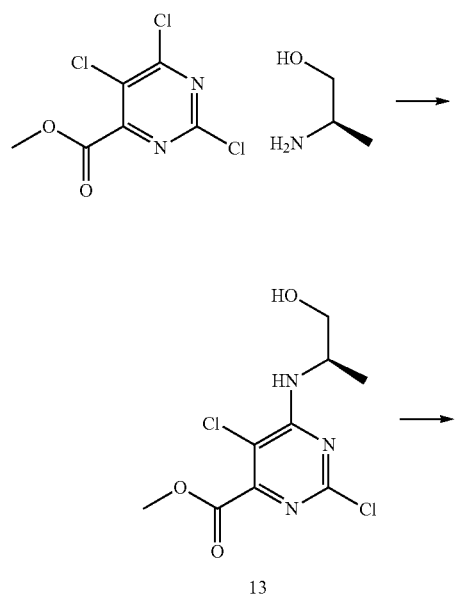

Starting from a nucleophilic replacement of the chloro pyrimidine derivative with (2R)-2-aminopropan-1-ol to 13 with or without addition of a base, followed by reaction with activated [(2R)-oxiran-2-yl]methyl, like 3-nitro-benzenesulfonic acid (S)-1-oxiranylmethyl ester.

Intermediate 1 can alternatively be synthesized starting from protected amino propanol as outlined in scheme 3

Scheme 3:

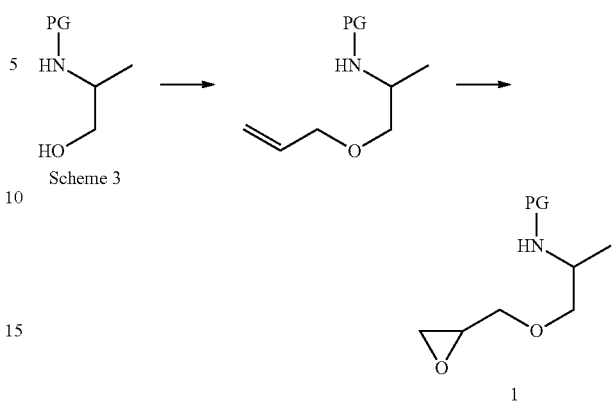

Intermediate 7 can be alternatively synthesized starting from morpholine as outlined in scheme 4.

Scheme 4:

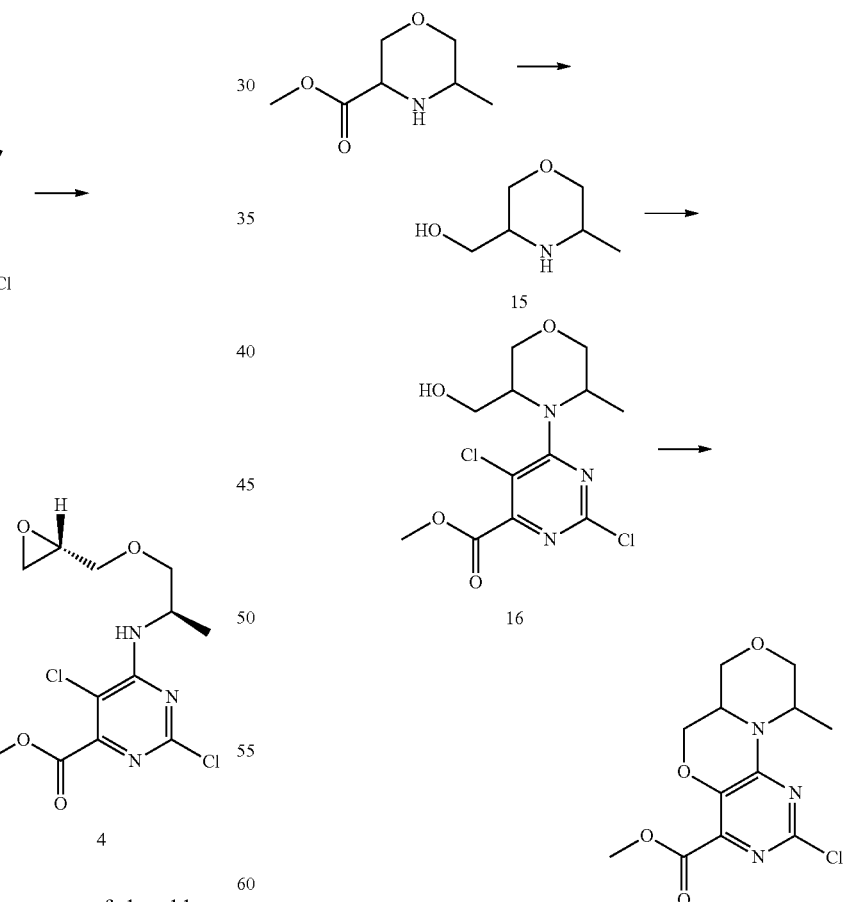

The ester morpholine derivative can be reduced to the alcohol 15 with a hydride source like NaBH$_4$ or LiAlH$_4$. After coupling with a chloropyrimidine under nucleophilic replacement or Buchwald Hartwig conditions, intermediate 16 can be isolated. Cylisation to 7 is possible under basic conditions.

Intermediate 8 can also be synthesized by reduction of the carboxylic acid 6, as outlined in Scheme 5.

Scheme 5:

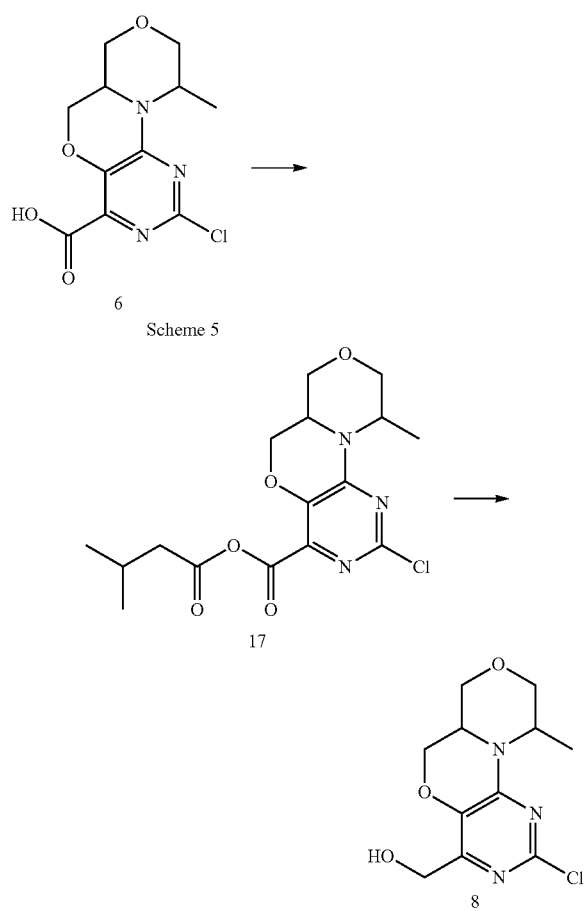

Scheme 5

Carboxylic acid 6 can be converted to an active ester 17 and then reduced to the alcohol 8.

Benzimidazole derivatives can be alternatively synthesized as described in scheme 6.

Scheme 6

Scheme 6:

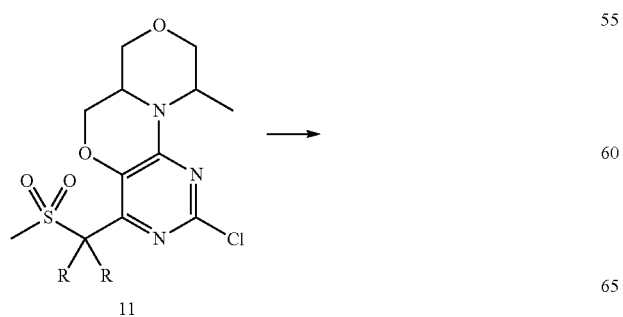

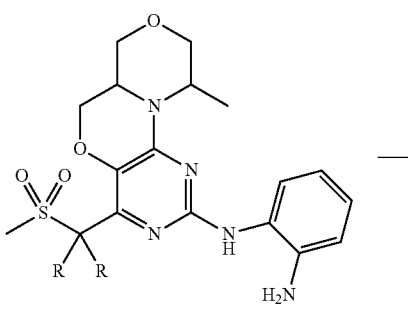

Chloropyrimidine 11 can be converted under nucleophilic replacement or Buchwald Hartwig conditions to amine 18. Ring closure to 14 is possible after reaction with methyl-isothiocyanate.

Triazole derivatives can be synthesized as outlined in scheme 7

Scheme 7:

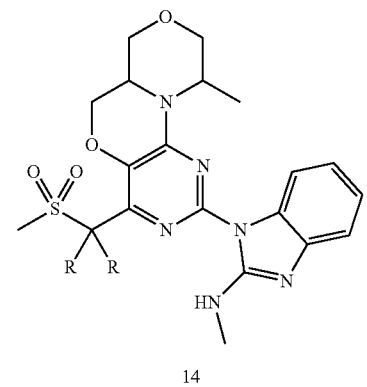

Scheme 7

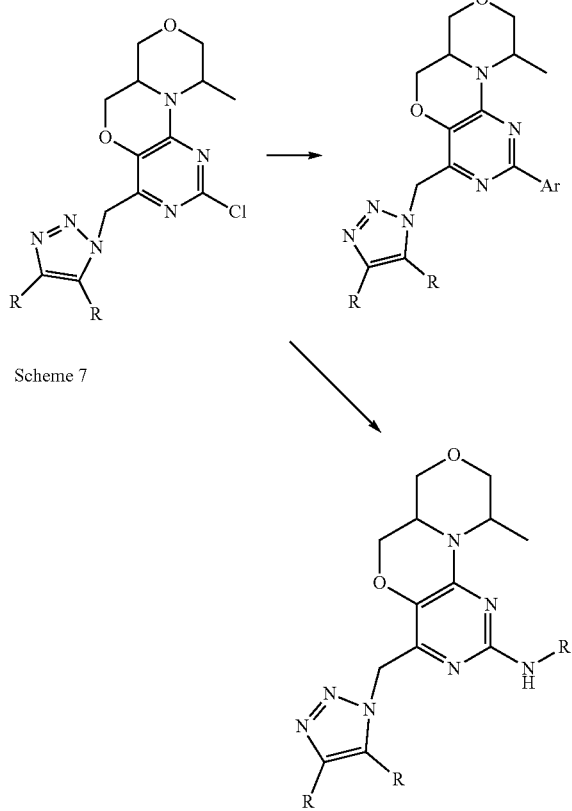

SYNTHESIS OF INTERMEDIATES

Boc-(R) Me-1: [(R)-1-Methyl-2-((S)-1-oxiranyl-methoxy)-ethyl]-carbamic Acid Tert-Butyl Ester

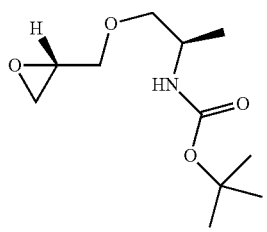 [SMILES: C[C@H](COC[C@@H]1CO1)NC(=O)OC(C)(C)C]

Boc-D-Alaninol (10.88 g; 60.849 mmol; 1.00 eq.) was suspended in tetrahydrofuran dried (600.00 ml; 7405.764 mmol; 121.71 eq.) and cooled down to 0° C. and sodium hydride (3.00 g; 125.010 mmol; 2.05 eq.) was added. After 15 min (S)-glycidyl 3-nitrobenzenesulfonate (14.28 g; 57.461 mmol; 0.94 eq.) was added and stirred for 6 hrs under cooling and for 14 h at room temperature. The reaction mixture was filtered and the precipitate washed with dichloromethane. After removal of the solvent of the filtrate, the precipitate was purified by flash chromatography by using cyclohexane and ethyl acetate. The product was isolated as a yellow oil (11.79 g; 82.1%). LCMS (method E): 0.61 min (purity 82.1%); [MH+] 132 m/z;

(R)-Me-2: (R)-1-((R)-2-Amino-propoxy)-3-chloro-propan-2-ol Hydrochloride

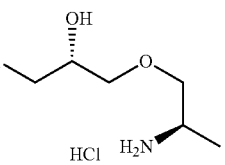

[(R)-1-Methyl-2-((S)-1-oxiranylmethoxy)-ethyl]-carbamic acid tert-butyl ester (11.79 g; 49.956 mmol; 1.00 eq.) was dissolved in [1,4]Dioxane (100.00 ml; 1.169 mol; 23.40 eq.) and Hydrogen chloride (4 M sol. in dioxane) (75.00 ml; 300.000 mmol; 6.01 eq.) was added and the reaction mixture was stirred overnight at room temperature. The product was isolated after removal of the solvent as an oil (10.50 g, 99.9%); LC/MS: (method E): 0.15 min (purity 97%); [MH+] 167.9.

(R)-Me-3: 2,5-Dichloro-6-[(R)-2-((R)-3-chloro-2-hydroxy-propoxy)-1-methyl-ethylamino]-pyrimidine-4-carboxylic Acid Methyl Ester

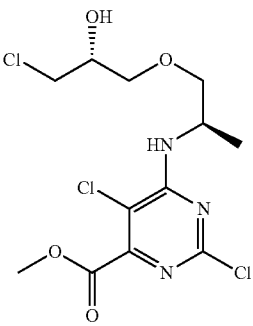 [SMILES: COC(=O)c1nc(Cl)nc(N[C@H](C)COC[C@@H](O)CCl)c1Cl]

To a solution of (R)-1-((R)-2-amino-propoxy)-3-chloro-propan-2-ol hydrochloride (10.50 g; 49.903 mmol; 1.06 eq.) in 2-propanol (140.00 ml; 1831.101 mmol; 38.78 eq.) was added N-ethyldiisopropylamine (24.00 ml; 141.127 mmol; 2.99 eq.) and the solution was stirred for 5 minutes. 2,5,6-Trichloropyrimidine-4-carboxylic acid methyl ester (11.40 g; 47.213 mmol; 1.00 eq.) was added and the reaction mixture was stirred 2 hrs at room temperature. The reaction mixture was treated with 2N HCl (300 ml) and extracted two times with methylene chloride. The combined organic phases were dried over sodium sulfate, filtered and evaporated under reduced pressure and lyophilized to give a yellow oil (20.11 g, 93.3%); LC/MS: 0.69 min (purity 86.1%); (M+H) 371.9 m/z.

(R)-Me-4: 2,5-Dichloro-6-[(R)-1-methyl-2-((S)-1-oxiranylmethoxy)-ethylamino]-pyrimidine-4-carboxylic Acid Methyl Ester

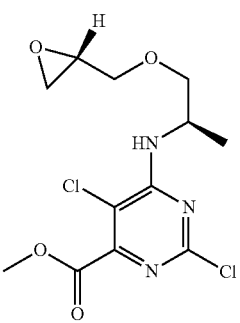 [SMILES: COC(=O)c1nc(Cl)nc(N[C@H](C)COC[C@@H]2CO2)c1Cl]

2,5-Dichloro-6-[(R)-2-((R)-3-chloro-2-hydroxy-propoxy)-1-methyl-ethylamino]-pyrimidine-4-carboxylic acid methyl ester (20.11 g; 44.038 mmol; 1.00 eq.) was dissolved in acetonitrile (150.00 ml; 2871.897 mmol; 65.21 eq.) and cesium carbonate (29.00 g; 89.004 mmol; 2.02 eq.) and stirred for 14 h at room temperature. After filtering and washing with acetonitrile, the solvent of the filtrate was evaporated and the residue purified by flash chromatography (cyclohexan/ethyl acetate) to afford the product as brown oil (10.38 g, 68.7%); LCMS (method E): 0.69 min (purity 98%); [MH+] 336.00 m/z.

Alternatively, intermediate (R)-Me-4 was synthesized as follows:

2,5-dichloro-6-[(R)-2-((R)-3-chloro-2-hydroxy-propoxy)-1-methyl-ethylamino]-pyrimidine-4-carboxylic acid methyl ester (917.00 mg; 1.95 mmol; 100.00 mol %), potassium carbonate (0.22 ml; 3.90 mmol; 200.00 mol %) and acetonitrile (4.00 ml; 76.58 mmol; 3929.36 mol %) were combined and stirred for 2 hours at room temperature and 14 h at 70° C. The reaction mixture was filtered and the solid residue was washed with acetonitrile. The solvent of the filtrate was evaporated and the residue purified by column chromatography (cyclohexan/ethyl acetate) to afford the title compound (376 mg, 57.4%); LCMS (method C): 1.517 min (purity 100%); [MH+] 336.1 m/z.

Li—(R)-Me-5: 2,5-Dichloro-6-[(R)-1-methyl-2-((S)-1-oxiranylmethoxy)-ethylamino]-pyrimidine-4-carboxylic Acid Lithium

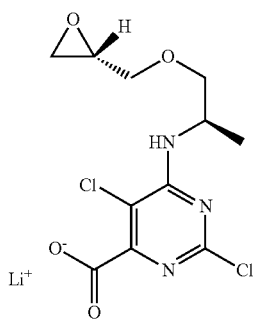 [SMILES: [Li+] ; C[C@H](COC[C@@H]1CO1)Nc1nc(Cl)nc(C(=O)[O-])c1Cl]

2,5-Dichloro-6-[(R)-1-methyl-2-((S)-1-oxiranyl-methoxy)-ethylamino]-pyrimidine-4-carboxylic acid methyl ester (10.38 g; 30.877 mmol; 1.00 eq.) was suspended in tetrahydrofuran (60.00 ml; 740.576 mmol; 23.98 eq.) and lithium hydroxide (905.00 mg; 37.034 mmol; 1.20 eq.) was added. The reaction mixture was stirred 4 hrs at room temperature. After removal of the solvent, the product was obtained as colorless solid (10.28 g, 99.3%); LCMS (method c): 0.58 min (purity 97.9%); [MH+] 322.00 m/z.

Na—(R)-5: 2,5-Dichloro-6-[(R)-1-methyl-2-((S)-1-oxiranylmethoxy)-ethylamino]-pyrimidine-4-carboxylic Acid Sodium 2,5-Dichloro-6-[(R)-2-((R)-3-chloro-2-hydroxy-propoxy)-1-methyl-ethylamino]-pyrimidine-4-carboxylic acid methyl ester (980.61 mg) was dissolved in Tetrahydrofuran (20.00 ml), sodium hydroxide (199.99 mg) was added and the mixture was stirred 5 h at room temperature. The solvent was removed under vacuo to afford the product as brown solid (1.085 g, quant.); LCMS (method E): 0.62 min (purity 100%); [MH+] 322 m/z.

(R)-Me-6: (5R,8aS)-3-Chloro-5-methyl-5,6,8a,9-tetrahydro-8H-7,10-dioxa-2,4,4b-triaza-phenanthrene-1-carboxylic Acid

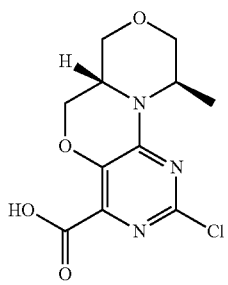 [SMILES: C[C@@H]1COC[C@H]2COc3c(C(=O)O)nc(Cl)nc3N21]

2,5-Dichloro-6-[(R)-1-methyl-2-((S)-1-oxiranyl-methoxy)-ethylamino]-pyrimidine-4-carboxylic acid lithium (10.28 g; 30.676 mmol; 1.00 eq.) was dissolved in tetrahydrofuran (250.00 ml; 3085.735 mmol; 100.59 eq.), 2-methyl-propan-2-ol lithium (1.0 M sol. in THF) (61.50 ml; 61.500 mmol; 2.00 eq.) was added dropwise at 0° C. After 4 hours, the reaction solution was allowed to warm to RT and stirred another 2 days. The reaction mixture was acidified with concentrated hydrochloric acid to pH ~2, washed with saturated sodium chloride solution and dried over sodium sulfate. After evaporation of the solvent, the product was isolated as beige solid (9.00 g, 65.5%, beige foam); LCMS (method E): 0.51 min (purity 63.8%); [MH+] 286.2 m/z.

(R)-Me-7: (5R,8aS)-3-Chloro-5-methyl-5,6,8a,9-tetrahydro-8H-7,10-dioxa-2,4,4b-triaza-phenanthrene-1-carboxylic Acid Methyl Ester

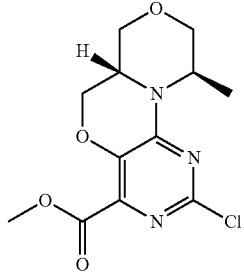

(5R,8aS)-3-Chloro-5-methyl-5,6,8a,9-tetrahydro-8H-7,10-dioxa-2,4,4b-triaza-phenanthrene-1-carboxylic acid (9.00 g; 20.099 mmol; 1.00 eq.) was dissolved in methanol (250.00 ml; 6163.785 mmol; 306.67 eq.) and sulfuric acid (8.60 ml; 161.339 mmol; 8.03 eq.) was added. The yellow reaction mixture was stirred for 14 h at 50° C. The reaction mixture was partially concentrated under reduced pressure and then diluted with ethyl acetate, washed twice with water. The organic layer was dried over $Na_2SO_4$, filtered and concentrated under reduced pressure. The residue was purified by flash chromatography (cyclohexane/ethyl acetate) to afford the product as off-white solid (4.3 g, 69.6%); LCMS (method E): 0.581 min (purity 97.5%); [MH+] 300.00 m/z.

(R)-Me-8: ((5R,8aS)-3-Chloro-5-methyl-5,6,8a,9-tetrahydro-8H-7,10-dioxa-2,4,4b-triaza-phenanthren-1-yl)-methanol

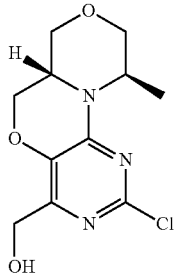 [SMILES: C[C@@H]1COC[C@H]2COc3c(CO)nc(Cl)nc3N21]

(5R,8aS)-3-Chloro-5-methyl-5,6,8a,9-tetrahydro-8H-7,10-dioxa-2,4,4b-triaza-phenanthrene-1-carboxylic acid methyl ester (4.30 g; 13.989 mmol; 1.00 eq.) was dissolved in tetrahydrofuran (135.00 ml; 1.666 mol; 119.12 eq.), lithium borohydride (2.0 M solution in THF) (10.50 ml; 21.000 mmol; 1.50 eq.) was added and the mixture was stirred for 1 hr at room temperature.

The reaction mixture was diluted with ethyl acetate and washed with saturated ammonium chloride. The organic layer was dried over sodium sulfate, filtered and concentrated under reduced pressure to afford the product as an off-white solid (3.85 g, 97.7%); LCMS (method E): 0.51 min (purity 96.4%); [MH+] 272.00 m/z.

Alternative synthesis of intermediate (R)-Me-8 ((5R,8aS)-3-Chloro-5-methyl-5,6,8a,9-tetrahydro-8H-7,10-dioxa-2,4,4b-triaza-phenanthren-1-yl)-methanol: (5R,8aS)-3-Chloro-5-methyl-5,6,8a,9-tetrahydro-8H-7,10-dioxa-2,4,4b-triaza-phenanthrene-1-carboxylic acid (28.19 g) was dissolved in tetrahydrofuran (200.00 ml) and isobutyl chloroformate (14.75 ml) was added. Triethylamine (15.72 ml) dissolved in tetrahydrofuran (15.00 ml) was added dropwise and the mixture was stirred for 30 min at room temperature. The reaction mixture was filtrated. Lithium borohydride (2 M sol. in THF) (161.96 ml) was added dropwise to the solution and the mixture was stirred for 14 h at room temperature. To the reaction mixture was added ammonium chloride solution (400 ml) and extracted with ethyl acetate. The combined organic layers were washed with saturated ammonium chloride solution and dried over sodium sulfate. After removal of the solvent in vacuo, the residue was purified by column chromatography to afford the product as colorless solid; LCMS (method E): 0.51 min (purity 99%), [MH+] 272.1 m/z.

Cl—(R)-Me-9: (5R,8aS)-3-Chloro-1-chloromethyl-5-methyl-5,6,8a,9-tetrahydro-8H-7,10-dioxa-2,4,4b-triaza-phenanthrene

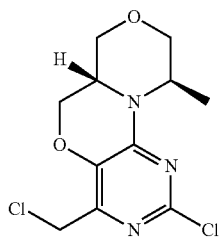 [SMILES: C[C@@H]1COC[C@H]2COc3c(CCl)nc(Cl)nc3N21]

((S)-3-Chloro-5,6,8a,9-tetrahydro-8H-7,10-dioxa-2,4,4b-triaza-phenanthren-1-yl)-methanol was dissolved in dichloromethane (35.00 ml; 0.548 mol; 40.12 eq.), thionyl chloride (3.00 ml; 41.355 mmol; 3.03 eq.) was added and the mixture was stirred for 4 hrs at room temperature. Thionyl chloride (0.99 ml; 13.660 mmol; 1.00 eq.) was added again and stirred for 3 days at room temperature. The reaction mixture was concentrated under reduced pressure, the residue was neutralized with saturated $NaHCO_3$-solution, extracted with ethyl acetate, the unified organic layer was washed once with de-ionized water and dried over $Na_2SO_4$. The product was isolated as yellow solid (3.955 g, 82.2%); LCMS (method E): 0.70 min (purity 82.4%); [MH+] 290 m/z.

(R)-Me-10: (5R,8aS)-3-Chloro-1-methanesulfonylmethyl-5-methyl-5,6,8a,9-tetrahydro-8H-7,10-dioxa-2,4,4b-triaza-phenanthrene

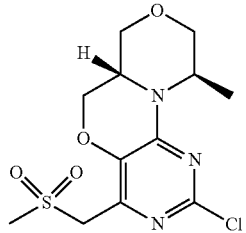 [SMILES: C[C@@H]1COC[C@H]2COc3c(CS(C)(=O)=O)nc(Cl)nc3N21]

(5R,8aS)-3-Chloro-1-chloromethyl-5-methyl-5,6,8a,9-tetrahydro-8H-7,10-dioxa-2,4,4b-triaza-phenanthrene (3.95 g; 11.218 mmol; 1.00 eq.) was suspended in propan-2-ol (25.00 ml; 326.982 mmol; 29.15 eq.), methanesulfinic acid sodium (1.50 g; 14.693 mmol; 1.31 eq.) was added and stirred for 4 hrs at 80° C. The reaction mixture was concentrated under reduced pressure, treated with de-ionized water, extracted twice with ethyl acetate, the unified organic layer was washed once with de-ionized water and dried over $Na_2CO_3$. After removing the solvent, the residue was purified by flash chromatography (cyclohexane/ethyl acetate) to afford the product as colorless solid (3.53 g, 92.3%); LCMS (method E): 0.56 min (purity 97.9%); [MH+] 334.00 m/z.

Di-Me-(R)-Me-11: (5R,8aS)-3-Chloro-1-(1-methanesulfonyl-1-methyl-ethyl)-5-methyl-5,6,8a,9-tetrahydro-8H-7,10-dioxa-2,4,4b-triaza-phenanthrene

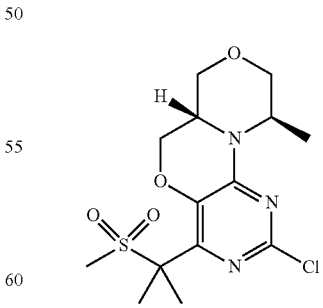

(5R,8aS)-3-Chloro-1-methanesulfonylmethyl-5-methyl-5,6,8a,9-tetrahydro-8H-7,10-dioxa-2,4,4b-triaza-phenanthrene (6.08 g; 17.432 mmol; 1.00 eq.) was dissolved in N,N-dimethyl-formamide (50.00 ml; 643.008 mmol; 36.89 eq.) and potassium tert-butylate (2.55 g; 22.725 mmol; 1.30 eq.) was added under ice bath cooling and after 10 mins iodomethane (1.45 ml; 23.292 mmol; 1.34 eq.) was added and stirred for 1 hr under initially ice bath cooling. Then potassium tert-butylate (2.55 g; 22.725 mmol; 1.30 eq.) was added again under ice bath cooling and after 10 mins iodomethane (1.45 ml; 23.292 mmol; 1.34 eq.) was added again and stirred for 1 hr initially under ice bath cooling. The reaction mixture was poured into 300 ml cold water and extracted 3 times with ethyl acetate. The unified organic layer was washed with brine, dried over Na$_2$SO$_4$ and the solvent removed under reduced pressure. The product was isolated after flash chromatography (cyclohexane/ethyl acetate) as yellow solid (2.69 g, 42.6%); LCMS (method E): 0.69 min (purity 100%); [MH+] 362 m/z.

Alternative Synthesis to (R)-Me-6: (5R,8aS)-3-Chloro-5-methyl-5,6,8a,9-tetrahydro-8H-7,10-dioxa-2,4,4b-triaza-phenanthrene-1-carboxylic Acid ((R)-2-Allyloxy-1-methyl-ethyl)-carbamic Acid Tert-Butyl Ester

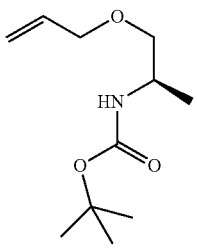

Boc-D-Alaninol (25.00 g; 138.393 mmol; 100.00 mol %) was suspended in sodium hydroxide (138.38 ml; 4670.754 mmol; 3375.00 mol %) and allyl bromide (14.82 ml; 166.071 mmol; 120.00 mol %) was added. The reaction mixture was stirred at RT for 2 days and then diluted with water and extracted with ethyl acetate. The combined organic layers were dried over sodium sulfate, filtered and evaporated. The residue was purified by flash column chromatography (cyclohexane/ethyl acetate) to afford the product as colorless oil (23.99 g, 80.5%); LCMS (method C): [MH+] 116.1 m/z.

((R)-1-Methyl-2-oxiranylmethoxy-ethyl)-carbamic Acid Tert-Butyl Ester

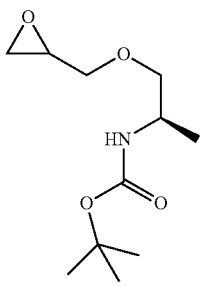 [SMILES: C[C@H](COCC1CO1)NC(=O)OC(C)(C)C]

To a solution of ((R)-2-allyloxy-1-methyl-ethyl)-carbamic acid tert-butyl ester (10.76 g; 50.000 mmol; 100.00 mol %) in dichloromethane (100.00 ml; 1566.000 mmol; 3132.00 mol %) was added 3-chloroperoxybenzoic acid (18.49 g; 75.000 mmol; 150.00 mol %) and the reaction mixture was stirred at room temperature for 1 day. The reaction mixture was filtered and the residue was washed with dichloromethane. The filtrate was extracted with sodium hydrogensulfite solution and with sodium carbonate solution. The organic layer was dried over sodium sulfate and evaporated to afford the product as colorless oil (11.286 g, 87.8%); LCMS (method C): [MH+] 132.2 m/z.

1-((R)-2-Amino-propoxy)-3-chloro-propan-2-ol Hydrochloride and 3-((R)-2-Amino-propoxy)-2-chloro-propan-1-ol Hydrochloride

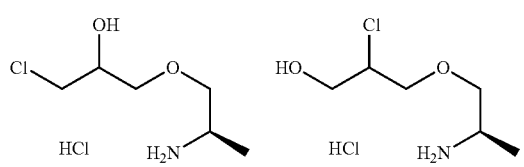

((R)-1-Methyl-2-oxiranylmethoxy-ethyl)-carbamic acid tert-butyl ester (8.99 g; 35.000 mmol; 100.00 mol %) was dissolved in Dioxane (179.63 ml; 2.100 mol; 6000.00 mol %) and treated with Hydrogen chloride (4 M solution in dioxane) (35.00 ml; 140.000 mmol; 400.00 mol %). The reaction mixture was stirred at RT overnight and the solvent removed under vacuo to afford the product as regioisomeric mixture as yellow oil (10.65 g, 80.5%); LCMS (method C): 1.400 min; [MH+] 168.1 m/z.

2,5-Dichloro-6-[(R)-2-(3-chloro-2-hydroxy-propoxy)-1-methyl-ethylamino]-pyrimidine-4-carboxylic Acid Methyl Ester

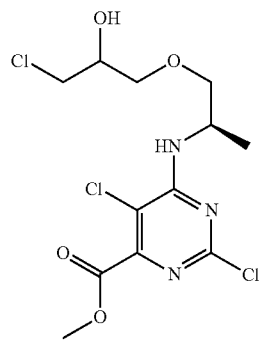 [SMILES: COC(=O)c1nc(Cl)nc(N[C@H](C)COCC(O)CCl)c1Cl]

To a solution of 1-((R)-2-amino-propoxy)-3-chloro-propan-2-ol hydrochloride and 3-((R)-2-amino-propoxy)-2-chloro-propan-1-ol hydrochloride (10.65 g; 52.157 mmol; 100.00 mol %) in 2-propanol (156.48 ml; 2046.654 mmol; 3924.00 mol %) was added N-ethyldiisopropylamine (26.61 ml; 156.472 mmol; 300.00 mol %) and stirred for 5 minutes. 2,5,6-Trichloro-pyrimidine-4-carboxylic acid methyl ester (12.59 g; 52.157 mmol; 100.00 mol %) was added and the reaction mixture was stirred at RT for 14 h. To the reaction mixture was added dichloromethane and 1 N HCl. The aqueous layer was extracted with dichloromethane. The combined organic layers were dried over sodium sulfate, the solvent removed under vacuo and the residue purified by column chromatography (petroleum benzene/ethyl acetate)

to afford the product as as yellow oil (10.8 g, 52%); LCMS (method C): 1.52 min (purity 94.1%); [MH+] 372.00 m/z.

2,5-Dichloro-6-((R)-1-methyl-2-oxiranylmethoxy-ethylamino)-pyrimidine-4-carboxylic Acid Methyl Ester

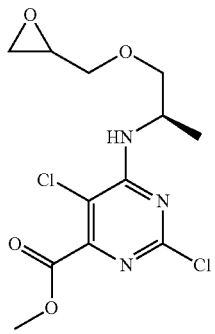 [SMILES: COC(=O)c1nc(Cl)nc(N[C@H](C)COCC2CO2)c1Cl]

2,5-Dichloro-6-[(R)-2-(3-chloro-2-hydroxy-propoxy)-1-methyl-ethylamino]-pyrimidine-4-carboxylic acid methyl ester (10.82 g; 27.321 mmol; 100.00 mol %) was dissolved in acetonitrile (72.53 ml; 1388.730 mmol; 5083.00 mol %) and cesium carbonate (4.37 ml; 54.642 mmol; 200.00 mol %) was added. The reaction mixture was stirred at RT for 2.75 h. The reaction mixture was filtered, washed with acetonitrile and the filtrate was concentrated under reduced pressure and dried in vacuo to afford the product as brown solid (9.95 g, 87.9%); LCMS (method C): 1.51 min (purity 81.1%); [MH+] 336.00 m/z.

2,5-Dichloro-6-((R)-1-methyl-2-oxiranylmethoxy-ethylamino)-pyrimidine-4-carboxylic Acid Lithium

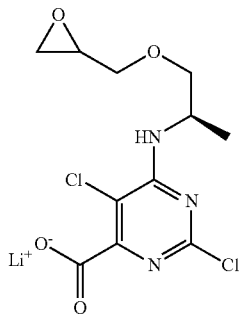 [SMILES: [Li+] ; C[C@H](COCC1CO1)Nc1nc(Cl)nc(C(=O)[O-])c1Cl]

2,5-Dichloro-6-((R)-1-methyl-2-oxiranylmethoxy-ethylamino)-pyrimidine-4-carboxylic acid methyl ester (4.97 g; 12.000 mmol; 100.00 mol %) was dissolved in tetrahydrofuran (24.12 ml; 297.720 mmol; 2481.00 mol %) and lithium hydroxide (351.89 mg; 14.400 mmol; 120.00 mol %) was added. The reaction mixture was stirred at room temperature for 14 h.

The reaction mixture was filtered and the solvent of the filtrate removed under vacuo to afford the product as ochre solid (4.671 g, 90.9%, ochre solid); LCMS (method C): 1.07 min (purity 76.6); [MH+] 322.10 m/z.

Intermediate 6: (5R,8aS)-3-Chloro-5-methyl-5,6,8a,9-tetrahydro-8H-7,10-dioxa-2,4,4b-triaza-phenanthrene-1-carboxylic Acid

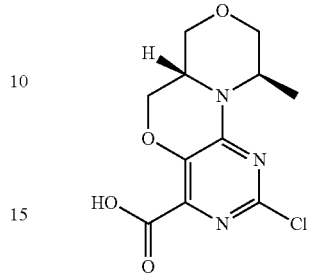

2,5-Dichloro-6-((R)-1-methyl-2-oxiranylmethoxy-ethylamino)-pyrimidine-4-carboxylic acid lithium (4.67 g; 10.906 mmol; 100.00 mol %) was dissolved in tetrahydrofuran (120.00 ml; 1481.153 mmol; 13581.16 mol %) and lithium tert-butoxide, 1.0 M solution in tetrahydrofuran (21.81 ml; 21.812 mmol; 200.00 mol %) was added. The reaction was stirred at RT for 3 days. The reaction mixture was extracted with saturated NaCl, the aqueous layer acidified with 2 N HCl and extracted with DCM. The combined organic layers were dried over sodium sulfate, filtered and concentrated under reduced pressure to obtain the product as beige solid (3.385 g, 53.6%); LCMS (method C): 1.10 min (purity 49.3%); [MH+] 286.00 m/z.

((S)-2-Allyloxy-1-methyl-ethyl)-carbamic Acid Tert-Butyl Ester

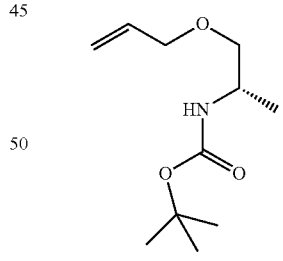

n-Boc-D-alaninol (5.00 g; 28.25 mmol; 1.00 eq.) was suspended in sodium hydroxide solution min. 32% (28.25 ml; 953.41 mmol; 33.75 eq.) and allyl bromide (3.02 ml; 33.90 mmol; 1.20 eq.) was added. The reaction mixture was stirred at RT for 20 days. The reaction mixture was diluted and extracted with ethyl acetate. The combined organic layers were dried over sodium sulfate, filtered and evaporated. The residue was purified by flash column chromatography (cyclohexane and ethyl acetate) to afford the product as colorless oil (4.772 g, 78.5%); LCMS (method C): 1.63 min (purity 100%); [MH+] 116.2 m/z.

Boc (S)-Me-1: ((S)-1-Methyl-2-oxiranylmethoxy-ethyl)-carbamic Acid Tert-Butyl Ester

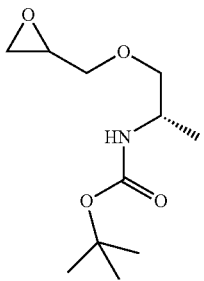 [SMILES: C[C@@H](COCC1CO1)NC(=O)OC(C)(C)C]

To a solution of ((S)-2-Allyloxy-1-methyl-ethyl)-carbamic acid tert-butyl ester (3.23 g; 15.00 mmol; 1.00 eq.) in dichloromethane (50.00 ml; 782.98 mmol; 52.20 eq.) was added 3-chloroperbenzoic acid (3.88 g; 22.50 mmol; 1.50 eq.) and the reaction mixture was stirred at room temperature for 20 hrs. 3-chloroperbenzoic acid (1294.24 mg; 7.50 mmol; 0.50 eq.) was added and the mixture was stirred at room temperature for another 2 hrs. 3-chloroperbenzoic acid (776.55 mg; 4.50 mmol; 0.30 eq.) was added and the reaction mixture was stirred at room temperature for 3 days. The reaction mixture was filtered and the residue was washed with dichloromethane. The filtrate was extracted with dilute sodium hydrogensulfite solution and with dilute sodium carbonate solution. The organic layer was dried over sodium sulfate and evaporated to dryness to afford the product as colorless oil (3.691 g, 95.7%); LCMS (method C): 1.40 min (purity 94.89%); [MH+] 132.1.

(S)-Me-2: 1-((S)-2-Amino-propoxy)-3-chloro-propan-2-ol Hydrochloride

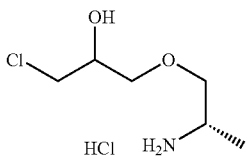

((S)-1-Methyl-2-oxiranylmethoxy-ethyl)-carbamic acid tert-butyl ester (3.69 g; 14.36 mmol; 1.00 eq.) was dissolved in dioxane (73.69 ml; 861.52 mmol; 60.00 eq.) and treated with hydrogen chloride solution (14.36 ml; 57.43 mmol; 4.00 eq.). The reaction mixture was stirred at RT for 3 days. The reaction mixture was concentrated under reduced pressure to afford the product as colorless oil (3.27 g, 102.8%); LCMS (method C): 1.40 min (purity 92.16%); [MH+] 168.2.

(S)-Me-3: 2,5-Dichloro-6-[(S)-2-(3-chloro-2-hydroxy-propoxy)-1-methyl-ethylamino]-pyrimidine-4-carboxylic Acid Methyl Ester

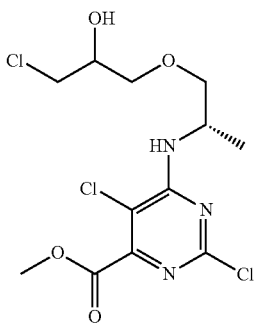 [SMILES: COC(=O)c1nc(Cl)nc(N[C@@H](C)COCC(O)CCl)c1Cl]

To a solution of 1-((S)-2-amino-propoxy)-3-chloro-propan-2-ol hydrochloride (3.27 g; 14.77 mmol; 1.00 eq.) in 2-propanol (44.32 ml; 579.67 mmol; 39.24 eq.) was added N-ethyldiisopropylamine (7.54 ml; 44.32 mmol; 3.00 eq.) and the solution was stirred for 5 minutes. 2,5,6-Trichloro-pyrimidine-4-carboxylic acid methyl ester (3.57 g; 14.77 mmol; 1.00 eq.) was added and the reaction mixture was stirred at RT for 14 h. To the reaction mixture was added dichloromethane and 1 N HCl. The organic layer was separated and the aqueous layer was extracted with dichloromethane. The combined organic layers were dried over sodium sulfate and filtered. The residue was purified by column chromatography (cyclohexane/ethyl acetate) to afford the product as yellow oil (2.131 g, 30.8%); LCMS (method C): 1.52 min (purity 79.63%); [MH+] 372.00 m/z.

(S)-Me-4: 2,5-Dichloro-6-((S)-1-methyl-2-oxiranylmethoxy-ethylamino)pyrimidine-4-carboxylic Acid Methyl Ester

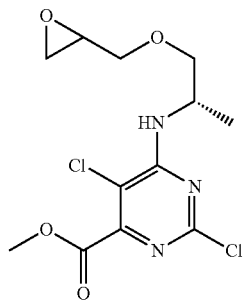 [SMILES: COC(=O)c1nc(Cl)nc(N[C@@H](C)COCC2CO2)c1Cl]

2,5-Dichloro-6-[(S)-2-(3-chloro-2-hydroxy-propoxy)-1-methyl-ethylamino]-pyrimidine-4-carboxylic acid methyl ester (2.13 g; 4.55 mmol; 1.00 eq.) was dissolved in acetonitrile (11.89 ml; 227.59 mmol; 50.00 eq.) and cesium carbonate (0.73 ml; 9.10 mmol; 2.00 eq.) was added. The reaction mixture was stirred at RT for 2.75 h. The reaction mixture was filtered and washed with acetonitrile. The filtrate was concentrated under reduced pressure and purified by column chromatography (cyclohexane/ethyl acetate) to afford the product as yellow oil (1.052 g, 68.3%); LCMS (method C): 1.51 min (purity 99.38%); [MH+] 336 m/z.

(S)-Me-5: 2,5-Dichloro-6-((S)-1-methyl-2-oxiranylmethoxy-ethylamino)pyrimidine-4-carboxylic Acid Lithium

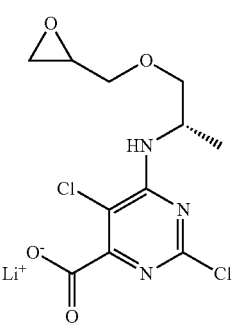 [SMILES: [Li+] ; C[C@@H](COCC1CO1)Nc1nc(Cl)nc(C(=O)[O-])c1Cl]

Lithium hydroxide (113.80 mg; 4.66 mmol; 1.50 eq.) and 2,5-dichloro-6-((S)-1 methyl-2-oxiranylmethoxy-ethyl-amino)-pyrimidine-4-carboxylic acid methyl ester (1.05 g; 3.10 mmol; 1.00 eq.) were suspended in tetrahydrofuran (6.29 ml; 77.62 mmol; 25.00 eq.) and stirred at room temperature for 2 hours. The reaction mixture was filtered and evaporated and the residue was dried under vacuum for 14 h to afford the product as colorless solid (885.7 mg, 75.3%); LCMS (method C): 1.08 min (purity 86.64%); [MH+] 322 m/z.

(S)-Me-6: (5S,8aR)-3-Chloro-5-methyl-5,6,8a,9-tetrahydro-8H-7,10-dioxa-2,4,4b-triaza-phenanthrene-1-carboxylic Acid

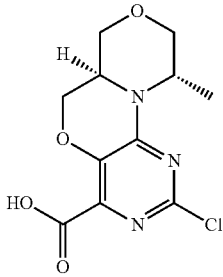 [SMILES: C[C@H]1COC[C@@H]2COc3c(C(=O)O)nc(Cl)nc3N21]

2,5-Dichloro-6-((S)-1-methyl-2-oxiranylmethoxy-ethyl-amino)-pyrimidine-4-carboxylic acid lithium (885.70 mg; 2.34 mmol; 1.00 eq.) was dissolved in tetrahydrofuran (23.68 ml; 292.24 mmol; 125.00 eq.) and lithium tert-butoxide, 1.0 m solution in tetrahydrofuran (4.71 ml; 0.06 mmol; 0.03 eq.) was added. The reaction mixture was stirred at room temperature for 4 days. The reaction mixture was treated with water and dichloromethane. The aqueous layer was acidified with 2 N HCl and extracted with dichloromethane. The combined organic layers were dried over sodium sulfate, filtered and evaporated under reduced pressure to afford the product as yellow oil (508.8 mg, 38.1%); LCMS (method C): 1.10 min (purity 50%); [MH+] 286 m/z (S)-Me-7: (5S,8aR)-3-Chloro-5-methyl-5,6,8a,9-tetrahydro-8H-7,10-dioxa-2,4,4b-triaza-phenanthrene-1-carboxylic Acid Methyl Ester

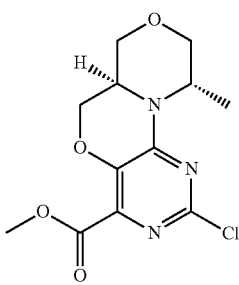 [SMILES: COC(=O)c1nc(Cl)nc2c1OC[C@H]1COC[C@H](C)N21]

(5S,8aR)-3-Chloro-5-methyl-5,6,8a,9-tetrahydro-8H-7,10-dioxa-2,4,4b-triaza-phenanthrene-1-carboxylic acid (508.80 mg; 0.89 mmol; 1.00 eq.) was dissolved in methanol (23.48 ml; 578.82 mmol; 650.00 eq.) and sulfuric acid (379.73 µl; 7.12 mmol; 8.00 eq.) was added and stirred at RT for 6 days. The solvent was removed under vacuo and the residue was extracted with DCM and water. The combined organic layers were extracted once with saturated NaHCO₃ solution and two times with water. The organic phase was dried over sodium sulfate, filtered and evaporated under reduced pressure. The residue was purified by flash chromatography (cyclohexane/ethyl acetate) to afford the product as a colorless oil (150.5 mg, 53.4%); LCMS (method C): 1.32 min (purity 94.77%); [MH+] 300.1 m/z.

(S)-Me-8: ((5S,8aR)-3-Chloro-5-methyl-5,6,8a,9-tetrahydro-8H-7,10-dioxa-2,4,4b-triaza-phenanthren-1-yl)-methanol

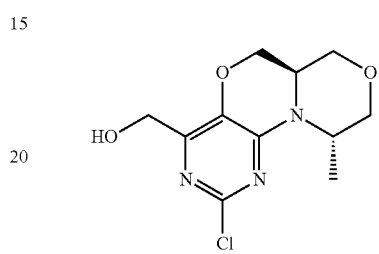

(5S,8aR)-3-Chloro-5-methyl-5,6,8a,9-tetrahydro-8H-7,10-dioxa-2,4,4b-triaza-phenanthrene-1-carboxylic acid methyl ester (150.00 mg; 0.47 mmol; 1.00 eq.) was dissolved in tetrahydrofuran (7.46 ml; 92.06 mmol; 194.04 eq.) and the solution was cooled in an ice bath. Under nitrogen, lithium borohydride solution 2.0 M in THF (355.84 µl; 0.71 mmol; 1.50 eq.) was added and the reaction solution was stirred for 3 hours at room temperature. Saturated ammonium chloride solution was added to the reaction solution and the mixture was extracted with ethyl acetate. The combined organic layers were dried over sodium sulfate, filtered and evaporated to afford the product as colorless oil (177 mg, 128%); LCMS (method C): 1.17 min (purity 93.22%); [MH+] 272.1 m/z.

Cl—(S)-Me-9: (5S,8aR)-3-Chloro-1-chloromethyl-5-methyl-5,6,8a,9-tetrahydro-8H-7,10-dioxa-2,4,4b-triaza-phenanthrene

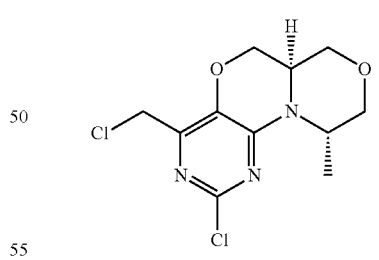

To a solution of ((5S,8aR)-3-Chloro-5-methyl-5,6,8a,9-tetrahydro-8H-7,10-dioxa-2,4,4b-triaza-phenanthren-1-yl)-methanol (177.00 mg; 0.61 mmol; 100.00 mol %) in dichloromethane (4.85 ml; 75.89 mmol; 12500.00 mol %) was added thionyl chloride (88.09 µl; 1.21 mmol; 200.00 mol %) and the solution was stirred at RT for 14 h. Thionyl chloride (44.05 µl; 0.61 mmol; 100.00 mol %) was added and the reaction mixture was stirred at RT for 6 hrs. Thionyl chloride (44.05 µl; 0.61 mmol; 100.00 mol %) was again added and the reaction mixture was stirred at RT for 14 h. Thionyl chloride for synthesis (176.18 µl; 2.43 mmol; 400.00 mol %)

was added and the reaction mixture was stirred at RT for 14 h. The solvent was removed under vacuo. The residue was dissolved in dichloromethane (500.00 µl; 7.83 mmol; 1289.57 mol %) and thionyl chloride for synthesis (100.00 µl; 1.38 mmol; 227.04 mol %) was added and the solution was stirred at RT for 2 hours. Dichloromethane and isopropyl acetate was added. The precipitate were filtered off and washed with little dichloromethane. The filtrate was evaporated and taken up in water and ethyl acetate. Saturated NaHCO$_3$ solution was added to reach a neutral pH value. The organic phase was separated and the aqueous phase was extracted three times with ethyl acetate. The combined organic phases were dried over sodium sulfate and evaporated. The residue was purified by column chromatography to afford the product (45 mg, 25%). LC/MS: (percent area) 98.323%; Rt 1.534 min; (M+H) 290.2.

(S)-Me-10: (5S,8aR)-3-Chloro-1-methanesulfonylmethyl-5-methyl-5,6,8a,9-tetrahydro-8H-7,10-dioxa-2,4,4b-triaza-phenanthrene

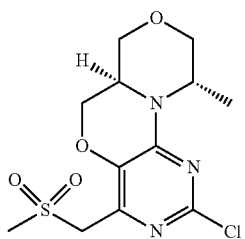 [SMILES: C[C@H]1COC[C@@H]2COc3c(CS(C)(=O)=O)nc(Cl)nc3N21]

(5S,8aR)-3-Chloro-1-chloromethyl-5-methyl-5,6,8a,9-tetrahydro-8H-7,10-dioxa-2,4,4b-triaza-phenanthrene (96.9 mg) was suspended in 2-propanol (1.00 ml; 13.08 mmol; 4014.87 mol %) and sodium methanesulfinate (50.86 mg; 0.42 mmol; 130.00 mol %) was added. The suspension was stirred at 80° for 3 days. Water was added and the mixture was extracted with ethyl acetate. The combined organic layers were dried over sodium sulfate, filtered and evaporated. The residue was purified by flash chromatography (cyclohexane/ethyl acetate) to afford the product as grey oil (63.1 mg, 55.2%); LCMS (method E): 0.56 min (purity 95.2%); [MH+] 334.1 m/z.

(S)-Me-11: (5S,8aR)-3-Chloro-1-(1-methanesulfonyl-1-methyl-ethyl)-5-methyl-5,6,8a,9-tetrahydro-8H-7,10-dioxa-2,4,4b-triaza-phenanthrene

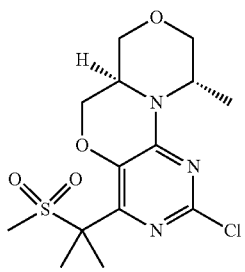 [SMILES: C[C@H]1COC[C@@H]2COc3c(nc(Cl)nc3C(C)(C)S(C)(=O)=O)N21]

(5S,8aR)-3-Chloro-1-methanesulfonylmethyl-5-methyl-5,6,8a,9-tetrahydro-8H-7,10-dioxa-2,4,4b-triaza-phenanthrene (63.10 mg; 0.18 mmol; 1.00 eq.) was dissolved in DMF (2.00 ml; 25.72 mmol; 142.92 eq.). Under ice cooling, potassium tert-butylate (26.25 mg; 0.23 mmol; 1.30 eq.) and iodomethane (14.56 µl; 0.23 mmol; 1.30 eq.) was added dropwise. The reaction mixture was stirred at 0° C. for 3 h. The reaction mixture was poured into 4 mL cold water and stirred for 30 minutes. The resulting light yellow suspension was filtered off and evaporated under reduced pressure. The residue was purified by column chromatography (cyclohexane/ethyl acetate) to afford the product as colorless oil (51.3 mg, 67%); LCMS (method E): 0.97 min (purity 85%); [MH+] 362.1 m/z.

(cis)-5-Methyl-morpholin-3-yl)-methanol

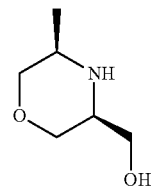

cis-5-Methylmorpholine-3-carboxylic acid hydrochloride (7.00 g; 36.616 mmol; 1.00 eq.) was suspended in tetrahydrofuran (200.00 ml; 2.469 mol; 67.42 eq.), cooled to 0° C. At this temperature lithium aluminum hydride, 1 M solution in tetrahydrofuran (80.00 ml; 80.000 mmol; 2.18 eq.) was added dropwise within 30 min. and stirred at 0° C. for 1.5 hrs and for 14 h at room temperature. Water was added dropwise under cooling. The reaction mixture was filtered over celite and washed with THF. The filtrate was concentrated under reduced pressure, extracted with dichloromethane and concentrated under reduced pressure to afford the product as a red oil (7.78 g, quant); LCMS (method E): 0.27 min (purity 100%); [MH+] 132.1 m/z.

cis-2,5-Dichloro-6-(3-hydroxymethyl-5-methyl-morpholin-4-yl)-pyrimidine-4-carboxylic Acid Methyl Ester

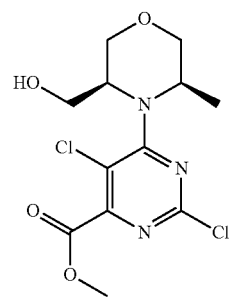 [SMILES: COC(=O)c1nc(Cl)nc(N2[C@@H](CO)COC[C@H]2C)c1Cl]

2,5,6-Trichloro-pyrimidine-4-carboxylic acid methyl ester (5.00 g; 20.086 mmol; 1.00 eq.), (cis)-5-methyl-morpholin-3-yl)-methanol (4.30 g; 31.798 mmol; 1.58 eq.) were dissolved in 2-propanol (50.00 ml; 653.965 mmol; 32.56 eq.) and N-ethyldiisopropylamine (6.85 ml; 40.280 mmol; 2.01 eq.) was added and the reaction mixture was stirred at RT for three days. The reaction mixture was purified by flash chromatography (cyclohexane/ethyl acetate) to afford the product as yellow solid (657 mg, 7%); LCMS (method C): Rt 1.434 min; (M+H) 336.

cis-3-Chloro-5-methyl-5,6,8a,9-tetrahydro-8H-7,10-dioxa-2,4,4b-triaza-phenanthrene-1-carboxylic Acid Methyl Ester

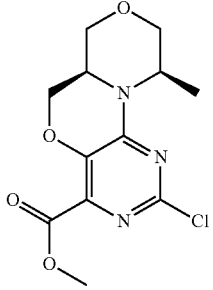 [SMILES: COC(=O)c1nc(Cl)nc2c1OC[C@H]1COC[C@@H](C)N21]

2,5-Dichloro-6-((cis)-3-hydroxymethyl-5-methyl-morpholin-4-yl)-pyrimidine-4-carboxylic acid methyl ester (607.00 mg; 1.244 mmol; 1.00 eq.) was dissolved in tetrahydrofuran (7.50 ml; 92.572 mmol; 74.41 eq.) and lithium tert-butoxide (150.00 mg; 1.874 mmol; 1.51 eq.) was added. The reaction mixture was stirred 3 hrs at room temperature and diluted with ethyl acetate and washed with 2N aqueous hydrochloric acid solution, the aqueous solution was washed with ethyl acetate. The unified organic layer was washed once with brine and dried over $Na_2SO_4$, filtered and concentrated under reduced pressure. The residue was purified by flash chromatography to afford the product as beige solid; LCMS (method C): 1.328 min, [MH+] 300.1 m/z.

((cis)-3-Chloro-5-methyl-5,6,8a,9-tetrahydro-8H-7,10-dioxa-2,4,4b-triaza-phenanthren-1-yl)-methanol

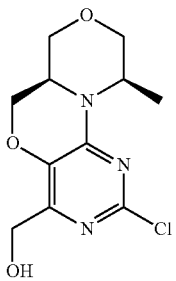 [SMILES: C[C@@H]1COC[C@@H]2COc3c(CO)nc(Cl)nc3N21]

(cis)-3-Chloro-5-methyl-5,6,8a,9-tetrahydro-8H-7,10-dioxa-2,4,4b-triaza-phenanthrene-1-carboxylic acid methyl ester (180.00 mg; 0.542 mmol; 1.00 eq.) was dissolved in tetrahydrofuran (2.00 ml; 24.686 mmol; 45.57 eq.), followed by the addition of lithium borohydride, 2M in THF (300.00 µl; 0.600 mmol; 1.11 eq.) at 0° C. The solution was stirred for 2 h at room temperature and then quenched with water and extracted with ethyl acetate. The organic layer was dried over $Na_2SO_4$, and the solvent removed in vacuo to afford the product as colorless solid; (158.00 mg; 80.9%) LCMS (method C): Rt 1.185 min (purity 96%); [MH+] 272.1 m/z.

(cis)-3-Chloro-1-chloromethyl-5-methyl-5,6,8a,9-tetrahydro-8H-7,10-dioxa-2,4,4b-triaza-phenanthrene

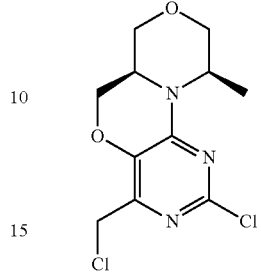

((cis)-3-Chloro-5,6,8a,9-tetrahydro-8H-7,10-dioxa-2,4,4b-triaza-phenanthren-1-yl)-methanol was suspended in dichloromethane (3.00 ml; 0.047 mol; 80.70 eq.) and thionyl chloride (84.50 µl; 0.001 mol; 2.00 eq.) was added dropwise. The reaction mixture was stirred 2 h at room temperature. The solvent was removed under vacuo to afford the product as beige solid. (188.00 mg; quant.); LCMS: (method C): Rt 1.556 min (purity 90%); [MH+] 290.2 m/z.

(cis)-3-Chloro-1-methanesulfonylmethyl-5-methyl-5,6,8a,9-tetrahydro-8H-7,10-dioxa-2,4,4b-triaza-phenanthrene

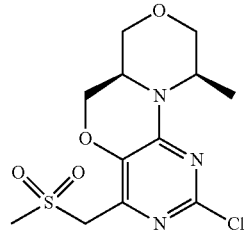

(cis)-3-Chloro-1-chloromethyl-5-methyl-5,6,8a,9-tetrahydro-8H-7,10-dioxa-2,4,4b-triaza-phenanthrene (188.00 mg; 0.616 mmol; 1.00 eq.) was dissolved in 2-propanol (2.50 ml; 0.033 mol; 53.12 eq.) and sodium methanesulfinate (100.00 mg; 0.833 mmol; 1.35 eq.) was added. The reaction mixture was stirred for 14 h at 80° C. Sodium methanesulfinate (26.00 mg; 0.216 mmol; 0.35 eq.) was added and stirred for 14 h at 80° C. The reaction mixture was purified by flash chromatography to afford the product as colorless solid (118.00 mg; 0.338 mmol; 54.9%); LCMS (method C): Rt 1.283 min (purity 96%); [M+H] 334 m/z.

(cis)-3-Chloro-1-(1-methanesulfonyl-1-methyl-ethyl)-5-methyl-5,6,8a,9-tetrahydro-8H-7,10-dioxa-2,4,4b-triaza-phenanthrene

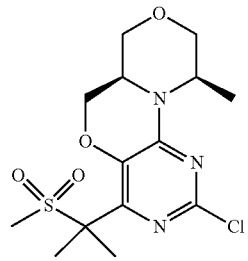

(cis)-3-Chloro-1-methanesulfonylmethyl-5-methyl-5,6,8a,9-tetrahydro-8H-7,10-dioxa-2,4,4b-triaza-phenanthrene (118.00 mg; 0.338 mmol; 1.00 eq.) was dissolved in DMF (1.25 ml; 16.075 mmol; 47.57 eq.) and cooled to 00° C. and potassium tert-butylate (50.00 mg; 0.446 mmol; 1.32 eq.) was added. After 10 min iodomethane (27.50 µl; 0.442 mmol; 1.31 eq.) was added. The reaction mixture was stirred for 14 h at room temperature. Potassium tert-butylate (50.00 mg; 0.446 mmol; 1.32 eq.) was added and stirred for 10 min and iodomethane (27.50 µl; 0.442 mmol; 1.31 eq.) was added and stirred for 4 hrs at room temperature. The reaction solution was quenched with water and the precipitate filtered off and washed with water and dried for 14 h in a vacuum dryer at 50° C. The filtrate was extracted with dichloromethane, the combined organic layers were dried over $Na_2SO_4$ and the solvent removed under vacuo. The combined residues were purified by flash chromatography to afford the product as yellow solid (72.50 mg); LCMS: (method C) Rt 1.524 min; [MH+] 362.1 m/z.

Example 1

Preparation of {4-[(S)-1-(1-Methanesulfonyl-1-methyl-ethyl)-5-(R)-methyl-5,6,8a,9-tetrahydro-8H-7,10-dioxa-2,4,4b-triaza-phenanthren-3-yl]-1H-pyrrolo[2,3-b]pyridin-5-yl}-methyl-amine ("A1")

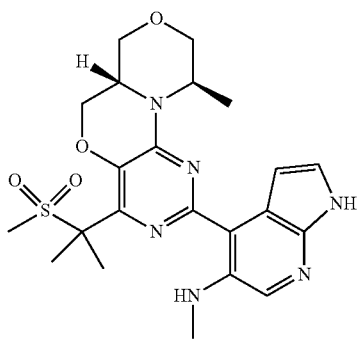 [SMILES: CNc1cnc2[nH]ccc2c1-c1nc2c(c(C(C)(C)S(C)(=O)=O)n1)OC[C@@H]1COC[C@@H](C)N21]

(5R,8aS)-1-(1-Methanesulfonyl-1-methyl-ethyl)-5-methyl-3-tributylstannanyl-5,6,8a,9-tetrahydro-8H-7,10-dioxa-2,4,4b-triaza-phenanthrene

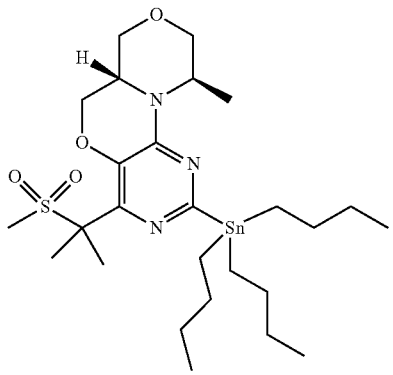 [SMILES: CCC[CH2][Sn]([CH2]CCC)([CH2]CCC)[c]1nc2c(c(C(C)(C)S(C)(=O)=O)n1)OC[C@@H]1COC[C@@H](C)N21]

(5R,8aS)-3-Chloro-1-(1-methanesulfonyl-1-methyl-ethyl)-5-methyl-5,6,8a,9-tetrahydro-8H-7,10-dioxa-2,4,4b-triaza-phenanthrene (937.00 mg; 2.590 mmol; 0.52 eq.) and bis(di-tert-butyl(4-dimethylaminophenyl)phosphine)dichloropalladium(ii) (355.00 mg; 0.501 mmol; 0.10 eq.) were suspended in 1,4-Dioxane (12.00 ml; 140.287 mmol; 28.05 eq.) and bis(tributyltin) (2.55 ml; 5.046 mmol; 1.01 eq.) was added and heated one hr at 160° C. in the microwave. Another bis(di-tert-butyl(4-dimethylaminophenyl)phosphine)dichloropalladium(ii) (90.00 mg; 0.127 mmol; 0.03 eq.) and bis(tributyltin) (2.55 ml; 5.046 mmol; 1.01 eq.) were added heated for 1 hr at 160° C. in the microwave. Another bis(tributyltin) (2.55 ml; 5.046 mmol; 1.01 eq.) was added and heated for 1 hr at 160° C. in the microwave. The compound was purified by flash chromatography (cyclohexane/ethyl acetate) to afford a colorless solid (0.788 g, 23%). LCMS (method E): 1.15 min (purity 90.1%); [MH+] 618.2 m/z.

1-Benzenesulfonyl-4-chloro-5-nitro-1H-pyrrolo[2,3-b]pyridine

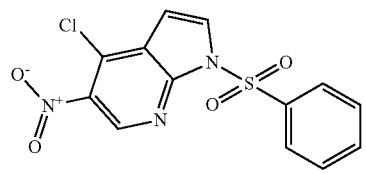 [SMILES: O=[N+]([O-])c1cnc2c(ccn2S(=O)(=O)c2ccccc2)c1Cl]

4-Chloro-1-benzenesulfonyl-7-azaindole (3.85 g; 13.125 mmol; 0.47 eq.) was dissolved in dichloromethane (50.00 ml; 782.970 mmol; 28.09 eq.) and tetramethylammonium nitrate (6.00 g; 42.306 mmol; 1.52 eq.) added at 0° C. To this solution trifluoroacetic anhydride (5.85 ml; 42.058 mmol; 1.51 eq.) was added and stirred for 6 hrs at 0° C. Then trifluoroacetic anhydride (2.90 ml; 20.850 mmol; 0.75 eq.) was added at 0° C. and stirred at room temperature overnight. The solvent was removed and the residue dissolved in dichloromethane, quenched with saturated aqueous $NH_4Cl$. The aqueous layer was extracted with dichloromethane and the combined organic layers dried over sodium sulfate and the solvent removed under vacuo. The product was obtained after recrystallization form methanol as yellow solid (5.74 g, 57.9%, yellow crystals); LCMS (method E): 0.86 min (purity 94.9%); [MH+] 338.00 m/z.

Example 1.1.1.1

(5R,8aS)-3-(1-Benzenesulfonyl-5-nitro-1H-pyrrolo[2,3-b]pyridin-4-yl)-1-(1-methanesulfonyl-1-methyl-ethyl)-5-methyl-5,6,8a,9-tetrahydro-8H-7,10-dioxa-2,4,4b-triaza-phenanthrene

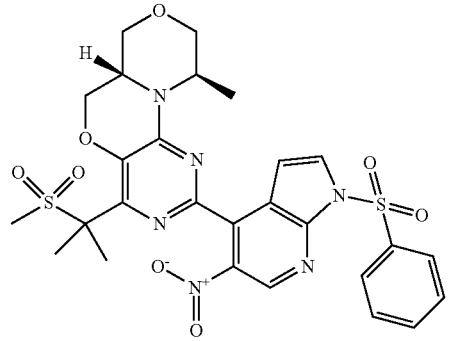 [SMILES: C[C@@H]1COC[C@H]2COc3c(nc(-c4c([N+](=O)[O-])cnc5c4ccn5S(=O)(=O)c4ccccc4)nc3C(C)(C)S(C)(=O)=O)N21]

(5R,8aS)-1-(1-Methanesulfonyl-1-methyl-ethyl)-5-methyl-3-tributylstannanyl-5,6,8a,9-tetrahydro-8H-7,10-dioxa-2,4,4b-triaza-phenanthrene (785.00 mg; 1.147 mmol; 1.00 eq.) and 1-benzenesulfonyl-4-chloro-5-nitro-1H-pyrrolo[2,3-b]pyridine (470.00 mg; 1.321 mmol; 1.15 eq.) were dissolved in DMF (2.45 ml; 31.552 mmol; 27.50 eq.). Bis(triphenylphosphine)palladium(II) chloride (15.2% Pd, 80.53 mg; 0.115 mmol; 0.10 eq.) was added and stirred for 14 h at 90° C. The product was purified by flash chromatography (cyclohexane/ethyl acetate) to afford 0.493 g (67.2%) as a yellow foam; LCMS (method E): 0.89 min (purity 98.4%); [MH+] 629.00 m/z.

Example 1.1.1

1-Benzenesulfonyl-4-[(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]-1H-pyrrolo[2,3-b]pyridin-5-ylamine

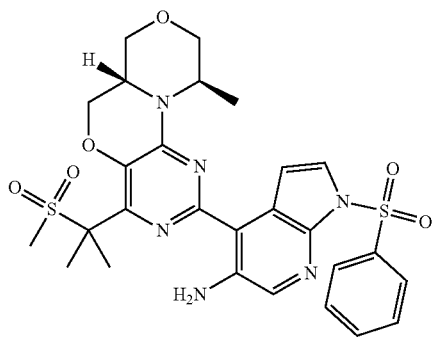 [SMILES: C[C@@H]1COC[C@H]2COc3c(nc(-c4c(N)cnc5c4ccn5S(=O)(=O)c4ccccc4)nc3C(C)(C)S(C)(=O)=O)N21]

(5R,8aS)-3-(1-Benzenesulfonyl-5-nitro-1H-pyrrolo[2,3-b]pyridin-4-yl)-1-(1-methanesulfonyl-1-methyl-ethyl)-5-methyl-5,6,8a,9-tetrahydro-8H-7,10-dioxa-2,4,4b-triaza-phenanthrene (490 mg, 0.779 mmol) was dissolved in THF (10 ml) and sponge Nickel (0.5 g) added and hydrogenated for 14 h at room temperature. After filtration, the solvent was removed under vacuo and the product obtained as yellow solid (0.495 g, 103.4%, yellow solid foam); LCMS (method C): 1.70 min (purity 95.9%); [MH+] 599.3 m/z.

Example 1.1

(1-Benzenesulfonyl-4-{(S)-1-[1-((R)-methanesulfonyl)-1-methyl-ethyl]-5-methyl-5,6,8a,9-tetrahydro-8H-7,10-dioxa-2,4,4b-triaza-phenanthren-3-yl}-1H-pyrrolo[2,3-b]pyridin-5-yl)-methyl-amine

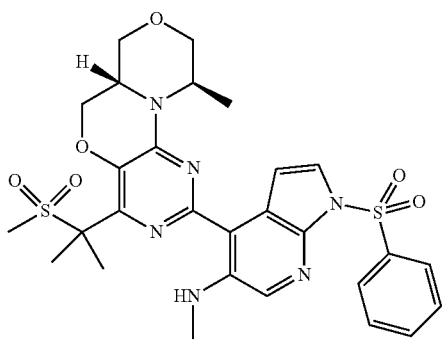 [SMILES: CNc1cnc2c(ccn2S(=O)(=O)c2ccccc2)c1-c1nc2c(c(C(C)(C)S(C)(=O)=O)n1)OC[C@@H]1COC[C@@H](C)N21]

To a solution of 1-Benzenesulfonyl-4-{(S)-1-[1-((R)-methanesulfonyl)-1-methyl-ethyl]-5-methyl-5,6,8a,9-tetrahydro-8H-7,10-dioxa-2,4,4b-triaza-phenanthren-3-yl}-1H-pyrrolo[2,3-b]pyridin-5-ylamine (61.09 mg; 0.10 mmol; 100.00 mol %) in Formic acid (100.00 µl; 2.65 mmol; 2650.73 mol %) was added formaldehyde, 1 M solution in formic acid (100.00 µl; 0.10 mmol; 100.00 mol %), heated to 100° C. and stirred at this temperature for 5 minutes. The reaction mixture was diluted with water and extracted with dichloromethane and with saturated NaHCO$_3$ the pH was set to neutral and extracted with dichloromethane. The combined organic phases was dried over sodium sulfate and evaporated. The residue was purified by column chromatography (cyclohexane/ethyl acetate) to afford the product (0.27 g, 41%); LCMS (method C): 1.817 min (purity 93%); [MH+] 613.3 m/z.

Preparation of {4-[(S)-1-(1-Methanesulfonyl-1-methyl-ethyl)-5-(R)-methyl-5,6,8a,9-tetrahydro-8H-7,10-dioxa-2,4,4b-triaza-phenanthren-3-yl]-1H-pyrrolo[2,3-b]pyridin-5-yl}-methyl-amine ("A1")

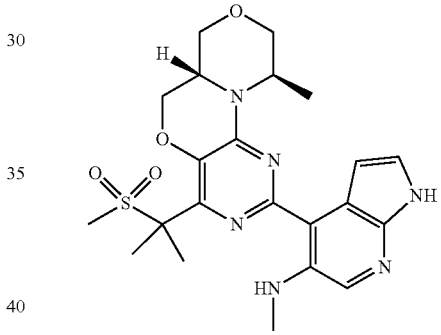

To a solution of (1-benzenesulfonyl-4-{(S)-1-[1-((R)-methanesulfonyl)-1-methyl-ethyl]-5-methyl-5,6,8a,9-tetrahydro-8H-7,10-dioxa-2,4,4b-triaza-phenanthren-3-yl}-1H-pyrrolo[2,3-b]pyridin-5-yl)-methyl-amine (131 mg) in tetrahydrofuran (2 ml) was added 2,2,2-trifluoroethanol (2 ml) and Cesium carbonate (246 mg). The suspension was heated to 100° and stirred for 14 h at this temperature. Then the reaction mixture was stirred at 30° C. for 3 days. The reaction solution was diluted with dichloromethane and purified by column chromatography (methanol and dichloromethane) to afford (46 mg) of the title compound as a yellow solid; LCMC (method C): 1.18 min (purity 100%); [MH+] 473.3 m/z; $^1$H NMR (400 MHz, DMSO-d$_6$) δ 11.19 (s, 1H), 7.87 (s, 1H), 7.78 (q, J=5.3 Hz, 1H), 7.33 (t, J=3.0 Hz, 1H), 6.91 (dd, J=3.3, 2.0 Hz, 1H), 4.71 (qd, J=6.7, 3.2 Hz, 1H), 4.42 (dd, J=10.8, 3.2 Hz, 1H), 4.02-3.93 (m, 2H), 3.89-3.82 (m, 2H), 3.68 (dd, J=11.6, 3.2 Hz, 1H), 3.23-3.10 (m, 1H), 2.99 (s, 3H), 2.91 (d, J=5.2 Hz, 3H), 1.87 (s, 3H), 1.82 (s, 3H), 1.33 (d, J=6.8 Hz, 3H).

Example 2

Preparation of 3-[(5R,8aS)-5-Methyl-3-(1H-pyrrolo[2,3-b]pyridin-4-yl)-5,6,8a,9-tetrahydro-8H-7,10-dioxa-2,4,4b-triaza-phenanthren-1-ylmethyl]-3H[1,2,3]triazole-4-carboxylic Acid ("A2")

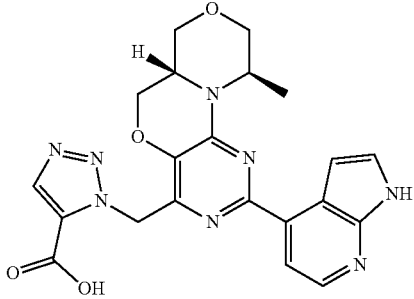 [SMILES: C[C@@H]1COC[C@H]2COc3c(Cn4nncc4C(=O)O)nc(-c4ccnc5[nH]ccc45)nc3N21]

Example 2.1.1.1

Methanesulfonic Acid (5R,8aS)-3-chloro-5-methyl-5,6,8a,9-tetrahydro-8H-7,10-dioxa-2,4,4b-triaza-phenanthren-1-ylmethyl Ester

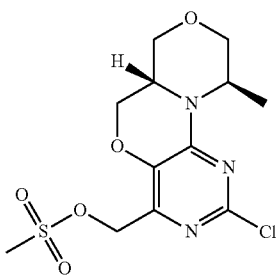

((5R,8aS)-3-Chloro-5-methyl-5,6,8a,9-tetrahydro-8H-7,10-dioxa-2,4,4b-triaza-phenanthren-1-yl)-methanol (260.000 mg; 0.9569 mmol; 1.00 eq.) was dissolved in dichloromethane (20.000 ml; 313.1880 mmol; 327.28 eq.) and triethylamine (198.975 μl; 1.4354 mmol; 1.50 eq.) added. At 5° C. methanesulfonyl chloride (96.417 μl; 1.2440 mmol; 1.30 eq.) in dichloromethane (5.000 ml; 78.2970 mmol; 81.82 eq.) was added and stirred for 3 hours. The reaction solution was diluted with dichloromethane and extracted with water and the organic layer was dried over $Na_2SO_4$. The product was obtained after removal of the solvent under vacuo as green solid (346 mg, 103.4%); LCMS (method F): 0.98 min (purity 100%); 350.00 m/z.

Example 2.1.1

(10S,14R)-4-chloro-14-methyl-6-[(2λ$^4$-triaz-2-yn-1-yl)methyl]-8,12-dioxa-1,3,5-triazatricyclo[8.4.0.0$^{2,7}$]tetradeca-2,4,6-triene

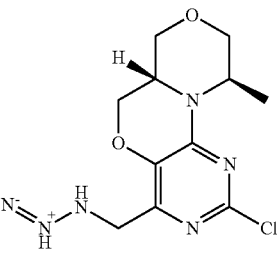 [SMILES: C[C@@H]1COC[C@H]2COc3c(CNN=[N-])nc(Cl)nc3N21]

Methanesulfonic acid (5R,8aS)-3-chloro-5-methyl-5,6,8a,9-tetrahydro-8H-7,10-dioxa-2,4,4b-triaza-phenanthren-1-ylmethyl ester (346.000 mg; 0.9892 mmol; 1.00 eq.) was dissolved in DMF (10.000 ml; 128.6015 mmol; 130.01 eq.). Sodium azide (173.801 μl; 4.9458 mmol; 5.00 eq.) was added and stirred at room temperature for 4 hours. The reaction mixture was poured into water and extracted with ethyl acetate. The combined organic layers were dried over $Na_2SO_4$, filtered and evaporated under reduced pressure. The product was purified by column chromatography (n-heptan/ethylacetate) to afford a colorless solid (210 mg, 71.1%); LCMS (method F): 1.06 min (purity 100%); [MH+] 297 m/z.

Example 2.1

3-((5R,8aS)-3-Chloro-5-methyl-5,6,8a,9-tetrahydro-8H-7,10-dioxa-2,4,4b-triaza-phenanthren-1-ylmethyl)-3H-[1,2,3]triazole-4-carboxylic Acid methyl Ester

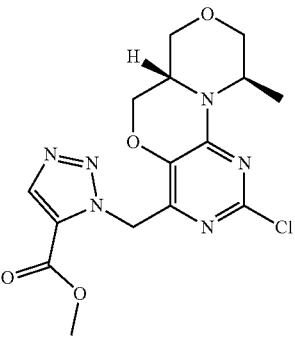 [SMILES: COC(=O)c1cnnn1Cc1nc(Cl)nc2c1OC[C@@H]1COC[C@@H](C)N21]

(10S,14R)-4-chloro-14-methyl-6-[(2A$^4$-triaz-2-yn-1-yl)methyl]-8,12-dioxa-1,3,5-triazatricyclo[8.4.0.0$^{2,7}$]tetradeca-2,4,6-triene (105.000 mg; 0.3515 mmol; 1.00 eq.) was dissolved in 1,4-Dioxane (5.000 ml; 0.0585 mol; 166.30 eq.) and Pentamethylcyclopentadienylbis(triphenylphosphine)ruthenium(II)chloride (2.451 μl; 0.0070 mmol; 0.02 eq.) and methylacetylencarboxylat (44.326 mg; 0.5272 mmol; 1.50 eq.) were added.

The reaction mixture was poured into brine and extracted with ethyl acetate. The combined organic layers were dried over $Na_2SO_4$, filtered and evaporated under reduced pressure. The product was purified by column chromatography (n-heptan/ethylacetate) to afford a brown solid (39 mg, 29.1%); LCMS (method F): 1.03 min (purity 100%); [MH+] 381.1 m/z.

Preparation of 3-[(5R,8aS)-5-Methyl-3-(1H-pyrrolo[2,3-b]pyridin-4-yl)-5,6,8a,9-tetrahydro-8H-7,10-dioxa-2,4,4b-triaza-phenanthren-1-ylmethyl]-3H[1,2,3]triazole-4-carboxylic Acid ("A2")

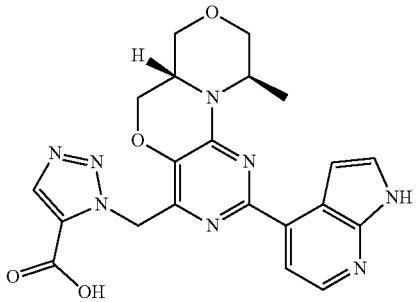 [SMILES: C[C@@H]1COC[C@H]2COc3c(Cn4nncc4C(=O)O)nc(-c4ccnc5[nH]ccc45)nc3N21]

3-((5R,8aS)-3-Chloro-5-methyl-5,6,8a,9-tetrahydro-8H-7,10-dioxa-2,4,4b-triaza-phenanthren-1-ylmethyl)-3H-[1,2,3]triazole-4-carboxylic acid methyl ester (18.000 mg; 0.0473 mmol; 1.00 eq.), 4-(tetramethyl-1,3,2-dioxaborolan-2-yl)-1H-pyrrolo[2,3-b]pyridine (13.085 mg; 0.0520 mmol; 1.10 eq.), potassium phosphate (45.834 mg; 0.1891 mmol; 4.00 eq.) and Pd(PCy3)2Cl2 (2.792 mg; 0.0038 mmol; 0.08 eq.) were dissolved in dioxane (1.500 ml; 17.5359 mmol; 370.97 eq.) and water (375.000 µl; 20.8160 mmol; 440.36 eq.) was added and stirred for 14 h at 90° C. The reaction mixture was poured into brine and extracted with ethylacetate. The combined organic layers were dried over Na$_2$SO$_4$, filtered and evaporated under reduced pressure. The product was purified by column chromatography (dichloromethane/methanol) to afford a yellow solid (5 mg, 23.6%); LCMS (method F): 0.81 min (purity 100%); [MH+] 449.2 m/z; $^1$H NMR (500 MHz, DMSO-d$_6$) δ 11.56 (s, 1H), 8.18 (d, J=5.0 Hz, 1H), 7.89 (s, 1H), 7.66 (d, J=5.0 Hz, 1H), 7.38 (dd, J=3.4, 2.5 Hz, 1H), 6.71 (dd, J=3.4, 2.0 Hz, 1H), 6.05 (s, 2H), 4.72 (qd, J=6.5, 2.7 Hz, 1H), 4.52-4.45 (m, 1H), 4.01-3.85 (m, 4H), 3.73 (dd, J=11.6, 3.2 Hz, 1H), 3.24-3.18 (m, 1H), 1.30 (d, J=6.7 Hz, 3H).

Example 3

3-[(5R,8aS)-5-Methyl-3-(2-methylamino-benzoimidazol-1-yl)-5,6,8a,9-tetrahydro-8H-7,10-dioxa-2,4,4b-triaza-phenanthren-1-ylmethyl]-3H[1,2,3]triazole-4-carboxylic Acid ("A3")

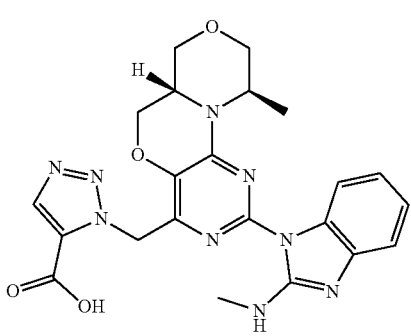 [SMILES: CNc1nc2ccccc2n1-c1nc(Cn2nncc2C(=O)O)c2c(n1)N1[C@@H](COC[C@H]1C)CO2]

3-((5R,8aS)-3-Chloro-5-methyl-5,6,8a,9-tetrahydro-8H-7,10-dioxa-2,4,4b-triaza-phenanthren-1-ylmethyl)-3H-[1,2,3]triazole-4-carboxylic acid methyl ester (18.000 mg; 0.0473 mmol; 1.00 eq.), Tris(dibenzylideneacetone)dipalladium(0) (8.657 mg; 0.0095 mmol; 0.20 eq.), dicyclohexyl-(2',4',6'-triisopropyl-biphenyl-2-yl)-phosphane (9.014 mg; 0.0189 mmol; 0.40 eq.) and (1H-benzimidazol-2-yl)-methyl-amine (7.323 mg; 0.0473 mmol; 1.00 eq.) were dissolved in dioxane (3.000 ml; 35.0718 mmol; 741.94 eq.). Lithium tert-butoxide (5.966 µl; 0.0662 mmol; 1.40 eq.) was added and stirred for 14 h at 90° C. The reaction mixture was poured into brine and extracted with ethylacetate. The combined organic layers were dried over Na$_2$SO$_4$, filtered and evaporated under reduced pressure. The product was purified by column chromatography (dichloromethane/methanol) to afford a yellow solid (6 mg, 26.6%); LCMS (method F): 0.86 min (purity 100%); [MH+] 478.2 m/z; $^1$H NMR (400 MHz, DMSO-d$_6$) δ 7.97 (d, J=8.0 Hz, 1H), 7.72-7.66 (m, 1H), 7.23-7.14 (m, 1H), 7.04 (dd, J=8.2, 7.0 Hz, 1H), 6.92 (t, J=7.4 Hz, 1H), 6.06 (s, 2H), 4.61-4.53 (m, 1H), 4.50 (dd, J=10.8, 3.0 Hz, 1H), 4.06-3.96 (m, 2H), 3.95-3.85 (m, 2H), 3.74 (dd, J=11.6, 3.2 Hz, 1H), 3.26-3.19 (m, 0H), 2.89 (d, J=4.8 Hz, 2H), 1.34 (d, J=6.8 Hz, 2H).

Example 4

1-[(5R,8aS)-5-Methyl-3-(1H-pyrrolo[2,3-b]pyridin-4-yl)-5,6,8a,9-tetrahydro-8H-7,10-dioxa-2,4,4b-triaza-phenanthren-1-ylmethyl]-1H-[1,2,3]triazole-4-carboxylic Acid ("A4")

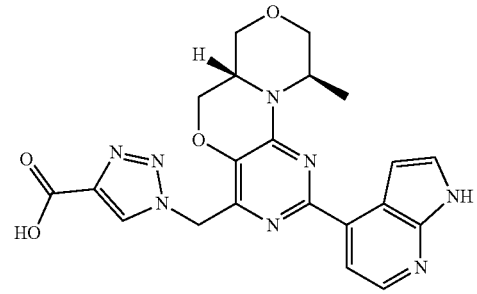 [SMILES: C[C@@H]1COC[C@H]2COc3c(Cn4cc(C(=O)O)nn4)nc(-c4ccnc5[nH]ccc45)nc3N21]

Example 4.1

1-((5R,8aS)-3-Chloro-5-methyl-5,6,8a,9-tetrahydro-8H-7,10-dioxa-2,4,4b-triaza-phenanthren-1-ylmethyl)-1H-[1,2,3]triazole-4-carboxylic Acid Methyl Ester

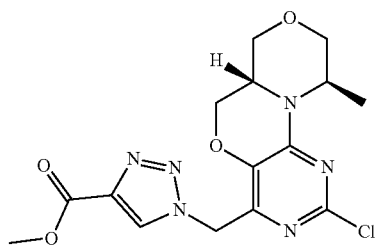

(10S,14R)-4-chloro-4-methyl-6-[(2λ⁴-triaz-2-yn-1-yl)methyl]-8,12-dioxa-1,3,5-triazatricyclo[8.4.0.0²,⁷]tetradeca-2,4,6-triene (105.000 mg; 0.3515 mmol; 1.00 eq.) was suspended in water (1.500 ml; 83.3333 mmol; 237.09 eq.) and tertbutanol (2.000 ml; 21.0464 mmol; 59.88 eq.). Then (0.002 ml; 0.2812 mmol; 0.80 eq.), copper(II) sulfate pentahydrate powder (4.912 µl; 0.0703 mmol; 0.20 eq.) and methylacetylencarboxylat (59.102 mg; 0.7030 mmol; 2.00 eq.) were added. The mixture was stirred at 90° C. for 3 hours. The reaction mixture was poured into brine and extracted twice with ethyl acetate. The combined organic layers were dried over $Na_2SO_4$, filtered and evaporated under reduced pressure. The product was purified by column chromatography (n-heptan/ethylacetate) to afford a brown solid (128 mg, 95.6%); LCMS (method F): 0.96 min (purity 100%); [MH+] 381.1 m/z.

Preparation of 1-[(5R,8aS)-5-Methyl-3-(1H-pyrrolo[2,3-b]pyridin-4-yl)-5,6,8a,9-tetrahydro-8H-7,10-dioxa-2,4,4b-triaza-phenanthren-1-ylmethyl]-1H[1,2,3]triazole-4-carboxylic Acid ("A4")

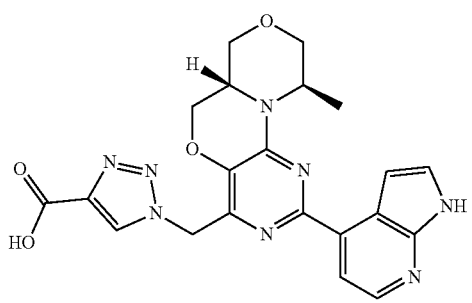 [SMILES: C[C@@H]1COC[C@H]2COc3c(Cn4cc(C(=O)O)nn4)nc(-c4ccnc5[nH]ccc45)nc3N21]

1-((5R,8aS)-3-Chloro-5-methyl-5,6,8a,9-tetrahydro-8H-7,10-dioxa-2,4,4b-triaza-phenanthren-1-ylmethyl)-1H-[1,2,3]triazole-4-carboxylic acid methyl ester (64.000 mg; 0.1681 mmol; 1.00 eq.), 4-(tetramethyl-1,3,2-dioxaborolan-2-yl)-1H-pyrrolo[2,3-b]pyridine (46.525 mg; 0.1849 mmol; 1.10 eq.), potassium phosphate (162.965 mg; 0.6723 mmol; 4.00 eq.) and Pd(PCy3)2Cl2 (9.925 mg; 0.0134 mmol; 0.08 eq.) were dissolved in dioxane (3.000 ml; 35.0718 mmol; 208.67 eq.) and water (750.000 µl; 41.6320 mmol; 247.70 eq.). The reaction was stirred at 90° C. for 14 h. The reaction mixture was poured into brine and extracted with ethyl acetate. The precipitate was isolated and dried under vacuo to obtain the product as brown solid (65 mg, 86.2%); LCMS (method F): 0.83 min (purity 100%); [MH+] 449.2 m/z; ¹H NMR (500 MHz, DMSO-d₆) δ 13.06 (bs, 1H), 11.78 (s, 1H), 8.79 (s, 1H), 8.28 (d, J=5.2 Hz, 1H), 7.80 (d, J=5.1 Hz, 1H), 7.45 (t, J=2.9 Hz, 1H), 6.88 (dd, J=3.4, 1.9 Hz, 1H), 5.80-5.72 (m, 2H), 4.75 (qd, J=6.7, 2.7 Hz, 1H), 4.56-4.49 (m, 1H), 4.03-3.93 (m, 3H), 3.89 (d, J=11.5 Hz, 1H), 3.74 (dd, J=11.6, 3.2 Hz, 1H), 3.27-3.19 (m, 1H), 1.32 (d, J=6.7 Hz, 3H).

Example 5

2-[(5R,8aS)-3-(5-Fluoro-3-methylaminomethyl-1H-pyrrolo[2,3-b]pyridin-4-yl)-5-methyl-5,6,8a,9-tetrahydro-8H-7,10-dioxa-2,4,4b-triaza-phenanthren-1-yl]-propan-2-ol ("A5")

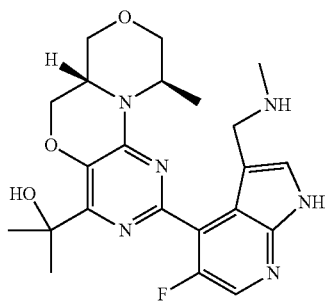 [SMILES: CNCc1c[nH]c2ncc(F)c(-c3nc4c(c(C(C)(C)O)n3)OC[C@@H]3COC[C@@H](C)N43)c12]

Example 5.1.1

2-((5R,8aS)-3-Chloro-5-methyl-5,6,8a,9-tetrahydro-8H-7,10-dioxa-2,4,4b-triaza-phenanthren-1-yl)-propan-2-ol

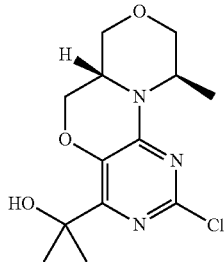 [SMILES: C[C@@H]1COC[C@H]2COc3c(nc(Cl)nc3C(C)(C)O)N21]

(5R,8aS)-3-Chloro-5-methyl-5,6,8a,9-tetrahydro-8H-7,10-dioxa-2,4,4b-triaza-phenanthrene-1-carboxylic acid methyl ester (1.85 g; 6.000 mmol; 100.00 mol %) was dissolved in tetrahydrofuran (25.42 ml; 313.800 mmol; 5230.00 mol %) and methylmagnesium chloride (solution in tetrahydrofuran) (6.00 ml; 18.000 mmol; 300.00 mol %) was added and the reaction was stirred for 50 min at ambient temperature. The reaction mixture was distributed between THF and saturated NaCl-solution. The resulted precipitate was filtered, the organic layer separated and dried over sodium sulfate, filtered and evaporated to dryness. The residue was heated in MTBE, allowed to cool down, withdrawn and washed with MTBE. The product was obtained as colorless solid (1.774 g, 89.4%); LCMS (method C): 1.49 min (purity 90.6%); [MH+] 300.1 m/z.

Example 5.1

2-[(5R,8aS)-3-(5-Fluoro-1H-pyrrolo[2,3-b]pyridin-4-yl)-5-methyl-5,6,8a,9-tetrahydro-8H-7,10-dioxa-2,4,4b-triaza-phenanthren-1-yl]-propan-2-ol ("A7")

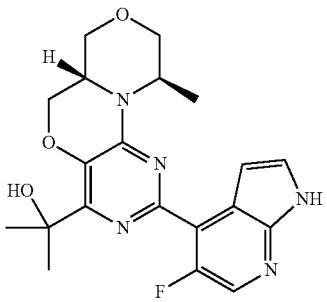 [SMILES: C[C@@H]1COC[C@H]2COc3c(nc(-c4c(F)cnc5[nH]ccc45)nc3C(C)(C)O)N21]

2-((5R,8aS)-3-Chloro-5-methyl-5,6,8a,9-tetrahydro-8H-7,10-dioxa-2,4,4b-triaza-phenanthren-1-yl)-propan-2-ol (330.85 mg; 1.000 mmol; 100.00 mol %), 5-fluoro-4-(4,4,5,5-tetramethyl-1,3,2-dioxaborolan-2-yl)-1-(triisopropylsilyl)-1H-pyrrolo[2,3-b]pyridine (502.11 mg; 1.200 mmol; 120.00 mol %) and sodium hydrogen carbonate (100.81 mg; 1.200 mmol; 120.00 mol %) were suspended in DMF (2.00 ml; 25.720 mmol; 2572.00 mol %) and water (1.00 ml; 55.490 mmol; 5549.00 mol %). The reaction mixture was heated to 80° C. and bis(triphenylphosphine)-palladium(II)-chlorid (14.04 mg; 0.020 mmol; 2.00 mol %) was added and stirred at 80° C. for 14 h. The reaction mixture was diluted with water and extracted with ethyl acetate. The combined organic layers were dried over sodium sulfate, filtered and concentrated under reduced pressure. The residue was purified by column chromatography to afford the product as yellow solid (130.9 mg, 31.0%); LCMS (method C): 1.31 min (purity 94.7%); [MH+] 400.3 m/z.

Preparation of 2-[(5R,8aS)-3-(5-Fluoro-3-methyl-aminomethyl-1H-pyrrolo[2,3-b]pyridin-4-yl)-5-methyl-5,6,8a,9-tetrahydro-8H-7,10-dioxa-2,4,4b-triaza-phenanthren-1-yl]-propan-2-ol ("A5")

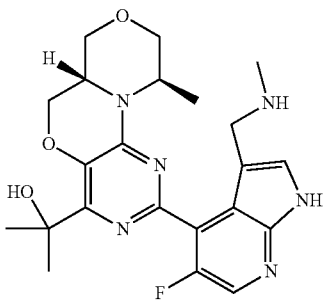 [SMILES: CNCc1c[nH]c2ncc(F)c(-c3nc4c(c(C(C)(C)O)n3)OC[C@@H]3COC[C@@H](C)N43)c12]

2-[(5R,8aS)-3-(5-Fluoro-1H-pyrrolo[2,3-b]pyridin-4-yl)-5-methyl-5,6,8a,9-tetrahydro-8H-7,10-dioxa-2,4,4b-triaza-phenanthren-1-yl]-propan-2-ol (42.18 mg; 0.10 mmol; 100.00 mol %) was dissolved in methylamine 33% wt. solution in ethanol (373.46 µl; 3.00 mmol; 3000.00 mol %) and stirred for 3 hours at 80° C. Methylamine 33% wt. solution in ethanol (373.46 µl; 3.00 mmol; 3000.00 mol %) was added and the reaction mixture was stirred for 14 h at 100° C. The solvent was removed under vacuo and the product was purified by preparative HPLC to afford a yellow solid (13.5 mg, 26.9%); LCMS (method C): 1.17 min (purity 97.2%); [MH+] 443.3 m/z; $^1$H NMR (400 MHz, DMSO-d$_6$) δ 11.87 (s, 1H), 8.30 (s, 1H, formate), 8.26 (d, J=2.4 Hz, 1H), 7.58 (s, 1H), 4.57-4.42 (m, 2H), 4.02-3.82 (m, 3H), 3.75 (d, J=11.5 Hz, 1H), 3.61 (dd, J=11.6, 3.3 Hz, 1H), 3.56-3.43 (m, 2H), 3.18 (t, J=11.6 Hz, 1H), 2.17 (s, 3H), 1.50 (s, 6H), 1.21 (d, J=6.8 Hz, 3H).

Example 6

2-[(5R,8aS)-5-Methyl-3-(1H-pyrrolo[2,3-b]pyridin-4-yl)-5,6,8a,9-tetrahydro-8H-7,10-dioxa-2,4,4b-triaza-phenanthren-1-yl]-propan-2-ol ("A6")

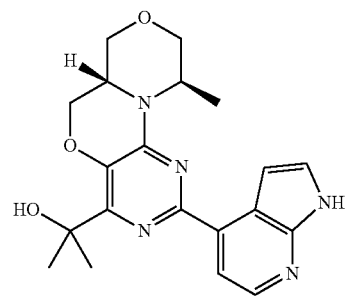

Example 6.1

2-[(5R,8aS)-3-(1-Benzenesulfonyl-1H-pyrrolo[2,3-b]pyridin-4-yl)-5-methyl-5,6,8a,9-tetrahydro-8H-7,10-dioxa-2,4,4b-triaza-phenanthren-1-yl]-propan-2-ol

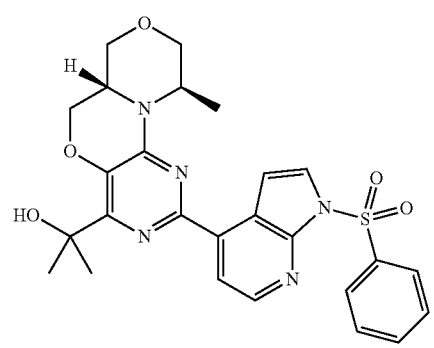 [SMILES: C[C@@H]1COC[C@H]2COc3c(nc(-c4ccnc5c4ccn5S(=O)(=O)c4ccccc4)nc3C(C)(C)O)N21]

2-((5R,8aS)-3-Chloro-5-methyl-5,6,8a,9-tetrahydro-8H-7,10-dioxa-2,4,4b-triaza-phenanthren-1-yl)-propan-2-ol (165.43 mg; 0.500 mmol; 100.00 mol %), 1-benzenesulfonyl-4-(4,4,5,5-tetramethyl-[1,3,2]dioxaborolan-2-yl)-1H-pyrrolo[2,3-b]pyridine (242.69 mg; 0.600 mmol; 120.00 mol %) and sodium hydrogen carbonate (50.40 mg; 0.600 mmol; 120.00 mol %) were suspended in DMF (3.00 ml; 38.580 mmol; 7716.00 mol %) and water (749.99 µl; 41.620 mmol; 8324.00 mol %). Bis(triphenylphosphine)-palladium(II)-chlorid (7.02 mg; 0.010 mmol; 2.00 mol %) was added. The reaction was stirred at 80° C. for 16 hrs. The reaction mixture was diluted with water. The resulting precipitate was filtered off and washed with water to obtain the product as beige solid (270 mg, 86.9%); LCMS (method C): 1.88 min (purity 83.9%); [MH+] 522.2 m/z.

Preparation of 2-[(5R,8aS)-5-Methyl-3-(1H-pyrrolo [2,3-b]pyridin-4-yl)-5,6,8a,9-tetrahydro-8H-7,10-dioxa-2,4,4b-triaza-phenanthren-1-yl]-propan-2-ol ("A6")

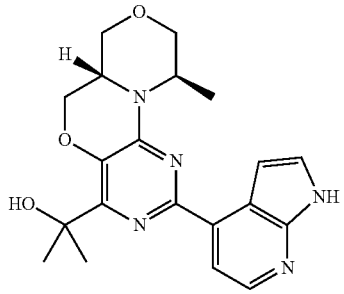 [SMILES: C[C@@H]1COC[C@H]2COc3c(nc(-c4ccnc5[nH]ccc45)nc3C(C)(C)O)N21]

2-[(5R,8aS)-3-(1-Benzenesulfonyl-1H-pyrrolo[2,3-b] pyridin-4-yl)-5-methyl-5,6,8a,9-tetrahydro-8H-7,10-dioxa-2,4,4b-triaza-phenanthren-1-yl]-propan-2-ol (270.00 mg; 0.434 mmol; 100.00 mol %) and cesium carbonate (104.31 µl; 1.303 mmol; 300.00 mol %) were suspended in 2,2,2-trifluoro-ethanol (868.64 µl; 11.983 mmol; 2759.00 mol %) and tetrahydrofuran (868.76 µl; 10.723 mmol; 2469.00 mol %) and the mixture was stirred at 80° C. for 16 hrs. The reaction mixture was filtered and the mother liquor was evaporated to dryness. The residue was purified by flash column chromatography (methanol/dichloromethane) to afford the product as colorless solid (90 mg, 54%); LCMS (method C): 1.32 min (purity 99.4%); [MH+] 382.2 m/z; $^1$H NMR (400 MHz, DMSO-d$_6$) δ 11.73 (s, 1H), 8.30 (d, J=5.0 Hz, 1H), 7.93 (d, J=5.0 Hz, 1H), 7.56 (dd, J=3.4, 2.5 Hz, 1H), 7.17 (dd, J=3.5, 2.0 Hz, 1H), 5.30 (s, 1H), 4.77 (qd, J=6.5, 2.9 Hz, 1H), 4.44 (dd, J=10.6, 2.8 Hz, 1H), 4.00-3.81 (m, 4H), 3.71 (dd, J=11.6, 3.2 Hz, 1H), 3.24-3.14 (m, 1H), 1.53 (s, 6H), 1.32 (d, J=6.8 Hz, 3H).

Example 7

2-[(5R,8aS)-3-(5-Fluoro-1H-pyrrolo[2,3-b]pyridin-4-yl)-5-methyl-5,6,8a,9-tetrahydro-8H-7,10-dioxa-2,4,4b-triaza-phenanthren-1-yl]-propan-2-ol ("A7")

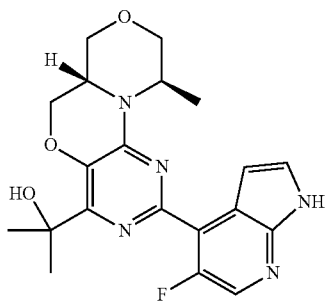 [SMILES: C[C@@H]1COC[C@H]2COc3c(nc(-c4c(F)cnc5[nH]ccc45)nc3C(C)(C)O)N21]

2-((5R,8aS)-3-Chloro-5-methyl-5,6,8a,9-tetrahydro-8H-7,10-dioxa-2,4,4b-triaza-phenanthren-1-yl)-propan-2-ol (330.85 mg; 1.000 mmol; 100.00 mol %), 5-fluoro-4-(4,4,5,5-tetramethyl-1,3,2-dioxaborolan-2-yl)-1-(triisopropylsilyl)-1H-pyrrolo[2,3-b]pyridine (502.11 mg; 1.200 mmol; 120.00 mol %) and sodium hydrogen carbonate (100.81 mg; 1.200 mmol; 120.00 mol %) were suspended in DMF (2.00 ml; 25.720 mmol; 2572.00 mol %) and water (1.00 ml; 55.490 mmol; 5549.00 mol %). The reaction mixture was heated to 80° C. and bis(triphenylphosphine)-palladium(II)-chlorid (14.04 mg; 0.020 mmol; 2.00 mol %) was added and stirred at 80° C. for 14 h. The reaction mixture was diluted with water and extracted with ethyl acetate. The combined organic layers were dried over sodium sulfate, filtered and concentrated under reduced pressure. The residue was purified by column chromatography to afford the product as yellow solid (130.9 mg, 31.0%); LCMS (method C): 1.31 min (purity 94.7%); [MH+] 400.3 m/z. $^1$H NMR (400 MHz, DMSO-d$_6$) δ 11.86 (s, 1H), 8.26 (d, J=3.7 Hz, 1H), 7.62 (t, J=2.6 Hz, 1H), 6.81 (d, J=2.9 Hz, 1H), 4.63 (qd, J=6.5, 3.0 Hz, 1H), 4.45 (dd, J=10.5, 2.8 Hz, 1H), 4.00-3.79 (m, 4H), 3.66 (dd, J=11.6, 3.2 Hz, 1H), 3.18 (t, J=11.6 Hz, 1H), 1.50 (s, 6H), 1.28 (d, J=6.7 Hz, 3H).

Example 8

{1-[(5R,8aR)-1-(1-Methanesulfonyl-1-methyl-ethyl)-5-methyl-5,6,8a,9-tetrahydro-8H-7,10-dioxa-2,4,4b-triaza-phenanthren-3-yl]-1H-benzimidazol-2-yl}-methyl-amine ("A8")

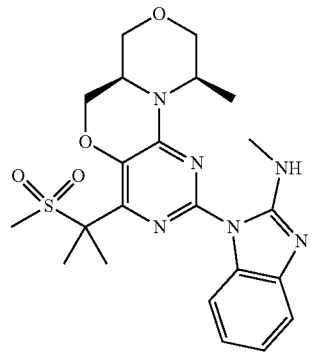

(cis)-3-Chloro-1-(1-methanesulfonyl-1-methyl-ethyl)-5-methyl-5,6,8a,9-tetrahydro-8H-7,10-dioxa-2,4,4b-triaza-phenanthrene (72.50 mg; 0.131 mmol; 1.00 eq.) was suspended in DMF (3.00 ml; 32.369 mmol; 246.64 eq.). Benzimidazole-2-yl-methylamine (35.00 mg; 0.226 mmol; 1.72 eq.), 2,6-lutidine, 98% (23.00 µl; 0.197 mmol; 1.50 eq.) and cesium carbonate were added and stirred at 120° C. for 14 h. Benzimidazole-2-yl-methylamine (20.00 mg; 0.129 mmol; 0.98 eq.) was added and stirred for 14 h at 120° C. The reaction mixture was allowed to cool to RT and water was added and extracted with ethyl acetate. The combined organic layer was dried over Na$_2$SO$_4$. The residue was purified by flash chromatography to afford the product as yellow solid (12.50 mg, 16.4%); LCMS: (method C); Rt 1.281 min (purity 81%); (M+H) 473.2; $^1$H NMR (500 MHz, DMSO-d$_6$) δ 8.31 (q, J=4.8 Hz, 1H), 8.14 (d, J=7.6 Hz, 1H), 7.30-7.22 (m, 2H), 7.08 (td, J=7.6, 1.2 Hz, 1H), 6.98 (td, J=7.7, 1.3 Hz, 1H), 4.44 (dd, J=10.6, 3.4 Hz, 1H), 4.42-4.35 (m, 1H), 4.33 (dd, J=11.7, 2.8 Hz, 1H), 4.30-4.26 (m, 1H), 4.02 (dd, J=10.3, 3.9 Hz, 1H), 3.80-3.69 (m, 3H), 3.05-3.35 (m, 6H), 1.86 (s, 3H), 1.83 (s, 3H), 1.51 (d, J=6.4 Hz, 3H).

Example 9

2-[(5R,8aS)-5-Methyl-3-(2-methylamino-benzimidazol-1-yl)-5,6,8a,9-tetrahydro-8H-7,10-dioxa-2,4,4b-triaza-phenanthren-1-yl]-propan-2-ol ("A9")

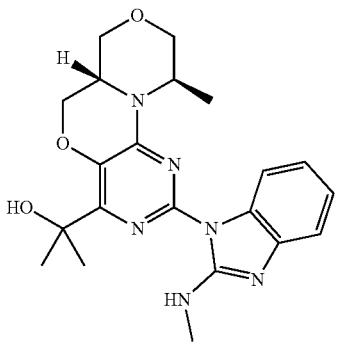 [SMILES: CNc1nc2ccccc2n1-c1nc2c(c(C(C)(C)O)n1)OC[C@@H]1COC[C@@H](C)N21]

2-((5R,8aS)-3-Chloro-5-methyl-5,6,8a,9-tetrahydro-8H-7,10-dioxa-2,4,4b-triaza-phenanthren-1-yl)-propan-2-ol (165.43 mg; 0.500 mmol; 100.00 mol %) was suspended in DMF (9.99 ml; 107.745 mmol; 21549.00 mol %). Benzimidazole-2-yl-methylamine (92.95 mg; 0.600 mmol; 120.00 mol %), 2,6-lutidine, 98% (58.24 µl; 0.500 mmol; 100.00 mol %) and cesium carbonate (325.83 mg; 1.000 mmol; 200.00 mol %) were added and stirred at 120° C. for three days and allowed to cool to room temperature and diluted with water (50 ml) and stirred for 30 min. The reaction solution was extracted with ethyl acetate. The organic layer was dried over $Na_2SO_4$. The residue was purified by flash chromatography (methanol/dichloromethane) to afford the product as yellow solid (46.5 mg, 22.4%); LCMS (method C): 1.29 min (purity 98.8%); [MH+] 411.3 m/z; $^1$H NMR (400 MHz, DMSO-$d_6$) δ 8.88 (q, J=4.8 Hz, 1H), 8.13 (d, J=7.4 Hz, 1H), 7.25 (dd, J=7.9, 1.3 Hz, 1H), 7.07 (td, J=7.6, 1.2 Hz, 1H), 6.97 (td, J=7.7, 1.3 Hz, 1H), 5.16 (s, 1H), 4.59 (qd, J=6.5, 2.8 Hz, 1H), 4.41 (dd, J=11.0, 3.2 Hz, 1H), 4.00-3.86 (m, 3H), 3.79 (dd, J=11.0, 8.8 Hz, 1H), 3.72 (dd, J=11.7, 3.2 Hz, 1H), 3.24-3.14 (m, 1H), 3.05 (d, J=4.8 Hz, 3H), 1.52 (s, 6H), 1.33 (d, J=6.8 Hz, 3H).

Example 10

{1-[(5R,8aS)-1-(1-Methanesulfonyl-1-methyl-ethyl)-5-methyl-5,6,8a,9-tetrahydro-8H-7,10-dioxa-2,4,4b-triaza-phenanthren-3-yl]-1H-imidazol-2-yl}-methylamine ("A10")

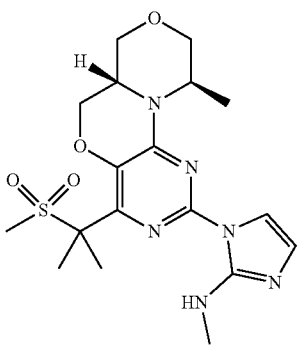 [SMILES: CNc1nccn1-c1nc2c(c(C(C)(C)S(C)(=O)=O)n1)OC[C@@H]1COC[C@@H](C)N21]

(5R,8aS)-3-Chloro-1-(1-methanesulfonyl-1-methyl-ethyl)-5-methyl-5,6,8a,9-tetrahydro-8H-7,10-dioxa-2,4,4b-triaza-phenanthrene (95.00 mg; 0.255 mmol; 1.00 eq.) was suspended in DMF (3.50 ml; 37.764 mmol; 148.29 eq.). (1H-Imidazol-2-yl)-methyl-amine hydrochloride (43.00 mg; 0.306 mmol; 1.20 eq.), 2,6-lutidine (30.00 µl; 0.258 mmol; 1.01 eq.) and cesium carbonate (250.00 mg; 0.767 mmol; 3.01 eq.) were added and stirred at 140° C. for 14 h. The solvent was removed under vacuo and purified by flash chromatography (cyclohexane/ethyl acetate) to afford the product as yellow solid (31.8 mg, 26.1%); LCMS (method E): 0.44 min (purity 98.1%); [MH+] 423.2 m/z; $^1$H NMR (400 MHz, DMSO-$d_6$) δ 8.20 (s, 1H), 7.41 (q, J=4.9 Hz, 1H), 7.32 (d, J=1.8 Hz, 1H), 6.53 (d, J=1.8 Hz, 1H), 4.64 (qd, J=6.8, 2.9 Hz, 1H), 4.39 (dd, J=11.1, 3.4 Hz, 1H), 4.00-3.90 (m, 3H), 3.85-3.74 (m, 2H), 3.64 (dd, J=11.6, 3.4 Hz, 1H), 3.20-3.10 (m, 1H), 2.98 (s, 3H), 2.91 (d, J=5.0 Hz, 3H), 1.80 (s, 3H), 1.77 (s, 3H), 1.25 (d, J=6.2 Hz, 3H).

Example 11

1-[(5R,8aS)-1-(1-Methanesulfonyl-1-methyl-ethyl)-5-methyl-5,6,8a,9-tetrahydro-8H-7,10-dioxa-2,4,4b-triaza-phenanthren-3-yl]-1H-benzimidazol-2-ylamine ("A11")

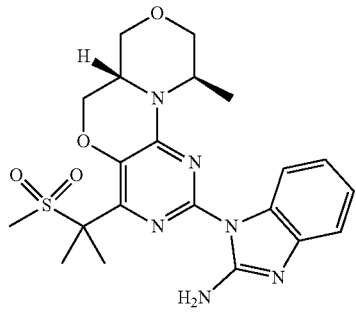 [SMILES: C[C@@H]1COC[C@H]2COc3c(nc(-n4c(N)nc5ccccc54)nc3C(C)(C)S(C)(=O)=O)N21]

(5R,8aS)-3-Chloro-1-(1-methanesulfonyl-1-methyl-ethyl)-5-methyl-5,6,8a,9-tetrahydro-8H-7,10-dioxa-2,4,4b-triaza-phenanthrene (150.00 mg; 0.402 mmol; 1.00 eq.) was suspended in DMF (6.00 ml; 64.738 mmol; 161.00 eq.). 2-Aminobenzimidazole (70.00 mg; 0.526 mmol; 1.31 eq.), 2,6-lutidine (47.00 µl; 0.404 mmol; 1.00 eq.) and cesium carbonate (262.00 mg; 0.804 mmol; 2.00 eq.) were added and stirred at 140° C. for 14 h. After removal of the solvent in vacuo, the residue was purified by flash chromatography (cyclohexane/methanol/ethyl acetate) and preparative HPLC to afford the product as beige solid (68.8 mg, 36.9%); LCMS (method E): 0.49 min (purity 98.9%); [MH+] 459.2 m/z; $^1$H NMR (400 MHz, DMSO-$d_6$) δ 7.99 (d, J=7.5 Hz, 1H), 7.41 (s, 2H), 7.23-7.16 (m, 1H), 7.07 (td, J=7.6, 1.3 Hz, 1H), 6.97 (td, J=7.7, 1.3 Hz, 1H), 4.68-4.57 (m, 1H), 4.43 (dd, J=10.9, 3.4 Hz, 1H), 4.07-3.94 (m, 2H), 3.91-3.81 (m, 3H), 3.70 (dd, J=11.6, 3.3 Hz, 1H), 3.24-3.15 (m, 1H), 3.01 (s, 3H), 1.86 (s, 3H), 1.81 (s, 3H), 1.36 (d, J=6.8 Hz, 3H).

Example 12

2-{(5R,8aS)-3-[(1H-Benzimidazol-2-yl)-methyl-amino]-5-methyl-5,6,8a,9-tetrahydro-8H-7,10-dioxa-2,4,4b-triaza-phenanthren-1-yl}-propan-2-ol ("A12")

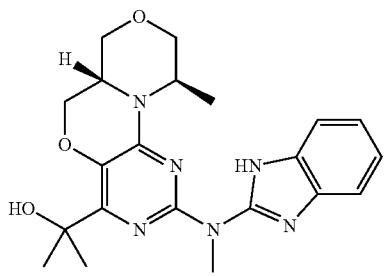 [SMILES: C[C@@H]1COC[C@H]2COc3c(nc(N(C)c4nc5ccccc5[nH]4)nc3C(C)(C)O)N21]

2-((5R,8aS)-3-Chloro-5-methyl-5,6,8a,9-tetrahydro-8H-7,10-dioxa-2,4,4b-triaza-phenanthren-1-yl)-propan-2-ol (154.51 mg; 0.500 mmol; 100.00 mol %), (1H-benzimidazol-2-yl)-methyl-amine (73.59 mg; 0.500 mmol; 100.00 mol %), tris(dibenzylideneacetone)dipalladium(0) (91.57 mg; 0.100 mmol; 20.00 mol %) and dicyclohexyl-(2',4',6'-triisopropyl-biphenyl-2-yl)-phosphane (95.34 mg; 0.200 mmol; 40.00 mol %) were dissolved in dioxane (1.36 ml; 15.845 mmol; 3169.00 mol %), lithium tert-butoxide (1.0 M solution in tetrahydrofuran) (700.00 µl; 0.700 mmol; 140.00 mol %) was added and the mixture was stirred for 1 h at 80° C. The reaction mixture was purified by column chromatography (petroleum benzene/ethyl acetate) to afford the product as yellow solid (14.8 mg, 6.5%); LCMS (method C): 1.29 min (purity 89.6%); [MH+] 411.3 m/z; $^1$H NMR (400 MHz, DMSO-$d_6$) δ 13.08 (s, 1H), 7.42 (d, J=7.1 Hz, 1H), 7.37-7.23 (m, 1H), 7.16-7.00 (m, 2H), 5.37 (s, 1H), 4.69-4.57 (m, 1H), 4.35 (dd, J=10.9, 3.2 Hz, 1H), 3.97-3.84 (m, 2H), 3.81 (d, J=11.5 Hz, 1H), 3.74-3.71 (m, 1H), 3.65 (dd, J=11.6, 3.3 Hz, 1H), 3.29 (s, 3H), 3.23-3.09 (m, 1H), 1.52 (s, 3H), 1.51 (s, 3H), 1.27 (d, J=6.8 Hz, 3H).

Example 13

(6R,8aS)-1-(1-Methanesulfonyl-1-methyl-ethyl)-5-methyl-3-(1H-pyrrolo[2,3-b]pyridin-4-yl)-5,6,8a,9-tetrahydro-8H-7,10-dioxa-2,4,4b-triaza-phenanthrene ("A13")

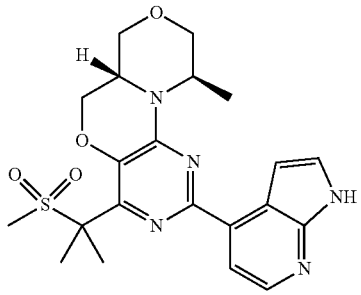 [SMILES: C[C@@H]1COC[C@H]2COc3c(nc(-c4ccnc5[nH]ccc45)nc3C(C)(C)S(C)(=O)=O)N21]

Example 13.1

(5R,8aS)-3-(1-Benzenesulfonyl-1H-pyrrolo[2,3-b]pyridin-4-yl)-1-(1-methanesulfonyl-1-methyl-ethyl)-5-methyl-5,6,8a,9-tetrahydro-8H-7,10-dioxa-2,4,4b-triaza-phenanthrene

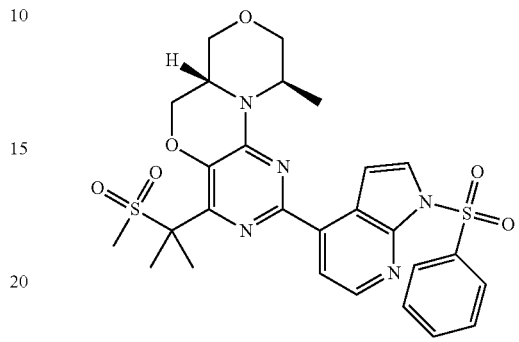

(5R,8aS)-3-Chloro-1-(1-methanesulfonyl-1-methyl-ethyl)-5-methyl-5,6,8a,9-tetrahydro-8H-7,10-dioxa-2,4,4b-triaza-phenanthrene (87.00 mg; 0.228 mmol; 100.00 mol %), 1-benzenesulfonyl-4-(4,4,5,5-tetramethyl-[1,3,2]dioxaborolan-2-yl)-1H-pyrrolo[2,3-b]pyridine (110.63 mg; 0.274 mmol; 120.00 mol %) and sodium hydrogen carbonate (22.98 mg; 0.274 mmol; 120.00 mol %) were suspended in DMF (1.37 ml; 17.587 mmol; 7716.00 mol %) and water (341.89 µl; 18.973 mmol; 8324.00 mol %). Bis(triphenylphosphine)-palladium(II)-chlorid (3.20 mg; 0.005 mmol; 2.00 mol %) was added. The reaction mixture was stirred at 80° C. for 16 hrs. The reaction mixture was diluted with water. The resulting precipitate was filtered off and washed with water. The residue was purified by flash chromatography (cyclohexane and ethyl acetate) to afford the product as colorless solid (100 mg, 74.3%); LCMS (method C): 1.83 min (purity 98.8%); [MH+] 584.3 m/z.

Preparation of (6R,8aS)-1-(1-Methanesulfonyl-1-methyl-ethyl)-5-methyl-3-(1H-pyrrolo[2,3-b]pyridin-4-yl)-5,6,8a,9-tetrahydro-8H-7,10-dioxa-2,4,4b-triaza-phenanthrene ("A13")

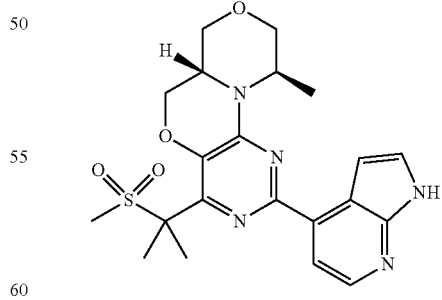

(5R,8aS)-3-(1-Benzenesulfonyl-1H-pyrrolo[2,3-b]pyridin-4-yl)-1-(1-methanesulfonyl-1-methyl-ethyl)-5-methyl-5,6,8a,9-tetrahydro-8H-7,10-dioxa-2,4,4b-triaza-phenanthrene (100.10 mg; 0.17 mmol; 100.00 mol %) and cesium carbonate (0.04 ml; 0.508 mmol; 300.00 mol %) were suspended in 2,2,2-trifluoroethanol (354.73 µl; 4.893 mmol;

2888.00 mol %) and tetrahydrofuran (354.72 µl; 4.378 mmol; 2584.00 mol %) and the mixture was stirred at 80° C. for 8 hrs. The reaction mixture was diluted with THF and filtered through a syringe filter. The filtrate was evaporated to dryness. The residue was purified by column chromatography. The residue was extracted with DCM/1 N HCl. The combined organic phases were dried over sodium sulfate and the solvent removed in vacuo to afford the product as yellow crystals (17 mg, 21.9%); LCMS (method C): 1.35 min (purity 97%); [MH+] 444.3 m/z; $^1$H NMR (400 MHz, DMSO-$d_6$) δ 11.72 (s, 1H), 8.30 (d, J=5.0 Hz, 1H), 7.89 (d, J=5.0 Hz, 1H), 7.56 (t, J=2.9 Hz, 1H), 7.22 (dd, J=3.5, 2.0 Hz, 1H), 4.87-4.76 (m, 1H), 4.42 (dd, J=10.9, 3.3 Hz, 1H), 4.02-3.90 (m, 2H), 3.88 (d, J=11.5 Hz, 1H), 3.82 (dd, J=10.9, 8.8 Hz, 1H), 3.70 (dd, J=11.6, 3.2 Hz, 1H), 3.18 (t, J=11.8 Hz, 1H), 2.95 (s, 3H), 1.90 (s, 3H), 1.88 (s, 3H), 1.33 (d, J=6.7 Hz, 3H).

Example 14

{1-[(5S,8aR)-1-(1-Methanesulfonyl-1-methyl-ethyl)-5-methyl-5,6,8a,9-tetrahydro-8H-7,10-dioxa-2,4,4b-triaza-phenanthren-3-yl]-1H-benzimidazol-2-yl}-methyl-amine ("A14")

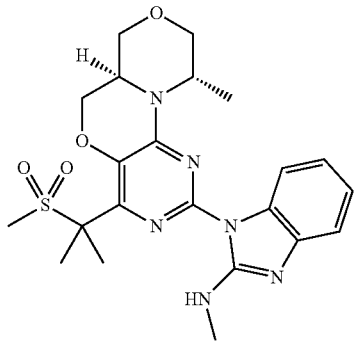 [SMILES: CNc1nc2ccccc2n1-c1nc2c(c(C(C)(C)S(C)(=O)=O)n1)OC[C@H]1COC[C@H](C)N21]

(5S,8aR)-3-Chloro-1-(1-methanesulfonyl-1-methyl-ethyl)-5-methyl-5,6,8a,9-tetrahydro-8H-7,10-dioxa-2,4,4b-triaza-phenanthrene (51.30 mg; 0.12 mmol; 1.00 eq.), benzimidazole-2-yl-methylamine (18.67 mg; 0.12 mmol; 1.00 eq.), tris(dibenzylideneacetone)dipalladium(0) (22.07 mg; 0.02 mmol; 0.20 eq.) and dicyclohexyl-(2',4',6'-triisopropyl-biphenyl-2-yl)-phosphane (22.98 mg; 0.05 mmol; 0.40 eq.) were dissolved in dioxane (1.00 ml; 11.69 mmol; 97.01 eq.), lithium tert-butoxide (1.0 M solution in tetrahydrofuran) (168.71 µl; 0.17 mmol; 1.40 eq.) was added and the mixture was stirred for 3 h at 100° C. The reaction mixture was purified by column chromatography (cyclohexane/ethyl acetate) to afford the product as a colorless solid (10.5 mg, 17.3%); LCMS (method E): 0.77 min (purity 93.9%); [MH+] 473.1 m/z; $^1$H NMR (400 MHz, DMSO-$d_6$) δ 8.20 (q, J=4.7 Hz, 1H), 8.01 (d, J=7.9 Hz, 1H), 7.33-7.21 (m, 1H), 7.08 (td, J=7.5, 1.2 Hz, 1H), 6.98 (td, J=7.7, 1.3 Hz, 1H), 4.78-4.56 (m, 1H), 4.44 (dd, J=10.9, 3.3 Hz, 1H), 4.07-3.95 (m, 2H), 3.93-3.80 (m, 2H), 3.78-3.68 (m, 1H), 3.24-3.15 (m, 1H), 3.05-3.02 (m, 6H), 1.85 (s, 3H), 1.82 (s, 3H), 1.36 (d, J=6.8 Hz, 3H).

Example 15

{1-[(5R,8aS)-1-(1-Methanesulfonyl-1-methyl-ethyl)-5-methyl-5,6,8a,9-tetrahydro-8H-7,10-dioxa-2,4,4b-triaza-phenanthren-3-yl]-1H-benzimidazol-2-yl}-methyl-amine ("A15")

and Example 16

(1H-Benzimidazol-2-yl)-[(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]-methyl-amine ("A16")

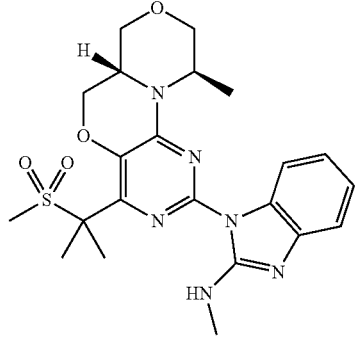

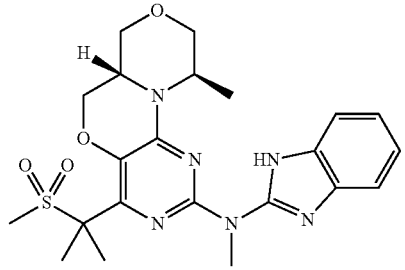

(5R,8aS)-3-Chloro-1-(1-methanesulfonyl-1-methyl-ethyl)-5-methyl-5,6,8a,9-tetrahydro-8H-7,10-dioxa-2,4,4b-triaza-phenanthrene (1.85 g), benzimidazole-2-yl-methyl-amine (719 mg), tris(dibenzylideneacetone)dipalladium(0) (895 mg; 0.2 eq.) and dicyclohexyl-(2',4',6'-triisopropyl-biphenyl-2-yl)-phosphane (932 mg) were dissolved in dioxane (10 ml), lithium tert-butoxide (1.0 M solution in tetrahydrofuran) (6.8 ml, 1.4 eq) was added and the mixture was stirred for 1 h at 80° C. The reaction mixture was purified by chromatography (dichloromethane/methanol) to afford {1-[(5R,8aS)-1-(1-Methanesulfonyl-1-methyl-ethyl)-5-methyl-5,6,8a,9-tetrahydro-8H-7,10-dioxa-2,4,4b-triaza-phenanthren-3-yl]-1H-benzimidazol-2-yl}-methyl-amine as a yellow solid (1.18 g); LCMS (method E): 0.50 min (purity 98%); [MH+] 473.3 m/z; $^1$H NMR (500 MHz, DMSO-$d_6$) δ 8.19 (q, J=4.8 Hz, 1H), 8.00 (d, J=7.6 Hz, 1H), 7.28-7.21 (m, 1H), 7.07 (td, J=7.6, 1.2 Hz, 1H), 6.97 (td, J=7.7, 1.3 Hz, 1H), 4.63 (qd, J=6.8, 2.9 Hz, 1H), 4.43 (dd, J=11.0, 3.4 Hz, 1H), 4.04-3.94 (m, 2H), 3.88 (d, J=11.6 Hz, 1H), 3.83 (dd, J=11.1, 9.2 Hz, 1H), 3.70 (dd, J=11.6, 3.2 Hz, 1H), 3.22-3.15 (m, 1H), 3.05-3.01 (m, 6H), 1.84 (s, 3H), 1.81 (s, 3H), 1.35 (d, J=6.8 Hz, 3H) and (1H-Benzimidazol-2-yl)-[(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]- methyl-amine as a beige solid (722 mg); LCMS (method E): 0.53 min (purity 94%); [MH+] 473.3 m/z; $^1$H NMR (400 MHz, DMSO-d$_6$) δ 12.40 (s, 1H), 7.45-7.38 (m, 1H), 7.34-7.27 (m, 1H), 7.11-7.00 (m, 2H), 4.67 (qd, J=6.5, 2.7 Hz, 1H), 4.38 (dd, J=11.0, 3.5 Hz, 1H), 3.99-3.89 (m, 2H), 3.82 (d, J=11.5 Hz, 1H), 3.76 (dd, J=11.0, 8.8 Hz, 1H), 3.72 (s, 3H), 3.65 (dd, J=11.7, 3.3 Hz, 1H), 3.15 (t, J=11.8 Hz, 1H), 3.04 (s, 3H), 1.83 (s, 3H), 1.81 (s, 3H), 1.29 (d, J=6.8 Hz, 3H).

Example 17

1-[(5R,8aS)-5-Methyl-3-(2-methylamino-benzimidazol-1-yl)-5,6,8a,9-tetrahydro-8H-7,10-dioxa-2,4,4b-triaza-phenanthren-1-ylmethyl]-1H[1,2,3]triazole-4-carboxylic Acid ("A17")

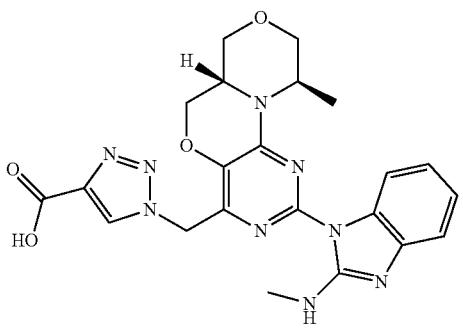 [SMILES: CNc1nc2ccccc2n1-c1nc(Cn2cc(C(=O)O)nn2)c2c(n1)N1[C@@H](COC[C@H]1C)CO2]

1-((5R,8aS)-3-Chloro-5-methyl-5,6,8a,9-tetrahydro-8H-7,10-dioxa-2,4,4b-triaza-phenanthren-1-ylmethyl)-1H-[1,2,3]triazole-4-carboxylic acid methyl ester (64.000 mg; 0.1681 mmol; 1.00 eq.), tris(dibenzylideneacetone)dipalladium(0) (30.782 mg; 0.0336 mmol; 0.20 eq.), dicyclohexyl-(2',4',6'-triisopropyl-biphenyl-2-yl)-phosphane (32.049 mg; 0.0672 mmol; 0.40 eq.) and (1H-benzimidazol-2-yl)-methyl-amine (26.038 mg; 0.1681 mmol; 1.00 eq.) were suspended in dioxane (5.000 ml; 58.4530 mmol; 347.78 eq.) and lithium tert-butoxide (21.213 µl; 0.2353 mmol; 1.40 eq.) was added. The reaction was stirred at 90° C. for 14 h. The reaction mixture was extracted with dichloromethane and water. The combined organic layer was dried over Na$_2$SO$_4$ and the solvent removed under vacuo. The residue was purified by column chromatography (dichloromethane/methanol) to afford the product as brown solid (35.000 mg; 0.073 mmol); LCMS (method D) Rt 2.039 min (purity 100%); [MH+] 478.2 m/z; $^1$H NMR (400 MHz, DMSO-d$_6$) δ 7.98 (d, J=8.0 Hz, 1H), 7.74-7.68 (m, 1H), 7.21 (d, J=7.7 Hz, 1H), 7.06 (t, J=7.6 Hz, 1H), 6.94 (t, J=7.7 Hz, 1H), 5.79-5.68 (m, 2H), 4.60-4.54 (m, 1H), 4.52 (dd, J=10.8, 3.0 Hz, 1H), 4.04-3.97 (m, 2H), 3.96-3.88 (m, 2H), 3.75 (dd, J=11.9, 2.4 Hz, 1H), 3.27-3.20 (m, 1H), 2.92 (d, J=4.8 Hz, 3H), 1.34 (d, J=6.7 Hz, 3H).

Example 18

1-[(5R,8aS)-5-Methyl-3-(1H-pyrrolo[2,3-b]pyridin-4-yl)-5,6,8a,9-tetrahydro-8H-7,10-dioxa-2,4,4b-triaza-phenanthren-1-ylmethyl]-1H-[1,2,3]triazole-4-carboxylic Acid Methyl Ester ("A18")

and Example 19

1-[(5R,8aS)-5-Methyl-3-(1-methyl-1H-pyrrolo[2,3-b]pyridin-4-yl)-5,6,8a,9-tetrahydro-8H-7,10-dioxa-2,4,4b-triaza-phenanthren-1-ylmethyl]-1H[1,2,3]triazole-4-carboxylic Acid Methyl Ester ("A19")

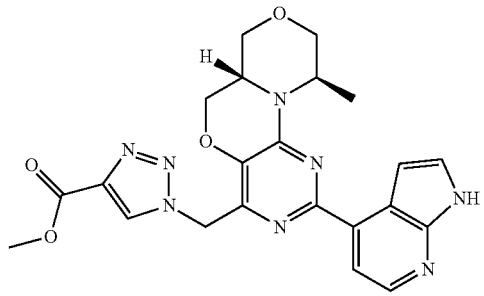
"A18"

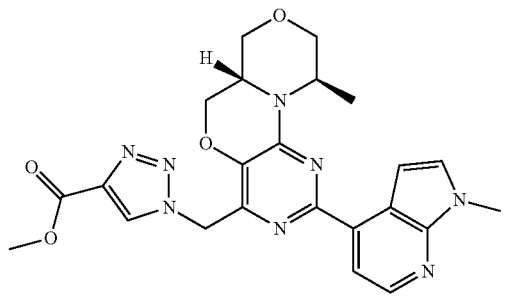
"A19"

1-[(5R,8aS)-5-Methyl-3-(1H-pyrrolo[2,3-b]pyridin-4-yl)-5,6,8a,9-tetrahydro-8H-7,10-dioxa-2,4,4b-triaza-phenanthren-1-ylmethyl]-1H-[1,2,3]triazole-4-carboxylic acid (54.000 mg; 0.1204 mmol; 1.00 eq.) was dissolved in DMF (2.000 ml; 25.7203 mmol; 213.59 eq.), cesiumcarbonat (11.086 µl; 0.1385 mmol; 1.15 eq.) was added and the reaction solution was stirred at RT for 15 minutes. Iodomethane (8.996 µl; 0.1445 mmol; 1.20 eq.) was added and the reaction mixture was stirred for 14 h at RT. The reaction mixture was poured into NaHCO$_3$ solution and extracted with ethylacetate. The combined organic layers were dried over Na$_2$SO$_4$, and the solvent removed under vacuo. The residue was purified by column chromatography to afford 1-[(5R,8aS)-5-Methyl-3-(1H-pyrrolo[2,3-b]pyridin-4-yl)-5,6,8a,9-tetrahydro-8H-7,10-dioxa-2,4,4b-triaza-phenanthren-1-ylmethyl]-1H-[1,2,3]triazole-4-carboxylic acid methyl ester as yellow solid (16.000 mg; 27%); LCMS: (method F): Rt 0.897 min (purity 94.9%); [MH+] 463.2 m/z; $^1$H NMR (500 MHz, DMSO-d$_6$) δ 11.65 (s, 1H), 8.88 (s, 1H), 8.24 (d, J=5.0 Hz, 1H), 7.74 (d, J=5.0 Hz, 1H), 7.41 (dd, J=3.4, 2.5 Hz, 1H), 6.81 (dd, J=3.4, 2.0 Hz, 1H), 5.78 (d, J=15.8 Hz, 1H), 5.74 (d, J=15.8 Hz, 1H), 4.74 (qd, J=6.8, 2.8 Hz, 1H), 4.55-4.46 (m, 1H), 4.02-3.91 (m, 3H), 3.88 (d, J=11.7 Hz, 1H), 3.86 (s, 3H), 3.72 (dd, J=11.6, 3.3 Hz, 1H), 3.25-3.18 (m, 1H), 1.31 (d, J=6.7 Hz, 3H) and 1-[(5R,8aS)-5-Methyl-3-(1-methyl-1H-pyrrolo[2,3-b]pyridin-4-yl)-5,6,8a,9-tetrahydro-8H-7,10-dioxa-2,4,4b-triaza-phenanthren-1-ylmethyl]-1H[1,2,3]triazole-4-carboxylic acid methyl ester as yellow solid (19 mg, 31%); LCMS: (method F) 93.65%; Rt 0.992 min (purity 93.7%); [MH+] 477.2 m/z; $^1$H NMR (500 MHz, DMSO-$d_6$) δ 8.89 (s, 1H), 8.29 (d, J=5.0 Hz, 1H), 7.78 (d, J=5.0 Hz, 1H), 7.46 (d, J=3.4 Hz, 1H), 6.78 (d, J=3.4 Hz, 1H), 5.78 (d, J=15.9 Hz, 1H), 5.74 (d, J=15.9 Hz, 1H), 4.74 (qd, J=6.7, 2.8 Hz, 1H), 4.55-4.45 (m, 1H), 4.02-3.91 (m, 3H), 3.89-3.86 (m, 4H), 3.82 (s, 3H), 3.72 (dd, J=11.7, 3.2 Hz, 1H), 3.25-3.17 (m, 1H), 1.30 (d, J=6.7 Hz, 3H).

Example 20

4-[(4bR,8S)-1-(1-Methanesulfonyl-1-methyl-ethyl)-5-methyl-5,6,8a,9-tetrahydro-8H-7,10-dioxa-2,4,4b-triaza-phenanthren-3-yl]-1H-pyrrolo[2,3-b]pyridin-5-ylamine ("A20")

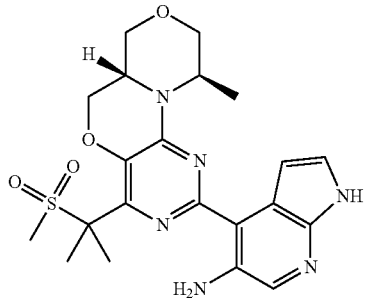 [SMILES: C[C@@H]1COC[C@H]2COc3c(nc(-c4c(N)cnc5[nH]ccc45)nc3C(C)(C)S(C)(=O)=O)N21]

1-Benzenesulfonyl-4-[(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]-1H-pyrrolo[2,3-b]pyridin-5-ylamine (124.86 mg; 0.200 mmol; 100.00 mol %) was dissolved in tetrahydrofuran (2.44 ml; 30.118 mmol) and 2,2,2-trifluoroethanol (2.44 ml; 33.660 mmol) and cesium carbonate (260.66 mg; 0.800 mmol) was added. The suspension was stirred at 90° for 2 days. After removal of the solvent in vacuo, the residue was purified by column chromatography to afford the product as ochre solid (57 mg, 62%); LCMS (method C): Rt 1.167 min (purity 98.7%), [MH+] 459.3 m/z; $^1$H NMR (400 MHz, DMSO-$d_6$) δ 11.15 (s, 1H), 7.87 (s, 1H), 7.27 (t, J=3.0 Hz, 1H), 6.91 (dd, J=3.3, 2.1 Hz, 1H), 6.19 (s, 2H), 4.75-4.64 (m, 1H), 4.41 (dd, J=10.8, 3.2 Hz, 1H), 4.03-3.91 (m, 2H), 3.85 (t, J=10.2 Hz, 2H), 3.68 (dd, J=11.6, 3.2 Hz, 1H), 3.24-3.13 (m, 1H), 2.97 (s, 3H), 1.87 (s, 3H), 1.82 (s, 3H), 1.32 (d, J=6.8 Hz, 3H).

Example 21

2-[(5R,8aS)-3-(5-Amino-1H-pyrrolo[2,3-b]pyridin-4-yl)-5-methyl-5,6,8a,9-tetrahydro-8H-7,10-dioxa-2,4,4b-triaza-phenanthren-1-yl]-propan-2-ol ("A21")

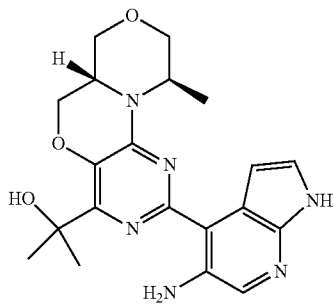 [SMILES: C[C@@H]1COC[C@H]2COc3c(nc(-c4c(N)cnc5[nH]ccc45)nc3C(C)(C)O)N21]

Example 21.1.1.1

2-((5R,8aS)-5-Methyl-3-tributylstannanyl-5,6,8a,9-tetrahydro-8H-7,10-dioxa-2,4,4b-triaza-phenanthren-1-yl)-propan-2-ol

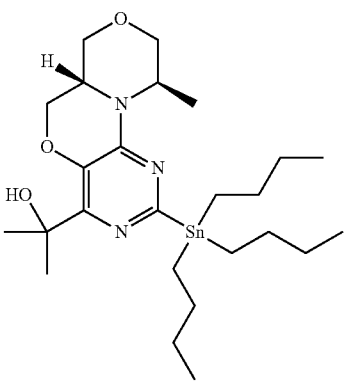 [SMILES: CCC[CH2][Sn]([CH2]CCC)([CH2]CCC)[c]1nc2c(c(C(C)(C)O)n1)OC[C@@H]1COC[C@@H](C)N21]

2-((5R,8aS)-3-Chloro-5-methyl-5,6,8a,9-tetrahydro-8H-7,10-dioxa-2,4,4b-triaza-phenanthren-1-yl)-propan-2-ol (609.60 mg; 1.843 mmol; 100.00 mol %) and bis(di-tert-butyl(4-dimethylaminophenyl)phosphine)dichloro palladium (II) (195.69 mg; 0.276 mmol; 15.00 mol %) were suspended in dioxane (10.00 ml; 116.906 mmol) and hexa-n-butylditin (1041.43 µl; 2.027 mmol; 110.00 mol %) was added and the reaction mixture was heated in the microwave for 1 h at 160° C. Bis(di-tert-butyl(4-dimethylaminophenyl)phosphine)dichloro palladium (II) (130.46 mg; 0.184 mmol; 10.00 mol %) and hexa-n-butylditin (852.08 µl; 1.658 mmol; 90.00 mol %) were added and the reaction mixture was heated in the microwave for 1 h at 160° C. The reaction mixture was quenched with DCM and filtered. The filtrate was washed with water and the separated aqueous layer was extracted with DCM and the combined organic layers were dried over sodium sulfate, filtered and concentrated under reduced pressure. The residue was purified by column chromatography over neutral alumina column to afford the product as yellow oil (28 mg, 3%); LCMS (method C): Rt 1.838 min. (purity 97.3%), [MH+] 556.3 m/z.

Example 21.1.1

2-[(5R,8aS)-3-(1-Benzenesulfonyl-5-nitro-1H-pyrrolo[2,3-b]pyridin-4-yl)-5-methyl-5,6,8a,9-tetrahydro-8H-7,10-dioxa-2,4,4b-triaza-phenanthren-1-yl]-propan-2-ol

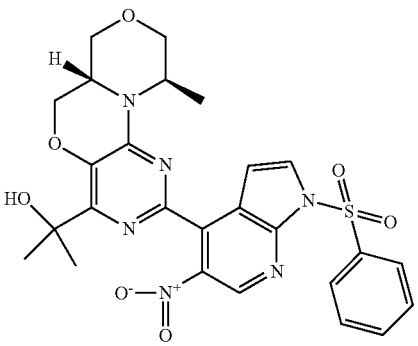 [SMILES: C[C@@H]1COC[C@H]2COc3c(nc(-c4c([N+](=O)[O-])cnc5c4ccn5S(=O)(=O)c4ccccc4)nc3C(C)(C)O)N21]

2-((5R,8aS)-5-Methyl-3-tributylstannanyl-5,6,8a,9-tetrahydro-8H-7,10-dioxa-2,4,4b-triaza-phenanthren-1-yl)-propan-2-ol (443.60 mg; 0.793 mmol; 94.22 mol %), 2-((5R, 8aS)-5-Methyl-3-tributylstannanyl-5,6,8a,9-tetrahydro-8H-7,10-dioxa-2,4,4b-triaza-phenanthren-1-yl)-propan-2-ol (27.70 mg; 0.049 mmol; 5.78 mol %) and 1-benzenesulfonyl-4-chloro-5-nitro-1H-pyrrolo[2,3-b]pyridine (305.52 mg; 0.858 mmol; 102.00 mol %) were dissolved in DMF (1.80 ml; 23.120 mmol). Bis(triphenylphosphine)palladium(II) chloride (15.2% Pd) (59.07 mg; 0.084 mmol; 10.00 mol %) was added. The reaction mixture was stirred at 80° C. for 14 h. The reaction mixture was diluted water and extracted with DCM. The combined organic layers were dried over sodium sulfate, filtered and purified by flash chromatography to afford the product as yellow solid (267 mg, 55%); LCMS (method C): Rt 1.919 min (purity 98.1%), [MH+] 567.2.

Example 21.1

2-[(5R,8aS)-3-(5-Amino-1-benzenesulfonyl-1H-pyrrolo[2,3-b]pyridin-4-yl)-5-methyl-5,6,8a,9-tetrahydro-8H-7,10-dioxa-2,4,4b-triaza-phenanthren-1-yl]-propan-2-ol

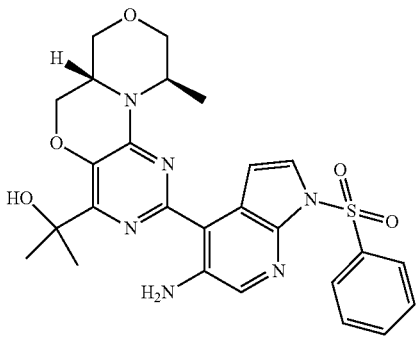 [SMILES: C[C@@H]1COC[C@H]2COc3c(nc(-c4c(N)cnc5c4ccn5S(=O)(=O)c4ccccc4)nc3C(C)(C)O)N21]

2-[(5R,8aS)-3-(1-Benzenesulfonyl-5-nitro-1H-pyrrolo[2,3-b]pyridin-4-yl)-5-methyl-5,6,8a,9-tetrahydro-8H-7,10-dioxa-2,4,4b-triaza-phenanthren-1-yl]-propan-2-ol (260 mg, 0.459 mmol) were dissolved in THF (10 ml) and sponge nickel (0.3 g) were added. The reaction solution was stirred at RT for 14 h under a $H_2$ atmosphere. The reaction mixture was filtrated and the solvent removed under vacuo to afford the product as yellow solid (249 mg, 94%); LCMS (method C): Rt 1.669 min (purity 93.9%), [MH+] 537.3 m/z.

Preparation of 2-[(5R,8aS)-3-(5-Amino-1H-pyrrolo[2,3-b]pyridin-4-yl)-5-methyl-5,6,8a,9-tetrahydro-8H-7,10-dioxa-2,4,4b-triaza-phenanthren-1-yl]-propan-2-ol ("A21")

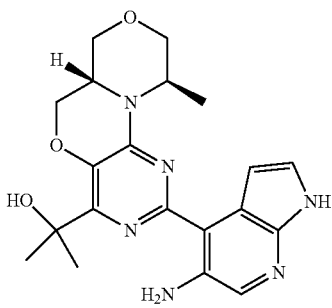 [SMILES: C[C@@H]1COC[C@H]2COc3c(nc(-c4c(N)cnc5[nH]ccc45)nc3C(C)(C)O)N21]

2-[(5R,8aS)-3-(5-Amino-1-benzenesulfonyl-1H-pyrrolo[2,3-b]pyridin-4-yl)-5-methyl-5,6,8a,9-tetrahydro-8H-7,10-dioxa-2,4,4b-triaza-phenanthren-1-yl]-propan-2-ol (57.15 mg; 0.100 mmol; 100.00 mol %) was dissolved in THF (500.00 µl) and 2,2,2-trifluoroethanol (500.00 µl; 6.897 mmol) and cesium carbonate (130.33 mg; 0.400 mmol) was added. The suspension was stirred at 90° for 15 hrs. The solvent was removed under vacuo and the residue purified by column chromatography to afford the product as beige solid (11 mg, 27%); LCMS (method C): Rt 1.126 min. (purity 100%), [MH+] 397.3 m/z; $^1$H NMR (500 MHz, DMSO-$d_6$) δ 11.16 (t, J=2.5 Hz, 1H), 7.88 (s, 1H), 7.28 (t, J=2.9 Hz, 1H), 6.93 (dd, J=3.3, 2.1 Hz, 1H), 6.40 (s, 2H), 5.09 (s, 1H), 4.63 (qd, J=6.7, 2.8 Hz, 1H), 4.42 (dd, J=10.8, 3.1 Hz, 1H), 3.98-3.90 (m, 2H), 3.89-3.81 (m, 2H), 3.70 (dd, J=11.5, 3.2 Hz, 1H), 3.22-3.14 (m, 1H), 1.52 (s, 6H), 1.30 (d, J=6.8 Hz, 3H).

Example 22

1-[(5R,8aS)-5-Methyl-3-(2-methylamino-benzoimidazol-1-yl)-5,6,8a,9-tetrahydro-8H-7,10-dioxa-2,4,4b-triaza-phenanthren-1-ylmethyl]-1H[1,2,3]triazole-4-carboxylic Acid Methyl Ester ("A22")

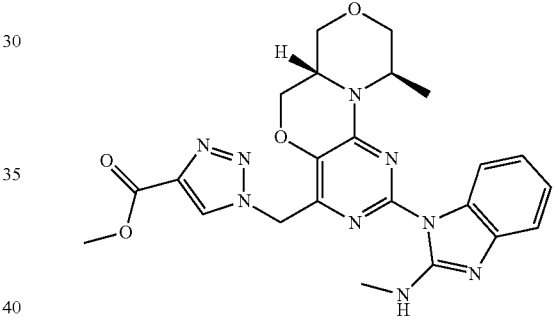

1-[(5R,8aS)-5-Methyl-3-(2-methylamino-benzoimidazol-1-yl)-5,6,8a,9-tetrahydro-8H-7,10-dioxa-2,4,4b-triaza-phenanthren-1-ylmethyl]-1H-[1,2,3]triazole-4-carboxylic acid (18.000 mg; 0.0377 mmol; 1.00 eq.) was dissolved in DMF (4.000 ml) and cesiumcarbonat (0.0565 mmol; 1.50 eq.) was added and the reaction mixture stirred for 15 minutes at RT. Iodomethane (2.816 µl; 0.0452 mmol; 1.20 eq.) was added and the reaction mixture was stirred for 14 h at RT. The reaction mixture was poured into NaHCO$_3$ solution and extracted with ethylacetate. The combined organic layers were dried over Na$_2$SO$_4$ and the solvent removed under vacuo to afford the product as yellow solid (6 mg, 32%); LCMS (method F) Rt 0.912 min (purity 100%), [MH+] 492.2 m/z. $^1$H NMR (500 MHz, DMSO-$d_6$) δ 8.97 (s, 1H), 7.92 (d, J=7.9 Hz, 1H), 7.72 (q, J=4.8 Hz, 1H), 7.22 (dd, J=8.0, 1.0 Hz, 1H), 7.06 (td, J=7.6, 1.2 Hz, 1H), 6.91 (ddd, J=8.4, 7.4, 1.2 Hz, 1H), 5.83 (d, J=16.4 Hz, 1H), 5.79 (d, J=16.4 Hz, 1H), 4.57 (qd, J=6.8, 2.9 Hz, 1H), 4.52 (dd, J=10.8, 3.1 Hz, 1H), 4.05-3.98 (m, 2H), 3.95-3.89 (m, 2H), 3.87 (s, 3H), 3.78-3.73 (m, 1H), 3.24 (t, J=11.9 Hz, 1H), 2.92 (d, J=4.9 Hz, 3H), 1.35 (d, J=6.7 Hz, 3H).

Example 23

2-[(5R,8aS)-5-Methyl-3-(5-methylamino-1H-pyrrolo[2,3-b]pyridin-4-yl)-5,6,8a,9-tetrahydro-8H-7,10-dioxa-2,4,4b-triaza-phenanthren-1-yl]-propan-2-ol ("A23")

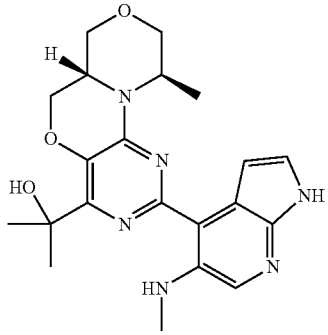 [SMILES: CNc1cnc2[nH]ccc2c1-c1nc2c(c(C(C)(C)O)n1)OC[C@@H]1COC[C@@H](C)N21]

Example 23.1

2-[(6R,9S)-3-(1-Benzenesulfonyl-5-methylamino-1H-pyrrolo[2,3-b]pyridin-4-yl)-5-methyl-5,6,8a,9-tetrahydro-8H-7,10-dioxa-2,4,4b-triaza-phenanthren-1-yl]-propan-2-ol

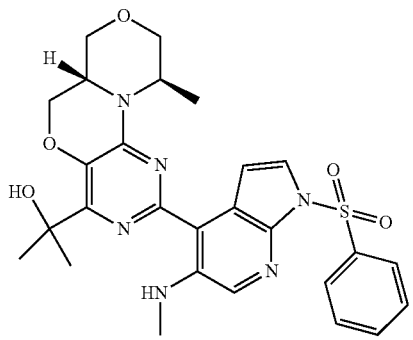 [SMILES: CNc1cnc2c(ccn2S(=O)(=O)c2ccccc2)c1-c1nc2c(c(C(C)(C)O)n1)OC[C@@H]1COC[C@@H](C)N21]

2-[(5R,8aS)-3-(5-Amino-1-benzenesulfonyl-1H-pyrrolo[2,3-b]pyridin-4-yl)-5-methyl-5,6,8a,9-tetrahydro-8H-7,10-dioxa-2,4,4b-triaza-phenanthren-1-yl]-propan-2-ol (191.30 mg; 0.335 mmol; 100.00 mol %) was dissolved in formic acid (334.79 µl; 8.874 mmol; 2651.00 mol %) and formaldehyde, 1 M solution in formic acid (284.54 µl; 0.285 mmol; 85.00 mol %) was added. The reaction solution was stirred at 100° C. for 5 minutes. The reaction mixture was treated with saturated NaHCO$_3$-solution and extracted with DCM. The combined organic layers were dried over sodium sulfate, filtered and concentrated under reduced pressure to afford the product as yellow solid (22 mg, 11%); LCMS (method C): Rt 1.768 min (purity 90%), [MH+] 551.3.

Preparation of 2-[(5R,8aS)-5-Methyl-3-(5-methylamino-1H-pyrrolo[2,3-b]pyridin-4-yl)-5,6,8a,9-tetrahydro-8H-7,10-dioxa-2,4,4b-triaza-phenanthren-1-yl]-propan-2-ol ("A23")

2-[(6R,9S)-3-(1-Benzenesulfonyl-5-methylamino-1H-pyrrolo[2,3-b]pyridin-4-yl)-5-methyl-5,6,8a,9-tetrahydro-8H-7,10-dioxa-2,4,4b-triaza-phenanthren-1-yl]-propan-2-ol (22.30 mg; 0.036 mmol; 100.00 mol %) and cesium carbonate (47.40 mg; 0.145 mmol; 400.00 mol %) were suspended in tetrahydrofuran (380.09 µl) and 2,2,2-trifluoroethanol (380.09 µl; 5.243 mmol) was added and the reaction mixture stirred for 14 h at 90° C. The solvent was removed under vacuo and the residue purified by column chromatography to afford the product as yellow solid (5 mg, 36%); LCMS (method C): (M+H) 411.3; (percent area) 100%; Rt 1.161 min (purity 100%); $^1$H NMR (500 MHz, DMSO-d$_6$) δ 11.20 (t, J=2.5 Hz, 1H), 8.39 (q, J=5.2 Hz, 1H), 7.88 (s, 1H), 7.34 (t, J=3.0 Hz, 1H), 6.98 (dd, J=3.3, 2.1 Hz, 1H), 5.10 (s, 1H), 4.62 (qd, J=6.7, 2.8 Hz, 1H), 4.42 (dd, J=10.8, 3.1 Hz, 1H), 3.94 (tt, J=13.0, 3.7 Hz, 2H), 3.87 (d, J=11.5 Hz, 1H), 3.83 (dd, J=10.8, 9.2 Hz, 1H), 3.71 (dd, J=11.5, 3.2 Hz, 1H), 3.23-3.14 (m, 1H), 2.94 (d, J=5.2 Hz, 3H), 1.53 (s, 6H), 1.31 (d, J=6.8 Hz, 3H).

Example 24

(5R,8aS)-1-(1-Methanesulfonyl-1-methyl-ethyl)-5-methyl-3-(2-methylbenzimidazol-1-yl)-5,6,8a,9-tetrahydro-8H-7,10-dioxa-2,4,4b-triaza-phenanthrene ("A24")

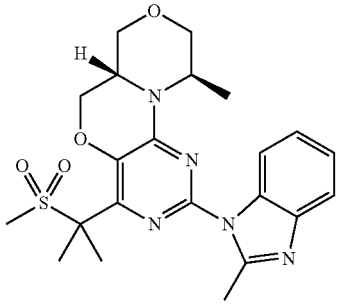 [SMILES: Cc1nc2ccccc2n1-c1nc2c(c(C(C)(C)S(C)(=O)=O)n1)OC[C@@H]1COC[C@@H](C)N21]

(5R,8aS)-3-Chloro-1-(1-methanesulfonyl-1-methyl-ethyl)-5-methyl-5,6,8a,9-tetrahydro-8H-7,10-dioxa-2,4,4b-triaza-phenanthrene (40,000 mg; 0,111 mmol; 1.00 eq.) was suspended in N,N-dimethylacetamide (1.000 ml) and 2-methyl benzimidazole (19.380 mg; 0.144 mmol; 1.30 eq.), 2,6-lutidine (12.875 μl; 0.111 mmol; 1.00 eq.) and cesium carbonate (72.037 mg; 0.221 mmol; 2.00 eq.) were added and stirred at 140° C. for 14 h. After removal of the solvent in vacuo, the residue was purified by column chromatography to afford the product as yellow solid (15 mg, 30%); LCMS (method D) Rt 2.117 min (purity 100%); (M+H) 458.

Example 25

{4-Fluoro-1-[(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]-1H-benzimidazol-2-yl}-methyl-amine ("A25")

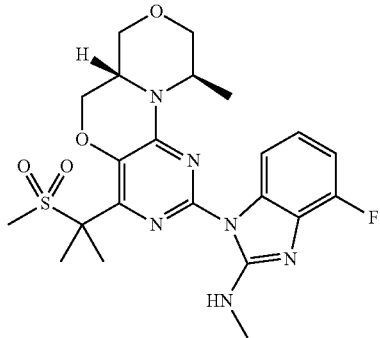 [SMILES: CNc1nc2c(F)cccc2n1-c1nc2c(c(C(C)(C)S(C)(=O)=O)n1)OC[C@@H]1COC[C@@H](C)N21]

(5R,8aS)-3-Chloro-1-(1-methanesulfonyl-1-methyl-ethyl)-5-methyl-5,6,8a,9-tetrahydro-8H-7,10-dioxa-2,4,4b-triaza-phenanthrene (40.000 mg; 0.111 mmol; 1.00 eq.) was suspended in N,N-dimethylacetamide (1.000 ml). (7-Fluoro-1H-benzimidazol-2-yl)-methyl-amine (23.736 mg; 0.144 mmol; 1.30 eq.), 2,6-lutidine (12.875 μl; 0.111 mmol; 1.00 eq.) and cesium carbonate (72.037 mg; 0.221 mmol; 2.00 eq.) were added and stirred at 140° C. for 3 hours and then stirred at RT for 14 h. The solvent was removed under vacuo and the residue purified by RP HPLC to afford the product as colorless solid (11 mg, 15%); LC/MS (method D) Rt 2.284 min; [MH+] 491 m/z.; $^1$H NMR (500 MHz, DMSO-d6) δ 8.78-8.37 (m, 1H), 7.92-7.88 (m, 1H), 7.16-7.00 (m, 2H), 4.64-4.57 (m, 1H), 4.48-4.43 (m, 1H), 4.05-3.96 (m, 2H), 3.90-3.82 (m, 2H), 3.70 (dd, J=11.7, 3.2 Hz, 1H), 3.23-3.15 (m, 1H), 3.10-3.02 (m, 6H), 1.87-1.82 (m, 3H), 1.81 (s, 3H), 1.34 (d, J=6.8 Hz, 3H).

Example 26

{1-[(4bR,8S)-1-(1-Methanesulfonyl-cyclopropyl)-5-methyl-5,6,8a,9-tetrahydro-8H-7,10-dioxa-2,4,4b-triaza-phenanthren-3-yl]-1H-benzimidazol-2-yl}-methylamine ("A26")

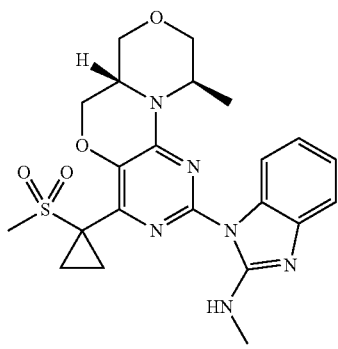 [SMILES: CNc1nc2ccccc2n1-c1nc2c(c(C3(S(C)(=O)=O)CC3)n1)OC[C@@H]1COC[C@@H](C)N21]

(4bR,8S)-3-Chloro-1-(1-methanesulfonyl-cyclopropyl)-5-methyl-5,6,8a,9-tetrahydro-8H-7,10-dioxa-2,4,4b-triaza-phenanthrene (136.30 mg; 0.300 mmol; 100.00 mol %), (1H-benzimidazol-2-yl)-methyl-amine (44.15 mg; 0.300 mmol; 100.00 mol %), tris(dibenzylideneacetone)dipalladium(0) (54.94 mg; 0.060 mmol; 20.00 mol %) and dicyclohexyl-(2',4',6'-triisopropyl-biphenyl-2-yl)phosphane (57.21 mg; 0.120 mmol; 40.00 mol %) were dissolved in dioxane (614.08 μl; 7.179 mmol; 2393.00 mol %), lithium tert-butoxide (1.0 M solution in tetrahydrofuran) (420.00 μl; 0.420 mmol; 140.00 mol %) was added and the mixture was stirred for 1 h at 80° C. After removal of the solvent in vacuo, the residue was purified by column chromatography to afford the product as beige solid (46.100 mg; 0.097 mmol); LCMS (method C): 1.27 min (purity 99%); [MH+] 471.2; $^1$H NMR (500 MHz, DMSO-d$_6$) δ 8.26 (q, J=4.8 Hz, 1H), 8.06 (d, J=7.7 Hz, 1H), 7.26 (dd, J=7.8, 1.2 Hz, 1H), 7.08 (td, J=7.6, 1.2 Hz, 1H), 6.98 (td, J=7.7, 1.3 Hz, 1H), 4.58 (qd, J=6.8, 2.9 Hz, 1H), 4.44 (dd, J=10.9, 3.2 Hz, 1H), 4.01-3.95 (m, 2H), 3.93-3.86 (m, 2H), 3.70 (dd, J=11.8, 3.2 Hz, 1H), 3.18 (t, J=11.9 Hz, 1H), 3.06 (s, 3H), 3.04 (d, J=4.9 Hz, 3H), 1.75-1.65 (m, 2H), 1.48-1.39 (m, 2H), 1.35 (d, J=6.8 Hz, 3H).

The following compounds are prepared analogously:

{4-[(5R,8aS)-1-(1-Methanesulfonyl-1-methyl-ethyl)-5-methyl-5,6,8a,9-tetrahydro-8H-7,10-dioxa-2,4,4b-triaza-phenanthren-3-yl]-1H-pyrrolo[2,3-c]pyridin-5-yl}-methyl-amine ("A27")

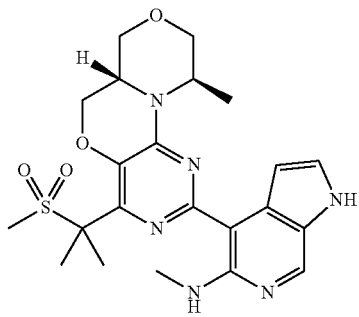 [SMILES: CNc1ncc2[nH]ccc2c1-c1nc2c(c(C(C)(C)S(C)(=O)=O)n1)OC[C@@H]1COC[C@@H](C)N21]

Scheme of Synthesis:

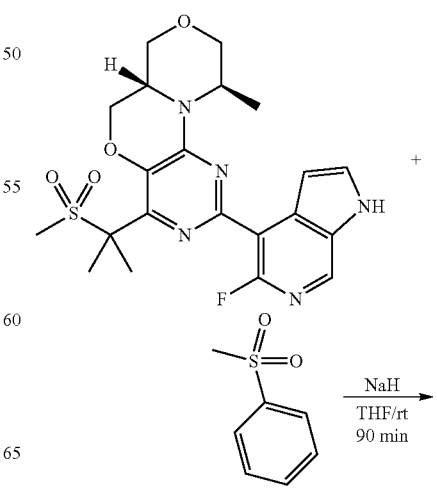

-continued

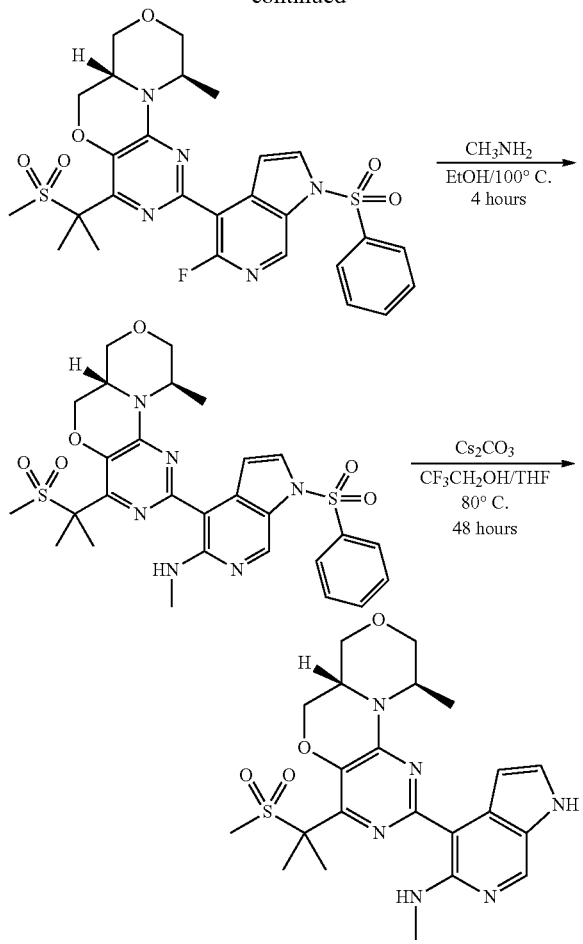

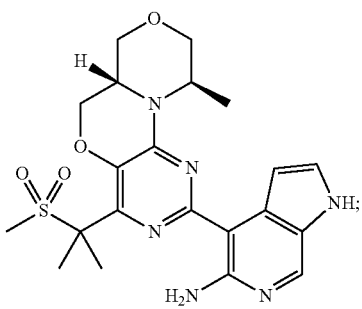 [SMILES: C[C@@H]1COC[C@H]2COc3c(nc(-c4c(N)ncc5[nH]ccc45)nc3C(C)(C)S(C)(=O)=O)N21]

LCMS (method C): 1.25 min (purity 99%); [MH+] 473.2; $^1$H NMR (400 MHz, DMSO-$d_6$) δ 11.07 (s, 1H), 8.67 (q, J=4.7 Hz, 1H), 8.39 (d, J=0.8 Hz, 1H), 7.44 (t, J=2.8 Hz, 1H), 7.02 (ddd, J=2.9, 2.0, 0.9 Hz, 1H), 4.71 (dd, J=6.9, 2.9 Hz, 1H), 4.40 (dd, J=10.8, 3.2 Hz, 1H), 4.01-3.77 (m, 4H), 3.69 (dd, J=11.6, 3.2 Hz, 1H), 3.23-3.12 (m, 1H), 3.04-2.94 (m, 6H), 1.85 (d, J=16.8 Hz, 6H), 1.33 (d, J=6.8 Hz, 3H).

4-[(10S,14R)-6-(2-Methanesulfonylpropan-2-yl)-14-methyl-8,12-dioxa-1,3,5-triazatricyclo[8.4.0.0$^{2,7}$]tetradeca-2,4,6-trien-4-yl]-1H-pyrrolo[2,3-c]pyridin-5-amine ("A28")

(5R,8aS)-3-(5-Fluoro-1H-pyrrolo[2,3-c]pyridin-4-yl)-1-(1-methanesulfonyl-1-methyl-ethyl)-5-methyl-5,6,8a,9-tetrahydro-8H-7,10-dioxa-2,4,4b-triaza-phenanthrene ("A29")

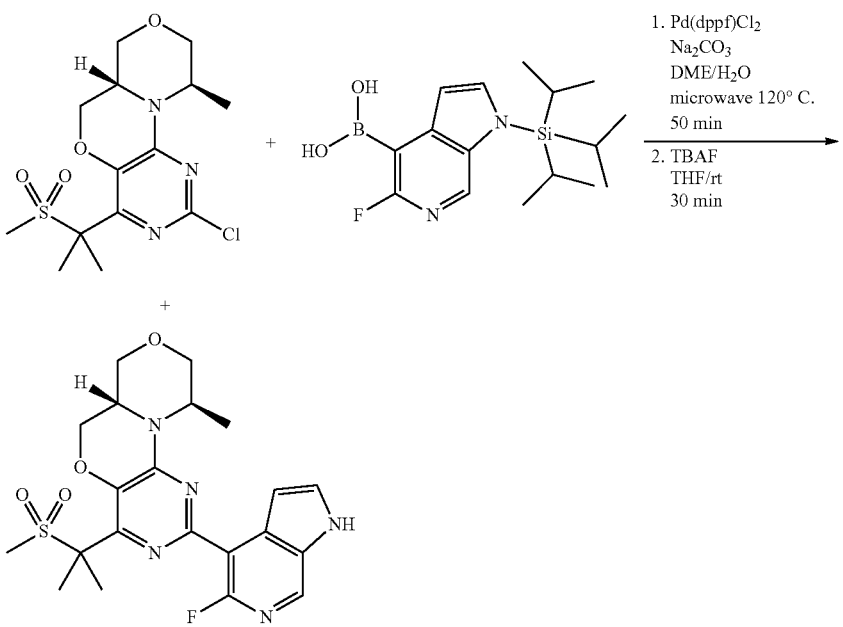

LCMS (method C): 1.44 min; [MH+] 462.1; ¹H NMR (500 MHz, DMSO-d₆) δ 11.74 (s, 1H), 8.38 (t, J=1.1 Hz, 1H), 7.74 (d, J=3.0 Hz, 1H), 6.93 (dd, J=2.9, 0.8 Hz, 1H), 4.67 (qd, J=6.7, 2.8 Hz, 1H), 4.41 (dd, J=11.0, 3.3 Hz, 1H), 3.94 (dd, J=10.8, 2.9 Hz, 2H), 3.87-3.78 (m, 2H), 3.64 (dd, J=11.6, 3.2 Hz, 1H), 3.21-3.12 (m, 1H), 2.95 (s, 3H), 1.85 (s, 3H), 1.81 (s, 3H), 1.28 (d, J=6.8 Hz, 3H).

4-[(10S,14R)-6-(2-Methanesulfonylpropan-2-yl)-14-methyl-8,12-dioxa-1,3,5-triazatricyclo[8.4.0.0²,⁷]tetradeca-2,4,6-trien-4-yl]-N-(oxetan-3-yl)-H-pyrrolo[2,3-b]pyridin-5-amine ("A30")

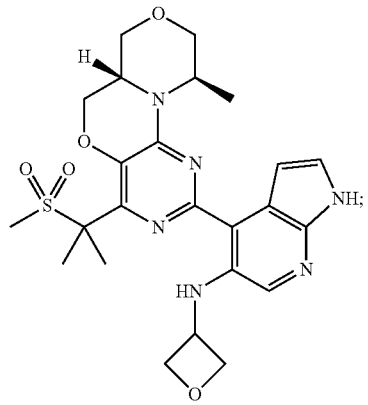 [SMILES: C[C@@H]1COC[C@H]2COc3c(nc(-c4c(NC5COC5)cnc5[nH]ccc45)nc3C(C)(C)S(C)(=O)=O)N21]

N-{4-[(10S,14R)-6-(2-Methanesulfonylpropan-2-yl)-14-methyl-8,12-dioxa-1,3,5-triazatricyclo[8.4.0.0²,⁷]tetradeca-2,4,6-trien-4-yl]-1H-pyrrolo[2,3-b]pyridin-5-yl}acetamide ("A31")

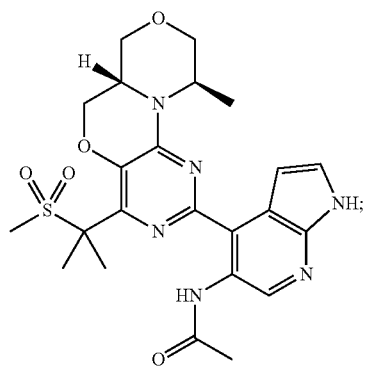 [SMILES: CC(=O)Nc1cnc2[nH]ccc2c1-c1nc2c(c(C(C)(C)S(C)(=O)=O)n1)OC[C@@H]1COC[C@@H](C)N21]

4-[(10S,14R)-6-(2-Methanesulfonylpropan-2-yl)-14-methyl-8,12-dioxa-1,3,5-triazatricyclo[8.4.0.0²,⁷]tetradeca-2,4,6-trien-4-yl]-N-2,2,2-trifluoroethyl)-1H-pyrrolo[2,3-b]pyridin-5-amine ("A32")

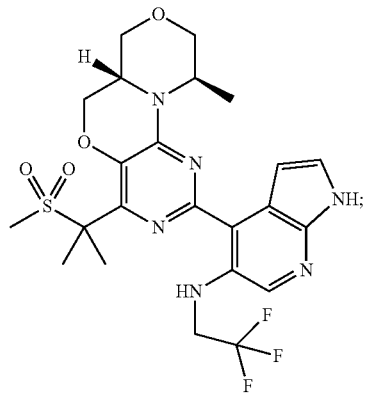 [SMILES: C[C@@H]1COC[C@H]2COc3c(nc(-c4c(NCC(F)(F)F)cnc5[nH]ccc45)nc3C(C)(C)S(C)(=O)=O)N21]

1-[(10S,14R)-6-(2-Methanesulfonylpropan-2-yl)-14-methyl-8,12-dioxa-1,3,5-triazatricyclo[8.4.0.0²,⁷]tetradeca-2,4,6-trien-4-yl]-N-(oxetan-3-yl)-1H-1,3-benzodiazol-2-amine ("A33")

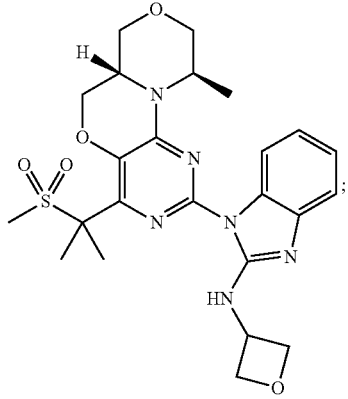 [SMILES: C[C@@H]1COC[C@H]2COc3c(nc(-n4c(NC5COC5)nc5ccccc54)nc3C(C)(C)S(C)(=O)=O)N21]

N-{1-[(10S,14R)-6-(2-Methanesulfonylpropan-2-yl)-14-methyl-8,12-dioxa-1,3,5-triazatricyclo[8.4.0.0²,⁷]tetradeca-2,4,6-trien-4-yl]-1H-1,3-benzodiazol-2-yl}acetamide ("A34")

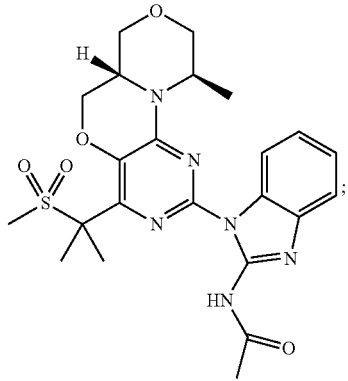 [SMILES: CC(=O)Nc1nc2ccccc2n1-c1nc2c(c(C(C)(C)S(C)(=O)=O)n1)OC[C@@H]1COC[C@@H](C)N21]

LCMS (method D) Rt 0.95 min; (M+H) 501.2;
¹H NMR (500 MHz, DMSO-d₆) δ 11.05 (s, 1H), 8.09-8.03 (m, 1H), 7.61-7.55 (m, 1H), 7.31-7.21 (m, 2H), 4.68-4.59 (m, 1H), 4.45 (dd, J=11.1, 3.7 Hz, 1H), 4.08-3.94 (m, 2H), 3.84 (dt, J=11.1, 9.8 Hz, 2H), 3.68 (dd, J=11.6, 3.3 Hz, 1H), 3.20 (t, J=10.9 Hz, 1H), 2.96 (s, 3H), 2.30 (s, 3H), 1.89 (s, 3H), 1.84 (s, 3H), 1.35 (d, J=6.8 Hz, 3H).

4-[(10S,14R)-6-(2-Methanesulfonylpropan-2-yl)-14-methyl-8,12-dioxa-1,3,5-triazatricyclo[8.4.0.0²,⁷]tetradeca-2,4,6-trien-4-yl]-1H-pyrrolo[2,3-b]pyridin-5-ol ("A35")

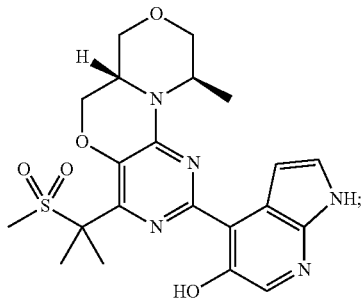 [SMILES: C[C@@H]1COC[C@H]2COc3c(nc(-c4c(O)cnc5[nH]ccc45)nc3C(C)(C)S(C)(=O)=O)N21]

4-[(10S,14R)-6-(1-methanesulfonylcyclopropyl)-14-methyl-8,12-dioxa-1,3,5-triazatricyclo[8.4.0.0²,⁷]tetradeca-2,4,6-trien-4-yl]-N-methyl-1H-pyrrolo[2,3-b]pyridin-5-amine ("A36")

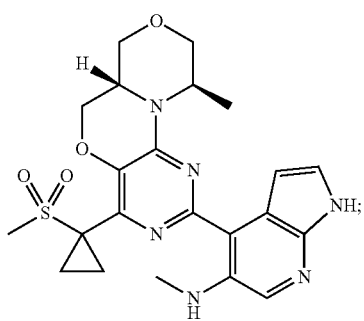 [SMILES: CNc1cnc2[nH]ccc2c1-c1nc2c(c(C3(S(C)(=O)=O)CC3)n1)OC[C@@H]1COC[C@@H](C)N21]

4-[(10S,14R)-6-(1-methanesulfonylcyclopropyl)-14-methyl-8,12-dioxa-1,3,5-triazatricyclo[8.4.0.0²,⁷]tetradeca-2,4,6-trien-4-yl]-1H-pyrrolo[2,3-b]pyridin-5-amine ("A37")

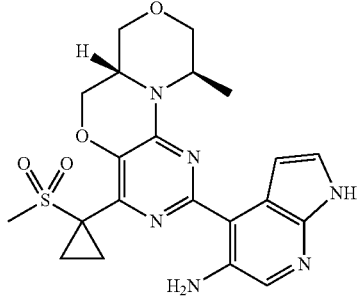 [SMILES: C[C@@H]1COC[C@H]2COc3c(nc(-c4c(N)cnc5[nH]ccc45)nc3C3(S(C)(=O)=O)CC3)N21]

"A37" has been prepared analogously to "A20" as follows:

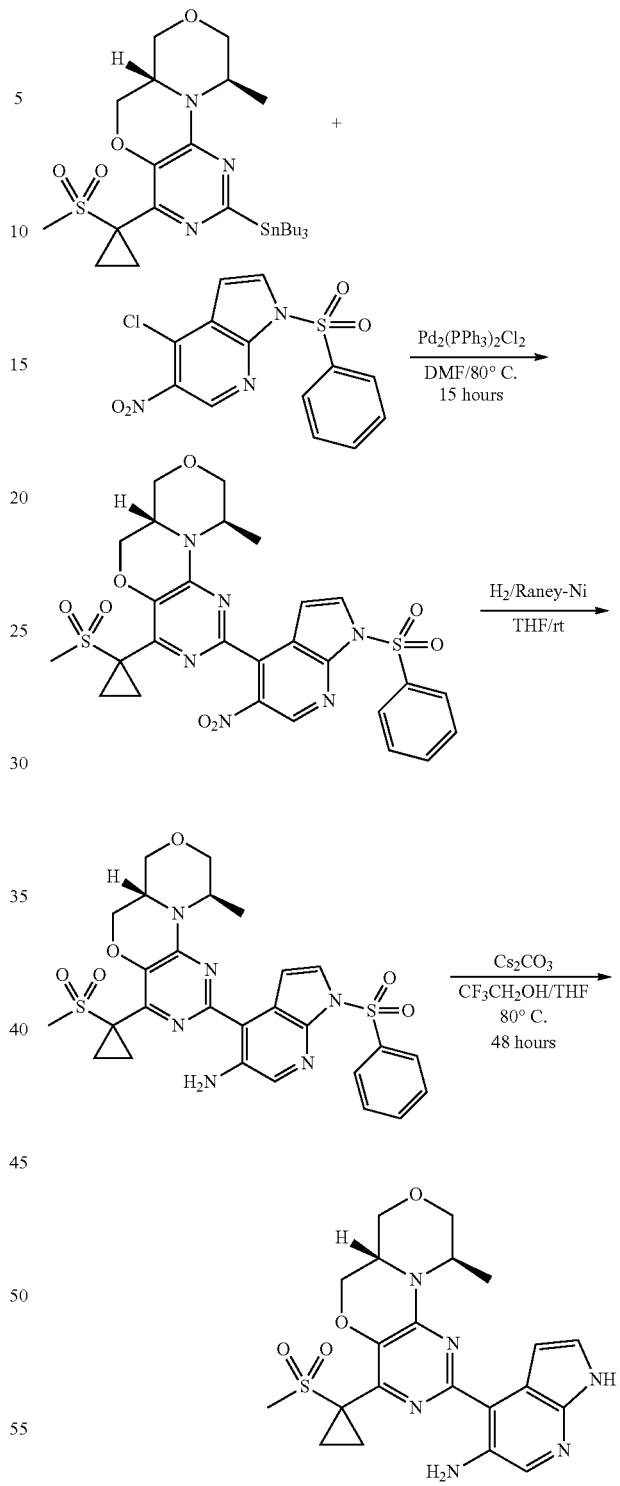

pale brown solid; LCMS (method C): 1.16 min; [MH⁺] 457.1 m/z. $^1$H NMR (500 MHz, DMSO-d$_6$) δ 11.16 (s, 1H), 7.88 (s, 1H), 7.27 (t, J=2.9 Hz, 1H), 7.00 (dd, J=3.2, 2.1 Hz, 1H), 6.39 (s, 2H), 4.64 (qd, J=6.7, 2.7 Hz, 1H), 4.43 (dd, J=10.4, 2.8 Hz, 1H), 4.00-3.93 ((m, 2H), 3.93-3.85 (m, 2H), 3.69 (dd, J=11.6, 3.2 Hz, 1H), 3.18 (t, J=11.6 Hz, 1H), 3.04 (s, 3H), 1.74-1.64 (m, 2H), 1.45-1.36 (m, 2H), 1.33 (d, J=6.8 Hz, 3H).

87

Synthesis of (5R,8aS)-3-(5-fluoro-1-methyl-1H-pyrrolo[2,3-c]pyridin-4-yl)-1-(1-methanesulfonyl-1-methyl-ethyl)-5-methyl-5,6,8a,9-tetrahydro-8H-7,10-dioxa-2,4,4b-triaza-phenanthrene ("A38")

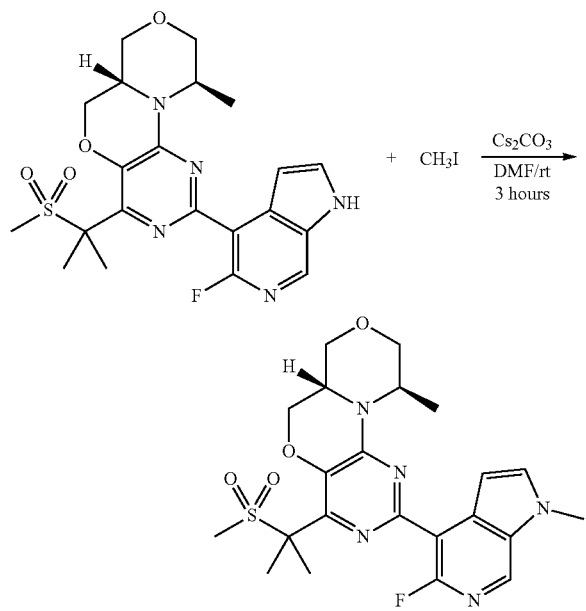

colourless foam; LCMS (method C): 1.54 min; [MH+] 476.2 m/z. ¹H NMR (500 MHz, DMSO-d₆) δ 8.48 (s, 1H), 7.69 (d, J=3.0 Hz, 1H), 6.90 (dd, J=2.9, 0.8 Hz, 1H), 4.66 (qd, J=6.7, 2.8 Hz, 1H), 4.41 (dd, J=10.9, 3.3 Hz, 1H), 3.98-3.90 (m, 5H), 3.87-3.77 (m, 2H), 3.64 (dd, J=11.6, 3.3 Hz, 1H), 3.21-3.13 (m, 1H), 2.95 (s, 3H), 1.85 (s, 3H), 1.80 (s, 3H), 1.27 (d, J=6.8 Hz, 3H).

Synthesis of (5R,8aS)-1-(1-methanesulfonyl-1-methyl-ethyl)-5-methyl-3-(1H-pyrrolo[2,3-c]pyridin-4-yl)-5,6,8a,9-tetrahydro-8H-7,10-dioxa-2,4,4b-triaza-phenanthrene ("A39")

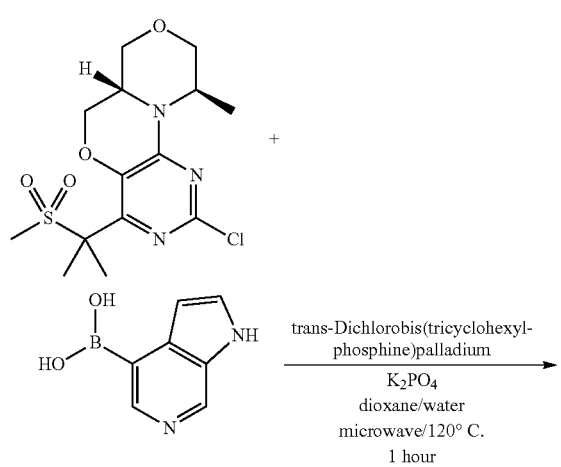

88

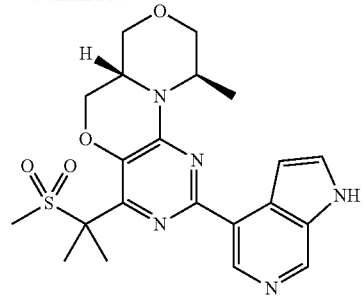

off-white powder; LCMS (method C): 1.16 min; [MH+] 444.1 m/z. ¹H NMR (400 MHz, DMSO-d₆) δ 11.72 (s, 1H), 9.00 (s, 1H), 8.80 (s, 1H), 7.70 (t, J=2.7 Hz, 1H), 7.28 (t, J=2.4 Hz, 1H), 4.83 (qd, J=6.6, 2.7 Hz, 1H), 4.42 (dd, J=10.8, 3.3 Hz, 1H), 4.01-3.92 (m, 2H), 3.88 (d, J=11.5 Hz, 1H), 3.82 (dd, J=10.9, 8.8 Hz, 1H), 3.71 (dd, J=11.5, 3.3 Hz, 1H), 3.19 (t, J=11.8 Hz, 1H), 2.96 (s, 3H), 1.90 (s, 3H), 1.88 (s, 3H), 1.34 (d, J=6.7 Hz, 3H).

Synthesis of {5-[(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]-pyridin-3-yl}-methanol ("A40")

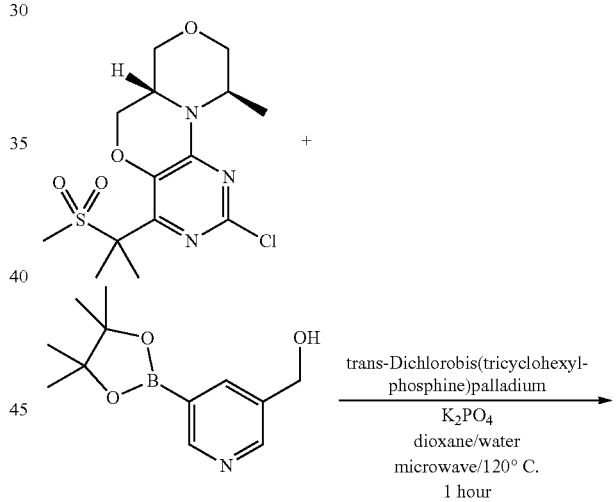

off-white powder; LCMS (method E): 0.47 min; [MH+] 435.2 m/z. ¹H NMR (400 MHz, DMSO-d₆) δ 9.29 (d, J=2.1 Hz, 1H), 8.57 (d, J=2.1 Hz, 1H), 8.47 (t, J=2.1 Hz, 1H), 5.40 (t, J=5.5 Hz, 1H), 4.85 (qd, J=6.5, 2.7 Hz, 1H), 4.62 (d, J=5.1 Hz, 2H), 4.41 (dd, J=10.9, 3.4 Hz, 1H), 3.99-3.91 (m, 2H), 3.85 (d, J=11.5 Hz, 1H), 3.79 (dd, J=11.0, 8.8 Hz, 1H), 3.67

(dd, J=11.6, 3.3 Hz, 1H), 3.17 (t, J=11.8 Hz, 1H), 2.94 (s, 3H), 1.87 (s, 3H), 1.85 (s, 3H), 1.29 (d, J=6.8 Hz, 3H).

Synthesis of {3-[(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]-phenyl}-methanol ("A41")

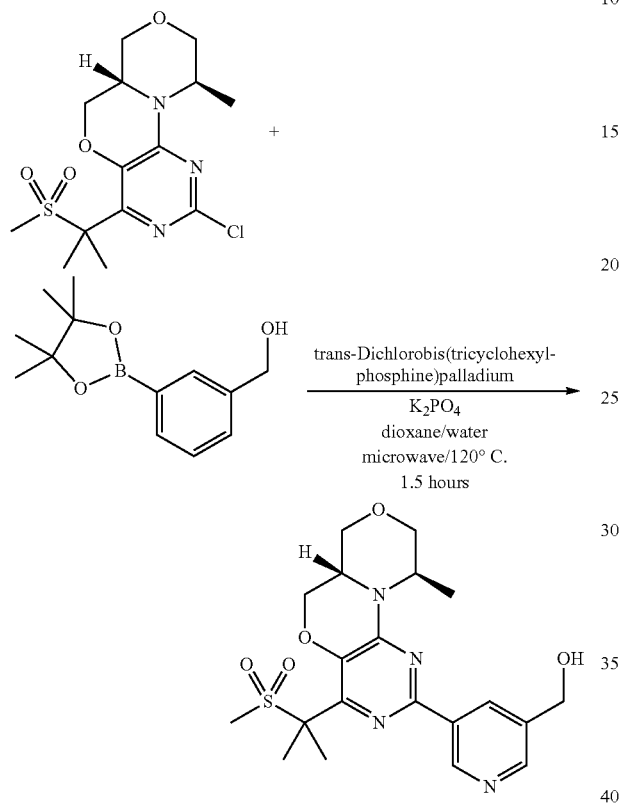

white powder; LCMS (method E): 0.71 min; [MH+] 434.2 m/z. ¹H NMR (400 MHz, DMSO-d₆) δ 8.21 (s, 1H), 8.14 (dt, J=7.1, 1.9 Hz, 1H), 7.47-7.37 (m, 2H), 5.23 (t, J=5.7 Hz, 1H), 4.84 (ddt, J=9.6, 6.8, 2.8 Hz, 1H), 4.57 (d, J=5.6 Hz, 2H), 4.39 (dd, J=10.9, 3.4 Hz, 1H), 3.98-3.89 (m, 2H), 3.85 (d, J=11.5 Hz, 1H), 3.78 (dd, J=11.0, 8.8 Hz, 1H), 3.67 (dd, J=11.6, 3.3 Hz, 1H), 3.16 (t, J=11.8 Hz, 1H), 2.94 (s, 3H), 1.86 (s, 3H), 1.84 (s, 3H), 1.29 (d, J=6.7 Hz, 3H).

Synthesis of 4-[(10S,14R)-6-(2-methanesulfonylpropan-2-yl)-14-methyl-8,12-dioxa-1,3,5-triazatricyclo[8.4.0.0²,⁷]tetradeca-2,4,6-trien-4-yl]-N-(²H₃)methyl-1H-pyrrolo[2,3-b]pyridin-5-amine ("A42")

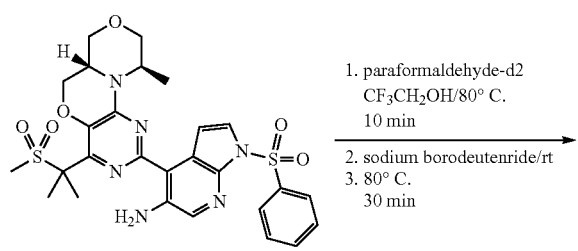

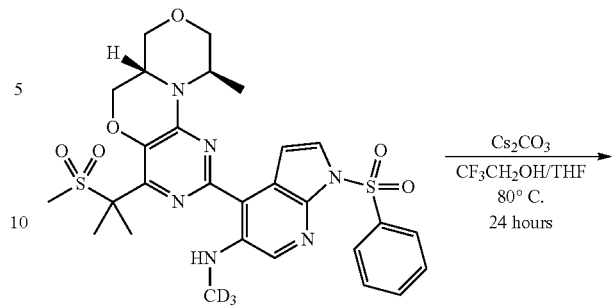

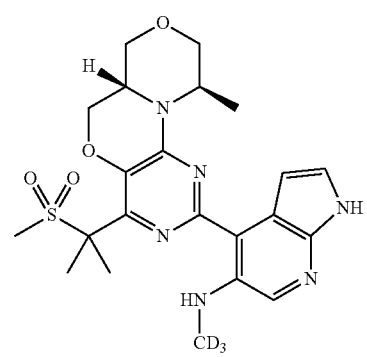

(explanation: D=²H)

yellow amorphous solid; LCMS (method C): 1.80 min; [MH+] 476.2 m/z. ¹H NMR (500 MHz, DMSO-d₆) δ 11.22 (s, 1H), 7.86 (s, 1H), 7.77 (s, 1H), 7.34 (t, J=2.9 Hz, 1H), 6.91 (dd, J=3.3, 2.1 Hz, 1H), 4.71 (qd, J=6.2, 2.6 Hz, 1H), 4.42 (dd, J=10.9, 3.3 Hz, 1H), 4.03-3.94 (m, 2H), 3.89-3.83 (m, 2H), 3.68 (dd, J=11.6, 3.2 Hz, 1H), 3.22-3.13 (m, 1H), 2.99 (s, 3H), 1.86 (s, 3H), 1.81 (s, 3H), 1.33 (d, J=6.8 Hz, 3H).

Synthesis of 1-[(10S,14R)-6-(2-methanesulfonylpropan-2-yl)-14-methyl-8,12-dioxa-1,3,5-triazatricyclo[8.4.0.0²,⁷]tetradeca-2,4,6-trien-4-yl]-N-methyl-1H-1,2,4-triazol-3-amine ("A43")

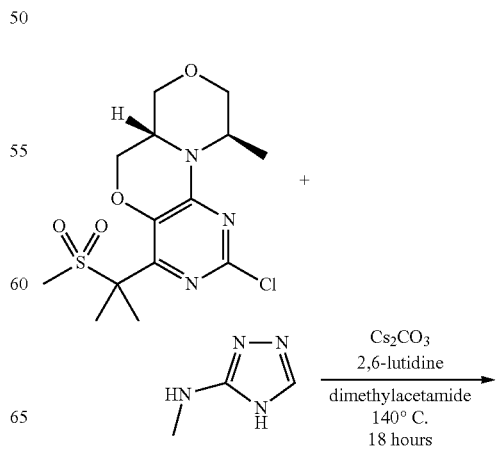

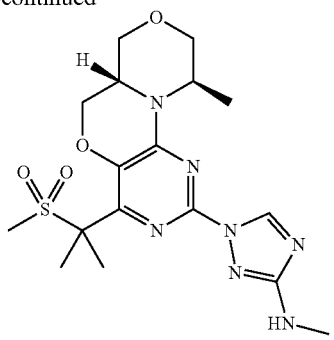

Pale orange solid; LCMS (method E): 0.56 min; [MH+] 434.2 m/z. ¹H NMR (400 MHz, DMSO-$d_6$) δ 8.89 (s, 1H), 6.18 (q, J=5.0 Hz, 1H), 4.75 (qd, J=6.5, 3.0 Hz, 1H), 4.38 (dd, J=11.1, 3.5 Hz, 1H), 4.00-3.89 (m, 2H), 3.81 (d, J=11.6 Hz, 1H), 3.75 (dd, J=11.1, 9.1 Hz, 1H), 3.63 (dd, J=11.6, 3.3 Hz, 1H), 3.20-3.11 (m, 1H), 3.07 (s, 3H), 2.78 (d, J=5.0 Hz, 3H), 1.79 (s, 3H), 1.77 (s, 3H), 1.27 (d, J=6.8 Hz, 3H).

Synthesis of (10S,14R)-4-[4-(1H-imidazol-2-yl)phenyl]-6-(2-methanesulfonylpropan-2-yl)-14-methyl-8,12-dioxa-1,3,5-triazatricyclo[8.4.0.0²,⁷]tetradeca-2,4,6-triene ("A44")

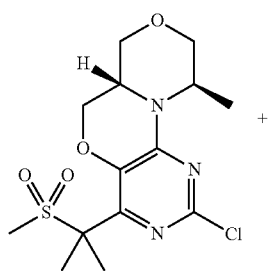

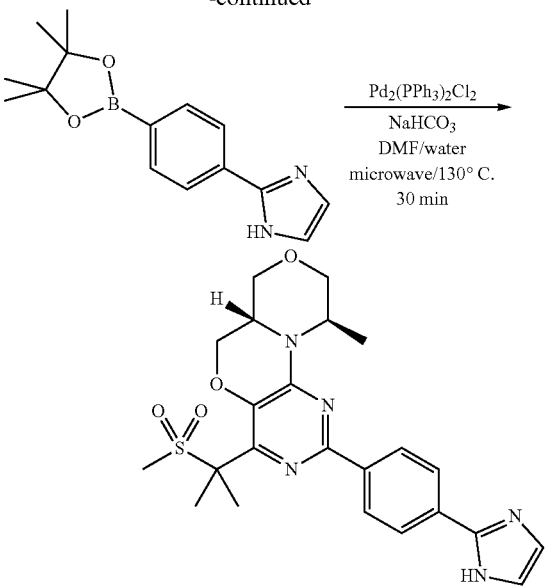

light yellow foam; LCMS (method C): 1.20 min; [MH+] 470.2 m/z. ¹H NMR (500 MHz, DMSO-$d_6$) δ 12.61 (s, 1H), 8.35-8.29 (m, 2H), 8.03-7.98 (m, 2H), 7.30 (dd, J=2.1, 1.1 Hz, 1H), 7.07 (t, J=1.3 Hz, 1H), 4.87 (qd, J=6.6, 2.8 Hz, 1H), 4.40 (dd, J=10.9, 3.4 Hz, 1H), 3.97-3.91 (m, 2H), 3.85 (d, J=11.4 Hz, 1H), 3.78 (dd, J=11.0, 8.8 Hz, 1H), 3.68 (dd, J=11.6, 3.3 Hz, 1H), 2.96 (s, 3H), 1.87 (s, 3H), 1.85 (s, 3H), 1.30 (d, J=6.8 Hz, 3H).

Synthesis of 2-{4-[(4bS,6R)-1-(1-methanesulfonyl-1-methyl-ethyl)-5-methyl-5,6,8a,9-tetrahydro-8H-7,10-dioxa-2,4,4b-triaza-phenanthren-3-yl]-phenyl}-ethylamine ("A45")

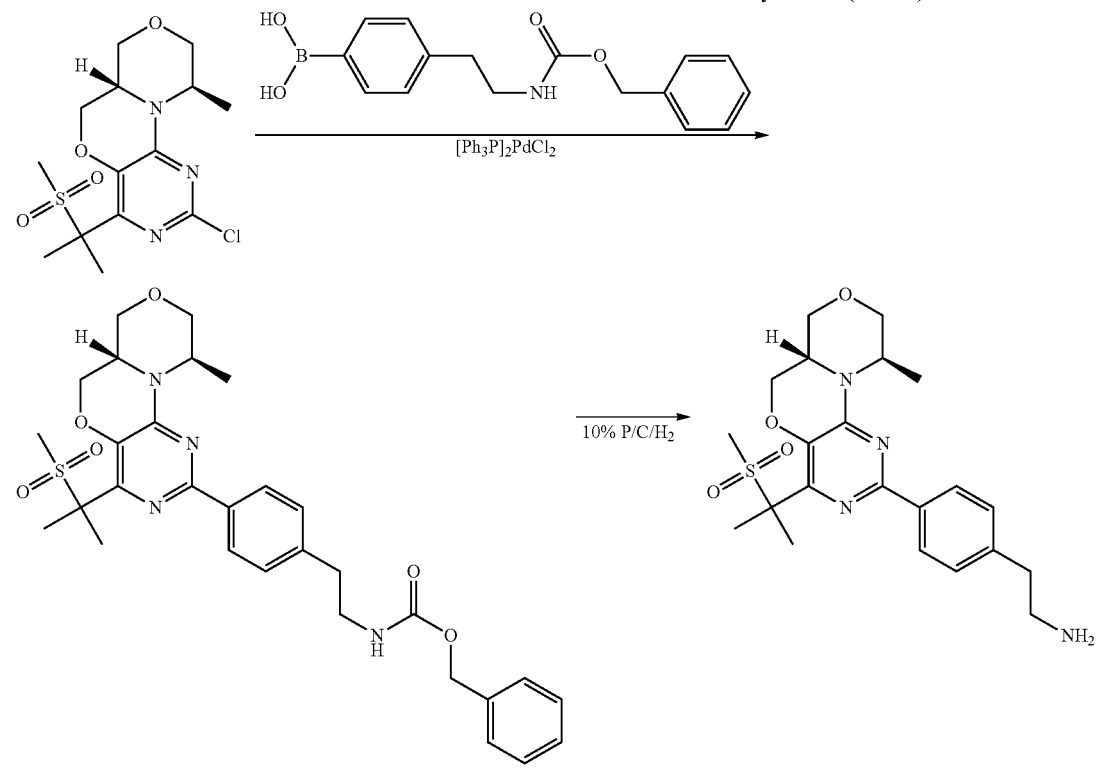

a) A microwave vial was charged with (4bS,6R)-3-Chloro-1-(1-methanesulfonyl-1-methyl-ethyl)-5-methyl-5,6,8a,9-tetrahydro-8H-7,10-dioxa-2,4,4b-triaza-phenanthrene (100 mg; 0.276 mmol), 4-(2-aminoethyl)benzeneboronic acid, N-CBZ protected (93 mg; 0.304 mmol), potassium phosphate tribasic monohydrate (255 mg; 1.105 mmol), bis(triphenylphosphine)-palladium(II)-chlorid (15.563 mg; 0.022 mmol) 2 ml 1,4-dioxane and 0.75 ml water. The reaction was sealed and heated in a Biotage microwave at 110° C. for 60 min. The reaction mixture was then poured into 100 ml water and extracted twice with each 100 ml ethylacetate. The combined organic layers were dried with waterfree Na2SO4, filtered and evaporated under reduced pressure. The crude product was purified by flash chromatography (75-0% n-heptane gradient in ethylacetate) to yield 126 mg (75%) (2-{4-[(4bS,6R)-1-(1-methanesulfonyl-1-methyl-ethyl)-5-methyl-5,6,8a,9-tetrahydro-8H-7,10-dioxa-2,4,4b-triaza-phenanthren-3-yl]-phenyl}-ethyl)-carbamic acid benzyl ester light brown foam; LCMS: [MH+] 581.

b) 125 mg (2-{4-[(4bS,6R)-1-(1-Methanesulfonyl-1-methyl-ethyl)-5-methyl-5,6,8a,9-tetrahydro-8H-7,10-dioxa-2,4,4b-triaza-phenanthren-3-yl]-phenyl}-ethyl)-carbamic acid benzyl ester were dissolved in 20 ml ethanol and hydrogenated over 10% Pd—C to afford 75 mg (78% yield) 2-{4-[(4bS,6R)-1-(1-methanesulfonyl-1-methyl-ethyl)-5-methyl-5,6,8a,9-tetrahydro-8H-7,10-dioxa-2,4,4b-triaza-phenanthren-3-yl]-phenyl}-ethylamine as white solid; LCMS: [MH+] 447. $^1$H NMR (500 MHz, DMSO-$d_6$) δ 8.20 (d, J=8.3 Hz, 2H), 7.33 (d, J=8.3 Hz, 2H), 6.78 (br. s, 2H), 4.81 (qd, J=6.6, 2.8 Hz, 1H), 4.39 (dd, J=10.9, 3.3 Hz, 1H), 3.96-3.88 (m, 2H), 3.83 (d, J=11.5 Hz, 1H), 3.76 (t, J=10.0 Hz, 1H), 3.66 (dd, J=11.6, 3.1 Hz, 1H), 3.19-3.12 (m, 1H), 3.00 (t, J=8.8, 6.6 Hz, 1H), 2.94 (s, 3H), 2.86 (t, J=8.9, 6.5 Hz, 1H), 1.85 (s, 3H), 1.82 (s, 3H), 1.26 (d, J=6.7 Hz, 3H).

Alternative Synthesis of "A18" and "A19"

1-[(5R,8aS)-5-Methyl-3-(1H-pyrrolo[2,3-b]pyridin-4-yl)-5,6,8a,9-tetrahydro-8H-7,10-dioxa-2,4,4b-triaza-phenanthren-1-ylmethyl]-1H-[1,2,3]triazole-4-carboxylic Acid Methyl Ester ("A18") and 1-[(5R,8aS)-5-Methyl-3-(1-methyl-1H-pyrrolo[2,3-b]pyridin-4-yl)-5,6,8a,9-tetrahydro-8H-7,10-dioxa-2,4,4b-triaza-phenanthren-1-ylmethyl]-1H-[1,2,3]triazole-4-carboxylic Acid Methyl Ester ("A19")

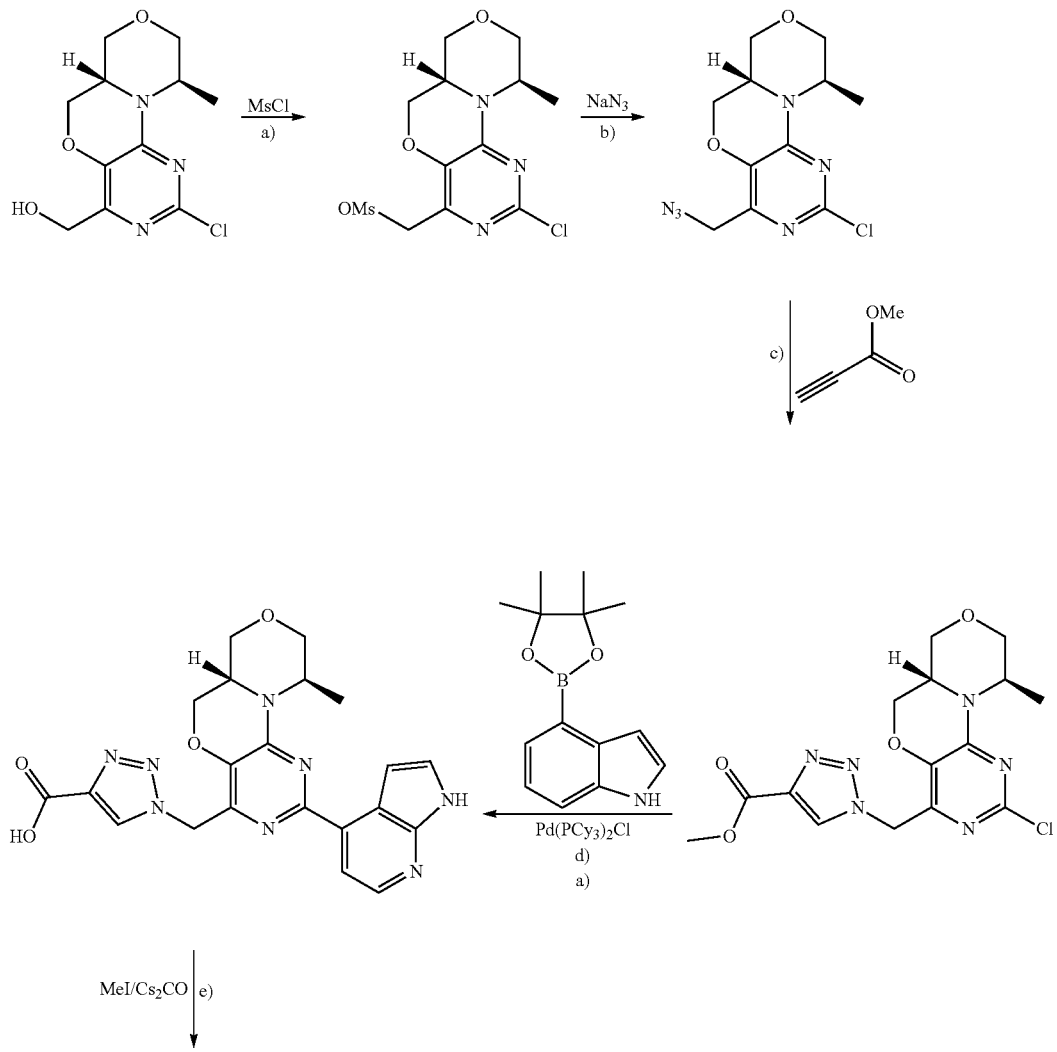

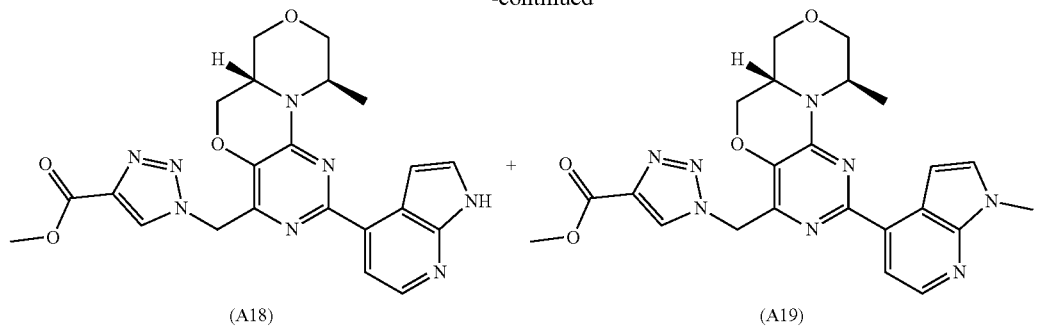

a) MsCl, TEA, DCM, 5° C. 3 h (100%); b) NaN₃, DMF, 4H RT (71, 1%); c) Cu(O), Cu(II)SO₄, tert.-ButOH, Water, 90° C. 3 h (95, 6%); d) Pd(PCy₃)₂Cl₂, K₃PO₄xH₂O, Dioxane, Water, 90° C. overnight (86, 2%); e) Cs₂CO₃, CH₃I, DMF, RT, 15 h, (("A18") 27%, ("A19") 31%).

1-[(5R,8aS)-5-Methyl-3-(1H-pyrrolo[2,3-b]pyridin-4-yl)-5,6,8a,9-tetrahydro-8H7,10-dioxa-2,4,4b-triaza-phenanthren-1-ylmethyl]-1H-[1,2,3]triazole-4-carboxylic Acid Methyl Ester ("A18")

LCMS: [MH+] 463; ¹H NMR (500 MHz, DMSO-d₆) δ 11.65 (s, 1H), 8.88 (s, 1H), 8.24 (d, J=5.0 Hz, 1H), 7.74 (d, J=5.0 Hz, 1H), 7.41 (dd, J=3.4, 2.5 Hz, 1H), 6.81 (dd, J=3.4, 2.0 Hz, 1H), 5.77-5.74 (m, 2H), 4.74 (dd, J=6.9, 2.9 Hz, 1H), 4.49 (dd, J=9.0, 6.8 Hz, 1H), 4.02-3.91 (m, 3H), 3.88 (d, J=11.7 Hz, 1H), 3.86 (s, 3H), 3.72 (dd, J=11.6, 3.3 Hz, 1H), 3.25-3.17 (m, 1H), 1.31 (d, J=6.7 Hz, 3H).

1-[(5R,8aS)-5-Methyl-3-(1-methyl-1H-pyrrolo[2,3-b]pyridin-4-yl)-5,6,8a,9-tetrahydro-8H-7,10-dioxa-2,4,4b-triaza-phenanthren-1-ylmethyl]-1H[1,2,3]triazole-4-carboxylic Acid Methyl Ester ("A19")

LCMS: [MH+] 477; ¹H NMR (500 MHz, DMSO-d₆) δ 8.89 (s, 1H), 8.29 (d, J=5.0 Hz, 1H), 7.78 (d, J=5.0 Hz, 1H), 7.46 (d, J=3.4 Hz, 1H), 6.78 (d, J=3.4 Hz, 1H), 5.79-5.71 (m, 2H), 4.74 (dd, J=6.8, 2.9 Hz, 1H), 4.49 (dd, J=8.9, 6.9 Hz, 1H), 4.05-3.91 (m, 3H), 3.89 (d, J=4.6 Hz, 1H), 3.86 (s, 3H), 3.82 (s, 3H), 3.72 (dd, J=11.7, 3.2 Hz, 1H), 3.26-3.16 (m, 1H), 1.30 (d, J=6.7 Hz, 3H).

Synthesis of 4-[(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]-benzylamine ("A46") Hydrochloride

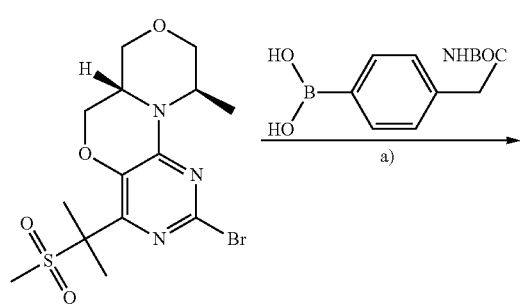

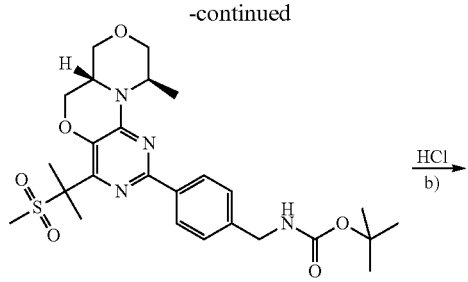

a) Pd(dppf)Cl₂*DCM, dioxane, water, K₃PO₄*H₂O, microwave 120° C., 1 h (35, 3%);
b) 4N HCl/dioxane, RT, 14 h (80%)

LCMS: [MH+] 433; ¹H NMR (500 MHz, DMSO-d₆) δ 8.36 (s, 3H), 8.27 (d, J=8.3 Hz, 2H), 7.56 (d, J=8.3 Hz, 2H), 4.83 (qd, J=6.7, 2.8 Hz, 1H), 4.40 (dd, J=11.0, 3.3 Hz, 1H), 4.08 (q, J=5.8 Hz, 2H), 3.97-3.89 (m, 2H), 3.83 (d, J=11.5 Hz, 1H), 3.77 (dd, J=11.0, 8.9 Hz, 1H), 3.66 (dd, J=11.5, 3.3 Hz, 1H), 3.20-3.10 (m, 1H), 2.94 (s, 3H), 1.85 (s, 3H), 1.83 (s, 3H), 1.27 (d, J=6.8 Hz, 3H).

Synthesis of (4bS,6R)-1-(1-methanesulfonyl-1-methyl-ethyl)-5-methyl-5,6,8a,9-tetrahydro-8H-7,10-dioxa-2,4,4b-triaza-phenanthrene-3-carboxylic Acid (2H-pyrazol-3-yl)-amide ("A47")

Synthesis of ((S)-3-hydroxy-pyrrolidin-1-yl)-[(4bS,6R)-1-(1-methanesulfonyl-1-methyl-ethyl)-5-methyl-5,6,8a,9-tetrahydro-8H-7,10-dioxa-2,4,4b-triaza-phenanthren-3-yl]-methanone ("A48")

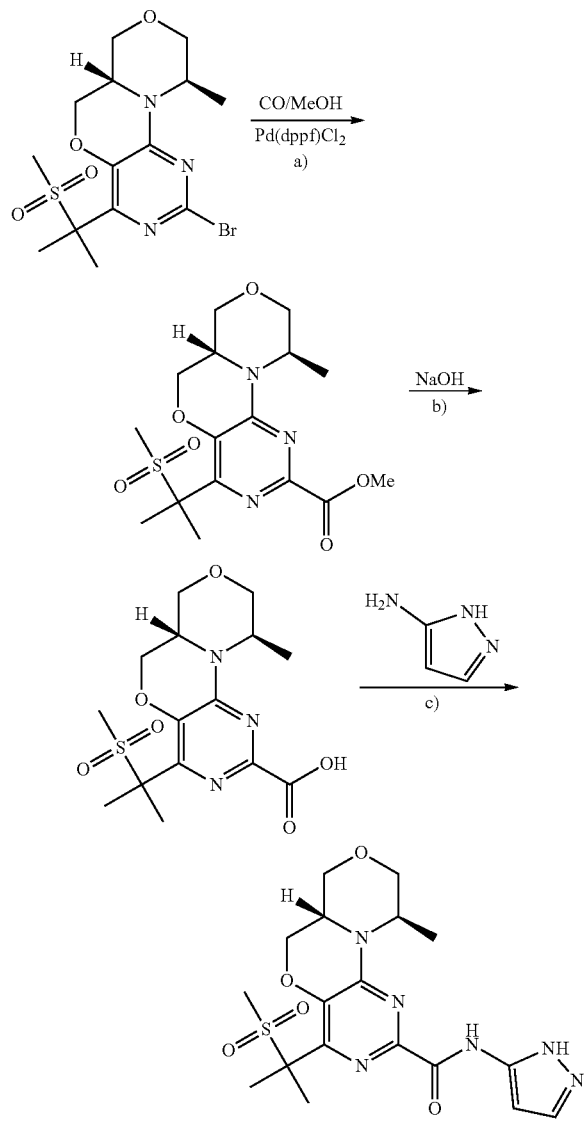
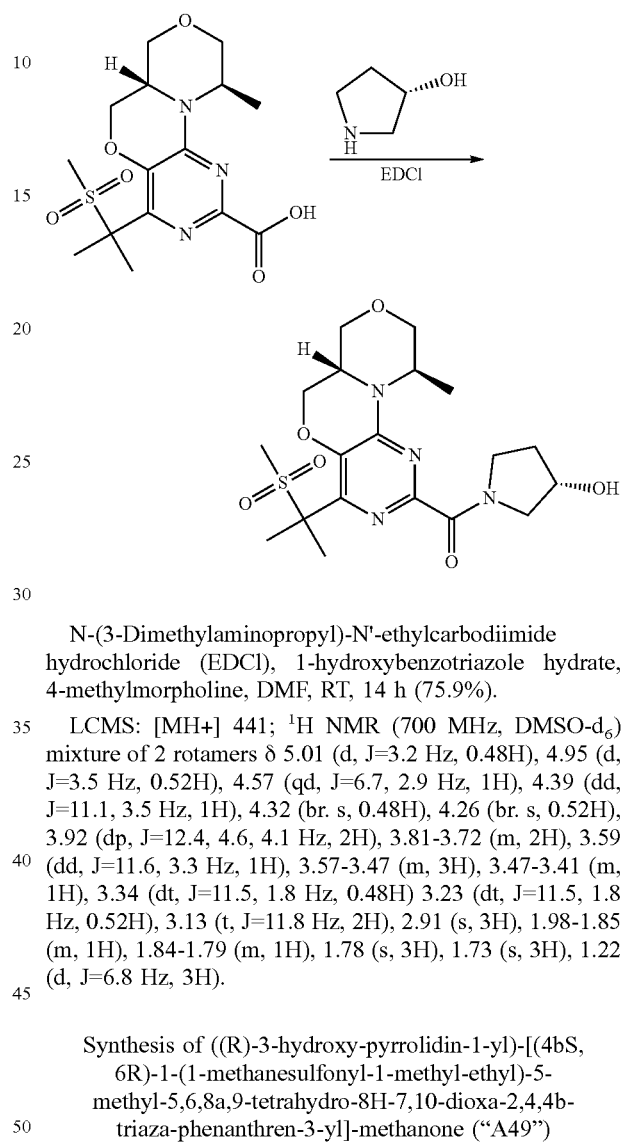

a) Carbon monoxide (CO), methanol, (1,1′-bis(diphenylphosphino)-ferrocen)dichloropalladium(II)*dichlormethan (Pd(dppf)Cl₂*DCM, 1,1-bis-(diphenylphosphino)-ferrocen, TEA, THF, 6 bar, 100° C., 15 h (88,2%);
b) 1N NaOH, methanol, (94,8%); c) 1-chloro-N,N,2-trimethyl-1-propenylamine, DCM, RT, 14 h (64,2%)

N-(3-Dimethylaminopropyl)-N′-ethylcarbodiimide hydrochloride (EDCl), 1-hydroxybenzotriazole hydrate, 4-methylmorpholine, DMF, RT, 14 h (75.9%).

LCMS: [MH+] 441; $^1$H NMR (700 MHz, DMSO-$d_6$) mixture of 2 rotamers δ 5.01 (d, J=3.2 Hz, 0.48H), 4.95 (d, J=3.5 Hz, 0.52H), 4.57 (qd, J=6.7, 2.9 Hz, 1H), 4.39 (dd, J=11.1, 3.5 Hz, 1H), 4.32 (br. s, 0.48H), 4.26 (br. s, 0.52H), 3.92 (dp, J=12.4, 4.6, 4.1 Hz, 2H), 3.81-3.72 (m, 2H), 3.59 (dd, J=11.6, 3.3 Hz, 1H), 3.57-3.47 (m, 3H), 3.47-3.41 (m, 1H), 3.34 (dt, J=11.5, 1.8 Hz, 0.48H) 3.23 (dt, J=11.5, 1.8 Hz, 0.52H), 3.13 (t, J=11.8 Hz, 2H), 2.91 (s, 3H), 1.98-1.85 (m, 1H), 1.84-1.79 (m, 1H), 1.78 (s, 3H), 1.73 (s, 3H), 1.22 (d, J=6.8 Hz, 3H).

Synthesis of ((R)-3-hydroxy-pyrrolidin-1-yl)-[(4bS,6R)-1-(1-methanesulfonyl-1-methyl-ethyl)-5-methyl-5,6,8a,9-tetrahydro-8H-7,10-dioxa-2,4,4b-triaza-phenanthren-3-yl]-methanone ("A49")

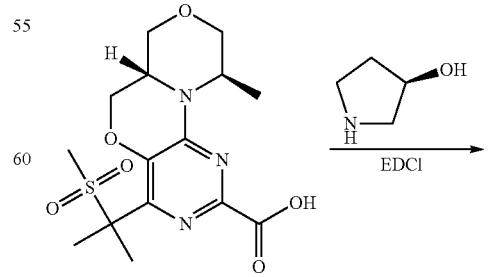

LCMS: [MH+] 437; $^1$H NMR (400 MHz, DMSO-$d_6$) δ 12.49 (s, 1H), 10.26 (s, 1H), 7.68 (s, 1H), 6.64 (s, 1H), 4.86 (dd, J=7.1, 2.9 Hz, 1H), 4.43 (dd, J=11.0, 3.4 Hz, 1H), 3.99-3.89 (m, 2H), 3.86-3.75 (m, 2H), 3.63 (dd, J=11.6, 3.2 Hz, 1H), 3.21-3.08 (m, 1H), 2.99 (s, 3H), 1.82 (s, 3H), 1.80 (s, 3H), 1.26 (d, J=6.7 Hz, 3H).

-continued

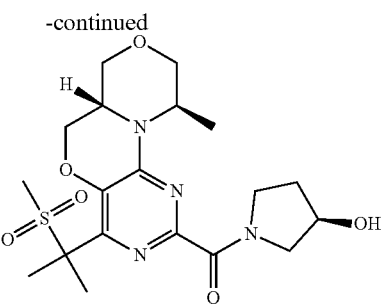

N-(3-Dimethylaminopropyl)-N'-ethylcarbodiimide hydrochloride (EDCl), 1-hydroxybenzotriazole hydrate, 4-methylmorpholine, DMF, RT, 14 h (67.5%). LCMS: [MH+] 441; $^1$H NMR (500 MHz, DMSO-d$_6$) mixture of 2 rotamers δ 5.00 (d, J=3.1 Hz, 0.48H), 4.96 (d, J=3.4 Hz, 0.52H), 4.62-4.53 (m, 1H), 4.39 (dd, J=11.0, 3.4 Hz, 1H), 4.31 (s, 0.48H), 4.25 (s, 0.52H), 3.91 (ddt, J=10.5, 6.9, 4.0 Hz, 2H), 3.81-3.73 (m, 2H), 3.60 (dd, J=11.7, 3.2 Hz, 1H), 3.56-3.43 (m, 3H), 3.39-3.35 (m, 0.45H), 3.27-3.21 (m, 0.55H), 3.13 (t, J=11.8 Hz, 1H), 2.91 (s, 3H), 1.98-1.85 (m, 1H), 1.83-1.79 (m, 1H), 1.78 (s, 3H), 1.74 (s, 3H), 1.21 (d, J=6.8 Hz, 3H).

Synthesis of ((R)-2-hydroxymethyl-pyrrolidin-1-yl)-[(4bS,6R)-1-(1-methanesulfonyl-1-methyl-ethyl)-5-methyl-5,6,8a,9-tetrahydro-8H-7,10-dioxa-2,4,4b-triaza-phenanthren-3-yl]-methanone ("A50")

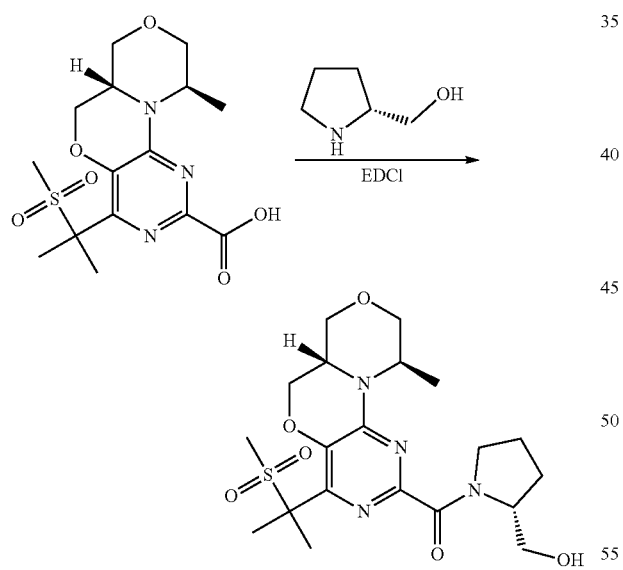

N-(3-Dimethylaminopropyl)-N'-ethylcarbodiimide hydrochloride (EDCl), 1-hydroxybenzotriazole hydrate, 4-methylmorpholine, DMF, RT, 48 h (47.4%). LCMS: [MH+] 455; $^1$H NMR (500 MHz, DMSO-d$_6$) mixture of 2 rotamers δ 4.86 (t, J=5.5 Hz, 0.56H), 4.67 (t, J=5.5 Hz, 0.44H), 4.63-4.50 (m, 1H), 4.39 (dt, J=11.0, 3.4 Hz, 1H), 3.97-3.86 (m, 2H), 3.76 (t, J=9.8 Hz, 2H), 3.70-3.63 (m, 1H), 3.60 (dd, J=11.7, 3.2 Hz, 1H), 3.21-3.03 (m, 3H), 2.92 (s, 1.6H), 2.90 (s, 1.4H), 2.01-1.81 (m, 4H), 1.78 (s, 3H), 1.73 (s, 3H), 1.28-1.16 (m, 3H).

Synthesis of ((R)-3-amino-pyrrolidin-1-yl)-[(4bS,6R)-1-(1-methanesulfonyl-1-methyl-ethyl)-5-methyl-5,6,8a,9-tetrahydro-8H-7,10-dioxa-2,4,4b-triaza-phenanthren-3-yl]-methanone ("A51") Hydrochloride

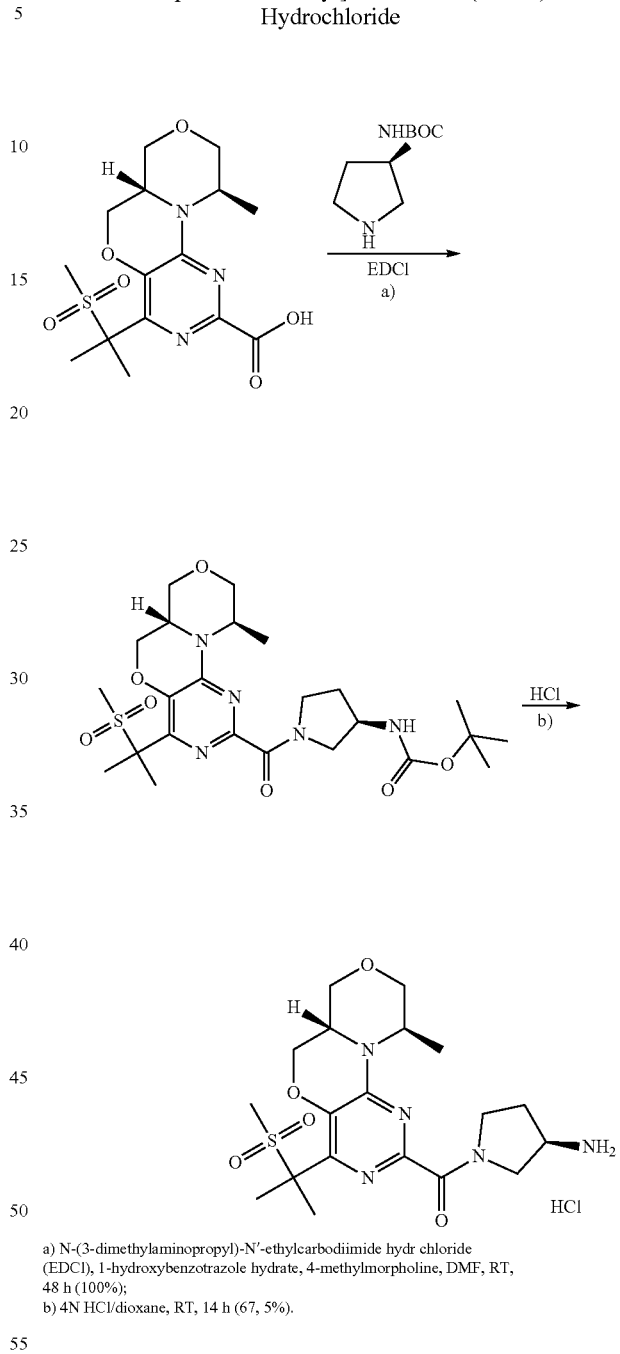

a) N-(3-dimethylaminopropyl)-N'-ethylcarbodiimide hydrochloride (EDCl), 1-hydroxybenzotrazole hydrate, 4-methylmorpholine, DMF, RT, 48 h (100%);
b) 4N HCl/dioxane, RT, 14 h (67, 5%).

LCMS: [MH+] 440; $^1$H NMR (400 MHz, DMSO-d$_6$) mixture of 2 rotamers δ 8.24 (s, 1.45H), 8.18 (s, 1.55H), 4.64-4.53 (m, 1H), 4.47-4.35 (m, 1H), 3.99-3.88 (m, 2H), 3.89-3.73 (m, 4H), 3.72-3.59 (m, 2H), 3.14 (td, J=11.8, 3.1 Hz, 1H), 2.92 (s, 3H), 2.21 (dt, J=13.9, 6.9 Hz, 1H), 1.97 (dt, J=10.7, 5.9 Hz, 1H), 1.79 (s, 3H), 1.75 (s, 3H), 1.22 (d, J=6.4 Hz, 3H).

101

Synthesis of ((S)-3-Amino-pyrrolidin-1-yl)-[(4bS,6R)-1-(1-methanesulfonyl-1-methyl-ethyl)-5-methyl-5,6,8a,9-tetrahydro-8H-7,10-dioxa-2,4,4b-triaza-phenanthren-3-yl]-methanone ("A52") Hydrochloride

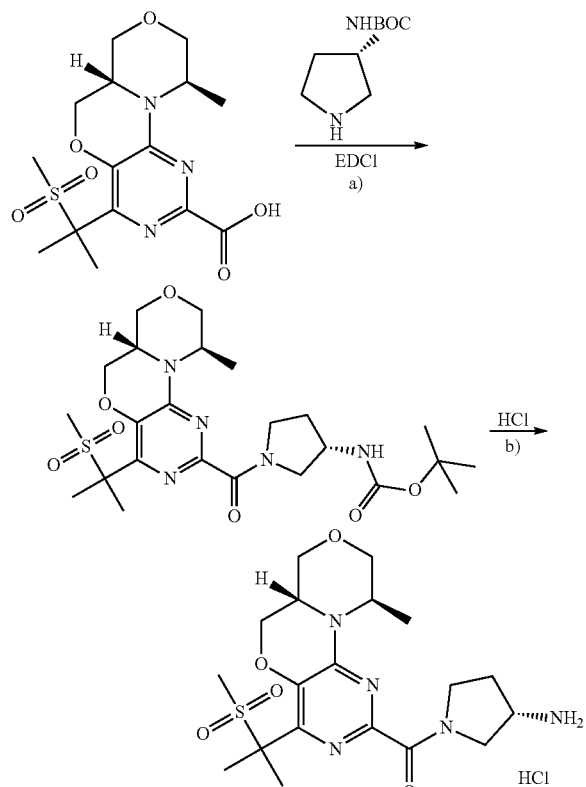

a) N-(3-dimethylaminopropyl)-N'-ethylcarbodiimide hydrochloride (EDCl), 1-hydroxybenzotrazole hydrate, 4-methylmorpholine, DMF, RT, 48 h (100%);
b) 4N HCl/dioxane, RT, 14 h (75, 1%).

LCMS: [MH+] 440; $^1$H NMR (400 MHz, DMSO-$d_6$) mixture of 2 rotamers δ 8.26 (s, 1.44H), 8.19 (s, 1.56H), 4.64-4.53 (m, 1H), 4.40 (dt, J=11.0, 3.6 Hz, 1H), 3.98-3.89 (m, 2H), 3.88-3.73 (m, 4H), 3.73-3.60 (m, 3H), 3.56-3.48 (m, 1H), 3.14 (t, J=11.8 Hz, 1H), 2.92 (s, 1.41H), 2.91 (s, 1.39H), 2.06-1.89 (m, 1H), 1.80 (s, 1.34H), 1.79 (s, 1.68H), 1.75 (s, 3H), 1.24 (d, J=4.0 Hz, 1.49H), 1.22 (d, J=4.1 Hz, 1.51H).

Synthesis of (4bS,6R)-1-(1-methanesulfonyl-1-methyl-ethyl)-5-methyl-5,6,8a,9-tetrahydro-8H-7,10-dioxa-2,4,4b-triaza-phenanthrene-3-carboxylic Acid ((R)-2-hydroxy-propyl)-amide ("A53")

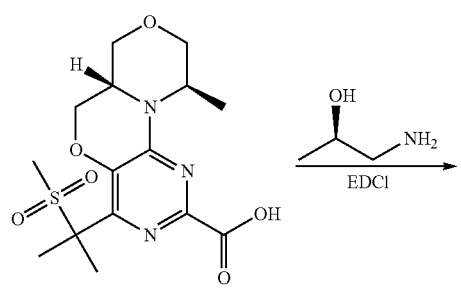

102

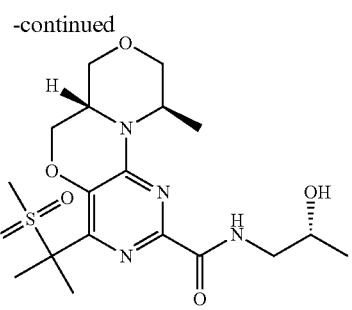

N-(3-dimethylaminopropyl)-N'-ethylcarbodiimide hydrochloride (EDCl), 1-hydroxybenzotriazole hydrate, 4-methylmorpholine, DMF, RT, 48 h (62.4%). LCMS: [MH+] 429; $^1$H NMR (500 MHz, DMSO-$d_6$) δ 8.33 (t, J=6.0 Hz, 1H), 4.79 (d, J=4.7 Hz, 1H), 4.78-4.74 (m, 1H), 4.40 (dd, J=11.0, 3.5 Hz, 1H), 3.97-3.87 (m, 2H), 3.85-3.71 (m, 3H), 3.61 (dd, J=11.6, 3.2 Hz, 1H), 3.24 (ddd, J=13.1, 6.4, 5.3 Hz, 1H), 3.21-3.08 (m, 2H), 2.97 (s, 3H), 1.79 (s, 3H), 1.77 (s, 3H), 1.23 (d, J=6.8 Hz, 3H), 1.05 (d, J=6.2 Hz, 3H).

Synthesis of (4bS,6R)-1-(1-methanesulfonyl-1-methyl-ethyl)-5-methyl-5,6,8a,9-tetrahydro-8H-7,10-dioxa-2,4,4b-triaza-phenanthrene-3-carboxylic Acid ((S)-2-hydroxy-propyl)-amide ("A54")

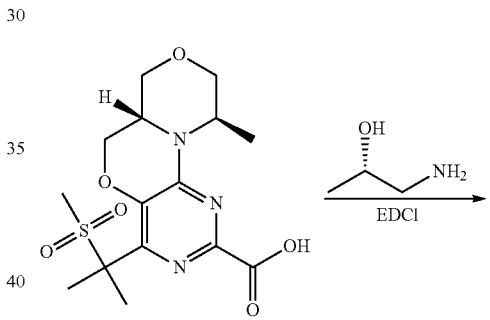

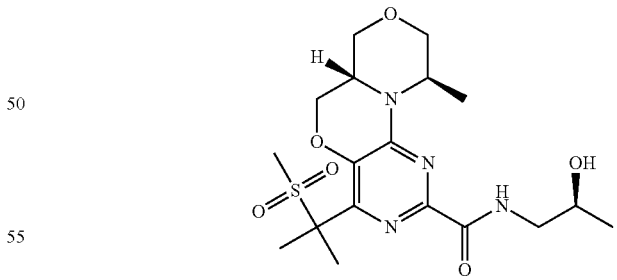

N-(3-dimethylaminopropyl)-N'-ethylcarbodiimide hydrochloride (EDCl), 1-hydroxybenzotriazole hydrate, 4-methylmorpholine, DMF, RT, 48 h (62.4%). LCMS: [MH+] 429; $^1$H NMR (500 MHz, DMSO-$d_6$) δ 8.37 (t, J=6.0 Hz, 1H), 4.82 (d, J=4.7 Hz, 1H), 4.80-4.77 (m, 1H), 4.40 (dd, J=11.0, 3.5 Hz, 1H), 3.97-3.87 (m, 2H), 3.85-3.71 (m, 3H), 3.61 (dd, J=11.6, 3.2 Hz, 1H), 3.24 (ddd, J=13.1, 6.4, 5.3 Hz, 1H), 3.21-3.08 (m, 2H), 2.98 (s, 3H), 1.80 (s, 3H), 1.77 (s, 3H), 1.23 (d, J=6.8 Hz, 3H), 1.06 (d, J=6.2 Hz, 3H).

Synthesis of (4bS,6R)-1-(1-methanesulfonyl-1-methyl-ethyl)-5-methyl-5,6,8a,9-tetrahydro-8H-7,10-dioxa-2,4,4b-triaza-phenanthrene-3-carboxylic Acid (4H-[1,2,4]triazol-3-yl)-amide ("A55")

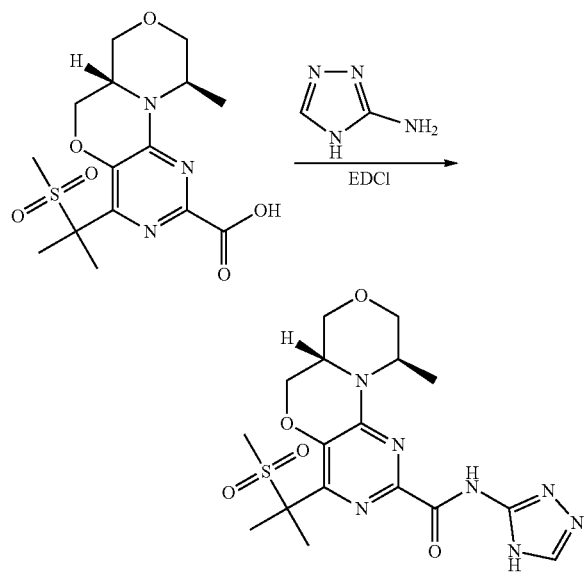

N-(3-dimethylaminopropyl)-N'-ethylcarbodiimide hydrochloride (EDCl), 1-hydroxybenzotriazole hydrate, 4-methylmorpholine, DMF, RT, 48 h (44.1%). LCMS: [MH+] 438; ¹H NMR (400 MHz, DMSO-$d_6$) δ 13.66 (br. s, 1H), 7.98 (br. s, 1H), 4.97 (s, 1H), 4.43 (dd, J=11.1, 3.4 Hz, 1H), 4.02-3.88 (m, 2H), 3.87-3.73 (m, 2H), 3.62 (dd, J=11.5, 3.2 Hz, 1H), 3.23-3.09 (m, 1H), 2.99 (s, 3H), 1.82 (s, 3H), 1.80 (s, 3H), 1.25 (d, J=6.8 Hz, 3H).

Synthesis of (4bS,6R)-1-(1-methanesulfonyl-1-methyl-ethyl)-5-methyl-5,6,8a,9-tetrahydro-8H-7,10-dioxa-2,4,4b-triaza-phenanthrene-3-carboxylic Acid (2-hydroxy-1-methyl-ethyl)-amide ("A56")

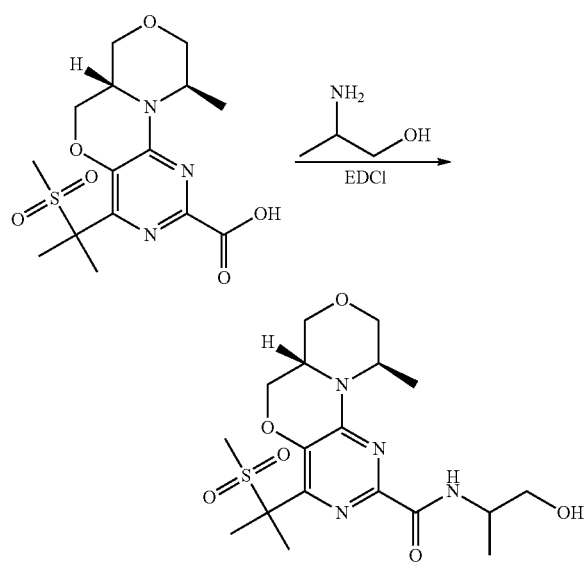

N-(3-dimethylaminopropyl)-N'-ethylcarbodiimide hydrochloride (EDCl), 1-hydroxybenzotriazole hydrate, 4-methylmorpholine, DMF, RT, 48 h 57.2%). LCMS: [MH+] 429; ¹H NMR (400 MHz, DMSO-$d_6$) mixture of 2 diastereomers δ 8.00 (dd, J=8.3, 2.6 Hz, 1H), 4.82 (td, J=5.4, 2.9 Hz, 1H), 4.76 (dt, J=6.9, 3.5 Hz, 1H), 4.41 (dd, J=11.0, 3.4 Hz, 1H), 4.00-3.86 (m, 3H), 3.86-3.71 (m, 2H), 3.63 (dd, J=11.6, 3.2 Hz, 1H), 3.55-3.36 (m, 2H), 3.14 (t, J=11.8 Hz, 1H), 2.99 (d, J=1.2 Hz, 3H), 1.80 (s, 3H), 1.77 (s, 3H), 1.23 (d, J=7.6 Hz, 3H), 1.15 (d, J=7.2 Hz, 3H).

Synthesis of (4bS,6R)-1-(1-methanesulfonyl-1-methyl-ethyl)-5-methyl-5,6,8a,9-tetrahydro-8H-7,10-dioxa-2,4,4b-triaza-phenanthrene-3-carboxylic Acid pyridazin-4-ylamide ("A57")

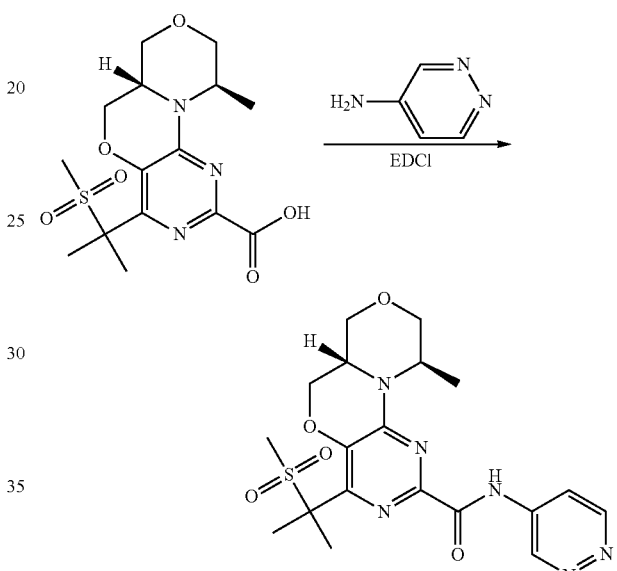

N-(3-dimethylaminopropyl)-N'-ethylcarbodiimide hydrochloride (EDCl), 1-hydroxybenzotriazole hydrate, 4-methylmorpholine, DMF, RT, 48 h (49.7%). LCMS: [MH+] 449; ¹H NMR (500 MHz, DMSO-$d_6$) δ 10.50 (s, 1H), 9.57 (dd, J=2.7, 1.0 Hz, 1H), 9.12 (dd, J=5.8, 1.0 Hz, 1H), 8.14 (dd, J=5.9, 2.7 Hz, 1H), 4.98-4.83 (m, 1H), 4.46 (dd, J=11.1, 3.4 Hz, 1H), 3.96 (ddd, J=12.4, 8.8, 4.2 Hz, 2H), 3.89-3.74 (m, 2H), 3.65 (dd, J=11.6, 3.2 Hz, 1H), 3.24-3.09 (m, 1H), 2.99 (s, 3H), 1.84 (s, 3H), 1.82 (s, 3H), 1.26 (d, J=6.8 Hz, 3H).

Synthesis of (4bS,6R)-1-(1-methanesulfonyl-1-methyl-ethyl)-5-methyl-5,6,8a,9-tetrahydro-8H-7,10-dioxa-2,4,4b-triaza-phenanthrene-3-carboxylic Acid pyrimidin-2-ylamide ("A58")

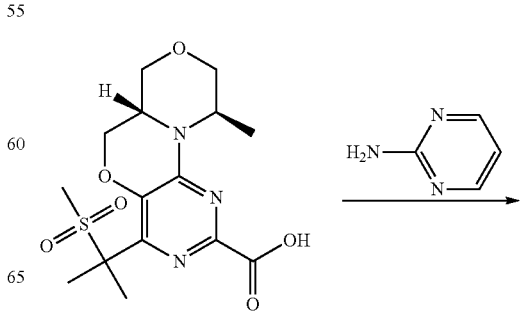

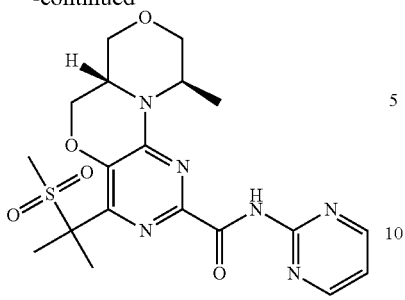

1-chloro-N,N,2-trimethyl-1-propenylamine, 2,6-dimethylpyridine, DCM, RT, 14 h (28.2%).

LCMS: [MH+] 449; ¹H NMR (400 MHz, DMSO-d$_6$) δ 10.52 (s, 1H), 8.71 (d, J=4.8 Hz, 2H), 7.25 (t, J=4.8 Hz, 1H), 4.75 (dd, J=6.8, 2.9 Hz, 1H), 4.44 (dd, J=11.1, 3.4 Hz, 1H), 4.03-3.89 (m, 2H), 3.81 (dd, J=11.3, 8.2 Hz, 2H), 3.63 (dd, J=11.6, 3.2 Hz, 1H), 3.20-3.07 (m, 1H), 2.96 (s, 3H), 1.82 (s, 3H), 1.79 (s, 3H), 1.25 (d, J=6.8 Hz, 3H).

Synthesis (4bS,6R)-1-(1-methanesulfonyl-1-methyl-ethyl)-5-methyl-5,6,8a,9-tetrahydro-8H-7,10-dioxa-2,4,4b-triaza-phenanthrene-3-carboxylic Acid ((S)-2-oxo-pyrrolidin-3-yl)-amide ("A59")

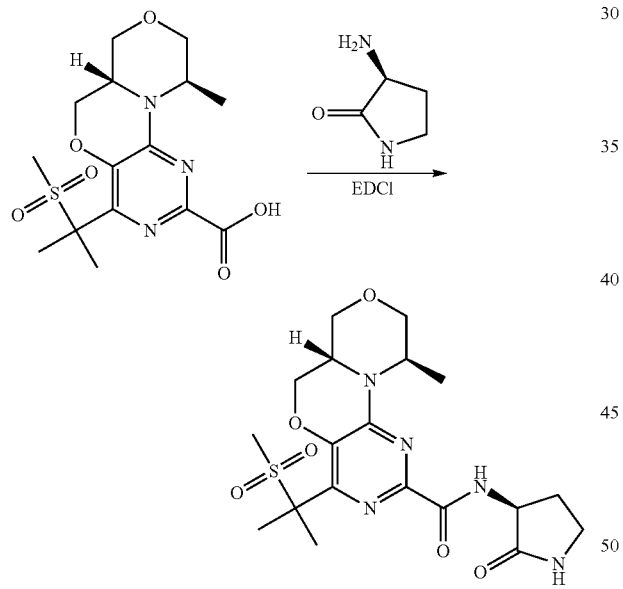

N-(3-dimethylaminopropyl)-N'-ethylcarbodiimide hydrochloride (EDCl), 1-hydroxybenzotriazole hydrate, 4-methylmorpholine, DMF, RT, 48 h (55.7%). LCMS: [MH+] 454; ¹H NMR (400 MHz, DMSO-d$_6$) δ 8.53 (d, J=7.9 Hz, 1H), 7.83 (s, 1H), 4.83 (dd, J=7.1, 2.7 Hz, 1H), 4.47-4.28 (m, 2H), 4.00-3.86 (m, 2H), 3.84-3.70 (m, 2H), 3.62 (dd, J=11.5, 3.2 Hz, 1H), 3.24 (dd, J=9.4, 4.4 Hz, 2H), 3.18-3.05 (m, 1H), 2.98 (s, 3H), 2.42-2.26 (m, 1H), 2.17-1.96 (m, 1H), 1.80 (s, 3H), 1.77 (s, 3H), 1.24 (d, J=6.7 Hz, 3H).

Synthesis of (5R,8aS)-1-(1-methanesulfonyl-1-methyl-ethyl)-5-methyl-3-[4-(2H-pyrazol-3-yl)-phenyl]-5,6,8a,9-tetrahydro-8H-7,10-dioxa-2,4,4b-triaza-phenanthrene ("A60")

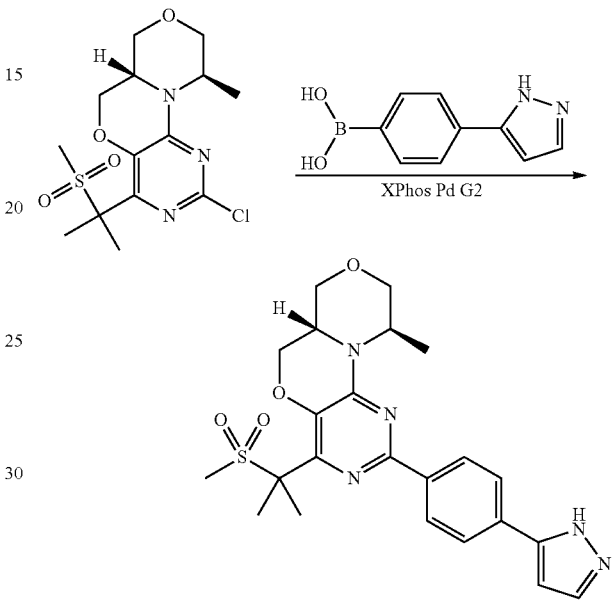

XPhos Pd G2, K$_3$PO$_4$*H$_2$O, THF, water, microwave 100° C., 1 h (16.3%); LCMS: [MH+] 470; ¹H NMR (500 MHz, DMSO-d$_6$) δ 12.93 (s, 1H), 8.28 (d, J=8.2 Hz, 2H), 7.90 (d, J=8.1 Hz, 2H), 7.80 (s, 1H), 6.76 (s, 1H), 4.85 (qd, J=6.6, 2.7 Hz, 1H), 4.39 (dd, J=11.0, 3.3 Hz, 1H), 4.02-3.89 (m, 2H), 3.84 (d, J=11.5 Hz, 1H), 3.77 (dd, J=10.9, 8.8 Hz, 1H), 3.67 (dd, J=11.6, 3.3 Hz, 1H), 3.16 (t, J=11.8 Hz, 1H), 2.95 (s, 3H), 1.86 (s, 3H), 1.84 (s, 3H), 1.29 (d, J=6.7 Hz, 3H).

Synthesis of (2-{4-[(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]-phenyl}-aziridin-2-yl)-methanol ("A61") and 3-{4-[(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]-phenyl}-oxetan-3-ylamine ("A62")

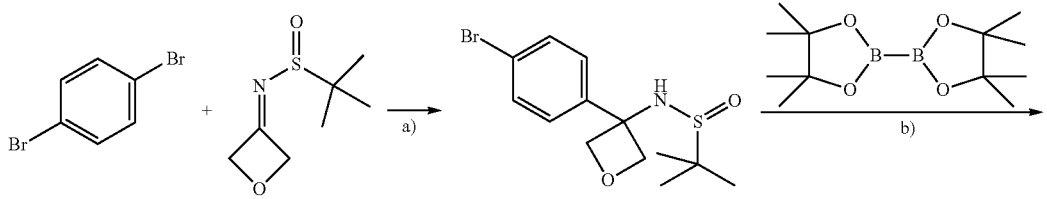

-continued

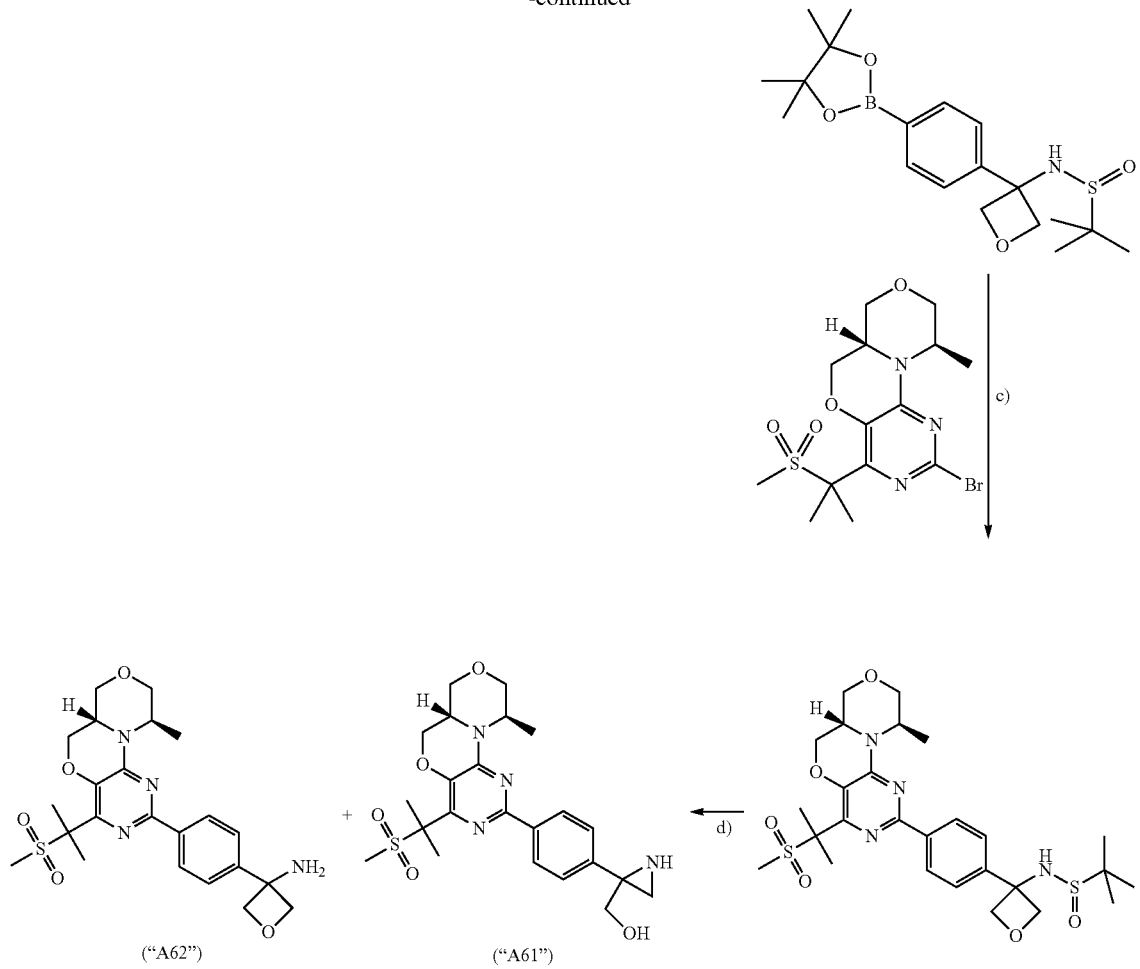

("A62")  ("A61")

a) BuLi (15% in Hexan), THF, -78° C., 30 min, then RT 14 h (45,8%);
b) Pd(dppf)Cl₂.CH₂Cl₂, KOAc, DMSO, 80° C., 2 h (97,8%);
c) XPhos Pd G2, K₃PO₄*H₂O, 1,4-dioxane, water, microwave 120° C., 1 h (59,9%);
d) Methanol, 4NHClin Dioxane, RT, 10 min (36,1% ("A61") and 59,9% ("A62"))

"A61":

LCMS: [MH+] 475; $^1$H NMR (500 MHz, DMSO-$d_6$) mixture of 2 diastereomers δ 8.16 (d, J=9.8 Hz, 2H), 7.46 (d, J=8.3 Hz, 2H), 5.02 (s, 1H), 4.81 (dd, J=6.8, 3.1 Hz, 1H), 4.38 (dd, J=10.9, 3.4 Hz, 1H), 3.98-3.86 (m, 2H), 3.87-3.71 (m, 3H), 3.66 (dd, J=11.6, 3.3 Hz, 1H), 3.22-3.09 (m, 1H), 2.93 (s, 3H), 2.15-1.92 (m, 1H), 1.84 (s, 3H), 1.83 (s, 3H), 1.48-1.35 (m, 1H), 1.26 (d, J=6.3 Hz, 3H), 1.26-1.18 (m, 1H).

"A62":

LCMS: [MH+] 475; $^1$H NMR (500 MHz, DMSO-$d_6$) δ 8.25 (d, J=8.4 Hz, 2H), 7.66 (d, J=8.4 Hz, 2H), 4.90-4.77 (m, 1H), 4.73 (d, J=5.9 Hz, 2H), 4.67 (d, J=5.9 Hz, 2H), 4.39 (dd, J=11.0, 3.3 Hz, 1H), 3.97-3.87 (m, 2H), 3.84 (d, J=11.5 Hz, 1H), 3.77 (dd, J=11.0, 8.8 Hz, 1H), 3.67 (dd, J=11.5, 3.3 Hz, 1H), 3.23-3.10 (m, 1H), 2.94 (s, 3H), 2.65-2.54 (m, 2H), 1.85 (s, 3H), 1.83 (s, 3H), 1.27 (d, J=6.8 Hz, 3H).

Synthesis of (2-{3-[(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]-phenyl}-aziridin-2-yl)-methanol ("A63") and 3-{3-[(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]-phenyl}-oxetan-3-ylamine ("A64")

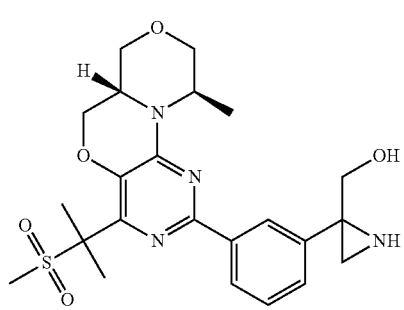

("A63")

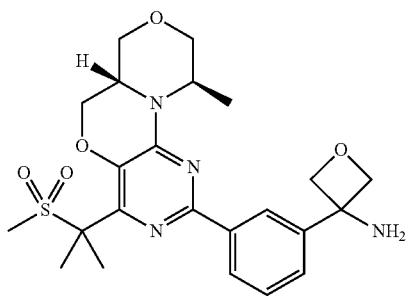

("A64")

The compounds are synthesized analogously to "A61" and "A62".

Compound ("A63"):

LCMS: [MH+] 475; ¹H NMR (500 MHz, DMSO-d₆) mixture of 2 diastereomers δ 8.27 (s, 1H), 8.09 (d, J=7.5 Hz, 1H), 7.45 (d, J=7.6 Hz, 1H), 7.37 (t, J=7.6 Hz, 1H), 5.03 (t, J=5.8 Hz, 1H), 4.86-4.75 (m, 1H), 4.39 (dd, J=11.0, 3.2 Hz, 1H), 3.97-3.87 (m, 2H), 3.84 (t, J=9.3 Hz, 2H), 3.80-3.74 (m, 1H), 3.67 (d, J=10.6 Hz, 1H), 3.19-3.11 (m, 1H), 2.94 (s, 3H), 2.08 (d, J=9.6 Hz, 1H), 1.85 (s, 3H), 1.83 (s, 3H), 1.49-1.31 (m, 2H), 1.27 (d, J=6.7 Hz, 3H).

Compound ("A64"):

LCMS: [MH+] 475; ¹H NMR (500 MHz, DMSO-d₆) δ 8.48 (s, 1H), 8.15 (d, J=7.8 Hz, 1H), 7.66 (d, J=8.3 Hz, 1H), 7.47 (t, J=7.7 Hz, 1H), 4.81 (dt, J=9.7, 4.8 Hz, 1H), 4.73 (dd, J=5.8, 3.8 Hz, 2H), 4.70 (d, J=5.9 Hz, 2H), 4.39 (dd, J=10.9, 3.3 Hz, 1H), 3.98-3.88 (m, 2H), 3.85 (d, J=11.5 Hz, 1H), 3.77 (dd, J=11.0, 8.8 Hz, 1H), 3.67 (dd, J=11.6, 3.3 Hz, 1H), 3.19-3.12 (m, 1H), 2.95 (s, 3H), 2.68-2.56 (m, 2H), 1.85 (s, 3H), 1.83 (s, 3H), 1.27 (d, J=6.7 Hz, 3H).

Synthesis of [(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]-(1H-pyrazol-4-ylmethyl)-amine ("A65")

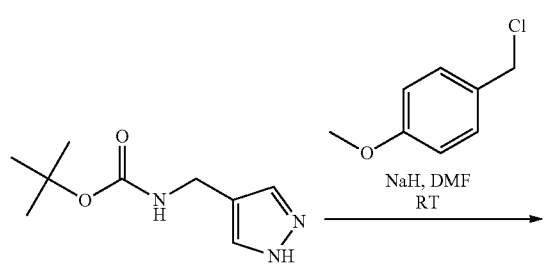

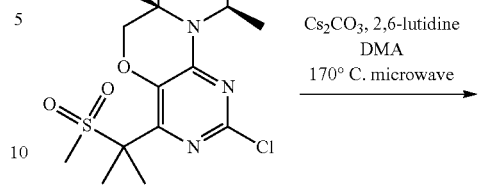

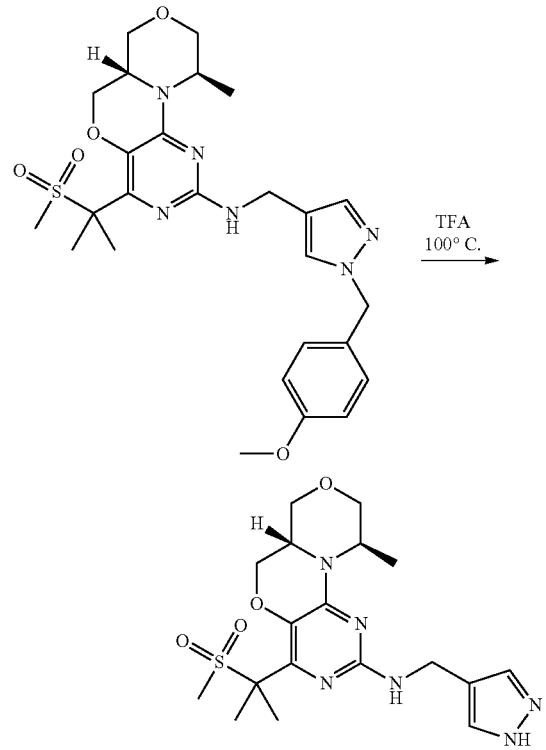

Yellow solid; LCMS (method F): 0.73 min; [MH+] 422.2.

¹H NMR (500 MHz, DMSO-d₆, TFA-d₁) δ 7.49 (s, 2H), 4.68-4.54 (m, 1H), 4.32-4.14 (m, 3H), 3.88-3.73 (m, 3H), 3.59-3.53 (m, 2H), 3.08 (t, J=10.5 Hz, 1H), 2.86 (s, 3H), 1.72 (s, 3H), 1.68 (s, 3H), 1.19 (d, J=6.9 Hz, 3H).

Synthesis of 7-[(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]-isoquinolin-3-ylamine ("A66")

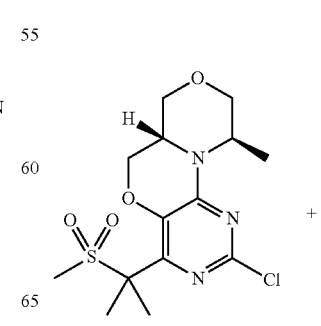

+

111

-continued

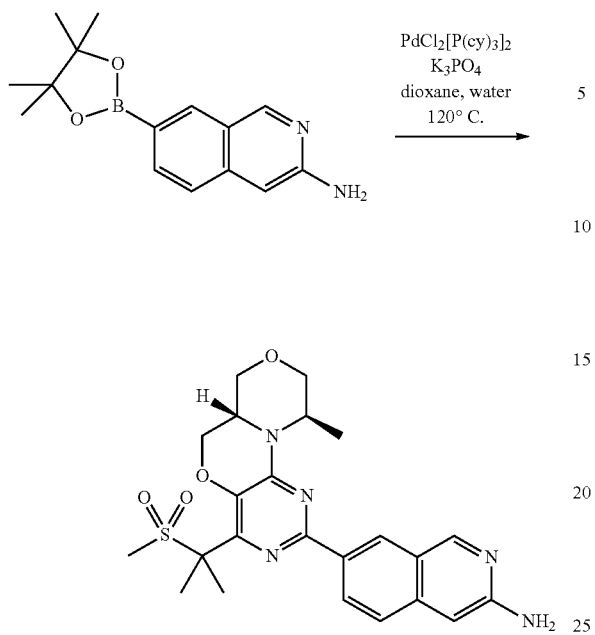

Yellow solid. LCMS (method F): 0.9 min; [MH+] 470.0.

$^1$H NMR (500 MHz, DMSO-d$_6$) δ 8.97 (s, 1H), 8.69 (s, 1H), 8.38-8.33 (m, 1H), 7.58 (d, J=8.8 Hz, 1H), 6.70 (s, 1H), 6.38-6.07 (m, 2H), 4.94-4.88 (m, 1H), 4.39 (dd, J=11.0, 3.4 Hz, 1H), 3.98-3.90 (m, 2H), 3.85 (d, J=11.4 Hz, 1H), 3.77 (dd, J=11.0, 8.7 Hz, 1H), 3.69 (dd, J=11.5, 3.3 Hz, 1H), 3.17 (t, J=11.8 Hz, 1H), 2.95 (s, 3H), 1.87 (s, 3H), 1.86 (s, 3H), 1.31 (d, J=6.7 Hz, 3H).

Synthesis of (5R,8aS)-3-(5-fluoro-1H-pyrrolo[2,3-c]pyridin-2-yl)-1-(1-methanesulfonyl-1-methyl-ethyl)-5-methyl-5,6,8a,9-tetrahydro-8H-7,10-dioxa-2,4,4b-triaza-phenanthrene ("A67") Trifluoroacetate

112

-continued

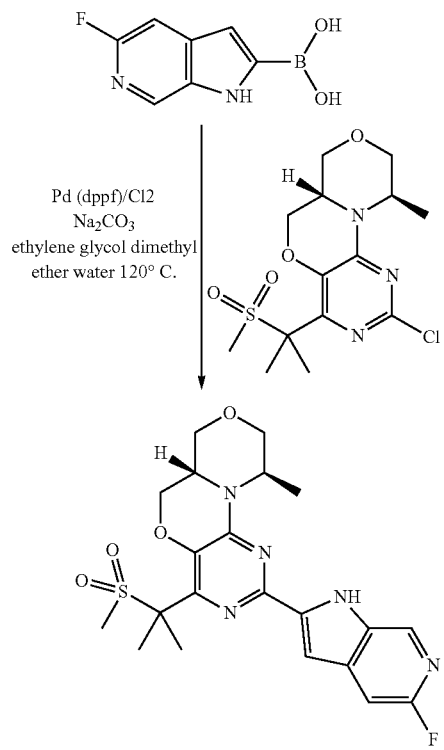

Yellow solid; LCMS (method D): 2.55 min; [MH+] 462.2.

$^1$H NMR (700 MHz, DMSO-d$_6$) δ 11.80-11.77 (m, 1H), 8.42-8.41 (m, 1H), 7.21-7.20 (m, 1H), 7.13-7.12 (m, 1H), 4.99-4.95 (m, 1H), 4.41 (dd, J=11.0, 3.5 Hz, 1H), 3.98-3.93 (m, 2H), 3.86 (d, J=11.4 Hz, 1H), 3.78 (dd, J=10.9, 9.1 Hz, 1H), 3.68 (dd, J=11.6, 3.3 Hz, 1H), 3.19-3.15 (m, 1H), 2.95 (s, 3H), 1.87 (s, 3H), 1.86 (s, 3H), 1.29 (d, J=6.8 Hz, 3H).

Synthesis of 1-[(S)-1-(1-methanesulfonyl-1-methyl-ethyl)-5-(R)-methyl-5,6,8a,9-tetrahydro-8H-7,10-dioxa-2,4,4b-triaza-phenanthren-3-yl]-1H-pyrazole-4-carboxylic Acid Amide ("A68")

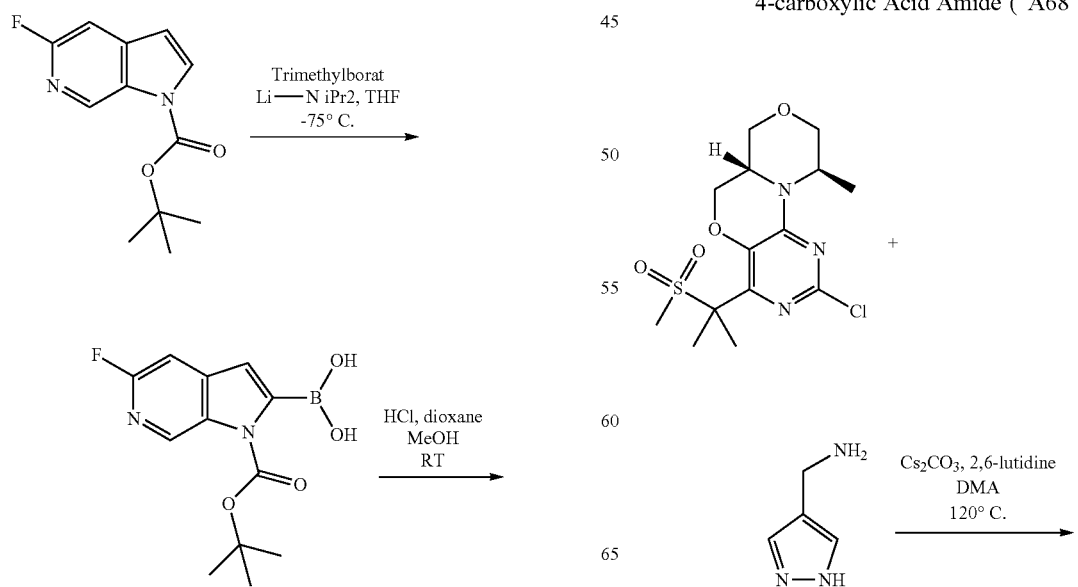

113

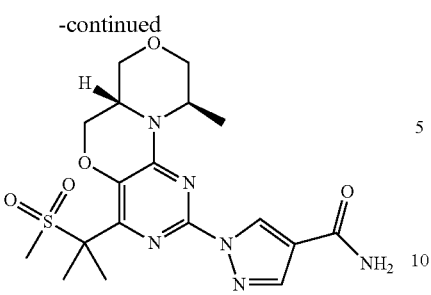

Yellow solid. LCMS (method F): 0.72 min; [MH+] 437.
¹H NMR (500 MHz, DMSO-d₆) δ 9.01 (s, 1H), 8.08 (s, 1H), 7.89 (s, 1H), 7.25 (s, 1H), 4.82-4.71 (m, 1H), 4.46-4.35 (m, 1H), 4.00-3.92 (m, 2H), 3.85-3.73 (m, 2H), 3.65 (dd, J=11.6, 3.4 Hz, 1H), 3.21-3.12 (m, 1H), 3.02 (s, 3H), 1.82 (s, 3H), 1.80 (s, 3H), 1.29 (d, J=6.8 Hz, 3H).

Synthesis of [(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]-(2H[1,2,3]triazol-4-yl)-amine ("A69")

114

Yellow solid; LCMS (method D): 1.72 min; [MH+] 410.0.
¹H NMR (400 MHz, DMSO-d₆) δ 14.16 (s, 1H), 9.35 (s, 1H), 7.90 (s, 1H), 4.64-4.57 (m, 1H), 4.26 (dd, J=11.0, 3.3 Hz, 1H), 3.92-3.83 (m, 2H), 3.82-3.77 (m, 1H), 3.67-3.58 (m, 2H), 3.15-3.07 (m, 1H), 2.93 (s, 3H), 1.76 (s, 3H), 1.73 (s, 3H), 1.25 (d, J=6.8 Hz, 3H).

Synthesis of 1-[(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]-1H-indole-3-carbonitrile ("A70")

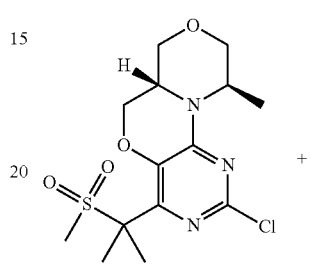

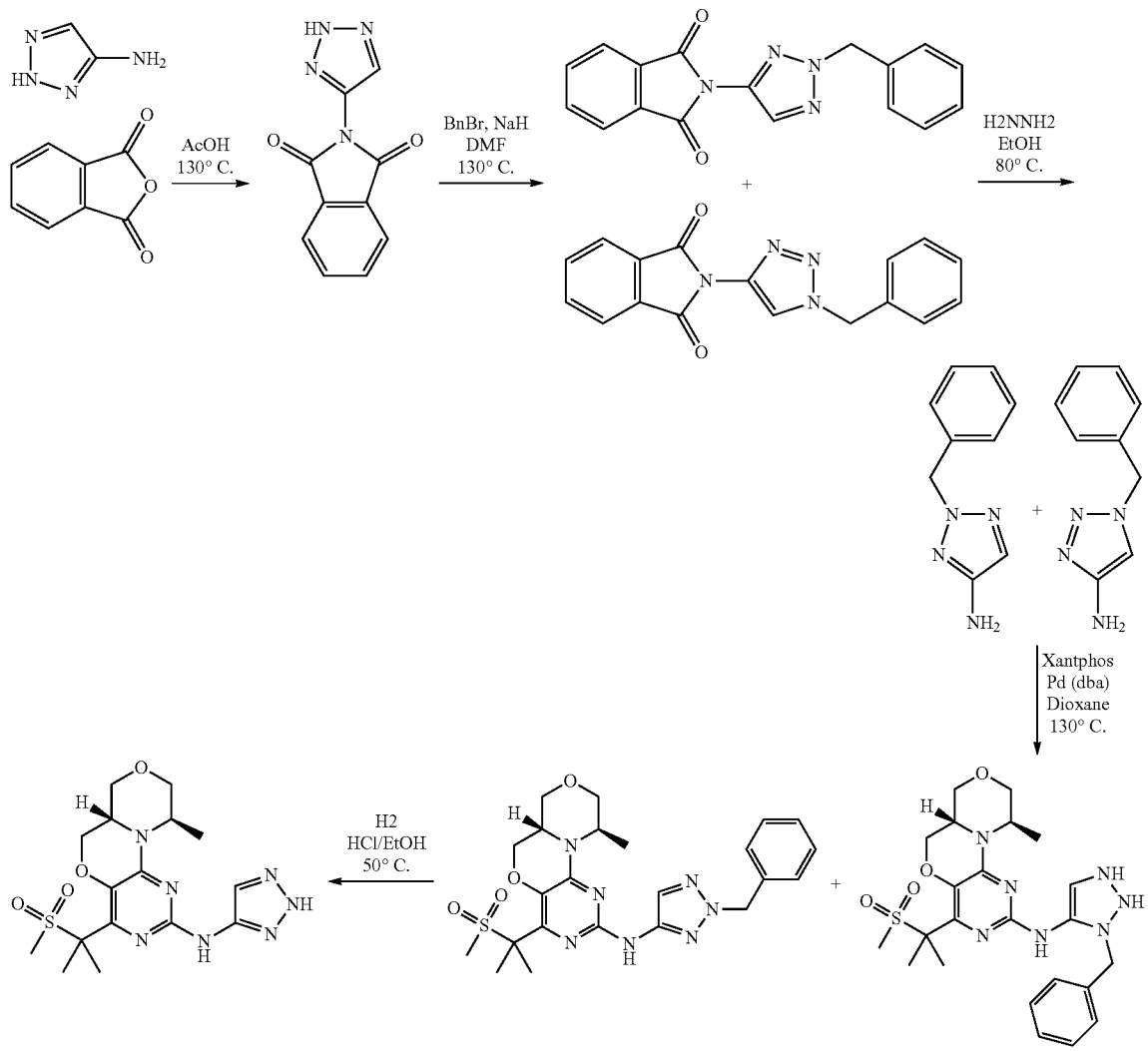

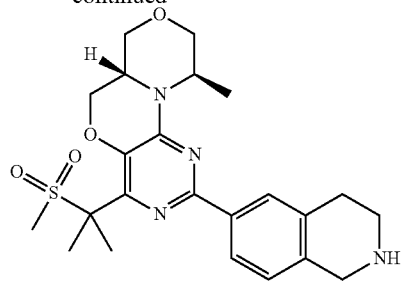

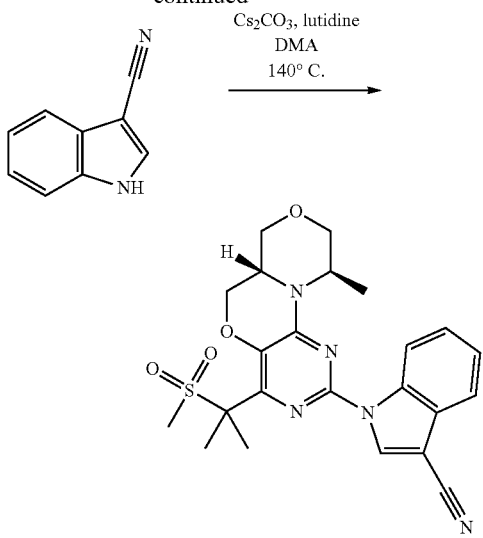

Yellow solid; LCMS (method D): 0.73 min; [MH+] 468.0.
$^1$H NMR (400 MHz, DMSO-d$_6$) δ 9.07 (s, 1H), 8.66 (d, J=8.4 Hz, 1H), 7.74-7.69 (m, 1H), 7.51-7.44 (m, 1H), 7.42-7.36 (m, 1H), 4.89-4.80 (m, 1H), 4.42 (dd, J=10.9, 3.4 Hz, 1H), 4.04-3.93 (m, 2H), 3.89-3.75 (m, 2H), 3.69 (dd, J=11.7, 3.2 Hz, 1H), 3.23-3.14 (m, 1H), 2.96 (s, 3H), 1.89 (s, 3H), 1.86 (s, 3H), 1.33 (d, J=6.8 Hz, 3H).

Synthesis of (5R,8aS)-1-(1-methanesulfonyl-1-methyl-ethyl)-5-methyl-3-(1,2,3,4-tetrahydro-isoquinolin-6-yl)-5,6,8a,9-tetrahydro-8H-7,10-dioxa-2,4,4b-triaza-phenanthrene ("A71")

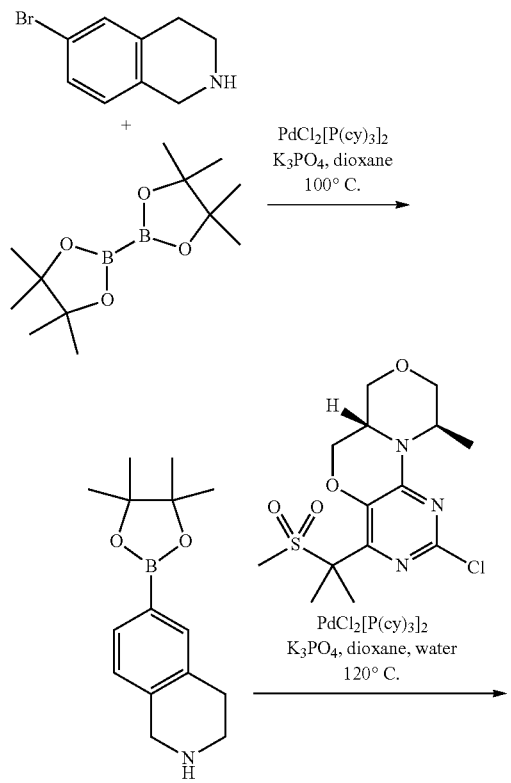

Yellow solid; LCMS (method F): 1.13 min; [MH+] 459.2.
$^1$H NMR (400 MHz, DMSO-d$_6$) δ 7.78 (dd, J=8.4, 2.1 Hz, 1H), 7.75-7.72 (m, 1H), 6.44 (d, J=8.4 Hz, 1H), 6.06-6.02 (m, 1H), 4.82-4.75 (m, 1H), 4.32 (dd, J=10.9, 3.3 Hz, 1H), 3.93-3.84 (m, 2H), 3.81 (d, J=11.5 Hz, 1H), 3.70 (dd, J=11.0, 9.1 Hz, 1H), 3.64 (dd, J=11.7, 3.2 Hz, 1H), 3.24-3.19 (m, 2H), 3.17-3.08 (m, 1H), 2.92 (s, 3H), 2.71 (t, J=6.3 Hz, 2H), 1.84-1.73 (m, 8H), 1.25 (d, J=6.7 Hz, 3H).

Synthesis of 6-[(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]-quinolin-2-ylamine ("A72")

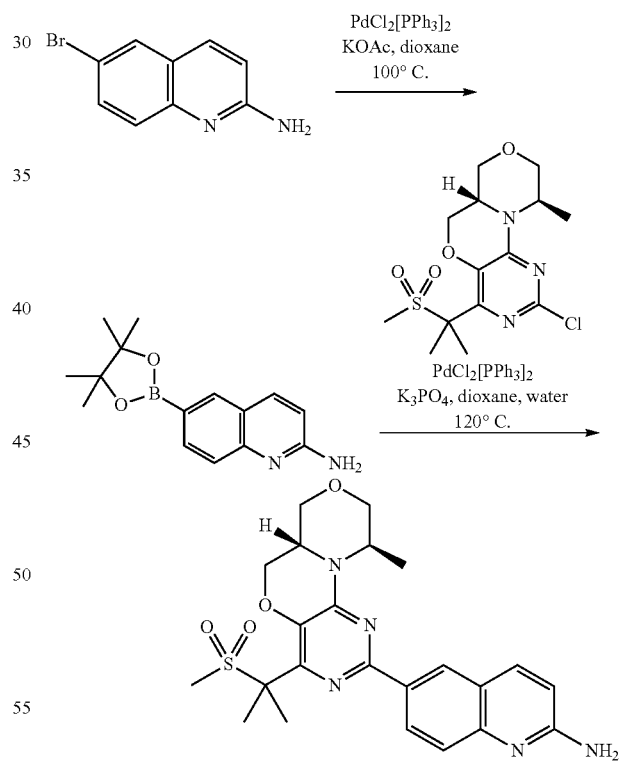

Colourless solid; LCMS (method F): 0.84 min; [MH+] 470.1.
$^1$H NMR (500 MHz, DMSO-d$_6$) δ 8.49 (d, J=2.0 Hz, 1H), 8.36 (dd, J=8.7, 2.0 Hz, 1H), 7.99 (d, J=8.9 Hz, 1H), 7.48 (d, J=8.8 Hz, 1H), 6.77 (d, J=8.9 Hz, 1H), 6.54 (s, 2H), 4.93-4.86 (m, 1H), 4.38 (dd, J=10.9, 3.4 Hz, 1H), 3.98-3.88 (m, 2H), 3.85 (d, J=11.5 Hz, 1H), 3.80-3.73 (m, 1H), 3.68 (dd, J=11.4, 3.2 Hz, 1H), 3.16 (t, J=11.8 Hz, 1H), 2.96 (s, 3H), 1.87 (s, 3H), 1.86 (s, 3H), 1.30 (d, J=6.7 Hz, 3H).

Synthesis of [(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]-(2H-pyrazol-3-yl)-amine ("A73") and [(5R,8aS)-1-(1-methanesulfonyl-1-methylethyl)-5-methyl-5,6,8a,9-tetrahydro-8H-7,10-dioxa-2,4,4b-triaza-phenanthren-3-yl]-methyl-(2H-pyrazol-3-yl)-amine ("A74")

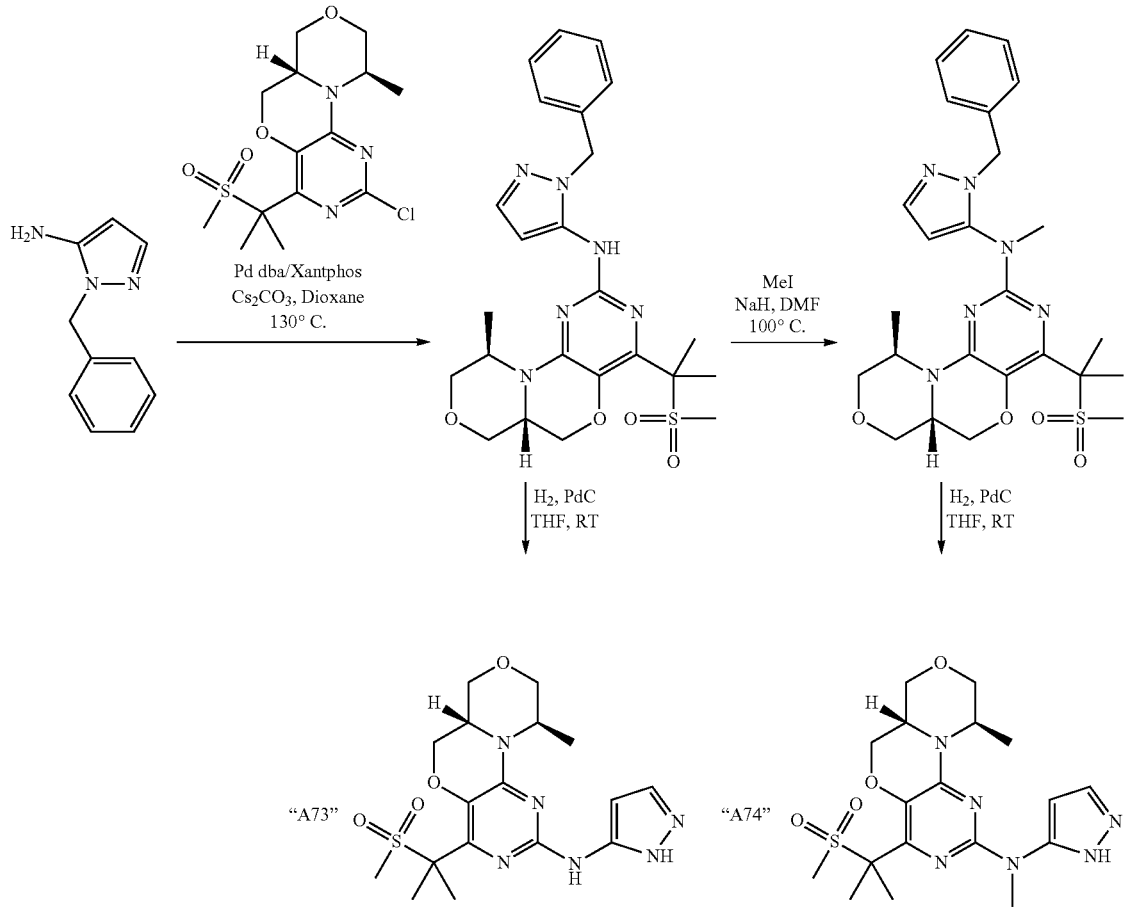

"A73": colourless solid; LCMS (method F): 0.78 min; [MH+] 409.2.

$^1$H NMR (400 MHz, DMSO-d$_6$) δ 12.00 (s, 1H), 9.53-8.70 (m, 1H), 7.57-7.21 (m, 1H), 6.56-5.80 (m, 1H), 4.63-4.56 (m, 1H), 4.29-4.22 (m, 1H), 3.92-3.77 (m, 3H), 3.67-3.57 (m, 2H), 3.15-3.07 (m, 1H), 2.93 (s, 3H), 1.75 (s, 3H), 1.72 (s, 3H), 1.24 (d, J=6.7 Hz, 3H).

"A74": colourless solid; LCMS (method F): 0.81 min; [MH+] 423.2.

$^1$H NMR (400 MHz, DMSO-d$_6$) δ 12.14 (s, 1H), 7.59-7.56 (m, 1H), 6.62-6.59 (m, 1H), 4.59-4.51 (m, 1H), 4.26 (dd, J=11.1, 3.0 Hz, 1H), 3.92-3.81 (m, 2H), 3.79 (d, J=11.4 Hz, 1H), 3.66-3.57 (m, 2H), 3.48 (s, 3H), 3.15-3.06 (m, 1H), 2.88 (s, 3H), 1.76 (s, 3H), 1.72 (s, 3H), 1.24 (d, J=6.8 Hz, 3H).

Synthesis of [(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]-(1H-pyrazol-4-yl)-amine ("A75")

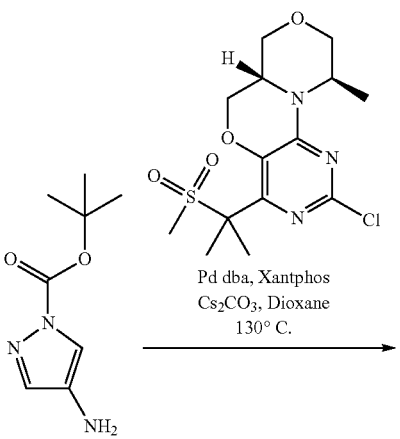

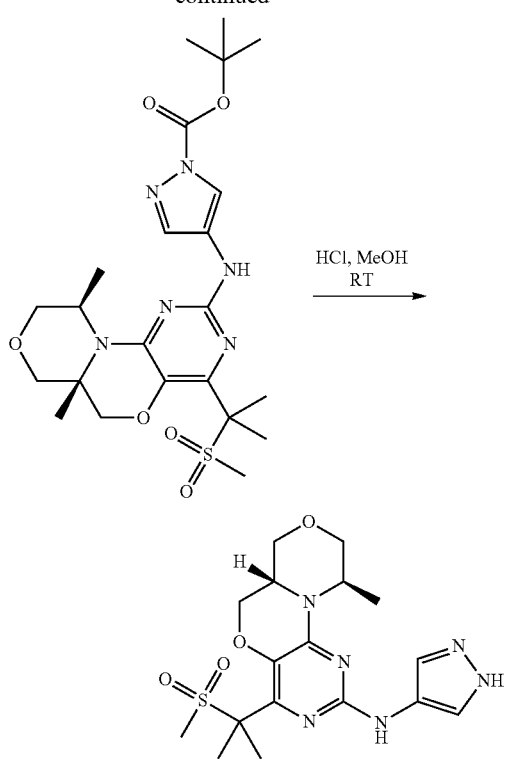

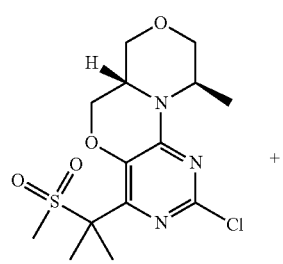

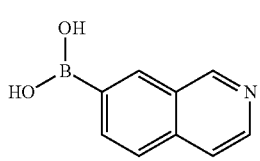

Yellow solid; LCMS (method D): 1.67 min; [MH+] 409.0.

$^1$H NMR (400 MHz, DMSO-d$_6$) δ 12.62-11.98 (m, 1H), 8.62 (s, 1H), 7.72-7.54 (m, 2H), 4.62-4.55 (m, 1H), 4.24 (dd, J=10.9, 3.3 Hz, 1H), 3.91-3.76 (m, 3H), 3.64-3.57 (m, 2H), 3.14-3.07 (m, 1H), 2.91 (s, 3H), 1.76 (s, 3H), 1.73 (s, 3H), 1.24 (d, J=6.7 Hz, 3H).

Synthesis of (5R,8aS)-3-isoquinolin-7-yl-1-(1-methanesulfonyl-1-methyl-ethyl)-5-methyl-5,6,8a,9-tetrahydro-8H-7,10-dioxa-2,4,4b-triaza-phenanthrene ("A76")

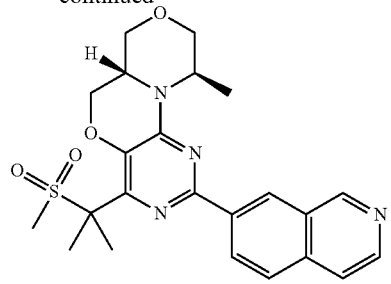

Colourless solid; LCMS (method F): 1.13 min; [MH+] 455.2.

$^1$H NMR (500 MHz, DMSO-d$_6$) δ 9.45 (s, 1H), 8.99-8.97 (m, 1H), 8.66 (dd, J=8.6, 1.7 Hz, 1H), 8.53 (d, J=5.7 Hz, 1H), 8.04 (d, J=8.7 Hz, 1H), 7.87-7.84 (m, 1H), 4.96 (dd, J=6.8, 2.9 Hz, 1H), 4.42 (dd, J=10.9, 3.3 Hz, 1H), 4.00-3.92 (m, 2H), 3.87 (d, J=11.4 Hz, 1H), 3.80 (dd, J=11.0, 8.8 Hz, 1H), 3.70 (dd, J=11.6, 3.2 Hz, 1H), 3.22-3.15 (m, 1H), 2.97 (s, 3H), 1.90 (s, 3H), 1.89 (s, 3H), 1.33 (d, J=6.7 Hz, 3H).

Synthesis of (5R,8aS)-1-(1-methanesulfonyl-1-methyl-ethyl)-5-methyl-3-quinolin-6-yl-5,6,8a,9-tetrahydro-8H-7,10-dioxa-2,4,4b-triaza-phenanthrene ("A77")

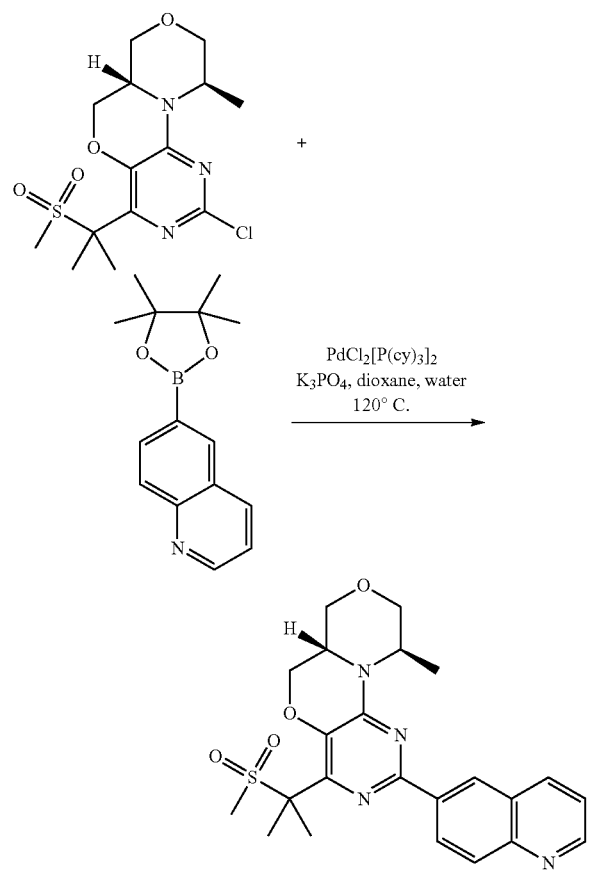

Colourless solid; LCMS (method F): 1.22 min; [MH+] 455.2.

$^1$H NMR (500 MHz, DMSO-d$_6$) δ 8.92 (dd, J=4.2, 1.7 Hz, 1H), 8.85 (d, J=1.9 Hz, 1H), 8.65 (dd, J=8.9, 1.9 Hz, 1H), 8.54-8.51 (m, 1H), 8.11-8.07 (m, 1H), 7.57 (dd, J=8.3, 4.2 Hz, 1H), 4.97-4.91 (m, 1H), 4.42 (dd, J=11.0, 3.3 Hz, 1H), 3.99-3.93 (m, 2H), 3.87 (d, J=11.4 Hz, 1H), 3.80 (dd, J=11.0, 8.9 Hz, 1H), 3.70 (dd, J=11.5, 3.2 Hz, 1H), 3.21-3.15 (m, 1H), 2.98 (s, 3H), 1.90 (s, 3H), 1.89 (s, 3H), 1.32 (d, J=6.8 Hz, 3H).

Synthesis of 6-[(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]-quinazolin-2-ylamine ("A78")

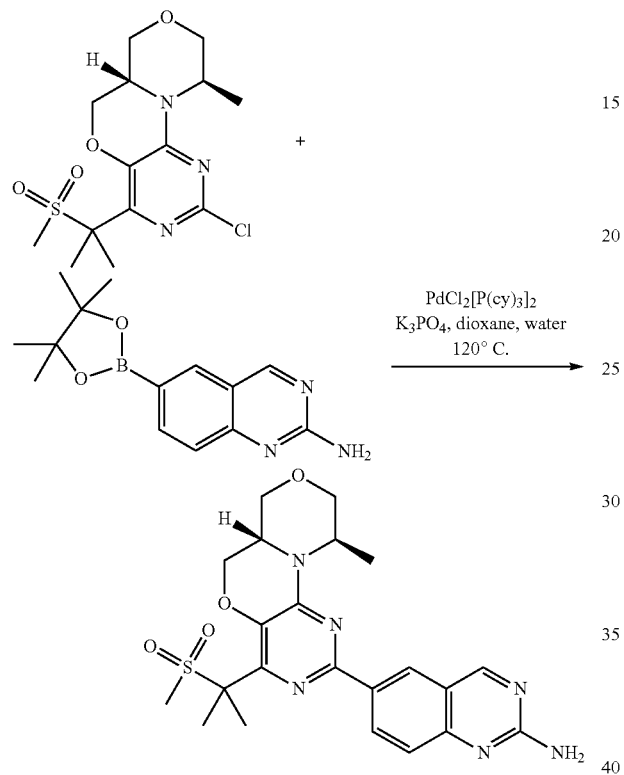

Beige solid; LCMS (method F): 0.86 min; [MH+] 471.2.
$^1$H NMR (400 MHz, DMSO-d$_6$) δ 9.24-9.22 (m, 1H), 8.67-8.64 (m, 1H), 8.57 (dd, J=8.9, 2.0 Hz, 1H), 7.49-7.45 (m, 1H), 6.94 (s, 2H), 4.94-4.87 (m, 1H), 4.39 (dd, J=11.0, 3.4 Hz, 1H), 3.98-3.89 (m, 2H), 3.85 (d, J=11.5 Hz, 1H), 3.77 (dd, J=11.0, 8.8 Hz, 1H), 3.68 (dd, J=11.5, 3.2 Hz, 1H), 3.17 (t, J=11.7 Hz, 1H), 2.95 (s, 3H), 1.87 (s, 3H), 1.86 (s, 3H), 1.30 (d, J=6.7 Hz, 3H).

Synthesis of [(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]-(1H[1,2,4]triazol-3-yl)-amine ("A79")

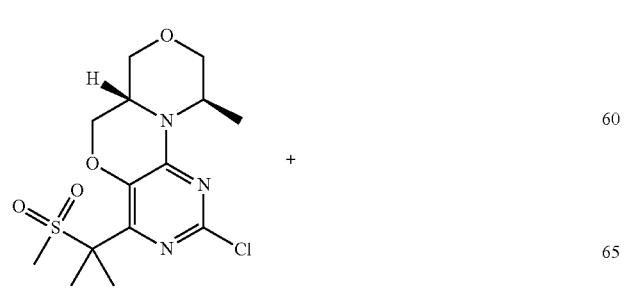

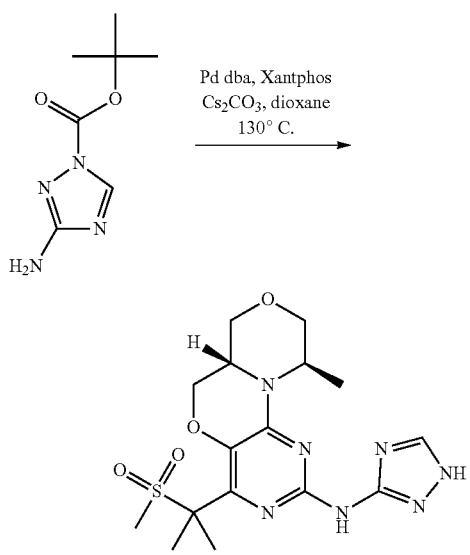

Yellow solid; LCMS (method D): 1.73 min; [MH+] 410.0.
$^1$H NMR (500 MHz, DMSO-d$_6$) δ 12.62 (s, 1H), 10.49 (s, 1H), 7.63 (d, J=1.6 Hz, 1H), 4.68-4.62 (m, 1H), 4.33 (dd, J=11.1, 3.5 Hz, 1H), 3.94-3.87 (m, 2H), 3.80 (d, J=11.5 Hz, 1H), 3.70 (dd, J=11.1, 8.8 Hz, 1H), 3.60 (dd, J=11.5, 3.2 Hz, 1H), 3.12 (t, J=11.8 Hz, 1H), 3.01 (s, 3H), 1.78 (s, 3H), 1.76 (s, 3H), 1.23 (d, J=6.8 Hz, 3H).

Synthesis of (5R,8aS)-1-(1-methanesulfonyl-1-methyl-ethyl)-5-methyl-3-(1H-pyrazol-4-yloxy)-5,6,8a,9-tetrahydro-8H-7,10-dioxa-2,4,4b-triaza-phenanthrene ("A80")

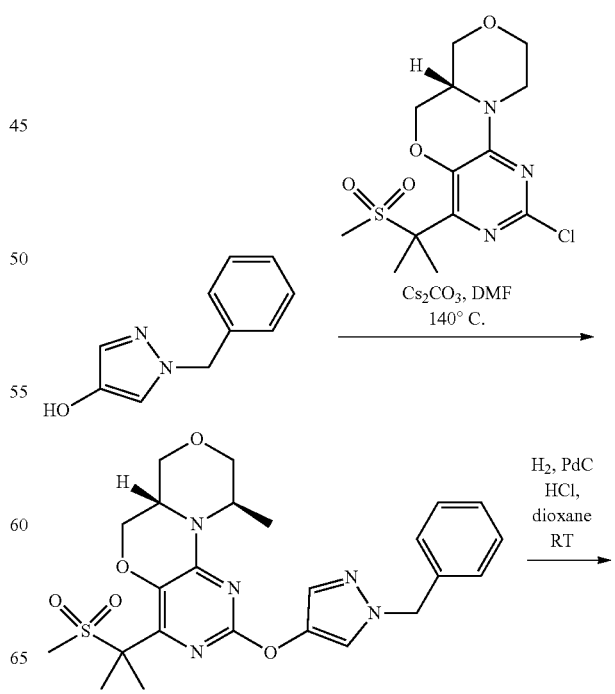

123

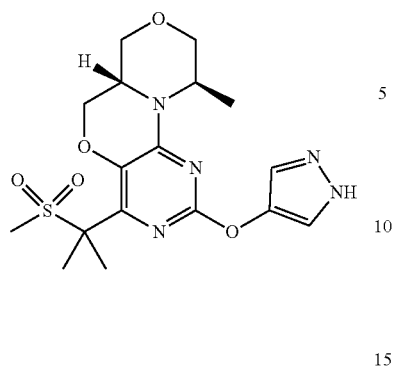

Colourless solid; LCMS (method D): 1.99 min; [MH+] 410.0.

$^1$H NMR (500 MHz, DMSO-d$_6$) δ 12.61 (s, 1H), 7.80 (s, 1H), 7.52 (s, 1H), 4.52-4.46 (m, 1H), 4.32 (dd, J=11.1, 3.5 Hz, 1H), 3.93-3.86 (m, 2H), 3.77 (d, J=11.6 Hz, 1H), 3.67 (dd, J=11.1, 8.9 Hz, 1H), 3.58 (dd, J=11.7, 3.3 Hz, 1H), 3.14-3.08 (m, 1H), 2.83 (s, 3H), 1.72 (s, 3H), 1.67 (s, 3H), 1.22 (d, J=6.8 Hz, 3H).

Synthesis of isopropyl-{4-[(S)-1-(1-methanesulfonyl-1-methyl-ethyl)-5-(R)methyl-5,6,8a,9-tetrahydro-8H-7,10-dioxa-2,4,4b-triaza-phenanthren-3-yl]-1H-pyrrolo[2,3-b]pyridin-5-yl}-amine ("A81")

124

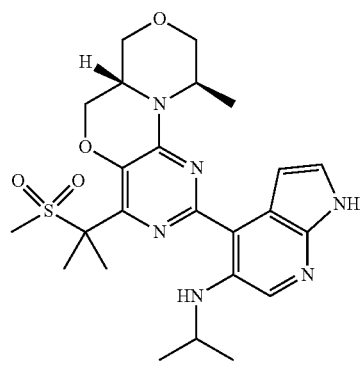

Yellow solid; LCMS (method F): 1.04 min; [MH+] 501.2.

$^1$H NMR (500 MHz, DMSO-d$_6$) δ 11.21-11.18 (m, 1H), 7.94 (s, 1H), 7.31 (t, J=2.9 Hz, 1H), 7.26 (d, J=8.7 Hz, 1H), 6.88 (dd, J=3.3, 2.1 Hz, 1H), 4.73-4.68 (m, 1H), 4.41 (dd, J=10.9, 3.5 Hz, 1H), 4.02-3.93 (m, 2H), 3.89-3.82 (m, 3H), 3.66 (dd, J=11.5, 3.2 Hz, 1H), 3.17 (t, J=10.7 Hz, 1H), 2.96 (s, 3H), 1.88 (s, 3H), 1.82 (s, 3H), 1.33 (d, J=6.8 Hz, 3H), 1.21 (d, J=6.3 Hz, 3H), 1.16 (d, J=6.5 Hz, 3H).

Synthesis of 1-[(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]-1H-pyrazol-3-ol ("A82")

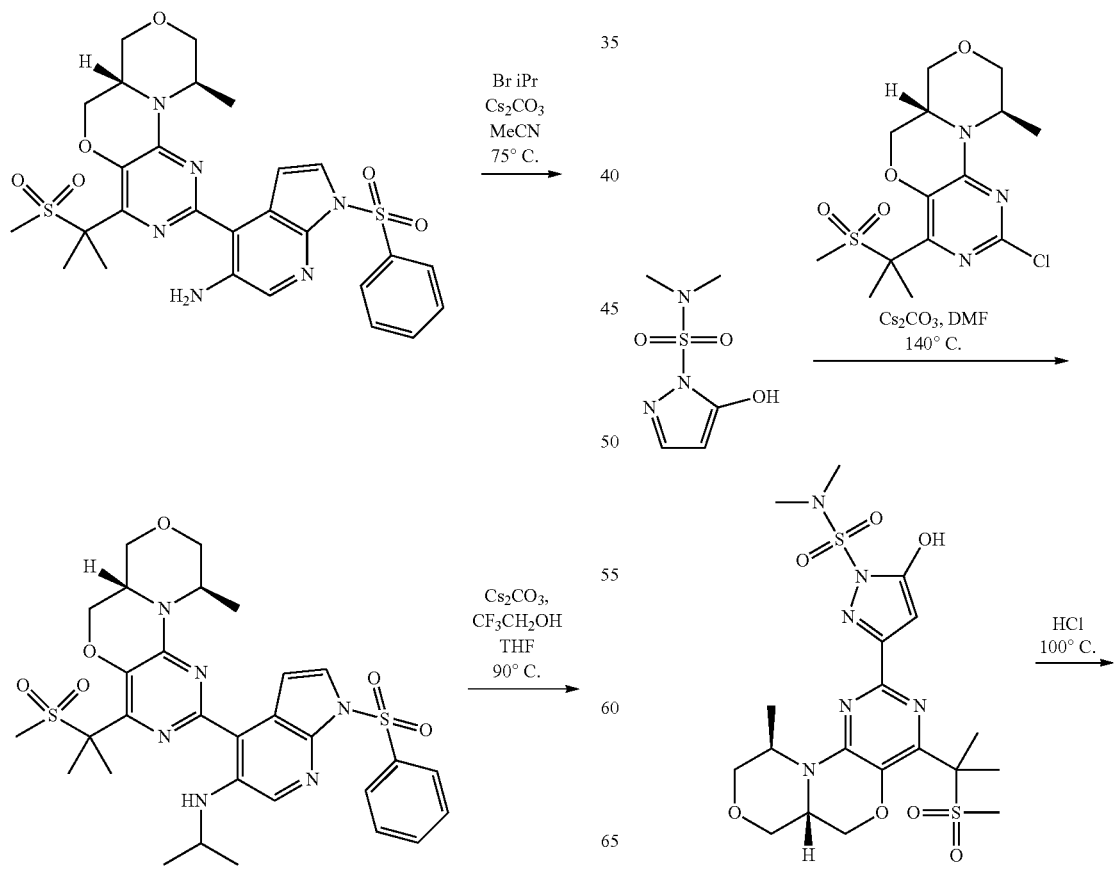

125

-continued

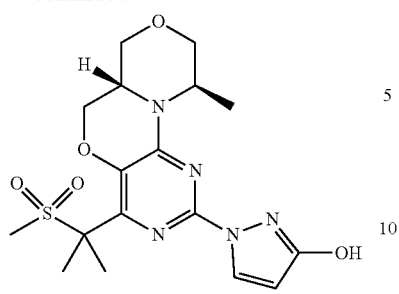

Beige solid; LCMS (method F): 1.11 min; [MH+] 410.2.
$^1$H NMR (400 MHz, DMSO-d$_6$) δ 10.50-10.37 (m, 1H), 8.27 (d, J=2.7 Hz, 1H), 5.81 (d, J=2.6 Hz, 1H), 4.76-4.69 (m, 1H), 4.35 (dd, J=11.0, 3.5 Hz, 1H), 3.98-3.89 (m, 2H), 3.80 (d, J=11.5 Hz, 1H), 3.71 (dd, J=11.1, 8.9 Hz, 1H), 3.61 (dd, J=11.5, 3.1 Hz, 1H), 3.19-3.10 (m, 1H), 2.99 (s, 3H), 1.79 (s, 3H), 1.76 (s, 3H), 1.25 (d, J=6.8 Hz, 3H).

126

Synthesis of {4-[(R)-1-(1-methanesulfonyl-1-methyl-ethyl)-5-(S)-methyl-5,6,8a,9-tetrahydro-8H-7,10-dioxa-2,4,4b-triaza-phenanthren-3-yl]-1H-pyrrolo[2,3-b]pyridin-5-yl}-methyl-amine ("A83") and 4-[(4bS,8R)-1-(1-methanesulfonyl-1-methyl-ethyl)-5-methyl-5,6,8a,9-tetrahydro-8H-7,10-dioxa-2,4,4b-triaza-phenanthren-3-yl]-1H-pyrrolo[2,3-b]pyridin-5-ylamine ("A84")

Scheme for the Preparation of "A83":

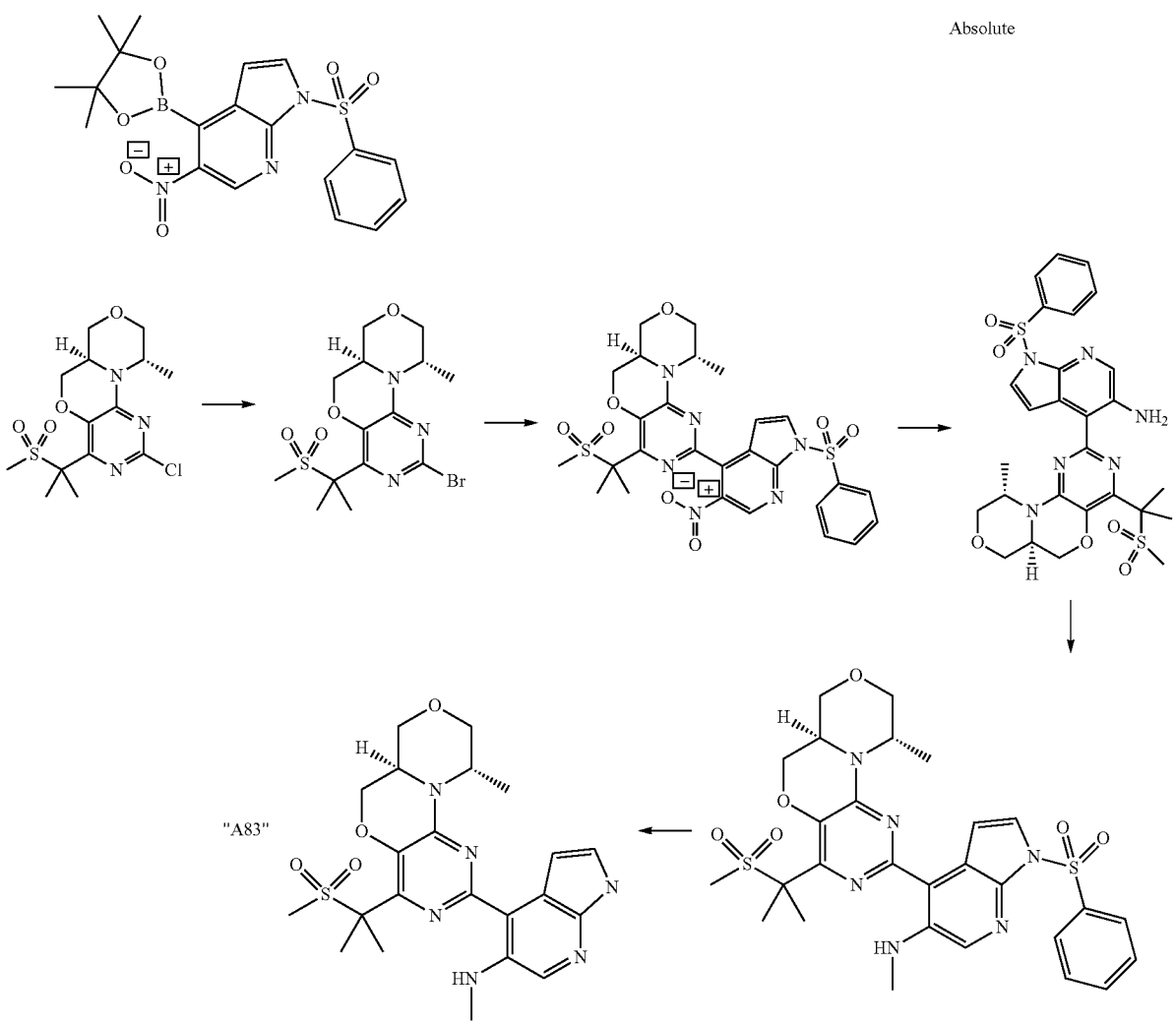

Scheme for the Preparation of "A84":

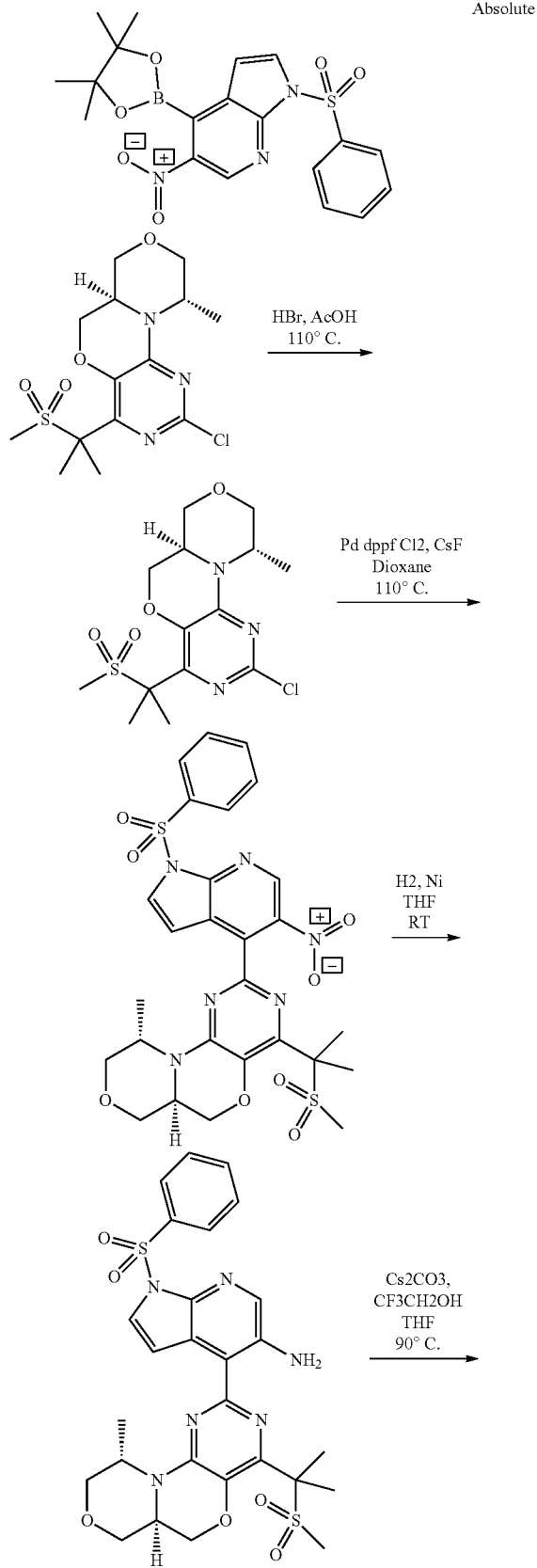

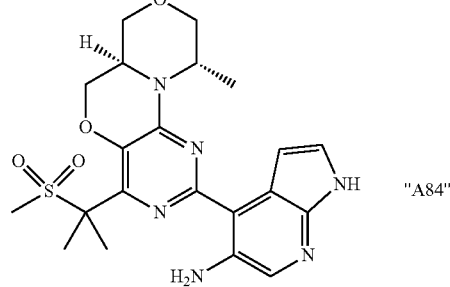

"A83": Yellow solid; LCMS (method D): 2.01 min; [MH+] 473.

$^1$H NMR (500 MHz, DMSO-d$_6$) δ 11.05-10.92 (m, 1H), 7.87 (s, 1H), 7.80 (q, J=5.2 Hz, 1H), 7.35 (t, J=2.9 Hz, 1H), 6.92 (dd, J=3.3, 2.1 Hz, 1H), 4.71 (qd, J=6.7, 2.7 Hz, 1H), 4.43 (dd, J=10.9, 3.3 Hz 1H), 4.02-3.93 (m, 2H) 3.90-3.82 (m, 2H), 3.68 (dd, J=11.6, 3.2 Hz, 1H), 3.22-3.13 (m, 1H), 3.00 (s, 3H), 2.91 (d, J=5.2 Hz, 3H), 1.87 (s, 3H), 1.82 (s, 3H), 1.34 (d, J=6.8 Hz, 3H).

"A84": Yellow solid; LCMS (method F): 0.82 min; [MH+] 459.3.

$^1$H NMR (400 MHz, DMSO-d$_6$) δ 11.15 (s, 1H), 7.87 (s, 1H), 7.27 (t, J=2.9 Hz, 1H), 6.91 (dd, J=3.3, 2.0 Hz, 1H), 6.29-6.17 (m, 2H), 4.74-4.67 (m, 1H), 4.41 (dd, J=10.8, 3.2 Hz, 1H), 4.01-3.92 (m, 2H), 3.89-3.81 (m, 2H), 3.68 (dd, J=11.6, 3.1 Hz, 1H), 3.21-3.14 (m, 1H), 2.96 (s, 3H), 1.87 (s, 3H), 1.82 (s, 3H), 1.32 (d, J=6.7 Hz, 3H).

Compounds 4-[(10S,14S)-6-(2-methanesulfonylpropan-2-yl)-14-methyl-8,12-dioxa-1,3,5-triazatricyclo[8.4.0.0^{2,7}]tetradeca-2,4,6-trien-4-yl]-N-methyl-1H-pyrrolo[2,3-b]pyridin-5-amine ("A85") and 4-[(S)-1-(1-methanesulfonyl-1-methyl-ethyl)-5-(S)-methyl-5,6,8a,9-tetrahydro-8H-7,10-dioxa-2,4,4b-triaza-phenanthren-3-yl]-1H-pyrrolo[2,3-b]pyridin-5-ylamine ("A86") have been prepared analogously to "A83" and "A84":

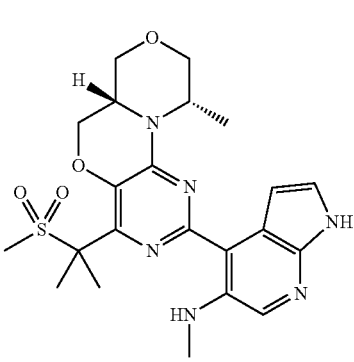

Yellow solid; LCMS (method D): 2.005 min; [MH+] 473.

$^1$H NMR (400 MHz, DMSO-d$_6$) δ 11.17 (s, 1H), 7.89-7.79 (m, 2H), 7.32 (t, J=3.0 Hz, 1H), 7.01 (dd, J=3.3, 2.0 Hz, 1H), 4.42 (dd, J=10.6, 3.2 Hz, 1H), 4.32-4.17 (m, 3H), 4.00 (dd, J=10.4, 3.9 Hz, 1H), 3.79 (dd, J=10.7, 9.3 Hz, 1H), 3.71-3.61 (m, 2H), 2.99 (s, 3H), 2.91 (d, J=5.2 Hz, 3H), 1.86 (s, 3H), 1.83 (s, 3H), 1.47 (d, J=6.4 Hz, 3H).

"A86"

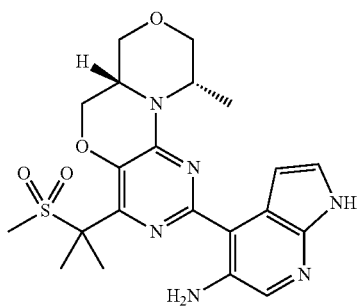

Yellow solid; LCMS (method D): 1.94 min; [MH+] 459. $^{1}$H NMR (500 MHz, DMSO-d$_{6}$) δ 11.16 (s, 1H), 7.86 (s, 1H), 7.26 (t, J=2.9 Hz, 1H), 7.00 (dd, J=3.2, 2.1 Hz, 1H), 6.24 (s, 2H), 4.42 (dd, J=10.6, 3.2 Hz, 1H), 4.32-4.17 (m, 3H), 4.00 (dd, J=10.3, 3.9 Hz, 1H), 3.78 (dd, J=10.7, 9.4 Hz, 1H), 3.70-3.62 (m, 2H), 2.98 (s, 3H), 1.86 (s, 3H), 1.83 (s, 3H), 1.46 (d, J=6.4 Hz, 3H).

Synthesis of 4-[(10S,14R)-6-(2-methanesulfonylpropan-2-yl)-14-methyl-8,12-dioxa-1,3,5-triazatricyclo[8.4.0.0^{2,7}]tetradeca-2,4,6-trien-4-yl]-1,3-dihydro-2lambda6,1-benzothiazole-2,2-dione ("A87")

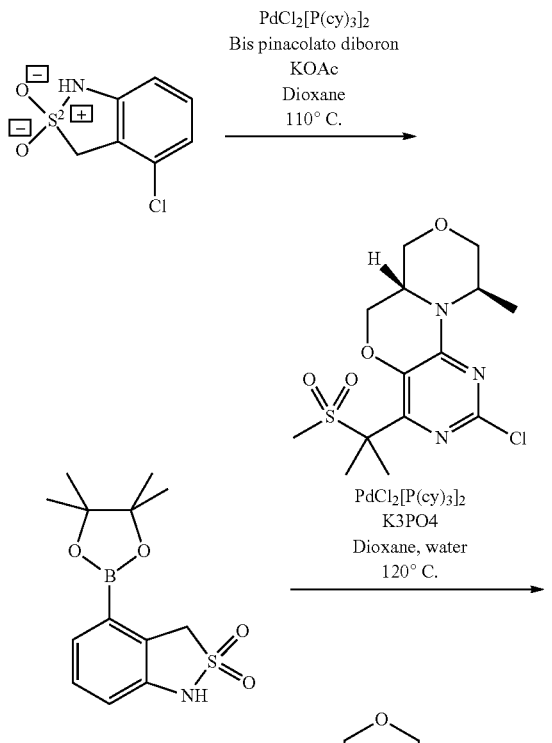

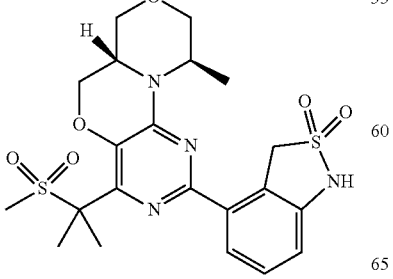

Yellow solid; LCMS (method F): 1.073 min; [MH+] 495. $^{1}$H NMR (500 MHz, DMSO-d$_{6}$) δ 10.63 (s, 1H), 7.84 (dd, J=8.1, 1.1 Hz, 1H), 7.37 (t, J=7.9 Hz, 1H), 6.90 (dd, J=7.8, 1.1 Hz, 1H), 4.86 (d, J=17.1 Hz, 1H), 4.80-4.67 (m, 2H), 4.40 (dd, J=10.9, 3.3 Hz, 1H), 3.97-3.88 (m, 2H), 3.87-3.74 (m, 2H), 3.65 (dd, J=11.6, 3.2 Hz, 1H), 3.19-3.10 (m, 1H), 2.91 (s, 3H), 1.85 (s, 3H), 1.82 (s, 3H), 1.28 (d, J=6.7 Hz, 3H).

Synthesis of (10S,14R)-6-(2-methanesulfonylpropan-2-yl)-4-{5-methoxy-1H-pyrrolo[2,3-b]pyridin-4-yl}-14-methyl-8,12-dioxa-1,3,5-triazatricyclo[8.4.0.0$^{2,7}$]tetradeca-2,4,6-triene ("A88")

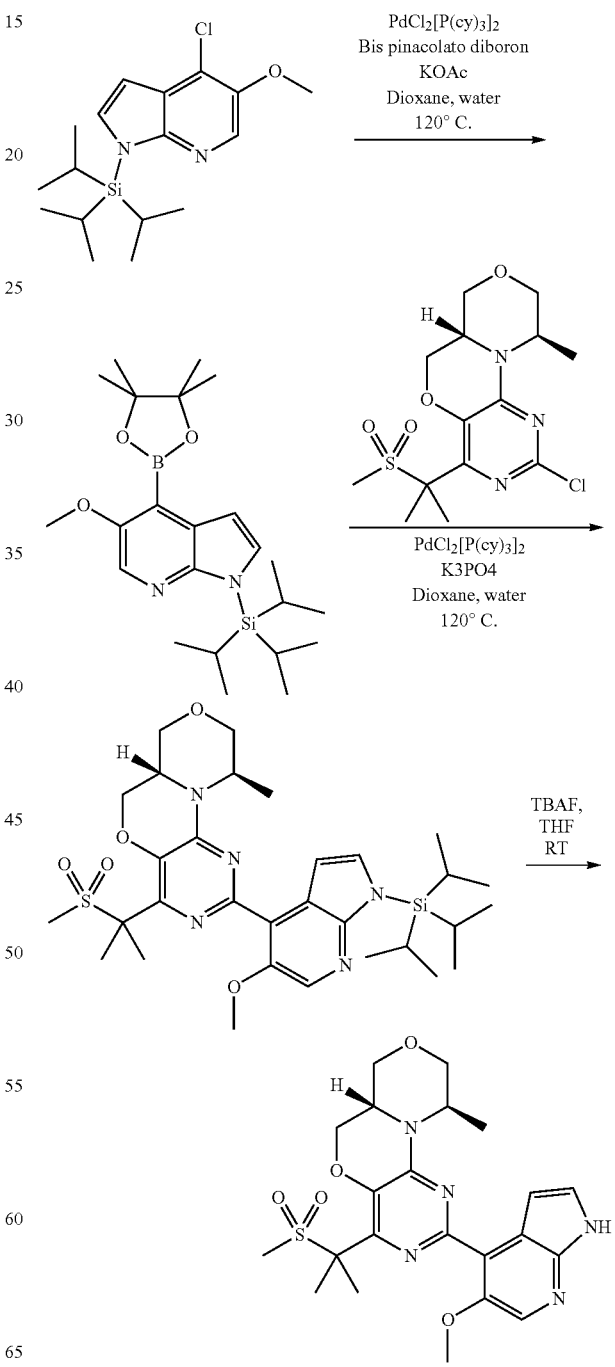

Colourless solid; LCMS (method F): 0.99 min; [MH+] 474.2.

$^1$H NMR (700 MHz, DMSO-d$_6$) δ 11.54 (s, 1H), 8.18 (s, 1H), 7.45 (t, J=2.9 Hz, 1H), 6.47 (dd, J=3.4, 1.9 Hz, 1H), 4.62-4.58 (m, 1H), 4.41 (dd, J=11.1, 3.3 Hz, 1H), 3.97-3.92 (m, 2H), 3.85-3.80 (m, 4H), 3.77 (d, J=11.5 Hz, 1H), 3.61 (dd, J=11.6, 3.3 Hz, 1H), 3.18-3.13 (m, 1H), 2.97 (s, 3H), 1.83 (s, 3H), 1.77 (s, 3H), 1.27 (d, J=6.8 Hz, 3H).

Synthesis of 4-[(10S,14R)-6-(2-methanesulfonylpropan-2-yl)-14-methyl-8,12-dioxa-1,3,5-triazatricyclo[8.4.0.0ˆ{2,7}]tetradeca-2,4,6-trien-4-yl]-1H-pyrrolo[2,3-b]pyridine-5-carbonitrile ("A89")

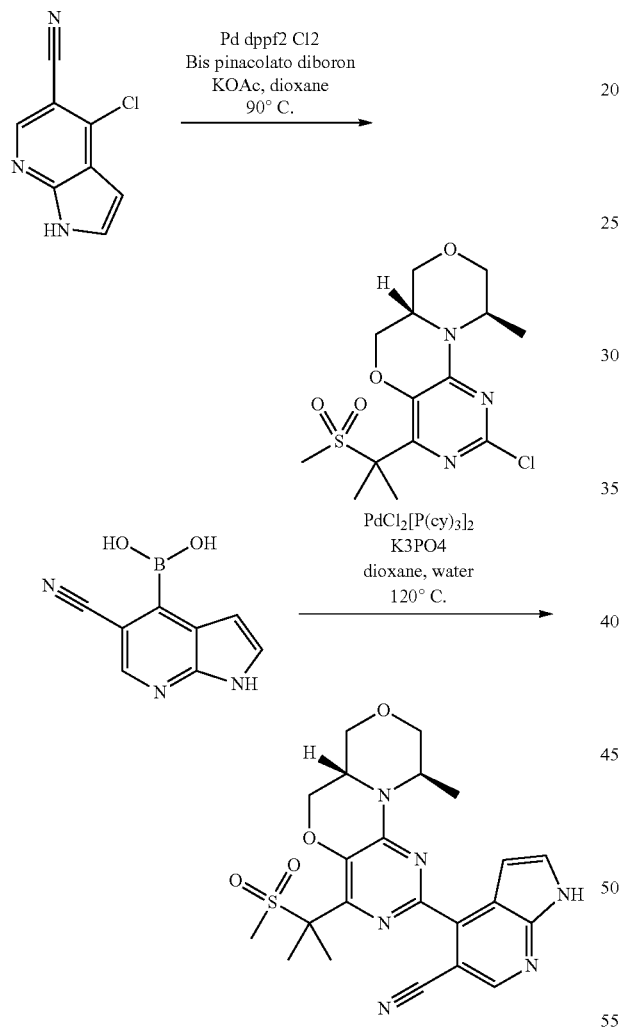

Synthesis of ethyl-{4-[(S)-1-(1-methanesulfonyl-1-methyl-ethyl)-5-(R)-methyl-5,6,8a,9-tetrahydro-8H-7,10-dioxa-2,4,4b-triaza-phenanthren-3-yl]-1H-pyrrolo[2,3-b]pyridin-5-yl}-amine ("A90")

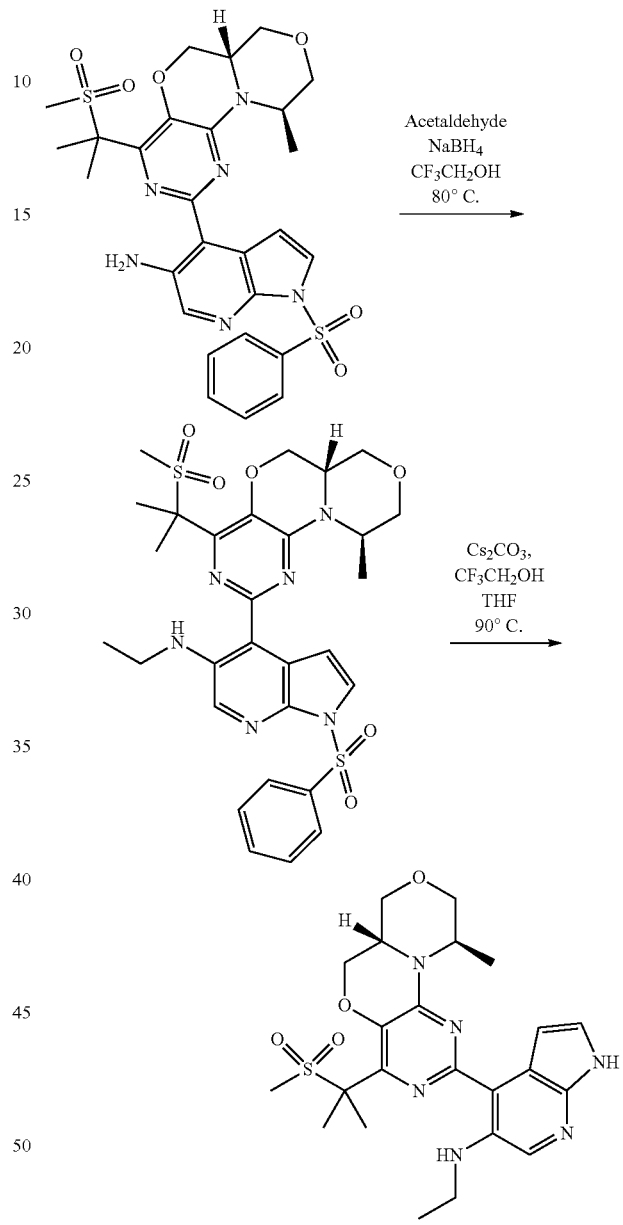

Yellow solid; LCMS (method F): 1.046 min; [MH+] 469.

$^1$H NMR (500 MHz, DMSO-d6) δ 12.38 (s, 1H), 8.66 (s, 1H), 7.77 (dd, J=3.5, 2.4 Hz, 1H), 7.24 (dd, J=3.5, 1.9 Hz, 1H), 4.90 (dt, J=9.2, 4.6 Hz, 1H), 4.46 (dd, J=11.0, 3.7 Hz, 1H), 4.08-3.81 (m, 4H), 3.66 (dd, J=11.5, 3.2 Hz, 1H), 3.19 (t, J=10.9 Hz, 1H), 2.95 (s, 3H), 1.91 (s, 3H), 1.87 (s, 3H), 1.33 (d, J=6.8 Hz, 3H).

Yellow solid; LCMS (method F): 0.95 min; [MH+] 487.2.

$^1$H NMR (400 MHz, DMSO-d$_6$) δ 11.19 (s, 1H), 7.91 (s, 1H), 7.57-7.47 (m, 1H), 7.32 (t, J=2.8 Hz, 1H), 6.93-6.90 (m, 1H), 4.75-4.67 (m, 1H), 4.42 (dd, J=10.8, 3.4 Hz, 1H), 4.03-3.93 (m, 2H), 3.90-3.83 (m, 2H), 3.67 (dd, J=11.5, 3.2 Hz, 1H), 3.31-3.22 (m, 2H), 3.21-3.13 (m, 1H), 2.96 (s, 3H), 1.88 (s, 3H), 1.83 (s, 3H), 1.33 (d, J=6.7 Hz, 3H), 1.24 (t, J=7.1 Hz, 3H).

133

Synthesis of 4-[(5R,8aS)-1-(1-methanesulfonyl-cyclopropyl)-5-methyl-5,6,8a,9-tetrahydro-8H-7,10-dioxa-2,4,4b-triaza-phenanthren-3-yl]-1H-pyrrolo[2,3-b]pyridin-5-ol ("A91")

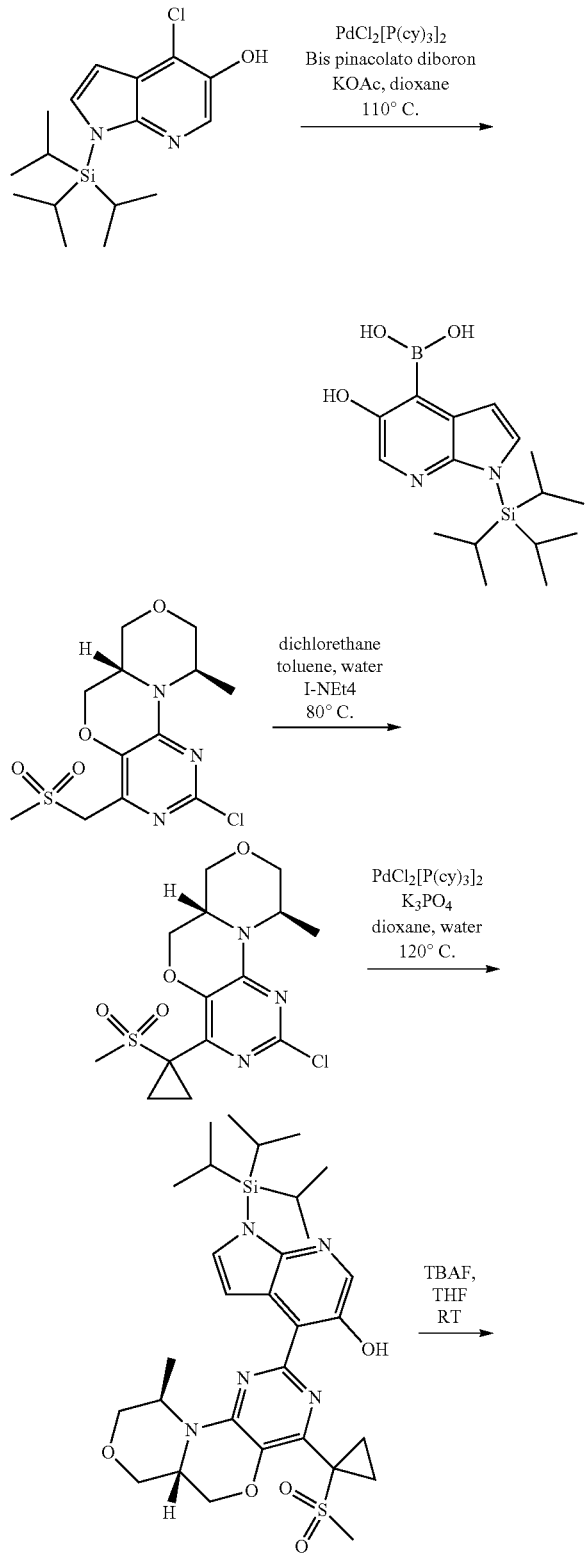

134

-continued

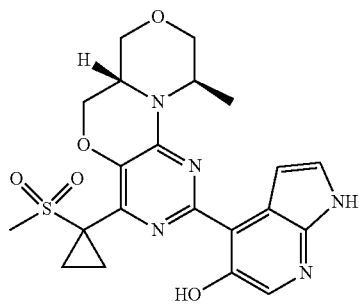 [SMILES: C[C@@H]1COC[C@H]2COc3c(nc(-c4c(O)cnc5[nH]ccc45)nc3C3(S(C)(=O)=O)CC3)N21]

Yellow solid; LCMS (method F): 0.93 min; [MH+] 458.2.

$^1$H NMR (400 MHz, DMSO-d$_6$) δ 13.28 (s, 1H), 11.52 (s, 1H), 7.97 (s, 1H), 7.46 (t, J=3.0 Hz, 1H), 7.18 (dd, J=3.3, 2.0 Hz, 1H), 4.73-4.65 (m, 1H), 4.48 (dd, J=10.5, 2.8 Hz, 1H), 4.06-3.90 (m, 4H), 3.74 (dd, J=11.7, 3.2 Hz, 1H), 3.24-3.17 (m, 1H), 3.05 (s, 3H), 1.77-1.68 (m, 2H), 1.46-1.40 (m, 2H), 1.37 (d, J=6.8 Hz, 3H).

Synthesis of 4-[(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]-1H-pyrrolo[2,3-b]pyridin-5-ol ("A92")

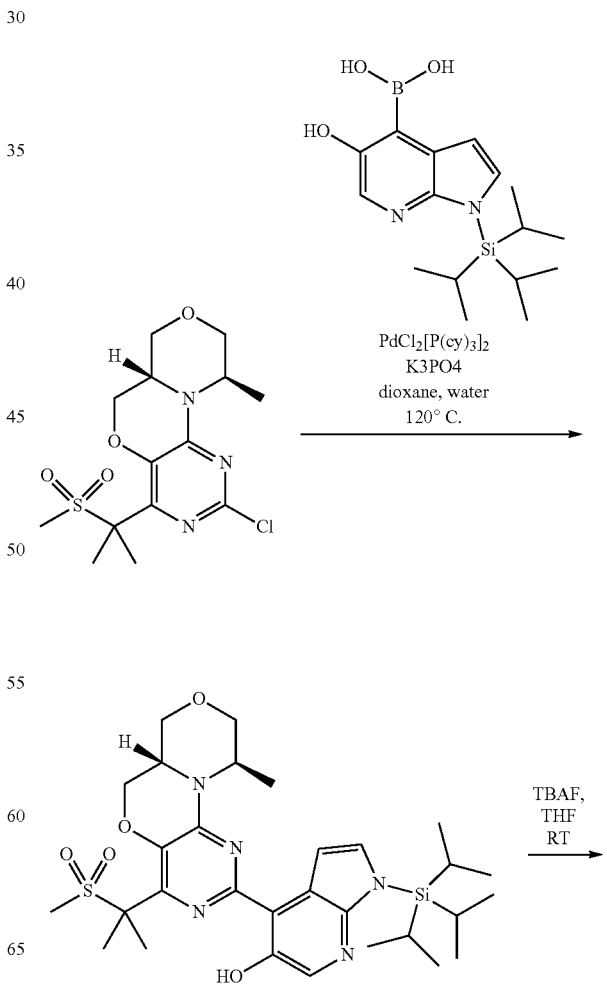

-continued

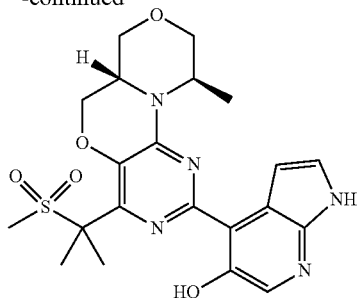

Yellow solid; LCMS (method F): 0.92 min; [MH+] 460.3.

¹H NMR (500 MHz, DMSO-d$_6$) δ 13.02 (s, 1H), 11.53 (s, 1H), 7.97 (s, 1H), 7.47 (t, J=3.0 Hz, 1H), 7.17-7.14 (m, 1H), 4.77-4.71 (m, 1H), 4.45 (dd, J=10.9, 3.5 Hz, 1H), 4.06-3.96 (m, 2H), 3.93 (d, J=11.6 Hz, 1H), 3.88 (dd, J=10.9, 9.0 Hz, 1H), 3.73 (dd, J=11.7, 3.3 Hz, 1H), 3.20 (t, J=10.8 Hz, 1H), 2.97 (s, 3H), 1.89 (s, 3H), 1.85 (s, 3H), 1.38 (d, J=6.8 Hz, 3H).

Synthesis of {1-[(5R,8aS)-1-(1-methanesulfonyl-1-methyl-ethyl)-5-methyl-5,6,8a,9-tetrahydro-8H-7,10-dioxa-2,4,4b-triaza-phenanthren-3-yl]-1H-benzoimidazol-2-yl}-oxetan-3-yl-amine ("A93")

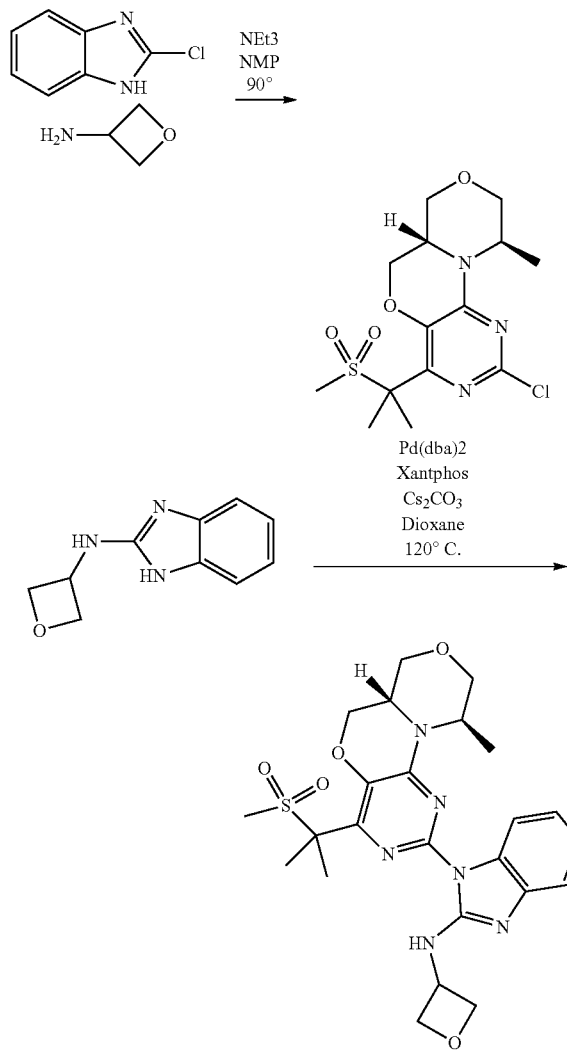

Colourless solid; LCMS (method F): 0.95 min; [MH+] 515.2.

¹H NMR (500 MHz, DMSO-d$_6$) δ 9.35-9.04 (m, 1H), 8.07 (d, J=8.0 Hz, 1H), 7.37 (d, J=7.8 Hz, 1H), 7.26-7.13 (m, 2H), 5.12-5.03 (m, 1H), 4.90-4.85 (m, 2H), 4.70-4.60 (m, 3H), 4.46 (dd, J=11.0, 3.6 Hz, 1H), 4.07-3.97 (m, 2H), 3.90-3.83 (m, 2H), 3.70 (dd, J=11.7, 3.3 Hz, 1H), 3.22-3.17 (m, 1H), 3.06 (s, 3H), 1.88 (s, 3H), 1.85 (s, 3H), 1.37 (d, J=6.9 Hz, 3H).

The following examples relate to medicaments:

Example A: Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B: Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

Example C: Solution

A solution is prepared from 1 g of an active ingredient of the formula I, 9.38 g of NaH$_2$PO$_4$.2 H$_2$O, 28.48 g of Na$_2$HPO$_4$.12 H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

Example D: Ointment 500 mg of an active ingredient of the formula I are mixed with 99.5 g of Vaseline under aseptic conditions.

Example E: Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

Example F: Dragees

Tablets are pressed analogously to Example E and subsequently coated in a conventional manner with a coating of sucrose, potato starch, talc, tragacanth and dye.

Example G: Capsules 2 kg of active ingredient of the formula I are introduced into hard gelatine capsules in a conventional manner in such a way that each capsule contains 20 mg of the active ingredient.

Example H: Ampoules

A solution of 1 kg of active ingredient of the formula I in 60 l of bidistilled water is sterile filtered, transferred into

The invention claimed is:
1. A compound of the formula I

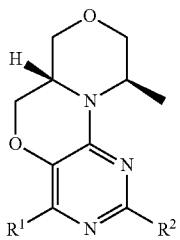

in which
R¹ denotes C(CH₃)₂SO₂A', CH₂OSO₂A', C(CH₃)₂OH, —[C(R³)₂]ₙHet¹, or 1-methylsulfonyl-cycloprop-1-yl,
R² denotes Het², NR³(CH₂)ₙHet², OHet², Ar¹, CONHHet³, COHet³ or CONHA,
R³ denotes H or A',
Het¹ denotes imidazolyl, pyrazolyl, triazolyl or pyridyl, each of which is unsubstituted or monosubstituted by COOH, COOA', CH₂OH, CH₂OA' or A,
Het² denotes 1H-pyrrolo[2,3-b]pyridinyl, 1H-pyrrolo[2,3-c]pyridinyl, indolyl, benzimidazolyl, imidazolyl, 1,2,3,4-tetrahydroisoquinolyl, pyridyl, triazolyl, pyrazolyl, quinolyl, isoquinolyl, quinazolinyl or 1,3-dihydro-2lamda6-2,2-dioxo-1-benzothiazolyl, each of which is unsubstituted or mono- or disubstituted by Hal, A', —[C(R³)₂]ₙOR³, CONH₂, SO₂phenyl, benzyl, CN, —[C(R³)₂]ₙNH₂, —[C(R³)₂]ₙNHA, oxetanyl-NH— and/or NHCOA,
Het³ denotes triazolyl, pyridazinyl, pyrimidinyl, pyrazolyl or pyrrolidinyl each of which is unsubstituted or monosubstituted by
—[C(R³)₂]ₙOR³, —[C(R³)₂]ₙNH₂ or =O,
Ar¹ denotes phenyl monosubstituted by —[C(R³)₂]ₙOR³, imidazolyl, —[C(R³)₂]ₙNH₂, pyrazolyl, aziridinyl or oxetanyl, each of which may be unsubstituted or monosubstituted by —[C(R³)₂]ₙOR³ or —[C(R³)₂]ₙNH₂,
A denotes unbranched or branched alkyl having 1-6 C-atoms, in which 1-7 H atoms may be replaced by OH, F, Cl and/or Br and/or in which one or two non-adjacent CH₂ groups may be replaced by O and/or NH groups,
A' denotes unbranched or branched alkyl having 1-4 C-atoms,
Hal denotes F, Cl, Br or I,
n denotes 0, 1, 2 or 3,
or a pharmaceutically acceptable salt, tautomer or stereoisomer thereof, including mixtures thereof in all ratios.
2. A compound according to claim 1 in which
R¹ denotes C(CH₃)₂SO₂A' or C(CH₃)₂OH,
or a pharmaceutically acceptable salt, tautomer or stereoisomer thereof, including mixtures thereof in all ratios.
3. A compound according to claim 1, in which
R² denotes Het²,
or a pharmaceutically acceptable salt, tautomer or stereoisomer thereof, including mixtures thereof in all ratios.
4. A compound according to claim 1, in which
R³ denotes H,
or a pharmaceutically acceptable salt, tautomer or stereoisomer thereof, including mixtures thereof in all ratios.
5. A compound according to claim 1, in which
A denotes unbranched or branched alkyl having 1-6 C-atoms, in which 1-5 H atoms may be replaced by OH and/or F,
or a pharmaceutically acceptable salt, tautomer or stereoisomer thereof, including mixtures thereof in all ratios.
6. A compound according to claim 1, in which
Het² denotes 1H-pyrrolo[2,3-b]pyridinyl, 1H-pyrrolo[2,3-c]pyridinyl, indolyl, benzimidazolyl or imidazolyl, each of which is mono- or disubstituted by Hal, —[C(R³)₂]ₙNH₂ and/or —[C(R³)₂]ₙNHA,
or a pharmaceutically acceptable salt, tautomer or stereoisomer thereof, including mixtures thereof in all ratios.
7. A compound according to claim 1, in which
R¹ denotes C(CH₃)₂SO₂A' or C(CH₃)₂OH,
R² denotes Het²,
Het² denotes 1H-pyrrolo[2,3-b]pyridinyl, 1H-pyrrolo[2,3-c]pyridinyl, indolyl, benzimidazolyl or imidazolyl, each of which is unsubstituted or mono- or disubstituted by Hal, OH, —[C(R³)₂]ₙNH₂, —[C(R³)₂]ₙNHA, oxetanyl-NH— and/or NHCOA,
A denotes denotes unbranched or branched alkyl having 1-6 C-atoms, in which 1-5 H atoms may be replaced by OH and/or F,
A' denotes unbranched or branched alkyl having 1-4 C-atoms,
Hal denotes F, Cl, Br or I,
n denotes 0, 1, 2 or 3
or a pharmaceutically acceptable salt, tautomer or stereoisomer thereof, including mixtures thereof in all ratios.
8. A compound according to claim 1, in which
R¹ denotes C(CH₃)₂SO₂CH₃ or C(CH₃)₂OH,
R² denotes Het²,
R³ denotes H,
Het² denotes 1H-pyrrolo[2,3-b]pyridinyl, 1H-pyrrolo[2,3-c]pyridinyl, indolyl, benzimidazolyl or imidazolyl, each of which is mono- or disubstituted by Hal, —[C(R³)₂]ₙNH₂ and/or —[C(R³)₂]ₙNHA,
A denotes denotes unbranched or branched alkyl having 1-6 C-atoms, in which 1-5 H atoms may be replaced by OH and/or F,
A' denotes unbranched or branched alkyl having 1-4 C-atoms,
Hal denotes F, Cl, Br or I,
n denotes 0, 1, 2 or 3
or a pharmaceutically acceptable salt, tautomer or stereoisomer thereof, including mixtures thereof in all ratios.
9. A compound according to claim 1, selected from the following compounds:

| No. | Structure |
|---|---|
| "A1" | ![structure] |

-continued

| No. | Structure |
|---|---|
| "A2" | 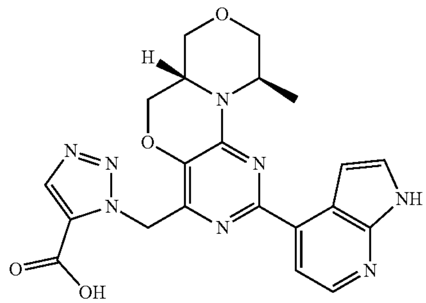 [SMILES: C[C@@H]1COC[C@H]2COc3c(Cn4nncc4C(=O)O)nc(-c4ccnc5[nH]ccc45)nc3N21] |
| "A3" | 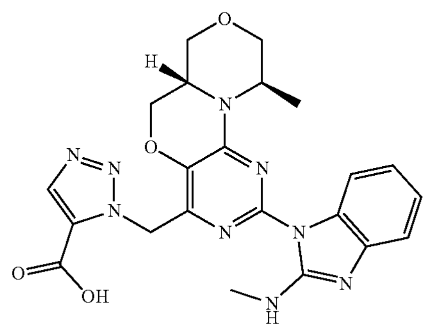 [SMILES: CNc1nc2ccccc2n1-c1nc(Cn2nncc2C(=O)O)c2c(n1)N1[C@@H](COC[C@H]1C)CO2] |
| "A4" | 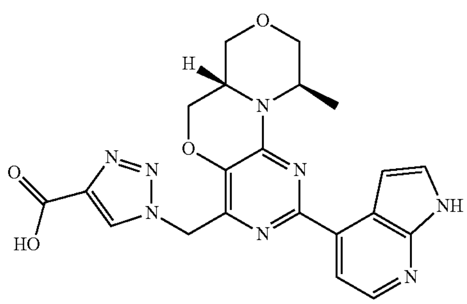 [SMILES: C[C@@H]1COC[C@H]2COc3c(Cn4cc(C(=O)O)nn4)nc(-c4ccnc5[nH]ccc45)nc3N21] |
| "A5" | 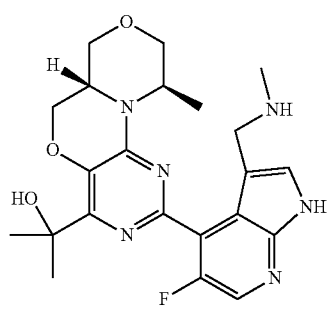 [SMILES: CNCc1c[nH]c2ncc(F)c(-c3nc4c(c(C(C)(C)O)n3)OC[C@@H]3COC[C@@H](C)N43)c12] |
| "A6" | 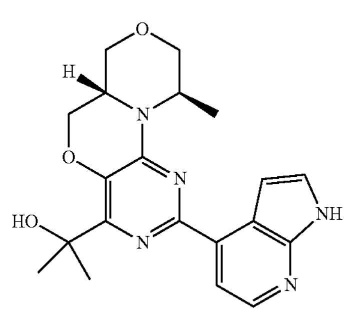 [SMILES: C[C@@H]1COC[C@H]2COc3c(nc(-c4ccnc5[nH]ccc45)nc3C(C)(C)O)N21] |

-continued

| No. | Structure |
|---|---|
| "A7" | 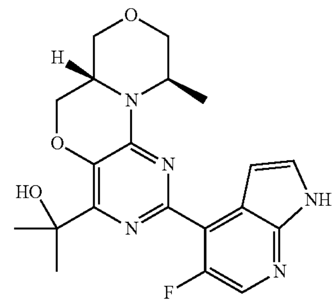 [SMILES: C[C@@H]1COC[C@H]2COc3c(nc(-c4c(F)cnc5[nH]ccc45)nc3C(C)(C)O)N21] |
| "A8" | 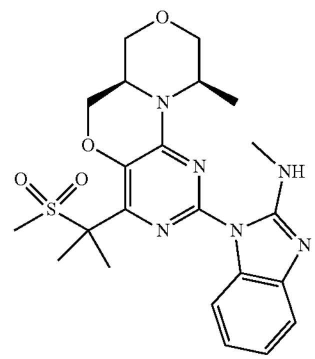 [SMILES: CNc1nc2ccccc2n1-c1nc2c(c(C(C)(C)S(C)(=O)=O)n1)OC[C@H]1COC[C@@H](C)N21] |
| "A9" | 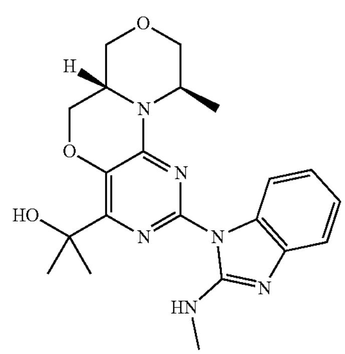 [SMILES: CNc1nc2ccccc2n1-c1nc2c(c(C(C)(C)O)n1)OC[C@@H]1COC[C@@H](C)N21] |
| "A10" | 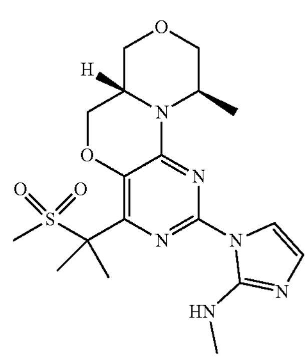 [SMILES: CNc1nccn1-c1nc2c(c(C(C)(C)S(C)(=O)=O)n1)OC[C@@H]1COC[C@@H](C)N21] |

-continued
| No. | Structure |
|---|---|
| "A11" | 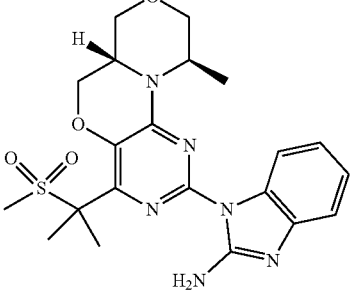 |
| "A12" | 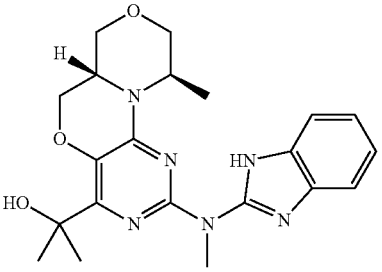 [SMILES: C[C@@H]1COC[C@H]2COc3c(nc(N(C)c4nc5ccccc5[nH]4)nc3C(C)(C)O)N21] |
| "A13" | 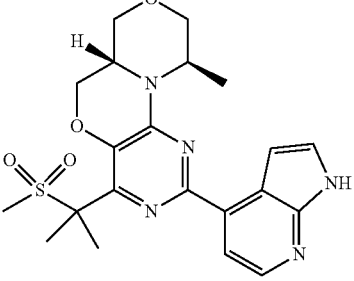 |
| "A14" | 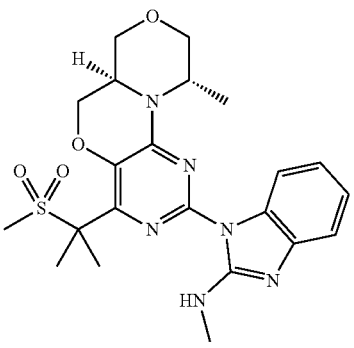 [SMILES: CNc1nc2ccccc2n1-c1nc2c(c(C(C)(C)S(C)(=O)=O)n1)OC[C@H]1COC[C@H](C)N21] |
| "A15" | 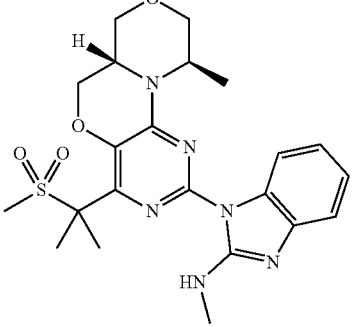 |
-continued
| No. | Structure |
|---|---|
| "A16" | 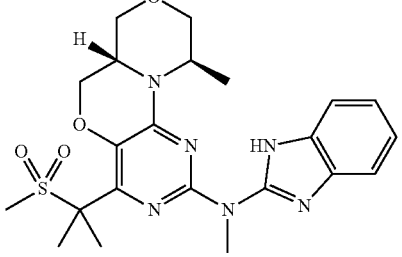 |
| "A17" | 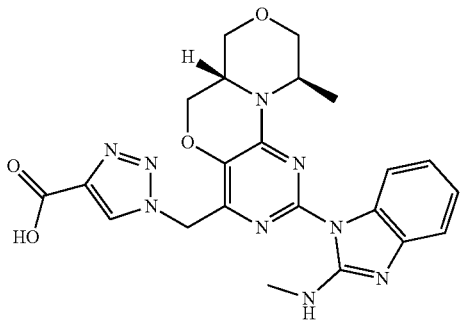 [SMILES: CNc1nc2ccccc2n1-c1nc(Cn2cc(C(=O)O)nn2)c2c(n1)N1[C@@H](COC[C@H]1C)CO2] |
| "A18" | 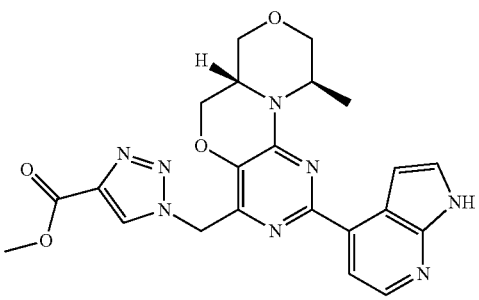 [SMILES: COC(=O)c1cn(Cc2nc(-c3ccnc4[nH]ccc34)nc3c2OC[C@@H]2COC[C@@H](C)N32)nn1] |
| "A19" | 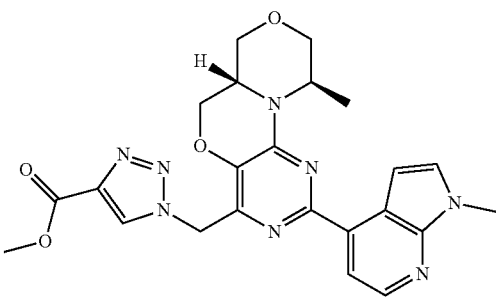 |
| "A20" | 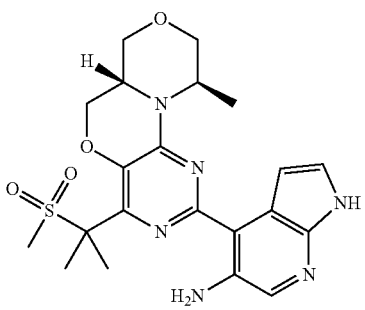 |

US 10,570,149 B2
143
-continued
| No. | Structure |
|---|---|
| "A21" | 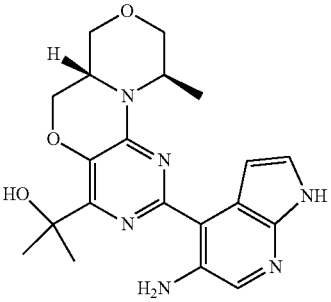 [SMILES: C[C@@H]1COC[C@H]2COc3c(nc(-c4c(N)cnc5[nH]ccc45)nc3C(C)(C)O)N21] |
| "A22" | 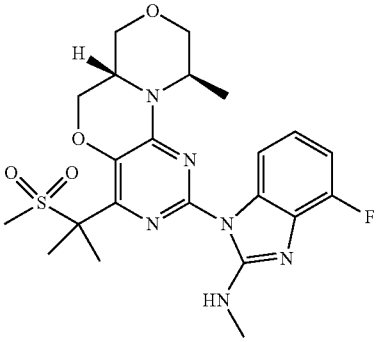 |
| "A23" | 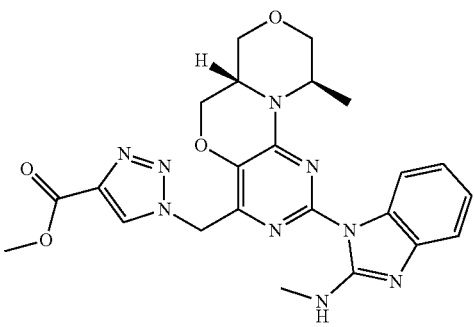 [SMILES: CNc1nc2ccccc2n1-c1nc(Cn2cc(C(=O)OC)nn2)c2c(n1)N1[C@@H](COC[C@H]1C)CO2] |
| "A24" | 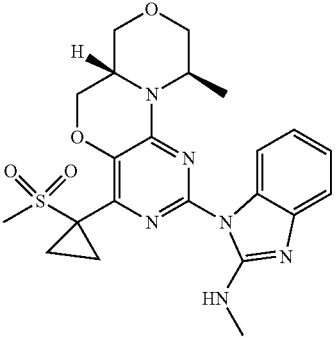 |
144
-continued
| No. | Structure |
|---|---|
| "A25" | 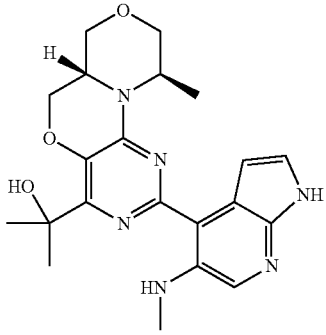 [SMILES: CNc1cnc2[nH]ccc2c1-c1nc2c(c(C(C)(C)O)n1)OC[C@@H]1COC[C@@H](C)N21] |
| "A26" | 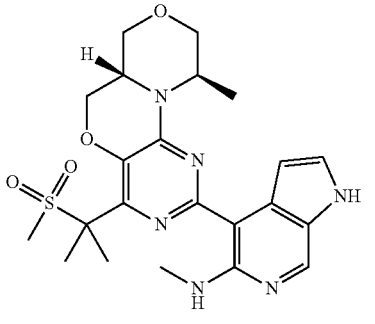 |
| "A27" | 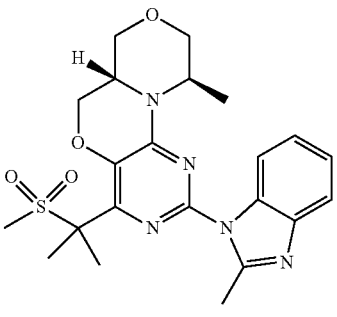 [SMILES: Cc1nc2ccccc2n1-c1nc2c(c(C(C)(C)S(C)(=O)=O)n1)OC[C@@H]1COC[C@@H](C)N21] |
| "A28" | 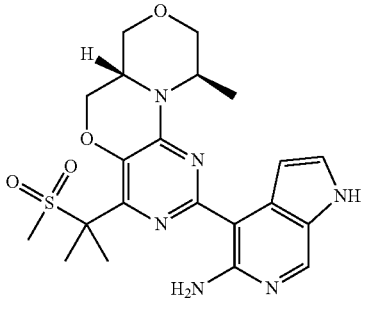 [SMILES: C[C@@H]1COC[C@H]2COc3c(nc(-c4c(N)ncc5[nH]ccc45)nc3C(C)(C)S(C)(=O)=O)N21] |

| No. | Structure |
|---|---|
| "A29" | 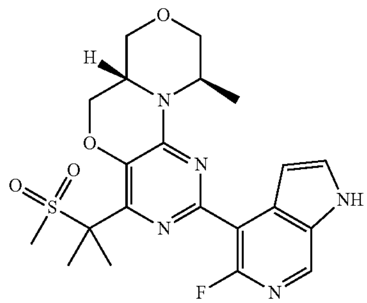 [SMILES: C[C@@H]1COC[C@H]2COc3c(nc(-c4c(F)ncc5[nH]ccc45)nc3C(C)(C)S(C)(=O)=O)N21] |
| "A30" | 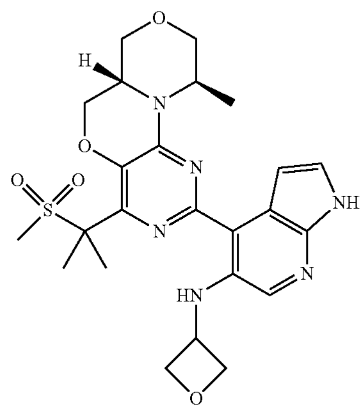 [SMILES: C[C@@H]1COC[C@H]2COc3c(nc(-c4c(NC5COC5)cnc5[nH]ccc45)nc3C(C)(C)S(C)(=O)=O)N21] |
| "A31" | 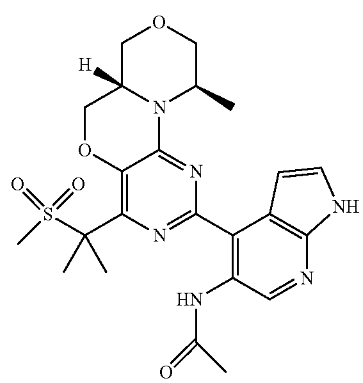 [SMILES: CC(=O)Nc1cnc2[nH]ccc2c1-c1nc2c(c(C(C)(C)S(C)(=O)=O)n1)OC[C@@H]1COC[C@@H](C)N21] |
| "A32" | 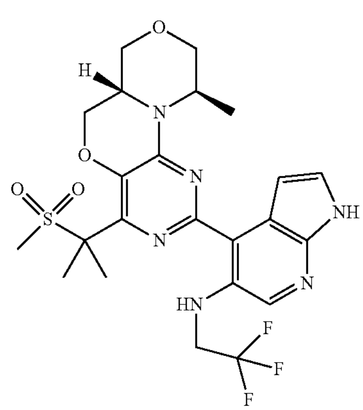 [SMILES: C[C@@H]1COC[C@H]2COc3c(nc(-c4c(NCC(F)(F)F)cnc5[nH]ccc45)nc3C(C)(C)S(C)(=O)=O)N21] |

| No. | Structure |
|---|---|
| "A33" | 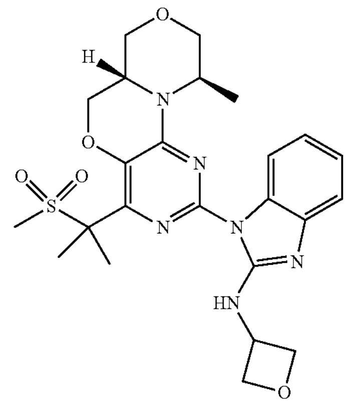 [SMILES: C[C@@H]1COC[C@H]2COc3c(nc(-n4c(NC5COC5)nc5ccccc54)nc3C(C)(C)S(C)(=O)=O)N21] |
| "A34" | 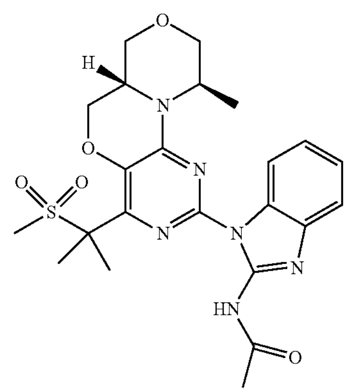 [SMILES: CC(=O)Nc1nc2ccccc2n1-c1nc2c(c(C(C)(C)S(C)(=O)=O)n1)OC[C@@H]1COC[C@@H](C)N21] |
| "A35" | 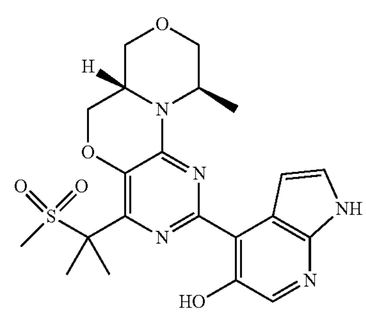 [SMILES: C[C@@H]1COC[C@H]2COc3c(nc(-c4c(O)cnc5[nH]ccc45)nc3C(C)(C)S(C)(=O)=O)N21] |
| "A36" | 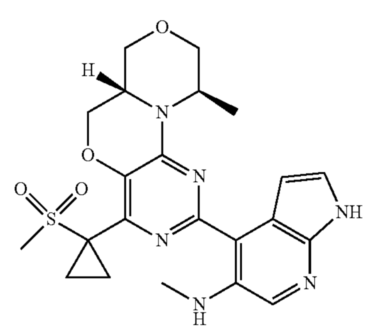 [SMILES: CNc1cnc2[nH]ccc2c1-c1nc2c(c(C3(S(C)(=O)=O)CC3)n1)OC[C@@H]1COC[C@@H](C)N21] |

| No. | Structure |
|---|---|
| "A37" | 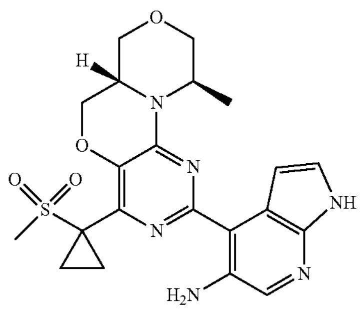 [SMILES: C[C@@H]1COC[C@H]2COc3c(nc(-c4c(N)cnc5[nH]ccc45)nc3C3(S(C)(=O)=O)CC3)N21] |
| "A38" | 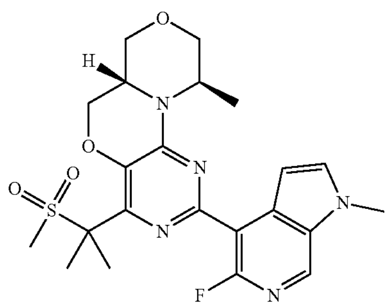 [SMILES: C[C@@H]1COC[C@H]2COc3c(nc(-c4c(F)ncc5c4ccn5C)nc3C(C)(C)S(C)(=O)=O)N21] |
| "A39" | 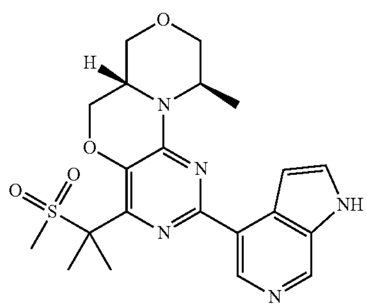 [SMILES: C[C@@H]1COC[C@H]2COc3c(nc(-c4cncc5[nH]ccc45)nc3C(C)(C)S(C)(=O)=O)N21] |
| "A40" | 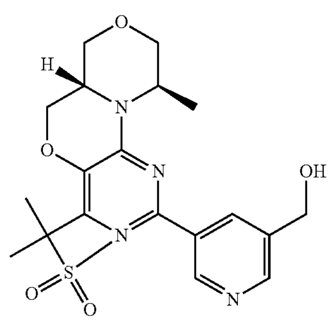 |
| "A41" | 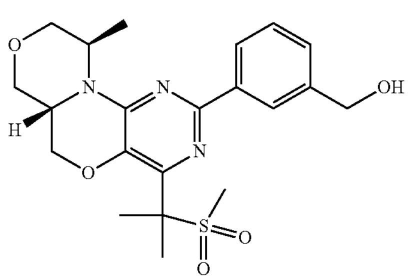 [SMILES: C[C@@H]1COC[C@H]2COc3c(nc(-c4cccc(CO)c4)nc3C(C)(C)S(C)(=O)=O)N21] |
| "A42" | |
| "A43" | |
| "A44" | |
| "A45" | |

| No. | Structure |
|---|---|
| "A46" | 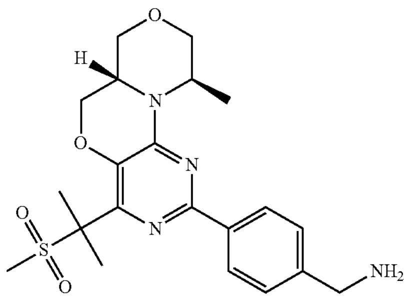 [SMILES: C[C@@H]1COC[C@H]2COc3c(nc(-c4ccc(CN)cc4)nc3C(C)(C)S(C)(=O)=O)N21] |
| "A47" | 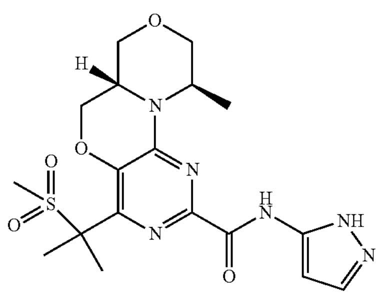 [SMILES: C[C@@H]1COC[C@H]2COc3c(nc(C(=O)Nc4ccn[nH]4)nc3C(C)(C)S(C)(=O)=O)N21] |
| "A48" | 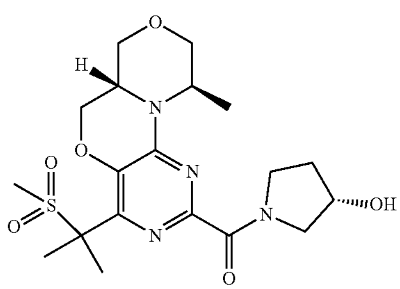 [SMILES: C[C@@H]1COC[C@H]2COc3c(nc(C(=O)N4CC[C@H](O)C4)nc3C(C)(C)S(C)(=O)=O)N21] |
| "A49" | 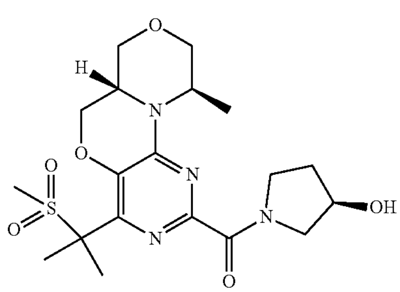 [SMILES: C[C@@H]1COC[C@H]2COc3c(nc(C(=O)N4CC[C@@H](O)C4)nc3C(C)(C)S(C)(=O)=O)N21] |
| "A50" | 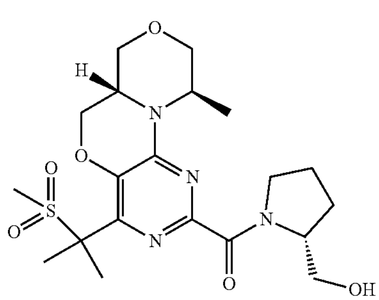 [SMILES: C[C@@H]1COC[C@H]2COc3c(nc(C(=O)N4CCC[C@@H]4CO)nc3C(C)(C)S(C)(=O)=O)N21] |

| No. | Structure |
|---|---|
| "A51" | 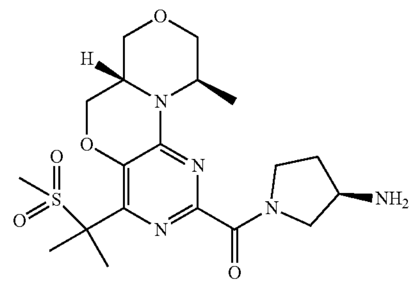 [SMILES: C[C@@H]1COC[C@H]2COc3c(nc(C(=O)N4CC[C@@H](N)C4)nc3C(C)(C)S(C)(=O)=O)N21] |
| "A52" | 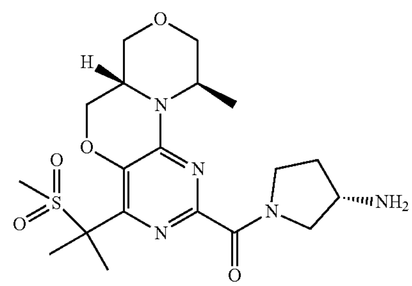 [SMILES: C[C@@H]1COC[C@H]2COc3c(nc(C(=O)N4CC[C@H](N)C4)nc3C(C)(C)S(C)(=O)=O)N21] |
| "A53" | 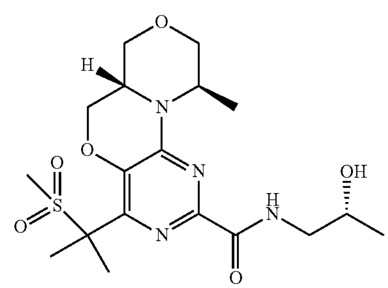 [SMILES: C[C@@H]1COC[C@H]2COc3c(nc(C(=O)NC[C@@H](C)O)nc3C(C)(C)S(C)(=O)=O)N21] |
| "A54" | 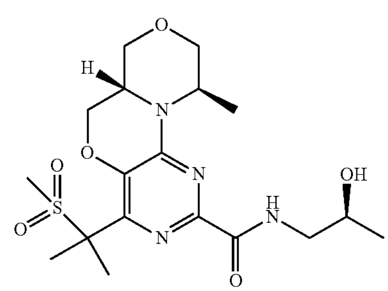 [SMILES: C[C@H](O)CNC(=O)c1nc2c(c(C(C)(C)S(C)(=O)=O)n1)OC[C@@H]1COC[C@@H](C)N21] |
| "A55" | 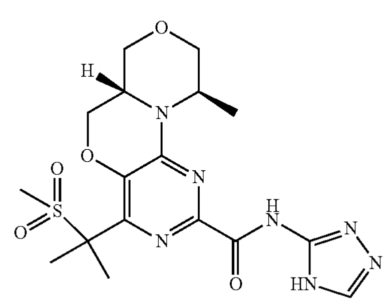 [SMILES: C[C@@H]1COC[C@H]2COc3c(nc(C(=O)Nc4nnc[nH]4)nc3C(C)(C)S(C)(=O)=O)N21] |

-continued

| No. | Structure |
|---|---|
| "A56" | 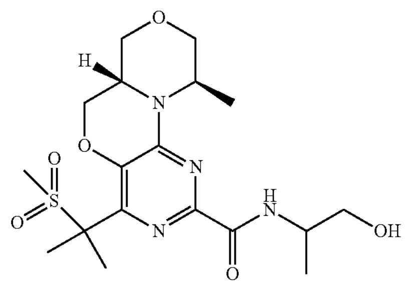 [SMILES: CC(CO)NC(=O)c1nc2c(c(C(C)(C)S(C)(=O)=O)n1)OC[C@@H]1COC[C@@H](C)N21] |
| "A57" | 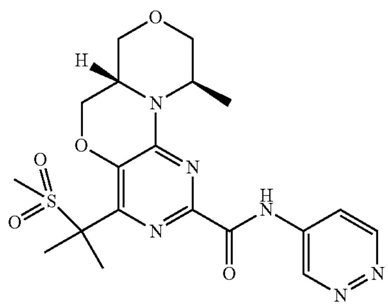 [SMILES: C[C@@H]1COC[C@H]2COc3c(nc(C(=O)Nc4ccnnc4)nc3C(C)(C)S(C)(=O)=O)N21] |
| "A58" | 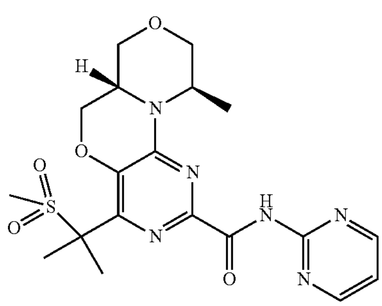 [SMILES: C[C@@H]1COC[C@H]2COc3c(nc(C(=O)Nc4ncccn4)nc3C(C)(C)S(C)(=O)=O)N21] |
| "A59" | 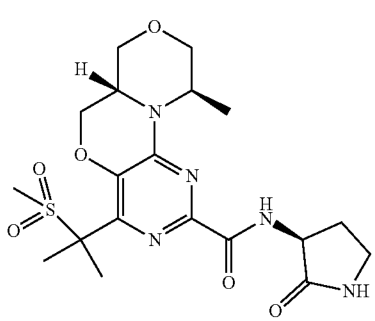 [SMILES: C[C@@H]1COC[C@H]2COc3c(nc(C(=O)N[C@H]4CCNC4=O)nc3C(C)(C)S(C)(=O)=O)N21] |
| "A60" | 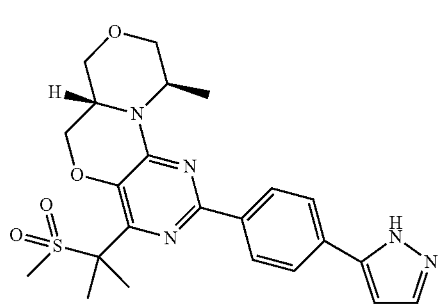 [SMILES: C[C@@H]1COC[C@H]2COc3c(nc(-c4ccc(-c5ccn[nH]5)cc4)nc3C(C)(C)S(C)(=O)=O)N21] |

-continued

| No. | Structure |
|---|---|
| "A61" | 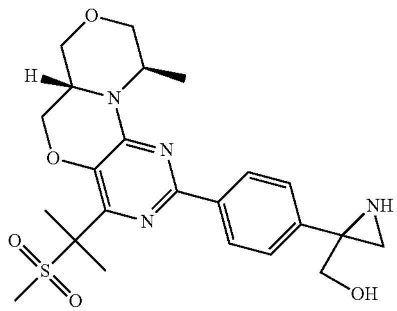 [SMILES: C[C@@H]1COC[C@H]2COc3c(nc(-c4ccc(C5(CO)CN5)cc4)nc3C(C)(C)S(C)(=O)=O)N21] |
| "A62" | 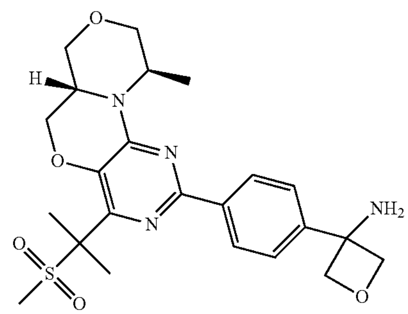 [SMILES: C[C@@H]1COC[C@H]2COc3c(nc(-c4ccc(C5(N)COC5)cc4)nc3C(C)(C)S(C)(=O)=O)N21] |
| "A63" | 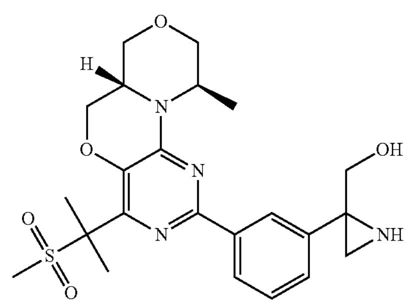 [SMILES: C[C@@H]1COC[C@H]2COc3c(nc(-c4cccc(C5(CO)CN5)c4)nc3C(C)(C)S(C)(=O)=O)N21] |
| "A64" | 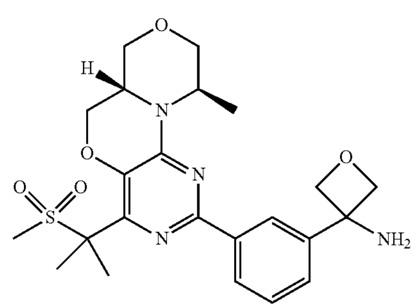 [SMILES: C[C@@H]1COC[C@H]2COc3c(nc(-c4cccc(C5(N)COC5)c4)nc3C(C)(C)S(C)(=O)=O)N21] |
| "A65" | 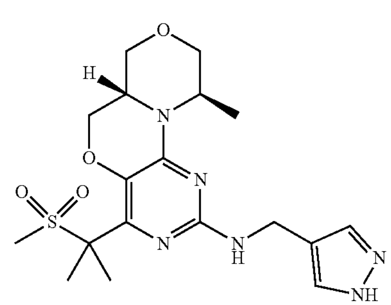 [SMILES: C[C@@H]1COC[C@H]2COc3c(nc(NCc4cn[nH]c4)nc3C(C)(C)S(C)(=O)=O)N21] |

-continued

| No. | Structure |
|---|---|
| "A66" | (structure) |
| "A67" | (structure) |
| "A68" | (structure) |
| "A69" | (structure) |
| "A70" | (structure) |

-continued

| No. | Structure |
|---|---|
| "A71" | (structure) |
| "A72" | (structure) |
| "A73" | (structure) |
| "A74" | (structure) |
| "A75" | (structure) |

| No. | Structure |
|---|---|
| "A76" | (structure) |
| "A77" | (structure) |
| "A78" | (structure) |
| "A79" | (structure) |
| "A80" | (structure) |
| "A81" | (structure) |
| "A82" | (structure) |
| "A83" | (structure) |
| "A84" | (structure) |
| "A85" | (structure) |

| No. | Structure |
|---|---|
| "A86" | (structure) |
| "A87" | (structure) |
| "A88" | (structure) |
| "A89" | (structure) |

| No. | Structure |
|---|---|
| "A90" | (structure) |
| "A91" | (structure) |
| "A92" | (structure) |
| "A93" | (structure) | or a pharmaceutically acceptable salt, tautomer or stereoisomer thereof, including mixtures thereof in all ratios.

10. A process for the preparation of a compound of the formula I according to claim 1 or a pharmaceutically acceptable salt, tautomer or stereoisomer thereof, comprising:

a) reacting a compound of the formula II

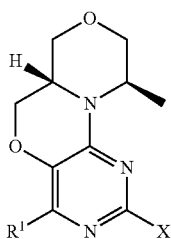

II in which R¹ has the meanings indicated in claim 1,
and X denotes Cl or Br,
with a compound of formula III

L-R²  III in which R² has the meanings indicated in claim 1,
and L denotes H, a boronic acid or a boronic acid ester group,
or
b) reacting a compound of the formula IIb

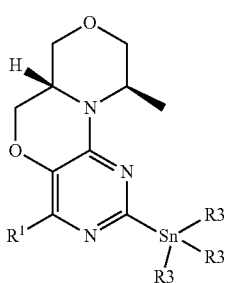

IIb in which R¹ has the meaning indicated in claim 1, and R³ denotes unbranched or branched alkyl having 1-4 C-atoms,
with a compound of formula III

X—R²  III in which R² has the meanings indicated in claim 1,
and X denotes Cl, Br or I,
and/or
c) converting a base or acid of the formula I into one of its salts.

11. A medicament composition comprising at least one compound of the formula I according to claim 1 or a pharmaceutically acceptable salt, tautomer or stereoisomer thereof, including mixtures thereof in all ratios, and optionally a pharmaceutically acceptable carrier, excipient or vehicle.

12. A medicament composition comprising at least one compound of the formula I according to claim 1 or a pharmaceutically acceptable salt, tautomer or stereoisomer thereof, including mixtures thereof in all ratios, and at least one further medicament active ingredient.

13. A kit consisting of separate packs of
(a) an effective amount of a compound of the formula I according to claim 1 or a pharmaceutically acceptable salt, tautomer or stereoisomer thereof, including mixtures thereof in all ratios,
and
(b) an effective amount of a further medicament active ingredient.

14. A method for the inhibiting ATR activity in a patient, comprising administering a compound of the formula I according to claim 1 or a pharmaceutically acceptable salt, tautomer or stereoisomer thereof, including mixtures thereof in all ratios.

* * * * *